US009221918B2

(12) United States Patent  
Dreier et al.

(10) Patent No.: US 9,221,918 B2
(45) Date of Patent: Dec. 29, 2015

(54) ANTIGEN BINDING POLYPEPTIDES

(71) Applicant: arGEN-X B.V., Rotterdam (NL)

(72) Inventors: Torsten Dreier, Sint Martens Latem (BE); Christophe Frederic Jerome Blanchetot, Gouda (NL); Johannes Joseph Wilhelmus De Haard, Oudelande (NL)

(73) Assignee: arGEN-X B.V., Breda (NL)

( * ) Notice: Subject to any disclaimer, the term of this patent is extended or adjusted under 35 U.S.C. 154(b) by 0 days.

(21) Appl. No.: 14/607,941

(22) Filed: Jan. 28, 2015

(65) Prior Publication Data

US 2015/0239990 A1    Aug. 27, 2015

Related U.S. Application Data

(62) Division of application No. 13/233,345, filed on Sep. 15, 2011, which is a division of application No. 12/497,239, filed on Jul. 2, 2009, now Pat. No. 8,444,976.

(60) Provisional application No. 61/077,730, filed on Jul. 2, 2008, provisional application No. 61/110,161, filed on Oct. 31, 2008.

(30) Foreign Application Priority Data

Jul. 2, 2008 (GB) .................................. 0812120.4

(51) Int. Cl.
*C07H 21/04* (2006.01)
*C07K 16/46* (2006.01)

(52) U.S. Cl.
CPC ........... *C07K 16/462* (2013.01); *C07K 2317/22* (2013.01); *C07K 2317/24* (2013.01); *C07K 2317/56* (2013.01)

(58) Field of Classification Search
None
See application file for complete search history.

(56) References Cited

U.S. PATENT DOCUMENTS

| | | | |
|---|---|---|---|
| 6,759,518 | B1 | 7/2004 | Kontermann et al. |
| 7,371,849 | B2 | 5/2008 | Honda et al. |
| 8,444,976 | B2 * | 5/2013 | Dreier et al. ............... 424/133.1 |
| 8,524,231 | B2 * | 9/2013 | Dreier et al. ............... 424/133.1 |
| 2003/0190598 | A1 | 10/2003 | Tanha et al. |
| 2004/0214990 | A1 | 10/2004 | Tribouley et al. |
| 2005/0037421 | A1 | 2/2005 | Honda et al. |
| 2006/0194212 | A1 | 8/2006 | Skurkovich et al. |
| 2006/0246058 | A1 | 11/2006 | Tanha et al. |
| 2007/0178082 | A1 | 8/2007 | Silence et al. |
| 2009/0111126 | A1 | 4/2009 | Akamatsu et al. |
| 2011/0300140 | A1 | 12/2011 | Dreier et al. |
| 2012/0148607 | A1 | 6/2012 | Hultberg et al. |
| 2012/0156206 | A1 | 6/2012 | Hultberg et al. |

FOREIGN PATENT DOCUMENTS

| | | |
|---|---|---|
| EP | 584421 | 2/1994 |
| EP | 1433793 A1 | 6/2004 |
| WO | WO 94/04678 A1 | 3/1994 |
| WO | WO 01/32714 A1 | 11/2001 |
| WO | WO 01/90190 A2 | 11/2001 |
| WO | WO 03/025020 A1 | 3/2003 |
| WO | WO 03/035694 A2 | 5/2003 |
| WO | WO 03/050531 A2 | 6/2003 |
| WO | WO 2004003019 A2 | 1/2004 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2004/062551 A2 | 7/2004 |
| WO | WO 2005/037989 A2 | 4/2005 |
| WO | WO 2005/044858 A1 | 5/2005 |
| WO | WO 2006/040153 A2 | 4/2006 |
| WO | WO 2006/074947 A2 | 7/2006 |
| WO | WO 2006/079372 A1 | 8/2006 |
| WO | WO 2006/122786 A2 | 11/2006 |
| WO | WO 2006/122825 A2 | 11/2006 |
| WO | WO 2007/025977 A2 | 3/2007 |
| WO | WO 2007/042289 A2 | 4/2007 |
| WO | WO 2007/104529 A2 | 9/2007 |
| WO | WO 2007/110219 A1 | 10/2007 |
| WO | WO 2007/118670 A1 | 10/2007 |
| WO | WO 2007/136525 A2 | 11/2007 |
| WO | WO 2008/020079 A1 | 2/2008 |

(Continued)

OTHER PUBLICATIONS

Brorson et al., "Mutational Analysis of Avidity and Fine Specificity of Anti-Levan Antibodies," J. Immunol. 163:6694-6701 (1999) D.
Brummell et al., "Probing the combining site of an anti-carbohydrate antibody by saturation-mutagenesis: role of the heavy chain CDR3 residues," Biochemistry 32:1180-1187 (1993) D.
Burks et al., "In Vitro scanning saturation mutagenesis of an antibody binding pocket," PNAS, 1997, 94:412-417.
Casset et al., "A peptide mimetic of an anti-CD4 monoclonal antibody by rational design," BBRC, 2003, vol. 307, 198-205.
Chen et al., "Selection and Analysis of an Optimized anti-VEGF Antibody: Crystal Structure of an Affinity-matured Fab in Complex with Antigen," J. Mol. Bio., 1999, 293, 865-881.
Coleman "Effects of amino acid sequence changes on antibody-antigen interactions," Research in Immunol., 145:33-36 (1994).
De Pascalis, R. et al.; "Grafting of "Abbreviated" Complementarity-Determining Regions Containing Specificity-Determining Residues Essential for Ligand Contact to Engineer a Less Immunogenic Humanized Monoclonal Antibody" The Journal of Immunology (2002) 169, 3076-3084.

(Continued)

*Primary Examiner* — Michael Burkhart
(74) *Attorney, Agent, or Firm* — Lathrop & Gage, LLP; James H. Velema, Esq.; Andrew T. Wilkins, Esq.

(57) ABSTRACT

The invention relates to a platform technology for production of antigen binding polypeptides having specificity for a desired target antigen which is based on the conventional antibody repertoire of species in the family Camelidae, and to antigen binding polypeptides obtained using this technology platform. In particular, the invention provides an antigen binding polypeptide comprising a VH domain and a VL domain, wherein at least one hypervariable loop or complementarity determining region (CDR) in the VH domain or the VL domain is obtained from a VH or VL domain of a species in the family Camelidae.

4 Claims, 5 Drawing Sheets

(56) References Cited

FOREIGN PATENT DOCUMENTS

| WO | WO 2008/028977 A2 | 3/2008 |
|---|---|---|
| WO | WO-2008/043821 A1 | 4/2008 |
| WO | WO 2008/043822 A2 | 4/2008 |
| WO | WO 2008/049897 A1 | 5/2008 |
| WO | WO 2008/068280 A1 | 6/2008 |
| WO | WO 2008/070344 A2 | 6/2008 |
| WO | WO 2008/071447 A2 | 6/2008 |
| WO | WO 2008/071685 A1 | 6/2008 |
| WO | WO 2008/074839 A2 | 6/2008 |
| WO | WO 2008/074840 A2 | 6/2008 |
| WO | WO 2008/074867 A2 | 6/2008 |
| WO | WO 2008/074868 A1 | 6/2008 |
| WO | WO 2008/077945 A2 | 7/2008 |
| WO | WO 2008/101985 A2 | 8/2008 |
| WO | WO 2008/142164 A2 | 11/2008 |
| WO | WO 2008/142165 A1 | 11/2008 |
| WO | WO 2009/004065 A2 | 11/2008 |
| WO | 2009/004066 A2 | 1/2009 |
| WO | WO 2009/027391 A1 | 3/2009 |
| WO | WO 2009/030285 A1 | 3/2009 |
| WO | WO 2009/068625 A2 | 6/2009 |
| WO | WO 2009/068627 A2 | 6/2009 |
| WO | WO 2009/068628 A1 | 6/2009 |
| WO | WO 2009/068630 A1 | 6/2009 |
| WO | WO 2009/068631 A1 | 6/2009 |
| WO | WO 2010/001251 A2 | 1/2010 |

OTHER PUBLICATIONS

De Simone et al., "Development of ELISAs for the measurement of IgM and IgG subclasses in sera from llamas (Lama glama) and assessment of the humoral immune response against different antigens," Vet. Immunol. Immunopathol. 126(1-2):64-73 (Nov. 5, 2008).

Decanniere et al., "Canonical Antigen-binding Loop Structures in Immunoglobulins: More Structures, More Canonical Classes?," J. Mol. Bioi., 300:83-91 (2000).

Fenwick et al., "Hybrid Monte Carlo with Multidimensional Replica Exchanges: Confromational Equilibria of hypervariable Regions of a Llama VHH Antibody Domain," Biopolymers, 68:160-177 (2003).

Holm et al., "Functional mapping and single chain construction of the anti-cytokeratin 8 monoclonal antibodi TS1," Mol. Immunol., 2007, 44: 1075-1084.

Jang et al., "The structural basis for DNA binding by an anti-DNA autoantibody," Molec. Immunol., 35:1207-1217 (1998).

Hwang, William Ying Khee et al., "Use of human germline genes in a CDR homology-based approach to antibody humanization," Methods, vol. 36:35-42 (2005).

Kobayashi et al., "Tryplophan H33 plays an important role in pyrimidine (6-4) pyrimidone photoproduct binding by a high-affinity antibody," Protein Engineering 12:879-844 (1999).

Kumar et al., "Molecular Cloning and Expression of the Fabs of Human Autoantibodies in *Escherichia coli*," J. Bioi. Chem. 275:(45) 35129-35136 (2000).

Morea, Veronica et al., "Antibody Modeling: Implications for Engineering and Design," Methods, vol. 20:267-279 Mar. 2000.

Rudikoff et al.,"Single amino acid substitution altering antigen-binding specificity," Proc Nail Acad Sci, USA 1982 vol. 79 page (1979) D.

Smith-Gill et al., "Contributions of Immunoglobulin Heavy and Light Chains to Antibody Specificity for Lysozyme and Two Haptens," J. Immunol., 139:4135-4144 (1987).

Song et al., "Light Chain of Natural Antibody Plays a Dominant Role in Protein Antigen Binding," Biochem Biophys Res Comm, 2000, vol. 268, pp. 390-394.

Vajdos et al., "Comprehensive Functional Maps of the Antigen-binding Site of an Anti-ErbB2 Antibody Obtained with Shotgun Scanning Mutagenesis," J. Mol. Bioi., 2002, vol. 320, pp. 415-428.

Wu et al., "Humanization of a Murine Monoclonal Antibody by simultaneous Optimization of Framework and CDR Residues," J. Mol. Bioi., 1999, vol. 294, pp. 251-162.

Christele, Martinez-Jean et al., "I MGT Repertoire (IG and TR) Protein display: Arabian camel (*Camelus dromedarius*) IGH C-Regions," I MGT, Immunogenetics Information Systems, retrieved online at: http://www.imgl.org (2002).

De Genst, Erwin et al., "Antibody repertoire development in camelids," Developmental and Comparative Immunology, vol. 30:187-198 (2006).

Gonzales, Noreen R. et al., "Minimizing the Immunogenicity of Antibodies for Clinical Application," TumorBiology, vol. 26:31-43 (2005).

Hamers-Casterman, C. et al., "Naturally occurring antibodies devoid of light chains," Nature, vol. 363:446-448 (1993).

Harmsen, Michiel M. et al., "Prolonged in vivo residence limes of llama single-domain antibody fragments in pigs by binding to porcine immunoglobulins," Vaccine, vol. 23:4926-4934 (2005).

Kim, Sang Jick et al., "Antibody Engineering for the Development of Therapeutic Antibodies," Molecules and Cells, vol. 20(1) : 17-29 (2005).

Legssyer, Ilham, "The camel (*Camelus dromedarius*) Immunoglobulin Light Chains," Thesis, Vrije Urtiversiteit 8 Brussel, Faculty of Sciences, Institute for Molecular Biology and Biotechnology, Laboratory of Ultrastructure, Academic year 2001-2002.

Nguyen. Viet Khong et al., "Camel heavy-chain antibodies: diverse germ line VHH and specific mechanisms enlarge the antigen-binding repertoire," The EMBO Journal, vol. 19(5):921-930 (2000).

Rahbarizadeh, Fatemeh et al., "The Production and Characterization of Novel Heavy-Chain Antibodies Against the Tandem Repeat Region of MUC1 Mucin," ImmunologicalInvesti. ations, vol. 34:431-452 (2005).

Saerens, Dirk et al., "Identification of a Universal VHH Framework to Graft Non-canonical Antigen-binding Loops of Camel Single-domain Antibodies," J. Mol. Bioi., vol. 352:597-607 k2005L, 2005.

Scaviner, Dominique, "Protein display: Llama (*Lama glama*)IGH V-REGIONs," retreived online at: http://www.imgt.org/lextes/IMGTrepertoire/Proteins/protein/Lama/IGH/IGHV/Lg_IGHV (2002), 1 page.

Scaviner, Dominique, "Protein display: Llama (*Lama glama*) IGH J-REGIONs," retreived online at: http://igmt.cines.fr/textes/IMGTrepertoire/Proteins/protein/Lama/IGH/IGHJ/Lg_IGHJallq . . . (2002), 1 page.

Scaviner, Dominique, "Table of alleles: Llama (*Lama glama*) IGHV," retreived online at: http://www.imgt.org/lextes/IMGTreperloire/Proteins/protein/laballeles/lama/IGH/IGHV/Ig_IGH . . . (2002), 2 pages.

Shen, Juqun et al., "Single variable domain antibody as a versatile building block for the construction of IgG-like bispecific antibodies," Journal of Immunological Methods, vol. 318:65-74 (2007).

Su, Chen et al., "Adaptive Evolution of Variable Region Genes Encoding an Unusual Type of Immuno•lobulin in Camelids," Mol. Bioi. Evol., vol. 19(3):205-215 (2002).

Tanha, Jamshid et al., "Selection by phage display of llama conventional VH fragments with heavy chain antibody VHH properties," Journal of Immunological Methods, vol. 263:97-109 2002.

Vu, Khoa Bang et al., "Comparison of Llama VH Sequences from Conventional and Heavy Chain Antibodies," Molecular Immunology, vol. 34(16-17):1121-1131 (1997).

Written Opinion for Application No. PCT/1B2009/006329, mailed Jan. 25, 2010, 9pages.

International Search Report for Application No. PCT/1B2009/006329, mailed Jan. 25, 2010, 8 pages.

Great Britain Examination Report for Application No. GB0812120.4, dated Oct. 21, 2009, 3 pages.

Great Britain Examination Report for Application No. GB0812120.4, dated Mar. 2, 2010, 3 pages.

Great Britain Examination Report for Application No. GB0812120.4, dated Dec. 4, 2008, 5 pages.

Christele, Martinez-Jean et al., "IMGT Repertoire (IG and TR) Protein display: Arabian camel (*Camelus dromedarius*) IGH C-REGIONs," IMGT, Immunogenetics Informations systems, retrieved online at: http://www.imgt.org (2002) 3 pages.

MacCallum, R.W. et al., Antibody-antigen Interactions: Contact Analysis and Binding Site Topography, J. Mol. Biol. (1996) 262, 732-745.

\* cited by examiner

Fig.2

SEQUENCE LISTING

<160> NUMBER OF SEQ ID NOS: 356

<210> SEQ ID NO 1
<211> LENGTH: 97
<212> TYPE: PRT
<213> ORGANISM: Homo sapiens

<400> SEQUENCE: 1

Glu Val Gln Leu Val Glu Ser Gly Gly Gly Leu Ile Gln Pro Gly Gly

```
1               5                   10                  15
Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 2
<211> LENGTH: 97
<212> TYPE: PRT
<213> ORGANISM: Camelus dromedarius

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
    50                  55                  60

Gly Arg Phe Thr Ile Ser Arg Asp Asn Ala Lys Asn Met Leu Tyr Leu
65                  70                  75                  80

Gln Met Asn Ser Leu Lys Pro Glu Asp Thr Ala Val Tyr Tyr Cys Ala
                85                  90                  95

Gly

<210> SEQ ID NO 3
<211> LENGTH: 95
<212> TYPE: PRT
<213> ORGANISM: Camelus dromedarius

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
    50                  55                  60

Gly Arg Phe Thr Ile Ser Arg Asp Asn Ala Lys Asn Met Leu Tyr Leu
65                  70                  75                  80

Gln Met Asn Ser Leu Lys Pro Glu Asp Thr Ala Met Tyr Tyr Cys
                85                  90                  95

<210> SEQ ID NO 4
<211> LENGTH: 95
<212> TYPE: PRT
<213> ORGANISM: Camelus dromedarius
```

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Ala Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
    50                  55                  60

Gly Arg Phe Thr Ile Ser Arg Asp Asn Ala Lys Asn Met Leu Tyr Leu
65                  70                  75                  80

Gln Met Asn Ser Leu Lys Pro Glu Asp Thr Ala Met Tyr Tyr Cys
                85                  90                  95

<210> SEQ ID NO 5
<211> LENGTH: 95
<212> TYPE: PRT
<213> ORGANISM: Camelus dromedarius

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Met Tyr Tyr Cys
                85                  90                  95

<210> SEQ ID NO 6
<211> LENGTH: 95
<212> TYPE: PRT
<213> ORGANISM: Camelus dromedarius

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
    50                  55                  60

Gly Arg Phe Thr Ile Ser Arg Asp Asn Ala Lys Asn Met Leu Tyr Leu
65                  70                  75                  80

Gln Val Asn Ser Leu Lys Pro Glu Asp Thr Ala Val Tyr Tyr Cys
                85                  90                  95

<210> SEQ ID NO 7
<211> LENGTH: 95
<212> TYPE: PRT
<213> ORGANISM: Camelus dromedarius

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
50                  55                  60

Gly Arg Phe Thr Ile Ser Arg Asp Asn Ala Lys His Met Leu Tyr Leu
65                  70                  75                  80

Gln Met His Ser Leu Lys Pro Glu Asp Thr Ala Met Tyr Tyr Cys
                85                  90                  95
```

<210> SEQ ID NO 8
<211> LENGTH: 95
<212> TYPE: PRT
<213> ORGANISM: Camelus dromedarius

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
50                  55                  60

Gly Arg Phe Thr Ile Ser Arg Asp Lys Ala Lys Asn Met Leu Tyr Leu
65                  70                  75                  80

Gln Met Asn Ser Leu Lys Pro Glu Asp Thr Ala Met Tyr Tyr Cys
                85                  90                  95
```

<210> SEQ ID NO 9
<211> LENGTH: 95
<212> TYPE: PRT
<213> ORGANISM: Camelus dromedarius

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Lys Ala Gln Gly Lys Gly Leu Glu Trp Val
        35                  40                  45

Ser Gly Ile Tyr Ser Asp Gly Ser Thr Tyr Tyr Gly Asp Ser Val Lys
50                  55                  60

Gly Arg Phe Thr Ile Ser Arg Asp Lys Ala Lys Asn Met Leu Tyr Leu
65                  70                  75                  80

Gln Met Asn Ser Leu Lys Pro Glu Asp Thr Ala Met Tyr Tyr Cys
                85                  90                  95
```

<210> SEQ ID NO 10
<211> LENGTH: 95
<212> TYPE: PRT
<213> ORGANISM: Camelus dromedarius

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ser Asn Thr Ser Asp Gly Ser Thr Tyr Tyr Gly Asp Ser Val Lys
    50                  55                  60

Gly Arg Phe Thr Ile Ser Arg Asp Asn Ala Lys Asn Met Leu Tyr Leu
65                  70                  75                  80

Gln Met Asn Ser Leu Lys Pro Glu Asp Thr Ala Met Tyr Tyr Cys
                85                  90                  95
```

<210> SEQ ID NO 11
<211> LENGTH: 95
<212> TYPE: PRT
<213> ORGANISM: Camelus dromedarius

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Tyr Met Ser Trp Val Arg Gln Ala Pro Gly Arg Gly Leu Glu Trp Val
        35                  40                  45

Ser Gly Ile Tyr Ser Asp Gly Gly Thr Tyr Tyr Gly Asp Ser Val Arg
    50                  55                  60

Gly Arg Phe Thr Ile Ser Arg Asp Asn Ala Lys Asn Met Leu Tyr Leu
65                  70                  75                  80

Gln Met Asn Ser Leu Lys Pro Glu Asp Thr Ala Met Cys Tyr Cys
                85                  90                  95
```

<210> SEQ ID NO 12
<211> LENGTH: 95
<212> TYPE: PRT
<213> ORGANISM: Camelus dromedarius

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
    50                  55                  60

Gly Arg Phe Thr Ile Ser Arg Asp Lys Ala Lys Asn Met Leu Tyr Leu
65                  70                  75                  80

Gln Met Asn Ser Leu Lys Pro Glu Asp Thr Ser Met Tyr Tyr Cys
                85                  90                  95
```

<210> SEQ ID NO 13
<211> LENGTH: 95
<212> TYPE: PRT
<213> ORGANISM: Camelus dromedarius

<400> SEQUENCE: 13

```
Glu Val Gln Leu Val Glu Ser Gly Gly Gly Leu Val Gln Pro Gly Gly
```

```
                 1               5                   10                  15
Ser Leu Arg Leu Ser Cys Ala Ala Ser Gly Phe Thr Phe Ser Ser Tyr
                20                  25                  30

Tyr Met Ser Trp Val Arg Gln Ala Pro Gly Lys Gly Leu Glu Trp Val
                35                  40                  45

Ser Gly Ile Tyr Ser Asp Gly Ser Thr Tyr Tyr Gly Asp Ser Val Lys
                50                  55                  60

Gly Arg Phe Thr Ile Ser Arg Asp Lys Ala Lys Asn Met Leu Tyr Leu
 65                 70                  75                  80

Gln Met Asn Ser Leu Lys Pro Glu Asp Thr Ala Met Tyr Tyr Cys
                    85                  90                  95

<210> SEQ ID NO 14
<211> LENGTH: 95
<212> TYPE: PRT
<213> ORGANISM: Camelus dromedarius

<400> SEQUENCE: 14

Ala Val Gln Leu Val Glu Ser Gly Gly Gly Ser Val Gln Ala Gly Gly
 1               5                   10                  15

Ser Leu Arg Leu Ser Cys Ala Ala Ser Gly Phe Thr Phe Ser Ser Tyr
                20                  25                  30

Tyr Met Ser Trp Val Arg Gln Ala Pro Gly Lys Gly Leu Glu Trp Val
                35                  40                  45

Ser Gly Ile Tyr Ser Asp Gly Ser Thr Tyr Tyr Gly Asp Ser Val Lys
                50                  55                  60

Gly Arg Phe Thr Ile Ser Arg Asp Lys Ala Lys Asn Met Leu Tyr Leu
 65                 70                  75                  80

Gln Met Asn Ser Leu Lys Pro Glu Asp Thr Ala Met Tyr Tyr Cys
                    85                  90                  95

<210> SEQ ID NO 15
<211> LENGTH: 95
<212> TYPE: PRT
<213> ORGANISM: Camelus dromedarius

<400> SEQUENCE: 15

Gln Val Gln Leu Val Glu Ser Gly Gly Gly Ser Val Gln Ala Gly Gly
 1               5                   10                  15

Ser Leu Arg Leu Ser Cys Ala Ala Ser Gly Phe Thr Phe Ser Ser Tyr
                20                  25                  30

Tyr Met Ser Trp Val Arg Gln Ala Pro Gly Lys Gly Leu Glu Trp Val
                35                  40                  45

Ser Gly Ile Tyr Ser Asp Gly Ser Thr Tyr Tyr Gly Asp Ser Val Lys
                50                  55                  60

Gly Arg Phe Thr Ile Ser Arg Asp Lys Ala Lys Asn Met Leu Tyr Leu
 65                 70                  75                  80

Gln Met Asn Ser Leu Lys Pro Glu Asp Thr Ala Met Tyr Tyr Cys
                    85                  90                  95

<210> SEQ ID NO 16
<211> LENGTH: 95
<212> TYPE: PRT
<213> ORGANISM: Camelus dromedarius

<400> SEQUENCE: 16

Ala Val Gln Leu Val Glu Ser Gly Gly Gly Leu Val Gln Pro Gly Gly
 1               5                   10                  15
```

-continued

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
    50                  55                  60

Gly Arg Phe Thr Ile Ser Arg Asp Lys Ala Lys Asn Met Leu Tyr Leu
65                  70                  75                  80

Gln Met Asn Ser Leu Lys Pro Glu Asp Thr Ala Met Tyr Tyr Cys
                85                  90                  95

<210> SEQ ID NO 17
<211> LENGTH: 95
<212> TYPE: PRT
<213> ORGANISM: Camelus dromedarius

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Arg Leu Glu Trp Val
        35                  40                  45

Ser Gly Ile Tyr Ser Asp Gly Ser Thr Tyr Tyr Gly Asp Ser Val Lys
    50                  55                  60

Gly Arg Phe Thr Ile Ser Arg Asp Lys Ala Lys Asn Met Leu Tyr Leu
65                  70                  75                  80

Gln Met Asn Ser Leu Lys Pro Glu Asp Thr Ala Met Tyr Tyr Cys
                85                  90                  95

<210> SEQ ID NO 18
<211> LENGTH: 95
<212> TYPE: PRT
<213> ORGANISM: Camelus dromedarius

<400> SEQUENCE: 18

Gln Val Gln Leu Val Glu Ser Gly Gly Gly Ser Val Gln Ala Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asn Ser Asp Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Met Tyr Tyr Cys
                85                  90                  95

<210> SEQ ID NO 19
<211> LENGTH: 95
<212> TYPE: PRT
<213> ORGANISM: Camelus dromedarius

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Arg Gly Ser Thr His Tyr Ala Asp Ser Met Lys
50                  55                  60

Gly Arg Phe Thr Ile Ser Arg Asp Asn Ala Lys Asn Val Leu Tyr Leu
65                  70                  75                  80

Gln Met Asn Ser Leu Lys Pro Glu Asp Thr Ala Met Tyr Tyr Cys
            85                  90                  95

<210> SEQ ID NO 20
<211> LENGTH: 95
<212> TYPE: PRT
<213> ORGANISM: Camelus dromedarius

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Ser Thr Tyr Tyr Gly Asp Ser Val Lys
50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys
            85                  90                  95

<210> SEQ ID NO 21
<211> LENGTH: 98
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 22
<211> LENGTH: 96
<212> TYPE: PRT
<213> ORGANISM: Camelus dromedarius

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Asn Ser Asp Gly Ser Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

<210> SEQ ID NO 23
<211> LENGTH: 96
<212> TYPE: PRT
<213> ORGANISM: Camelus dromedarius

<400> SEQUENCE: 23

Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Thr Gly Gly Gly Ser Thr Tyr Tyr Ala Asp Ser Val
    50                  55                  60

Lys Gly Arg Phe Thr Ile Ser Arg Asp Asn Ala Lys Asn Val Leu Tyr
65                  70                  75                  80

Leu Lys Leu Ser Ser Leu Lys Pro Glu Asp Thr Ala Met Tyr Tyr Cys
                85                  90                  95

<210> SEQ ID NO 24
<211> LENGTH: 96
<212> TYPE: PRT
<213> ORGANISM: Camelus dromedarius

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ser Thr Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Met Leu Tyr
65                  70                  75                  80

Leu Gln Met Asn Ser Leu Lys Pro Glu Asp Thr Ala Met Tyr Tyr Cys
                85                  90                  95

<210> SEQ ID NO 25
<211> LENGTH: 96
<212> TYPE: PRT
<213> ORGANISM: Camelus dromedarius

<400> SEQUENCE: 25

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
            35                  40                  45

Ser Thr Ile Asn Ser Gly Gly Gly Ser Thr Tyr Tyr Ala Asp Ser Val
            50                  55                  60

Lys Gly Arg Phe Thr Ile Ser Arg Asp Asn Ala Lys Asn Met Leu Tyr
 65                  70                  75                  80

Leu Gln Met Asn Ser Leu Lys Pro Glu Asp Thr Ala Val Tyr Tyr Cys
                85                  90                  95
```

<210> SEQ ID NO 26
<211> LENGTH: 96
<212> TYPE: PRT
<213> ORGANISM: Camelus dromedarius

<400> SEQUENCE: 26

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Pro Glu Trp Val
            35                  40                  45

Ser Thr Ile Asn Ser Gly Gly Gly Ser Thr Tyr Tyr Ala Asp Ser Val
            50                  55                  60

Lys Gly Arg Phe Thr Ile Ser Arg Asp Asn Ala Lys Asn Met Leu Tyr
 65                  70                  75                  80

Leu Gln Met Asn Ser Leu Lys Pro Glu Asp Thr Ala Met Tyr Tyr Cys
                85                  90                  95
```

<210> SEQ ID NO 27
<211> LENGTH: 96
<212> TYPE: PRT
<213> ORGANISM: Camelus dromedarius

<400> SEQUENCE: 27

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Arg Lys Gly Leu Glu Trp Val
            35                  40                  45

Ser Thr Ile Asn Ser Ala Gly Gly Ser Thr Tyr Tyr Ala Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Met Tyr Tyr Cys
                85                  90                  95
```

<210> SEQ ID NO 28
<211> LENGTH: 96
<212> TYPE: PRT
<213> ORGANISM: Camelus dromedarius

<400> SEQUENCE: 28

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
```

```
                    20                  25                  30

Trp Met Tyr Trp Val Arg Gln Ala Pro Gly Lys Gly Leu Glu Trp Val
            35                  40                  45

Ser Thr Ile Asn Ser Ala Gly Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

<210> SEQ ID NO 29
<211> LENGTH: 96
<212> TYPE: PRT
<213> ORGANISM: Camelus dromedarius

<400> SEQUENCE: 29

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45

Ser Ala Ile Asn Ser Gly Gly Gly Ser Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

<210> SEQ ID NO 30
<211> LENGTH: 96
<212> TYPE: PRT
<213> ORGANISM: Camelus dromedarius

<400> SEQUENCE: 30

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45

Ser Ala Ile Asn Ser Gly Gly Gly Ser Thr Tyr Tyr Ala Asp Ser Val
 50                  55                  60

Lys Gly Gln Phe Thr Ile Ser Arg Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

<210> SEQ ID NO 31
<211> LENGTH: 96
<212> TYPE: PRT
<213> ORGANISM: Camelus dromedarius

<400> SEQUENCE: 31

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30
```

```
Ala Ile Ser Trp Val Arg Gln Ala Pro Gly Lys Gly Leu Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Met Tyr Tyr Cys
                85                  90                  95

<210> SEQ ID NO 32
<211> LENGTH: 96
<212> TYPE: PRT
<213> ORGANISM: Camelus dromedarius

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Leu Asn Ser Leu Lys Thr Glu Asp Thr Ala Met Tyr Tyr Cys
                85                  90                  95

<210> SEQ ID NO 33
<211> LENGTH: 96
<212> TYPE: PRT
<213> ORGANISM: Camelus dromedarius

<400> SEQUENCE: 33

Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Ile Ser Trp Val Arg Gln Ala Pro Gly Lys Gly Leu Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Thr Glu Asp Thr Ala Met Tyr Tyr Cys
                85                  90                  95

<210> SEQ ID NO 34
<211> LENGTH: 96
<212> TYPE: PRT
<213> ORGANISM: Camelus dromedarius

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30
```

```
Trp Val Tyr Trp Val Arg Gln Ala Pro Gly Lys Gly Leu Glu Trp Val
            35                  40                  45

Ser Ser Ile Tyr Thr Gly Gly Ser Thr Tyr Tyr Ala Asp Ser Val
 50                  55                  60

Lys Gly Arg Phe Thr Ile Ser Lys Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

<210> SEQ ID NO 35
<211> LENGTH: 96
<212> TYPE: PRT
<213> ORGANISM: Camelus dromedarius

<400> SEQUENCE: 35

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met Tyr Trp Val Arg Gln Ala Pro Gly Lys Gly Leu Glu Trp Val
            35                  40                  45

Ser Ser Ile Tyr Thr Gly Gly Ser Thr Tyr Tyr Ala Asp Ser Val
 50                  55                  60

Lys Gly Arg Phe Thr Ile Ser Lys Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

<210> SEQ ID NO 36
<211> LENGTH: 96
<212> TYPE: PRT
<213> ORGANISM: Camelus dromedarius

<400> SEQUENCE: 36

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met Tyr Trp Val Arg Gln Ala Pro Gly Lys Ala Leu Gln Trp Val
            35                  40                  45

Ser Ser Ile Tyr Thr Gly Gly Ser Thr Tyr Tyr Ala Asp Ser Val
 50                  55                  60

Lys Gly Pro Leu Thr Ile Ser Lys Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

<210> SEQ ID NO 37
<211> LENGTH: 96
<212> TYPE: PRT
<213> ORGANISM: Camelus dromedarius

<400> SEQUENCE: 37

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met Tyr Trp Val Arg Gln Ala Pro Gly Lys Gly Leu Glu Trp Val
```

```
                35                  40                  45
Ser Ala Ile Asn Ser Gly Gly Gly Ser Thr Tyr Tyr Ala Asp Ser Val
     50                  55                  60
Lys Gly Arg Phe Thr Ile Ser Gln Asp Asn Ala Lys Asn Thr Arg Tyr
65                  70                  75                  80
Leu Gln Met Asn Ser Leu Lys Pro Glu Asp Thr Ala Met Tyr Tyr Cys
                85                  90                  95
```

<210> SEQ ID NO 38
<211> LENGTH: 96
<212> TYPE: PRT
<213> ORGANISM: Camelus dromedarius

<400> SEQUENCE: 38

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ala Met Ser Trp Val Arg Gln Ala Pro Gly Lys Gly Leu Glu Trp Val
                35                  40                  45
Ser Ala Ile Tyr Thr Gly Gly Ser Thr Tyr Tyr Ala Asp Ser Val
     50                  55                  60
Lys Gly Arg Phe Thr Ile Ser Gln Asp Asn Ala Lys Asn Thr Val Tyr
65                  70                  75                  80
Leu Gln Met Asn Ser Leu Lys Thr Glu Asp Thr Ala Met Tyr Tyr Cys
                85                  90                  95
```

<210> SEQ ID NO 39
<211> LENGTH: 96
<212> TYPE: PRT
<213> ORGANISM: Camelus dromedarius

<400> SEQUENCE: 39

```
Glu Val Gln Leu Val Glu Ser Gly Gly Gly Ser Val Gln Ala Gly Gly
1               5                   10                  15
Ser Leu Arg Leu Ser Cys Ala Ala Ser Gly Phe Thr Phe Ser Ser Tyr
                20                  25                  30
Asp Met Ser Trp Val Arg Gln Ala Pro Gly Lys Gly Leu Glu Trp Val
                35                  40                  45
Ser Ala Ile Asn Ser Gly Gly Gly Ser Thr Tyr Tyr Ala Asp Ser Val
     50                  55                  60
Lys Gly Arg Phe Thr Ile Ser Gln Asp Asn Ala Lys Asn Met Leu Tyr
65                  70                  75                  80
Leu Gln Met Asn Ser Leu Lys Pro Glu Asp Thr Ala Met Tyr Tyr Cys
                85                  90                  95
```

<210> SEQ ID NO 40
<211> LENGTH: 96
<212> TYPE: PRT
<213> ORGANISM: Camelus dromedarius

<400> SEQUENCE: 40

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Ser Ser Ser Tyr
                20                  25                  30
Trp Met Tyr Trp Val Arg Gln Ala Pro Gly Lys Gly Leu Glu Trp Val
                35                  40                  45
```

Ser Ser Ile Tyr Thr Gly Gly Ser Thr Tyr Tyr Ala Asp Ser Val
    50                  55                  60

Lys Gly Arg Phe Thr Ile Ser Lys Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95

<210> SEQ ID NO 41
<211> LENGTH: 96
<212> TYPE: PRT
<213> ORGANISM: Camelus dromedarius

<400> SEQUENCE: 41

Glu Val Gln Leu Val Glu Ser Gly Gly Gly Leu Val Gln Pro Gly Gly
 1               5                  10                  15

Ser Leu Arg Leu Ser Cys Ala Ala Ser Ala Phe Thr Tyr Ser Ser Cys
                 20                  25                  30

Cys Met Tyr Trp Val Arg Gln Ala Pro Gly Lys Gly Phe Glu Trp Val
                 35                  40                  45

Ser Ala Ile Asn Ser Gly Gly Gly Ser Thr Tyr Tyr Ala Asp Ser Val
    50                  55                  60

Lys Gly Arg Phe Thr Ile Ser Gln Asp Asn Ala Lys Asn Thr Arg Tyr
 65                  70                  75                  80

Leu Gln Met Asn Ser Leu Lys Pro Glu Asp Thr Ala Met Tyr Tyr Cys
                 85                  90                  95

<210> SEQ ID NO 42
<211> LENGTH: 96
<212> TYPE: PRT
<213> ORGANISM: Camelus dromedarius
<220> FEATURE:
<221> NAME/KEY: MISC_FEATURE
<222> LOCATION: (26)..(26)
<223> OTHER INFORMATION: Unknown amino acid

<400> SEQUENCE: 42

Glu Val Gln Leu Val Glu Ser Gly Gly Gly Leu Val Gln Pro Gly Gly
 1               5                  10                  15

Ser Leu Arg Leu Ser Cys Ala Ala Ser Xaa Phe Thr Phe Ser Ser Tyr
                 20                  25                  30

Ala Ile Ser Trp Val Arg Gln Ala Pro Gly Lys Gly Leu Glu Trp Val
                 35                  40                  45

Ser Ala Ile Asn Ser Gly Gly Gly Ser Thr Tyr Tyr Ala Asp Ser Val
    50                  55                  60

Lys Gly Arg Phe Thr Ile Ser Gln Asp Asn Ala Lys Asn Thr Arg Tyr
 65                  70                  75                  80

Leu Gln Met Asn Ser Leu Lys Pro Glu Asp Thr Ala Met Tyr Tyr Cys
                 85                  90                  95

<210> SEQ ID NO 43
<211> LENGTH: 98
<212> TYPE: PRT
<213> ORGANISM: Lama glama

<400> SEQUENCE: 43

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
                 20                  25                  30

```
Ala Met Ser Trp Val Arg Gln Ala Pro Gly Lys Gly Leu Glu Trp Val
            35                  40                  45

Ser Ser Ile Tyr Ser Tyr Ser Ser Asn Thr Tyr Tyr Ala Asp Ser Val
    50                  55                  60

Lys Ser Arg Phe Thr Ile Ser Thr Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala

<210> SEQ ID NO 44
<211> LENGTH: 99
<212> TYPE: PRT
<213> ORGANISM: Homo sapiens

<400> SEQUENCE: 44

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 45
<211> LENGTH: 112
<212> TYPE: PRT
<213> ORGANISM: Camelus dromedarius

<400> SEQUENCE: 45

Gln Ser Val Leu Thr Gln Pro Pro Ser Met Ser Gly Ser Leu Gly Gln
1               5                   10                  15

Arg Val Thr Ile Ser Cys Thr Gly Ser Ser Ser Asn Ile Gly Gly Gly
            20                  25                  30

Ser Gly Val Gln Trp Phe Gln Gln Leu Pro Gly Thr Ala Pro Lys Leu
        35                  40                  45

Leu Ile Tyr Gly Asn Ser Asn Arg Ala Ser Gly Ile Pro Asp Arg Phe
    50                  55                  60

Ser Glu Ser Lys Ser Gly Ser Ser Ala Ser Leu Thr Ile Thr Gly Leu
65                  70                  75                  80

Gln Ala Asp Asp Glu Ala Asp Tyr Tyr Cys Ala Ser Tyr Asp Asn Arg
                85                  90                  95

Leu Ser Gly Pro Val Phe Gly Gly Gly Thr Lys Leu Thr Val Leu Gly
            100                 105                 110

<210> SEQ ID NO 46
<211> LENGTH: 99
<212> TYPE: PRT
<213> ORGANISM: Homo Sapiens

<400> SEQUENCE: 46
```

```
Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Arg Val Ser Trp Tyr Gln Gln Pro Pro Gly Thr Ala Pro Lys Leu
        35                  40                  45

Met Ile Tyr Glu Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Leu Tyr Thr Ser Ser
            85                  90                  95

Ser Thr Phe

<210> SEQ ID NO 47
<211> LENGTH: 130
<212> TYPE: PRT
<213> ORGANISM: Camelus dromedarius

<400> SEQUENCE: 47

Met Ala Trp Ala Leu Leu Leu Thr Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Ser Cys Thr Gly Thr Ser Asn Asp Val
        35                  40                  45

Gly Gly Tyr Asn Tyr Val Ser Trp Tyr Gln Gln Leu Pro Gly Thr Ala
    50                  55                  60

Pro Lys Leu Leu Ile Tyr Gln Asp Ser Lys Arg Asn Ser Gly Ile Pro
65              70                  75                  80

Asp Arg Phe Ser Gly Ser Lys Ser Asp Asn Thr Ala Ser Met Thr Ile
            85                  90                  95

Ser Gly Leu Gln Ser Ala Asp Glu Ala Asp Tyr Tyr Cys Ala Ser Tyr
            100                 105                 110

Arg Ser Thr Tyr His Ser Leu Phe Gly Gly Thr His Leu Thr Val
            115                 120                 125

Leu Gly
    130

<210> SEQ ID NO 48
<211> LENGTH: 130
<212> TYPE: PRT
<213> ORGANISM: Camelus dromedarius

<400> SEQUENCE: 48

Met Ala Trp Ala Leu Leu Leu Thr Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Thr Cys Thr Gly Thr Arg Asp Asp Val
        35                  40                  45

Gly Gly Tyr Asn Tyr Val Ser Trp Tyr Gln Gln Leu Pro Gly Thr Ala
    50                  55                  60

Pro Lys Leu Leu Ile Tyr Gln Ile Asn Lys Arg Leu Ser Gly Ile Pro
65              70                  75                  80
```

```
Asp Arg Phe Ser Gly Ser Lys Ser Gly Asn Thr Ala Ser Met Thr Ile
            85                  90                  95

Ser Gly Leu Gln Ser Ala Asp Glu Ala Asp Tyr Tyr Cys Ala Ser Tyr
            100                 105                 110

Arg Asp Leu Asn Thr Leu Val Phe Gly Gly Thr His Leu Thr Val
            115                 120                 125

Leu Gly
    130

<210> SEQ ID NO 49
<211> LENGTH: 130
<212> TYPE: PRT
<213> ORGANISM: Camelus dromedarius

<400> SEQUENCE: 49

Met Ala Trp Ala Leu Leu Leu Thr Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Ser Cys Thr Gly Thr Ser Asn Asp Val
            35                  40                  45

Gly Gly Tyr Asn Tyr Val Ser Arg Tyr Gln Gln Leu Pro Gly Thr Ala
        50                  55                  60

Pro Lys Leu Leu Ile Tyr Gln Ile Asn Lys Arg Ala Ser Gly Ile Pro
65                  70                  75                  80

Asp Arg Phe Ser Gly Ser Arg Ser Gly Asn Thr Ala Ser Met Thr Ile
            85                  90                  95

Ser Gly Leu Gln Ser Ala Asp Glu Ala Asp Tyr Tyr Cys Ala Ser Tyr
            100                 105                 110

Arg Ala Thr Asn Ser Ile Val Phe Gly Gly Thr His Leu Thr Val
            115                 120                 125

Leu Gly
    130

<210> SEQ ID NO 50
<211> LENGTH: 130
<212> TYPE: PRT
<213> ORGANISM: Camelus dromedarius

<400> SEQUENCE: 50

Met Ala Trp Ala Leu Leu Leu Thr Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Ser Cys Thr Gly Thr Ser Asn Asp Val
            35                  40                  45

Gly Arg Tyr Asn Tyr Val Ser Trp Tyr Gln Gln Leu Pro Gly Thr Ala
        50                  55                  60

Pro Lys Phe Leu Ile Tyr Gln Val Asn Lys Arg Ala Ser Gly Ile Pro
65                  70                  75                  80

Asp Arg Phe Ser Gly Ser Lys Ser Gly Asn Thr Ala Ser Met Thr Ile
            85                  90                  95

Ser Gly Leu Gln Ser Ala Asp Glu Ala Asp Tyr Tyr Cys Ala Ser Leu
            100                 105                 110

Arg Ser Ser Gly Asn Ala Val Phe Gly Gly Thr His Leu Thr Val
            115                 120                 125
```

Leu Gly
    130

<210> SEQ ID NO 51
<211> LENGTH: 130
<212> TYPE: PRT
<213> ORGANISM: Camelus dromedarius

<400> SEQUENCE: 51

Met Ala Trp Ala Leu Leu Leu Thr Leu Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Ser Cys Thr Gly Thr Ser Asn Asp Val
            35                  40                  45

Gly Arg Tyr Asn Tyr Val Ser Trp Tyr Gln Gln Phe Pro Gly Thr Ala
        50                  55                  60

Pro Lys Leu Leu Ile Tyr Gln Val Asn Lys Arg Ala Ser Gly Ile Pro
65                  70                  75                  80

Asp Arg Phe Ser Gly Ser Lys Ser Gly Asn Thr Ala Ser Met Thr Ile
                85                  90                  95

Ser Gly Leu Gln Ser Ala Asp Glu Ala Asp Tyr Tyr Cys Ala Ser Tyr
            100                 105                 110

Arg Asn Trp Ala Asn Leu Pro Phe Gly Gly Gly Thr His Leu Thr Val
        115                 120                 125

Leu Gly
    130

<210> SEQ ID NO 52
<211> LENGTH: 130
<212> TYPE: PRT
<213> ORGANISM: Camelus dromedarius

<400> SEQUENCE: 52

Met Ala Trp Ala Leu Leu Leu Thr Leu Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Ser Cys Thr Gly Thr Ser Asn Gly Val
            35                  40                  45

Gly Gly Tyr Asn Tyr Val Ser Trp Tyr Arg Gln Leu Pro Gly Thr Ala
        50                  55                  60

Pro Lys Leu Leu Ile Tyr Gln Val Asn Lys Arg Ala Ser Gly Ile Pro
65                  70                  75                  80

Asp Arg Phe Ser Gly Ser Lys Ser Gly Asn Thr Ala Ser Met Thr Ile
                85                  90                  95

Ser Gly Leu Gln Ser Ala Asp Glu Ala Asp Tyr Tyr Cys Ala Ser Tyr
            100                 105                 110

Arg Asn Gly Asn Asn Ala Val Phe Gly Gly Gly Thr His Leu Thr Val
        115                 120                 125

Leu Gly
    130

<210> SEQ ID NO 53
<211> LENGTH: 130
<212> TYPE: PRT
<213> ORGANISM: Camelus dromedarius

<400> SEQUENCE: 53

```
Met Ala Trp Ala Leu Leu Leu Thr Leu Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Ser Cys Thr Gly Thr Ser Asn Asp Val
        35                  40                  45

Gly Gly Tyr Asn Tyr Val Ser Trp Tyr Gln Gln Leu Pro Gly Thr Ala
    50                  55                  60

Pro Lys Leu Leu Ile Tyr Gln Val Asn Lys Arg Ala Ser Gly Ile Pro
65                  70                  75                  80

Asp Arg Phe Ser Ser Ser Lys Ser Asp Asn Thr Ala Ser Met Thr Ile
                85                  90                  95

Ser Gly Leu Gln Ser Ala Asp Glu Ala Asp Tyr Tyr Cys Ala Ser Tyr
            100                 105                 110

Arg Ser Arg Asp Asn Ala Val Phe Gly Gly Gly Thr His Leu Thr Val
        115                 120                 125

Leu Gly
    130
```

<210> SEQ ID NO 54
<211> LENGTH: 130
<212> TYPE: PRT
<213> ORGANISM: Camelus dromedarius

<400> SEQUENCE: 54

```
Met Ala Trp Ala Leu Leu Leu Thr Leu Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Ser Cys Thr Gly Thr Ser Asn Asp Val
        35                  40                  45

Gly Arg Tyr Asn Tyr Val Ser Trp Tyr Gln Gln Leu Pro Glu Thr Ala
    50                  55                  60

Pro Lys Leu Leu Ile Tyr Asp Val Asp Lys Arg Ala Ser Gly Ile Pro
65                  70                  75                  80

Asp Arg Phe Ser Gly Ser Lys Ser Gly Asn Thr Ala Ser Met Thr Ile
                85                  90                  95

Ser Gly Leu Gln Ser Ala Asp Glu Ala Asp Tyr Tyr Cys Ala Ser Tyr
            100                 105                 110

Arg Ser Gly Asp Asn Ala Ala Phe Gly Gly Gly Thr Arg Leu Thr Val
        115                 120                 125

Leu Gly
    130
```

<210> SEQ ID NO 55
<211> LENGTH: 111
<212> TYPE: PRT
<213> ORGANISM: Camelus dromedarius

<400> SEQUENCE: 55

```
Gln Ala Val Leu Thr Gln Pro Ser Ser Val Ser Gly Thr Pro Gly Gln
1               5                   10                  15

Thr Val Thr Ile Ser Cys Thr Gly Thr Ser Asn Asp Val Gly Lys Tyr
            20                  25                  30

Asn Tyr Val Ser Trp Tyr Gln Gln Phe Pro Gly Thr Ala Pro Lys Leu
```

```
                35                  40                  45
Leu Ile Tyr Gln Val Asn Lys Arg Gly Ser Gly Ile Pro Asp Arg Phe
 50                  55                  60

Ser Gly Ser Lys Ser Gly Asn Thr Ala Ser Met Thr Ile Ser Gly Leu
 65                  70                  75                  80

Gln Ser Ala Asp Glu Ala Asp Tyr Tyr Cys Ala Ser Leu Ser Ser Gly
                 85                  90                  95

Asn Asn Ala Val Phe Gly Gly Gly Thr His Leu Thr Val Leu Gly
            100                 105                 110

<210> SEQ ID NO 56
<211> LENGTH: 130
<212> TYPE: PRT
<213> ORGANISM: Camelus dromedarius

<400> SEQUENCE: 56

Met Ala Trp Ala Leu Leu Leu Thr Leu Leu Thr Gln Gly Thr Gly
 1               5                  10                  15

Ser Trp Ala Gln Ser Ala Leu Thr Gln Pro Ser Ser Val Ser Gly Thr
             20                  25                  30

Pro Gly Gln Thr Val Thr Ile Ser Cys Thr Gly Thr Ser Asn Asp Val
         35                  40                  45

Gly Gly Tyr Asn Tyr Val Ser Trp His Gln Gln Val Pro Gly Thr Ala
 50                  55                  60

Pro Lys Leu Ile Leu Tyr Gln Val Lys Glu Arg Pro Ser Gly Ile Pro
 65                  70                  75                  80

Asp Arg Phe Ser Gly Ser Lys Phe Gly Asn Thr Ala Ser Met Thr Ile
                 85                  90                  95

Ser Gly Leu Gln Ser Ala Asp Glu Ala Asp Tyr Tyr Cys Ala Ser Tyr
            100                 105                 110

Ser Ser Pro Asn Asn Val Leu Phe Gly Gly Thr His Leu Thr Val
        115                 120                 125

Leu Gly
    130

<210> SEQ ID NO 57
<211> LENGTH: 130
<212> TYPE: PRT
<213> ORGANISM: Camelus dromedarius

<400> SEQUENCE: 57

Met Ala Trp Ala Leu Leu Leu Thr Leu Leu Thr Gln Gly Thr Gly
 1               5                  10                  15

Ser Trp Ala Gln Ser Ala Leu Ala Gln Pro Ser Ser Val Ser Gly Thr
             20                  25                  30

Pro Gly Gln Thr Val Thr Ile Ser Cys Thr Gly Thr Ser Asp Asp Val
         35                  40                  45

Gly Ala Tyr Asn Tyr Val Ser Trp Tyr Gln Gln Leu Pro Gly Thr Ala
 50                  55                  60

Pro Lys Leu Leu Ile Tyr Gln Val Asn Lys Arg Pro Ser Gly Ile Pro
 65                  70                  75                  80

Asp Arg Phe Ser Gly Ser Lys Ser Gly Asn Thr Val Ser Leu Thr Ile
                 85                  90                  95

Ser Gly Leu Gln Ser Ala Asp Glu Ala Asp Tyr Thr Cys Ala Ser Tyr
            100                 105                 110

Lys His Thr Tyr Asn Ala Val Phe Gly Gly Gly Thr His Leu Thr Val
```

<210> SEQ ID NO 58
<211> LENGTH: 133
<212> TYPE: PRT
<213> ORGANISM: Camelus dromedarius

<400> SEQUENCE: 58

Met Ala Trp Ala Leu Leu Leu Thr Leu Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Ser Cys Thr Gly Thr Arg Asp Asp Val
        35                  40                  45

Gly Lys Tyr Asn Tyr Val Ser Trp Tyr Gln Gln Leu Pro Gly Thr Ala
    50                  55                  60

Pro Lys Leu Leu Ile Tyr Gln Val Asn Lys Arg Ala Ser Gly Ile Pro
65                  70                  75                  80

Asp Arg Phe Ser Gly Ser Lys Ser Gly Asn Thr Ala Ser Met Thr Ile
                85                  90                  95

Ser Gly Leu Gln Ser Ala Asp Glu Ala Asp Tyr Tyr Cys Ala Ser Val
            100                 105                 110

Arg Asp Tyr Asp Asn Asn Glu Phe Val Val Phe Gly Gly Gly Thr His
        115                 120                 125

Leu Thr Val Leu Gly
        130

<210> SEQ ID NO 59
<211> LENGTH: 130
<212> TYPE: PRT
<213> ORGANISM: Camelus dromedarius

<400> SEQUENCE: 59

Met Ala Trp Ala Leu Leu Leu Thr Leu Leu Thr Gln Gly Thr Gly
1               5                   10                  15

Ser Trp Ala Gln Ser Ala Leu Thr Gln Pro Ser Ser Val Ser Gly Thr
            20                  25                  30

Pro Gly Gln Thr Val Thr Ile Ser Cys Thr Gly Thr Ser Asn Asp Val
        35                  40                  45

Gly Arg Tyr Ala Tyr Val Ser Trp Tyr Gln His Leu Pro Gly Thr Ala
    50                  55                  60

Pro Lys Leu Leu Ile Tyr Gln Val Asn Lys Arg Ala Ser Gly Thr Pro
65                  70                  75                  80

Asp Arg Phe Ser Gly Ser Lys Ser Gly Asn Thr Ala Ser Met Thr Thr
                85                  90                  95

Ser Gly Leu Gln Ser Ala Asp Glu Ala Asp Tyr Tyr Cys Ser Ala Tyr
            100                 105                 110

Arg Ser Asn Asp Gly Pro Val Phe Gly Gly Gly Thr His Leu Thr Val
        115                 120                 125

Leu Gly
    130

<210> SEQ ID NO 60
<211> LENGTH: 95
<212> TYPE: PRT

<213> ORGANISM: Homo Sapiens

<400> SEQUENCE: 60

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                85                  90                  95

<210> SEQ ID NO 61
<211> LENGTH: 108
<212> TYPE: PRT
<213> ORGANISM: Camelus dromedarius

<400> SEQUENCE: 61

Gln Ser Val Leu Thr Gln Pro Ser Ala Val Ser Val Ser Leu Gly Glu
1               5                   10                  15

Thr Ala Arg Ile Thr Cys Gln Gly Gly Asn Phe Gly Ser Tyr Tyr Ala
            20                  25                  30

Asn Trp Tyr Gln Gln Lys Pro Gly Gln Ala Pro Val Leu Val Leu Tyr
        35                  40                  45

Lys Asp Ser Ala Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Ala Asp Tyr Tyr Cys Gln Ser Gly Ser Ser Ala Ser Ala
                85                  90                  95

Val Phe Gly Gly Gly Thr His Leu Thr Val Leu Gly
                100                 105

<210> SEQ ID NO 62
<211> LENGTH: 107
<212> TYPE: PRT
<213> ORGANISM: Camelus dromedarius

<400> SEQUENCE: 62

Gln Ser Val Leu Thr Gln Pro Ser Ala Val Ser Val Pro Leu Gly Glu
1               5                   10                  15

Thr Ala Arg Ile Thr Cys Gln Gly Gly Asp Phe Gly Asp Tyr Tyr Val
            20                  25                  30

Ser Trp Tyr Gln Gln Lys Pro Gly Gln Ser Pro Val Leu Val Ile Tyr
        35                  40                  45

Lys Asp Thr Leu Arg Pro Ser Gly Ile Pro Glu Arg Phe Thr Gly Ser
    50                  55                  60

Ser Ser Gly Gly Ala Ala Thr Leu Thr Ile Ser Gly Ala Gln Ala Glu
65                  70                  75                  80

Asp Glu Ala Asp Tyr Tyr Cys Gln Ser Glu Thr Ser Ser Ala Thr Val
                85                  90                  95

Phe Gly Gly Gly Thr His Leu Thr Val Leu Gly
                100                 105

<210> SEQ ID NO 63
<211> LENGTH: 108
<212> TYPE: PRT
<213> ORGANISM: Camelus dromedarius

<400> SEQUENCE: 63

Thr Ala Leu Thr Gln Pro Ser Ala Val Ser Val Ser Leu Gly Glu Thr
1               5                   10                  15

Ala Arg Ile Thr Cys Gln Gly Gly Asn Phe Gly Ser Tyr Tyr Thr Ser
            20                  25                  30

Trp Tyr Gln Gln Lys Pro Glu Glu Ala Pro Val Val Ile Tyr Lys
        35                  40                  45

Asp Thr Glu Arg Pro Ser Gly Ile Pro Glu Arg Phe Ser Ala Ser Ser
    50                  55                  60

Ser Gly Asp Thr Ala Thr Leu Thr Ile Ser Gly Ala Gln Ala Glu Asp
65                  70                  75                  80

Glu Ala Asp Tyr Tyr Cys Gln Ser Gly Ser Ser Ser Ala Asn Ala Pro
                85                  90                  95

Val Phe Gly Gly Gly Thr Lys Leu Thr Val Leu Gly
            100                 105

<210> SEQ ID NO 64
<211> LENGTH: 110
<212> TYPE: PRT
<213> ORGANISM: Camelus dromedarius

<400> SEQUENCE: 64

Gln Ala Val Leu Ser Gln Pro Ser Ala Val Ser Val Ser Leu Gly Glu
1               5                   10                  15

Thr Ala Arg Ile Thr Cys Gln Gly Asp Asn Phe Gly Ser Tyr Tyr Phe
            20                  25                  30

Ser Trp Tyr Gln Gln Lys Pro Gly Gln Ala Pro Val Leu Val Ile Tyr
        35                  40                  45

Arg Asn Ser Asn Arg Pro Ser Gly Ile Pro Glu Arg Phe Ser Ala Ser
    50                  55                  60

Ser Ser Gly Gly Thr Ala Thr Leu Thr Ile Ser Gly Ala Gln Ala Glu
65                  70                  75                  80

Asp Glu Ala Asp Tyr Tyr Cys Gln Ser Ala Asp Ser Ser Gly Arg Asn
                85                  90                  95

Ala Arg Ala Phe Gly Gly Gly Thr Lys Leu Thr Val Leu Gly
            100                 105                 110

<210> SEQ ID NO 65
<211> LENGTH: 111
<212> TYPE: PRT
<213> ORGANISM: Camelus dromedarius

<400> SEQUENCE: 65

Gln Ser Val Leu Thr Gln Pro Ser Ala Val Ser Val Ser Leu Gly Gln
1               5                   10                  15

Thr Ala Arg Ile Thr Cys Gln Gly Gly Ile Leu Gly Ser Lys Lys Thr
            20                  25                  30

Asn Trp Tyr Gln Gln Lys Pro Gly Gln Ala Pro Val Leu Val Ile Tyr
        35                  40                  45

Gly Asp Asp Ser Arg Pro Ser Gly Ile Pro Glu Arg Phe Ser Gly Ser
    50                  55                  60

```
Arg Ser Gly Gly Thr Ala Thr Leu Thr Ile Ser Gly Ala Gln Ala Glu
 65                  70                  75                  80

Asp Glu Ala Asp Tyr Tyr Cys Gln Leu Leu Asp Ser Thr Asp Ser Ser
                 85                  90                  95

Ser Tyr Trp Val Phe Gly Gly Gly Thr His Leu Thr Val Leu Gly
            100                 105                 110

<210> SEQ ID NO 66
<211> LENGTH: 96
<212> TYPE: PRT
<213> ORGANISM: Homo sapiens

<400> SEQUENCE: 66

Ser Tyr Glu Leu Thr Gln Pro His Ser Val Ser Val Ala Thr Ala Gln
  1               5                  10                  15

Met Ala Arg Ile Thr Cys Gly Gly Asn Asn Ile Gly Ser Lys Ala Val
                 20                  25                  30

His Trp Tyr Gln Gln Lys Pro Gly Gln Asp Pro Val Leu Val Ile Tyr
             35                  40                  45

Ser Asp Ser Asn Arg Pro Ser Gly Ile Pro Glu Arg Phe Ser Gly Ser
         50                  55                  60

Asn Pro Gly Asn Thr Thr Thr Leu Thr Ile Ser Arg Ile Glu Ala Gly
 65                  70                  75                  80

Asp Glu Ala Asp Tyr Tyr Cys Gln Val Trp Asp Ser Ser Ser Asp His
                 85                  90                  95

<210> SEQ ID NO 67
<211> LENGTH: 110
<212> TYPE: PRT
<213> ORGANISM: Camelus dromedarius

<400> SEQUENCE: 67

Gln Ser Val Leu Thr Gln Pro Ser Thr Ala Ser Met Ser Leu Gly Gln
  1               5                  10                  15

Thr Ala Lys Ile Thr Cys Gln Gly Gly Ser Leu Arg Asn Tyr Ala Ala
                 20                  25                  30

His Trp Tyr Gln Gln Lys Pro Gly Ala Ala Pro Val Leu Val Ile Tyr
             35                  40                  45

Asn Asp Asn Asn Arg Pro Ser Gly Ile Pro Glu Arg Phe Ser Gly Ser
         50                  55                  60

Lys Ser Gly Gly Thr Ala Thr Leu Thr Ile Ser Arg Thr Lys Ala Glu
 65                  70                  75                  80

Asp Glu Ala Asp Tyr Tyr Cys Leu Ser Arg Asp Met Ser Asp Ser Asn
                 85                  90                  95

Arg Val Val Phe Gly Gly Gly Thr His Leu Thr Val Leu Gly
            100                 105                 110

<210> SEQ ID NO 68
<211> LENGTH: 101
<212> TYPE: PRT
<213> ORGANISM: Homo Sapiens

<400> SEQUENCE: 68

Asp Ile Val Met Thr Gln Thr Pro Leu Ser Leu Pro Val Thr Pro Gly
  1               5                  10                  15

Glu Pro Ala Ser Ile Ser Cys Arg Ser Ser Gln Ser Leu Leu Asp Ser
                 20                  25                  30

Asp Asp Gly Asn Thr Tyr Leu Asp Trp Tyr Leu Gln Lys Pro Gly Gln
```

```
                35                  40                  45
Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Ile Glu Phe Pro
                100

<210> SEQ ID NO 69
<211> LENGTH: 114
<212> TYPE: PRT
<213> ORGANISM: Camelus dromedarius

<400> SEQUENCE: 69

Asp Ile Val Met Thr Gln Ser Pro Ser Val Thr Ala Ser Val Gly
 1               5                  10                  15

Glu Lys Val Thr Ile Asn Cys Lys Ser Ser Gln Ser Val Phe Asp Thr
                 20                  25                  30

Ser Arg Gln Lys Ser Phe Leu Asn Trp His Arg Gln Arg Pro Gly Gln
                 35                  40                  45

Ser Pro Arg Arg Leu Ile Tyr Tyr Ala Ser Thr Arg Gln Ser Gly Val
 50                  55                  60

Pro Asp Arg Phe Ser Gly Ser Gly Ser Thr Thr Asp Phe Thr Leu Thr
 65                  70                  75                  80

Ile Ser Ser Val Gln Pro Glu Asp Ala Ala Val Tyr Tyr Cys Gln Gln
                 85                  90                  95

Ala Phe Asn Val Gln Pro Ser Phe Gly Ser Gly Thr Arg Leu Glu Ile
                100                 105                 110

Lys Arg

<210> SEQ ID NO 70
<211> LENGTH: 114
<212> TYPE: PRT
<213> ORGANISM: Camelus dromedarius

<400> SEQUENCE: 70

Asp Ile Val Met Thr Gln Ser Pro Ser Val Thr Ala Ser Val Gly
 1               5                  10                  15

Glu Lys Val Thr Ile Asn Cys Lys Ser Ser Gln Ser Val Phe Ser Ser
                 20                  25                  30

Ser Ser Gln Lys Ser Leu Leu Asp Trp His Gln Gln Arg Pro Gly Gln
                 35                  40                  45

Ser Pro Arg Arg Leu Ile Tyr Tyr Ala Ser Ala Arg Ala Ser Gly Val
 50                  55                  60

Pro Asp Arg Phe Ser Gly Ser Gly Ser Thr Thr Asp Phe Thr Leu Thr
 65                  70                  75                  80

Ile Ser Ser Val Gln Pro Glu Asp Ala Ala Val Tyr Tyr Cys Gln Gln
                 85                  90                  95

Tyr Ser Gly Ser Pro Pro Thr Phe Gly Ser Gly Thr Arg Leu Glu Ile
                100                 105                 110

Lys Arg

<210> SEQ ID NO 71
<211> LENGTH: 114
```

```
<212> TYPE: PRT
<213> ORGANISM: Camelus dromedarius

<400> SEQUENCE: 71

Asp Ile Val Met Thr Gln Ser Pro Ser Ser Val Thr Ala Ser Val Gly
 1               5                  10                  15

Glu Lys Val Thr Ile Asn Cys Lys Ser Ser Gln His Val Ile Ser Val
                20                  25                  30

Ser Asn Gln Lys Ser Tyr Leu Asn Trp Tyr Gln Gln Arg Pro Gly Gln
            35                  40                  45

Ser Pro Arg Leu Leu Ile Tyr Tyr Ala Ser Thr Arg Glu Ser Gly Ile
        50                  55                  60

Pro Asp Arg Phe Ser Gly Ser Gly Ser Thr Thr Asp Phe Ala Leu Thr
 65                 70                  75                  80

Ile Ser Ser Val Gln Pro Glu Asp Ala Ala Val Tyr Tyr Cys Gln Gln
                85                  90                  95

Ala Tyr Ser Thr Pro Tyr Ser Phe Gly Ser Gly Thr Arg Leu Glu Ile
           100                 105                 110

Lys Arg

<210> SEQ ID NO 72
<211> LENGTH: 114
<212> TYPE: PRT
<213> ORGANISM: Camelus dromedarius

<400> SEQUENCE: 72

Asp Ile Val Met Thr Gln Ser Pro Ser Ser Val Thr Ala Ser Val Gly
 1               5                  10                  15

Glu Lys Val Thr Ile Asn Cys Lys Ser Ser Gln Ser Val Leu Ser Ser
                20                  25                  30

Ser Asn Gln Lys Ser Tyr Leu Asn Trp Tyr Gln Gln Arg Pro Gly Gln
            35                  40                  45

Ser Pro Arg Leu Leu Ile Tyr Tyr Ala Ser Thr Arg Glu Ser Gly Ile
        50                  55                  60

Pro Asp Arg Phe Ser Gly Ser Gly Ser Thr Thr Asp Phe Thr Leu Thr
 65                 70                  75                  80

Ile Ser Ser Val Gln Pro Glu Asp Ala Ala Val Phe Tyr Cys Gln Gln
                85                  90                  95

Ala Tyr Ser Ala Pro Tyr Ser Phe Gly Ser Gly Thr Arg Leu Glu Ile
           100                 105                 110

Lys Arg

<210> SEQ ID NO 73
<211> LENGTH: 114
<212> TYPE: PRT
<213> ORGANISM: Camelus dromedarius

<400> SEQUENCE: 73

Asp Ile Val Met Thr Gln Ser Pro Ser Ser Val Leu Ala Ser Val Gly
 1               5                  10                  15

Glu Lys Val Thr Ile Asn Cys Lys Ser Ser Gln Ser Val Leu Ser Ser
                20                  25                  30

Ser Asn Gln Lys Ser Tyr Leu Asn Trp Tyr Gln Gln Arg Pro Gly Gln
            35                  40                  45

Ser Pro Arg Leu Leu Ile Thr Tyr Ala Ser Thr Arg Glu Ser Gly Ile
        50                  55                  60
```

```
Pro Asp Arg Phe Ser Gly Ser Gly Ser Thr Thr Asp Phe Thr Leu Thr
 65                  70                  75                  80

Ile Ser Ser Val Gln Pro Glu Asp Ala Val Tyr Tyr Cys Gln Gln
                 85                  90                  95

Ala Tyr Ser Lys Pro Tyr Asn Phe Gly Asn Gly Thr Arg Leu Glu Ile
            100                 105                 110

Lys Arg

<210> SEQ ID NO 74
<211> LENGTH: 114
<212> TYPE: PRT
<213> ORGANISM: Camelus dromedarius

<400> SEQUENCE: 74

Asp Ile Val Met Thr Gln Ser Pro Thr Ser Val Thr Ala Ser Val Gly
  1               5                  10                  15

Glu Lys Val Thr Ile Asn Cys Lys Ser Ser Gln Ser Val Phe Ala Ser
                 20                  25                  30

Ser Ser Gln Lys Ser Gln Leu Ala Trp His Gln Gln Arg Pro Gly Gln
             35                  40                  45

Ser Pro Arg Arg Leu Ile Tyr Tyr Ala Ser Thr Arg Glu Ser Gly Val
 50                  55                  60

Pro Asp Arg Phe Ser Gly Ser Gly Ser Thr Thr Asp Phe Thr Leu Thr
 65                  70                  75                  80

Ile Ser Ser Val Gln Pro Glu Asp Ala Ala Val Tyr Tyr Cys Gln His
                 85                  90                  95

Leu Tyr Ser Ala Pro Tyr Ser Phe Gly Ser Gly Thr Arg Leu Glu Ile
            100                 105                 110

Lys Arg

<210> SEQ ID NO 75
<211> LENGTH: 114
<212> TYPE: PRT
<213> ORGANISM: Camelus dromedarius

<400> SEQUENCE: 75

Asp Ile Val Met Thr Gln Ser Pro Ser Ser Val Thr Ala Ser Val Gly
  1               5                  10                  15

Glu Lys Val Thr Ile Asn Cys Lys Ser Ser Gln Asn Leu Val Ser Asp
                 20                  25                  30

Ser Asn Gln Arg Ser Leu Leu Ala Trp His Gln Gln Arg Pro Gly Gln
             35                  40                  45

Ser Pro Arg Lys Leu Ile Tyr Tyr Ala Ser Arg Thr Ser Gly Thr
 50                  55                  60

Pro Asp Arg Phe Ser Gly Ser Gly Ser Thr Thr Asp Phe Thr Leu Thr
 65                  70                  75                  80

Ile Ser Ser Val Gln Pro Glu Asp Ala Ala Val Tyr Tyr Cys Gln Gln
                 85                  90                  95

Gly Lys Lys Asp Pro Leu Ser Phe Gly Ser Gly Thr Arg Leu Glu Ile
            100                 105                 110

Lys Arg

<210> SEQ ID NO 76
<211> LENGTH: 17
<212> TYPE: PRT
<213> ORGANISM: Homo Sapiens
```

```
<400> SEQUENCE: 76

Ala Glu Tyr Phe Gln His Trp Gly Gln Gly Thr Leu Val Thr Val Ser
1               5                   10                  15

Ser

<210> SEQ ID NO 77
<211> LENGTH: 17
<212> TYPE: PRT
<213> ORGANISM: Homo Sapiens

<400> SEQUENCE: 77

Tyr Trp Tyr Phe Asp Leu Trp Gly Arg Gly Thr Leu Val Thr Val Ser
1               5                   10                  15

Ser

<210> SEQ ID NO 78
<211> LENGTH: 15
<212> TYPE: PRT
<213> ORGANISM: Homo Sapiens

<400> SEQUENCE: 78

Ala Phe Asp Val Trp Gly Gln Gly Thr Met Val Thr Val Ser Ser
1               5                   10                  15

<210> SEQ ID NO 79
<211> LENGTH: 15
<212> TYPE: PRT
<213> ORGANISM: Homo Sapiens

<400> SEQUENCE: 79

Tyr Phe Asp Tyr Trp Gly Gln Gly Thr Leu Val Thr Val Ser Ser
1               5                   10                  15

<210> SEQ ID NO 80
<211> LENGTH: 16
<212> TYPE: PRT
<213> ORGANISM: Homo Sapiens

<400> SEQUENCE: 80

Asn Trp Phe Asp Ser Trp Gly Gln Gly Thr Leu Val Thr Val Ser Ser
1               5                   10                  15

<210> SEQ ID NO 81
<211> LENGTH: 20
<212> TYPE: PRT
<213> ORGANISM: Homo Sapiens

<400> SEQUENCE: 81

Tyr Tyr Tyr Tyr Tyr Gly Met Asp Val Trp Gly Gln Gly Thr Thr Val
1               5                   10                  15

Thr Val Ser Ser
            20

<210> SEQ ID NO 82
<211> LENGTH: 18
<212> TYPE: PRT
<213> ORGANISM: Lama glama

<400> SEQUENCE: 82

Gly Tyr Arg Tyr Leu Glu Val Trp Gly Gln Gly Thr Leu Val Thr Val
1               5                   10                  15

Ser Ser
```

```
<210> SEQ ID NO 83
<211> LENGTH: 16
<212> TYPE: PRT
<213> ORGANISM: Lama glama

<400> SEQUENCE: 83

Asn Ala Leu Asp Ala Trp Gly Gln Gly Thr Leu Val Thr Val Ser Ser
1               5                   10                  15

<210> SEQ ID NO 84
<211> LENGTH: 15
<212> TYPE: PRT
<213> ORGANISM: Lama glama

<400> SEQUENCE: 84

Glu Tyr Asp Tyr Trp Gly Gln Gly Thr Gln Val Thr Val Ser Ser
1               5                   10                  15

<210> SEQ ID NO 85
<211> LENGTH: 15
<212> TYPE: PRT
<213> ORGANISM: Lama glama

<400> SEQUENCE: 85

Pro Gln Phe Glu Tyr Trp Gly Gln Gly Thr Leu Val Thr Val Ser
1               5                   10                  15

<210> SEQ ID NO 86
<211> LENGTH: 14
<212> TYPE: PRT
<213> ORGANISM: Lama glama

<400> SEQUENCE: 86

Asp Phe Gly Ser Trp Gly Gln Gly Thr Leu Val Thr Val Ser
1               5                   10

<210> SEQ ID NO 87
<211> LENGTH: 12
<212> TYPE: PRT
<213> ORGANISM: Homo Sapiens

<400> SEQUENCE: 87

Tyr Val Phe Gly Thr Gly Thr Lys Val Thr Val Leu
1               5                   10

<210> SEQ ID NO 88
<211> LENGTH: 12
<212> TYPE: PRT
<213> ORGANISM: Homo Sapiens

<400> SEQUENCE: 88

Val Val Phe Gly Gly Gly Thr Lys Leu Thr Val Leu
1               5                   10

<210> SEQ ID NO 89
<211> LENGTH: 12
<212> TYPE: PRT
<213> ORGANISM: Homo Sapiens

<400> SEQUENCE: 89

Val Val Phe Gly Gly Gly Thr Lys Leu Thr Val Leu
1               5                   10
```

```
<210> SEQ ID NO 90
<211> LENGTH: 12
<212> TYPE: PRT
<213> ORGANISM: Homo Sapiens

<400> SEQUENCE: 90

Phe Val Phe Gly Gly Gly Thr Gln Leu Ile Ile Leu
1               5                   10

<210> SEQ ID NO 91
<211> LENGTH: 12
<212> TYPE: PRT
<213> ORGANISM: Homo Sapiens

<400> SEQUENCE: 91

Trp Val Phe Gly Glu Gly Thr Glu Leu Thr Val Leu
1               5                   10

<210> SEQ ID NO 92
<211> LENGTH: 12
<212> TYPE: PRT
<213> ORGANISM: Homo Sapiens

<400> SEQUENCE: 92

Asn Val Phe Gly Ser Gly Thr Lys Val Thr Val Leu
1               5                   10

<210> SEQ ID NO 93
<211> LENGTH: 12
<212> TYPE: PRT
<213> ORGANISM: Homo Sapiens

<400> SEQUENCE: 93

Ala Val Phe Gly Gly Gly Thr Gln Leu Thr Val Leu
1               5                   10

<210> SEQ ID NO 94
<211> LENGTH: 11
<212> TYPE: PRT
<213> ORGANISM: Camelus dromedarius

<400> SEQUENCE: 94

Phe Gly Gly Gly Thr His Leu Thr Val Leu Gly
1               5                   10

<210> SEQ ID NO 95
<211> LENGTH: 11
<212> TYPE: PRT
<213> ORGANISM: Camelus dromedarius

<400> SEQUENCE: 95

Phe Gly Gly Gly Thr Lys Leu Thr Val Leu Gly
1               5                   10

<210> SEQ ID NO 96
<211> LENGTH: 11
<212> TYPE: PRT
<213> ORGANISM: Camelus dromedarius

<400> SEQUENCE: 96

Phe Gly Gly Gly Thr Arg Leu Thr Val Leu Gly
1               5                   10

<210> SEQ ID NO 97
<211> LENGTH: 12
```

```
<212> TYPE: PRT
<213> ORGANISM: Homo Sapiens

<400> SEQUENCE: 97

Trp Thr Phe Gly Gln Gly Thr Lys Val Glu Ile Lys
1               5                   10

<210> SEQ ID NO 98
<211> LENGTH: 12
<212> TYPE: PRT
<213> ORGANISM: Homo Sapiens

<400> SEQUENCE: 98

Tyr Thr Phe Gly Gln Gly Thr Lys Leu Glu Ile Lys
1               5                   10

<210> SEQ ID NO 99
<211> LENGTH: 12
<212> TYPE: PRT
<213> ORGANISM: Homo Sapiens

<400> SEQUENCE: 99

Phe Thr Phe Gly Pro Gly Thr Lys Val Asp Ile Lys
1               5                   10

<210> SEQ ID NO 100
<211> LENGTH: 12
<212> TYPE: PRT
<213> ORGANISM: Homo Sapiens

<400> SEQUENCE: 100

Leu Thr Phe Gly Gly Gly Thr Lys Val Glu Ile Lys
1               5                   10

<210> SEQ ID NO 101
<211> LENGTH: 12
<212> TYPE: PRT
<213> ORGANISM: Homo Sapiens

<400> SEQUENCE: 101

Ile Thr Phe Gly Gln Gly Thr Arg Leu Glu Ile Lys
1               5                   10

<210> SEQ ID NO 102
<211> LENGTH: 11
<212> TYPE: PRT
<213> ORGANISM: Camelus dromedarius

<400> SEQUENCE: 102

Phe Gly Ser Gly Thr Arg Leu Glu Ile Lys Arg
1               5                   10

<210> SEQ ID NO 103
<211> LENGTH: 11
<212> TYPE: PRT
<213> ORGANISM: Camelus dromedarius

<400> SEQUENCE: 103

Phe Gly Asn Gly Thr Arg Leu Glu Ile Lys Arg
1               5                   10

<210> SEQ ID NO 104
<211> LENGTH: 109
<212> TYPE: PRT
<213> ORGANISM: Homo Sapiens
```

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
            100                 105

<210> SEQ ID NO 105
<211> LENGTH: 122
<212> TYPE: PRT
<213> ORGANISM: Lama glama

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Glu Trp Val
        35                  40                  45

Ser Ala Ile Asn Ser Gly Gly Ile Ser Thr Tyr Asn Ala Asp Ser Met
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Asp Thr Trp Tyr Cys Asp Gln Leu Asp Ser Ser Asp Tyr Trp
            100                 105                 110

Gly Gln Gly Thr Gln Val Thr Val Ser Ser
        115                 120

<210> SEQ ID NO 106
<211> LENGTH: 118
<212> TYPE: PRT
<213> ORGANISM: Lama glama

<400> SEQUENCE: 106

Glu Val Gln Leu Val Glu Ser Gly Gly Gly Leu Val Gln Pro Gly Arg
1               5                   10                  15

Ser Leu Arg Val Ser Tyr Ala Ala Ser Gly Phe Thr Phe Ser Ser His
            20                  25                  30

Tyr Met Ser Trp Val Arg Gln Asp Pro Glu Lys Gly Leu Glu Trp Val
        35                  40                  45

Ser Glu Ile Ala Thr Gly Gly Thr Ile Thr Tyr Ala Asp Ser Val
    50                  55                  60

Lys Gly Arg Phe Thr Ile Ser Arg Asp Asn Ala Asn Asn Met Leu Phe
65                  70                  75                  80

```
Leu Gln Met Asn Asn Leu Lys Pro Glu Asp Thr Ala Leu Tyr Tyr Cys
                 85                  90                  95

Val Arg Arg Gly Arg Ala Ile Ala Phe Asp Val Trp Gly Gln Gly Thr
            100                 105                 110

Leu Val Thr Val Ser Ser
        115

<210> SEQ ID NO 107
<211> LENGTH: 122
<212> TYPE: PRT
<213> ORGANISM: Lama glama

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Asp Asp Tyr
            20                  25                  30

Ala Met Ser Trp Val Arg Gln Ala Pro Gly Lys Gly Leu Glu Trp Val
        35                  40                  45

Ser Thr Ile Tyr Thr His Ser Arg Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Asp Asp Thr Ala Leu Tyr Tyr Cys
                85                  90                  95

Ala Lys Glu Trp Val Gly Ser Val Val Glu Gly Arg Tyr Arg Gly Trp
            100                 105                 110

Gly Gln Gly Thr Leu Val Thr Val Ser Ser
        115                 120

<210> SEQ ID NO 108
<211> LENGTH: 122
<212> TYPE: PRT
<213> ORGANISM: Lama glama
<220> FEATURE:
<221> NAME/KEY: MISC_FEATURE
<222> LOCATION: (36)..(36)
<223> OTHER INFORMATION: Unknown amino acid

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Xaa Val Arg Gln Ala Pro Gly Lys Gly Pro Glu Trp Val
        35                  40                  45

Ser Gly Val Asn Thr Asp Gly Arg Ser Ile Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Thr Lys Ile Cys Thr Val Ile Thr Gly Arg Pro Gly Tyr Asp Tyr Trp
            100                 105                 110

Gly Gln Gly Thr Leu Val Thr Val Ser Ser
        115                 120

<210> SEQ ID NO 109
```

```
<211> LENGTH: 117
<212> TYPE: PRT
<213> ORGANISM: Lama glama

<400> SEQUENCE: 109
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Val | Ser | Cys | Ala | Ala | Ser | Gly | Phe | Thr | Phe | Ser | Ser | Leu |
| | | | 20 | | | | | 25 | | | | | 30 | | |
| Tyr | Met | Ser | Trp | Val | Arg | Gln | Val | Pro | Gly | Lys | Gly | Leu | Glu | Trp | Val |
| | | 35 | | | | | 40 | | | | | 45 | | | |
| Ser | Thr | Ile | His | Thr | Ala | Ser | Gly | Ser | Thr | Phe | Tyr | Ala | Asp | Ser | Val |
| | 50 | | | | | 55 | | | | | 60 | | | | |
| Gln | Gly | Arg | Phe | Leu | Val | Ser | Arg | Asp | Asn | Ala | Lys | Asn | Thr | Leu | Tyr |
| 65 | | | | | 70 | | | | | 75 | | | | | 80 |
| Leu | Gln | Met | Asp | Ser | Leu | Lys | Pro | Glu | Asp | Thr | Ala | Arg | Tyr | Tyr | Cys |
| | | | | 85 | | | | | 90 | | | | | 95 | |
| Ala | Ser | Ala | Ile | Leu | Gly | Trp | Tyr | Asp | Tyr | Trp | Gly | Gln | Gly | Thr | Leu |
| | | | 100 | | | | | 105 | | | | | 110 | | |
| Val | Thr | Val | Ser | Ser | | | | | | | | | | | |
| | | | 115 | | | | | | | | | | | | |

```
<210> SEQ ID NO 110
<211> LENGTH: 117
<212> TYPE: PRT
<213> ORGANISM: Lama glama

<400> SEQUENCE: 110
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Asp | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Gly | Ile | Tyr | Ser | Asp | Gly | Thr | Thr | Thr | Tyr | Asp | Gly | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Asn | Met | Leu | Tyr |
| 65 | | | | | 70 | | | | | 75 | | | | | 80 |
| Leu | Gln | Met | Asn | Ser | Leu | Lys | Pro | Glu | Asp | Ala | Ala | Val | Tyr | Tyr | Cys |
| | | | | 85 | | | | | 90 | | | | | 95 | |
| Ala | Ser | Ala | Ile | Arg | Gly | Trp | Tyr | Asp | Tyr | Trp | Gly | Gln | Gly | Thr | Leu |
| | | | 100 | | | | | 105 | | | | | 110 | | |
| Val | Thr | Val | Ser | Ser | | | | | | | | | | | |
| | | | 115 | | | | | | | | | | | | |

```
<210> SEQ ID NO 111
<211> LENGTH: 98
<212> TYPE: PRT
<213> ORGANISM: Homo Sapiens

<400> SEQUENCE: 111
```

| | | | | | | | | | | | | | | |
|---|---|---|---|---|---|---|---|---|---|---|---|---|---|---|
| Gln | Ser | Val | Leu | Thr | Gln | Pro | Pro | Ser | Val | Ser | Glu | Ala | Pro | Arg | Gln |
| 1 | | | | 5 | | | | | 10 | | | | | 15 | |
| Arg | Val | Thr | Ile | Ser | Cys | Ser | Gly | Ser | Ser | Ser | Asn | Ile | Gly | Asn | Asn |
| | | | 20 | | | | | 25 | | | | | 30 | | |
| Ala | Val | Asn | Trp | Tyr | Gln | Gln | Leu | Pro | Gly | Lys | Ala | Pro | Lys | Leu | Leu |
| | | | 35 | | | | | 40 | | | | | 45 | | |

```
Ile Tyr Tyr Asp Asp Leu Leu Pro Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly
```

<210> SEQ ID NO 112
<211> LENGTH: 110
<212> TYPE: PRT
<213> ORGANISM: Lama glama

<400> SEQUENCE: 112

```
Gln Pro Val Leu Thr Gln Pro Ser Val Ser Gly Ser Pro Gly Gln
 1               5                   10                  15

Lys Phe Thr Ile Ser Cys Thr Gly Ser Ser Asn Ile Gly Asn Asn
                 20                  25                  30

Tyr Val Asn Trp Tyr Gln His Leu Pro Gly Thr Ala Pro Arg Leu Leu
                 35                  40                  45

Ile Tyr Ser Asn Asn Arg Ala Ser Gly Val Pro Asp Arg Phe Ser
 50                  55                  60

Gly Ser Lys Ser Gly Ser Ser Ala Ser Leu Thr Ile Thr Gly Leu Gln
 65                  70                  75                  80

Ala Glu Asp Glu Ala Glu Tyr Tyr Cys Ser Ser Trp Asp Asp Ser Leu
                 85                  90                  95

Ser Gly Thr Val Phe Gly Gly Gly Thr His Leu Thr Val Leu
                100                 105                 110
```

<210> SEQ ID NO 113
<211> LENGTH: 111
<212> TYPE: PRT
<213> ORGANISM: Lama glama

<400> SEQUENCE: 113

```
Gln Ser Ala Leu Thr Gln Pro Ser Val Ser Gly Ser Pro Gly Gln
 1               5                   10                  15

Lys Phe Thr Ile Ser Cys Thr Gly Ser Ser Asn Ile Gly Asp Asn
                 20                  25                  30

Tyr Val Asn Trp Tyr Gln His Leu Pro Gly Thr Ala Pro Lys Leu Leu
                 35                  40                  45

Ile Tyr Ser Asn Ser Asn Arg Ala Ser Gly Val Pro Asp Arg Phe Ser
 50                  55                  60

Gly Ser Lys Ser Gly Ser Ser Ala Ser Leu Thr Ile Thr Gly Leu Gln
 65                  70                  75                  80

Ala Glu Asp Glu Ala Asp Tyr Tyr Cys Ser Ser Trp Asp Asp Ser Leu
                 85                  90                  95

Ser Gly His Pro Val Phe Gly Gly Gly Thr Lys Leu Thr Val Leu
                100                 105                 110
```

<210> SEQ ID NO 114
<211> LENGTH: 110
<212> TYPE: PRT
<213> ORGANISM: Lama glama

<400> SEQUENCE: 114

```
Asn Phe Met Leu Thr Gln Pro Ser Val Ser Gly Ser Pro Gly Gln
 1               5                   10                  15
```

```
Lys Phe Thr Ile Ser Cys Thr Gly Ser Ser Asp Ile Gly Asn Asn
             20                  25                  30

Tyr Val Asn Trp Tyr Gln His Leu Pro Gly Thr Ala Pro Lys Leu Leu
             35                  40                  45

Ile Tyr Ser Thr Asp Lys Arg Ala Ser Gly Val Pro Asp Arg Phe Ser
         50                  55                  60

Gly Ser Lys Ser Gly Ser Ser Ala Ser Leu Thr Ile Thr Gly Leu Gln
65                  70                  75                  80

Ala Glu Asp Glu Ala Asp Tyr Tyr Cys Ser Ser Trp Asp Asp Asn Leu
                 85                  90                  95

Gly Thr Tyr Val Phe Gly Gly Gly Thr Ser Val Thr Val Leu
                100                 105                 110

<210> SEQ ID NO 115
<211> LENGTH: 110
<212> TYPE: PRT
<213> ORGANISM: Lama glama

<400> SEQUENCE: 115

Asn Phe Met Leu Thr Gln Pro Pro Ser Val Ser Gly Ser Pro Gly Gln
1               5                   10                  15

Lys Phe Thr Ile Ser Cys Thr Gly Ser Ser Asn Ile Gly Glu Asn
             20                  25                  30

Phe Val Asn Trp Tyr Gln His Leu Pro Gly Thr Ala Pro Lys Leu Leu
             35                  40                  45

Ile Tyr Ser Thr Asp Lys Arg Ala Ser Gly Val Pro Asp Arg Phe Ser
         50                  55                  60

Gly Ser Lys Ser Gly Ser Ser Ala Ser Leu Thr Ile Thr Gly Leu Gln
65                  70                  75                  80

Ala Glu Asp Glu Ala Asp Tyr Tyr Cys Ser Ser Trp Asp Asp Asn Leu
                 85                  90                  95

Gly Thr Tyr Val Phe Gly Gly Gly Thr Ser Val Thr Val Leu
                100                 105                 110

<210> SEQ ID NO 116
<211> LENGTH: 111
<212> TYPE: PRT
<213> ORGANISM: Lama glama

<400> SEQUENCE: 116

Asn Phe Met Leu Thr Gln Pro Pro Ser Val Ser Gly Ser Pro Gly Gln
1               5                   10                  15

Lys Phe Thr Ile Ser Cys Thr Gly Ser Asn Asn Ile Gly Asn Asn
             20                  25                  30

Tyr Val Asn Trp Tyr Gln His Leu Pro Gly Thr Ala Pro Lys Leu Leu
             35                  40                  45

Ile Tyr Ser Asn Asn Tyr Arg Ala Ser Gly Val Pro Asp Arg Phe Ser
         50                  55                  60

Gly Ser Lys Ser Gly Ser Ser Ala Ser Leu Thr Ile Thr Gly Leu Gln
65                  70                  75                  80

Ala Glu Asp Glu Ala Asp Tyr Tyr Cys Ser Ser Trp Asp Glu Ser Leu
                 85                  90                  95

Ser Gly Arg Tyr Val Phe Gly Gly Gly Thr Lys Leu Ala Val Leu
                100                 105                 110

<210> SEQ ID NO 117
```

<211> LENGTH: 99
<212> TYPE: PRT
<213> ORGANISM: Homo Sapiens

<400> SEQUENCE: 117

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 118
<211> LENGTH: 110
<212> TYPE: PRT
<213> ORGANISM: Lama glama

<400> SEQUENCE: 118

Gln Ser Ala Leu Thr Gln Pro Pro Ser Val Ser Gly Thr Leu Gly Lys
1               5                   10                  15

Thr Val Thr Ile Ser Cys Ala Gly Thr Ser Asn Asp Ile Gly Arg Tyr
            20                  25                  30

Asn Tyr Val Ala Trp Tyr Gln Gln Leu Pro Gly Thr Ala Pro Lys Leu
        35                  40                  45

Leu Ile Tyr Ala Val Ser Tyr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Gly Asp Glu Ala Asp Tyr Tyr Cys Val Ser Tyr Arg Ser Gly
                85                  90                  95

Gly Thr Asn Val Phe Gly Gly Gly Thr His Leu Thr Val Leu
            100                 105                 110

<210> SEQ ID NO 119
<211> LENGTH: 112
<212> TYPE: PRT
<213> ORGANISM: Lama glama

<400> SEQUENCE: 119

Gln Ser Ala Leu Thr Gln Pro Pro Ser Val Ser Gly Thr Leu Gly Lys
1               5                   10                  15

Thr Leu Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
        35                  40                  45

Leu Ile Tyr Arg Val Ser Tyr Arg Pro Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Thr Ser Tyr Thr Tyr Lys

```
                        85                  90                  95

Gly Gly Gly Thr Ala Val Phe Gly Gly Gly Thr His Leu Thr Val Leu
                100                 105                 110

<210> SEQ ID NO 120
<211> LENGTH: 110
<212> TYPE: PRT
<213> ORGANISM: Lama glama

<400> SEQUENCE: 120

Gln Ser Ala Leu Thr Gln Pro Pro Ser Val Ser Gly Thr Leu Gly Lys
1               5                   10                  15

Thr Val Thr Ile Ser Cys Ala Gly Thr Arg Thr Asp Val Gly Tyr Gly
                20                  25                  30

Asp Tyr Val Ser Trp Tyr Gln His Val Pro Asn Thr Ala Pro Arg Leu
            35                  40                  45

Leu Ile Tyr Ala Val Ser Ala Arg Ala Ser Gly Ile Pro Ser Arg Phe
        50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asp Gly
                85                  90                  95

Asn Tyr Ala Val Phe Gly Gly Gly Thr His Leu Thr Val Leu
                100                 105                 110

<210> SEQ ID NO 121
<211> LENGTH: 110
<212> TYPE: PRT
<213> ORGANISM: Lama glama

<400> SEQUENCE: 121

Gln Ala Val Leu Thr Gln Pro Pro Ser Val Ser Gly Thr Leu Gly Lys
1               5                   10                  15

Ala Val Thr Ile Ser Cys Ala Gly Thr Gly Ser Asp Val Gly Tyr Gly
                20                  25                  30

Asp Tyr Val Ser Trp Tyr Gln Gln Leu Pro Asp Thr Ala Pro Lys Leu
            35                  40                  45

Leu Val Tyr Ala Val Asn Thr Arg Ala Ser Gly Ile Pro Asp Arg Phe
        50                  55                  60

Ser Gly Ser Arg Ser Gly Asn Thr Ala Ser Leu Thr Ile Ser Gly Leu
65                  70                  75                  80

Gln Ser Glu Asp Glu Gly Asp Tyr Tyr Cys Ala Ser Tyr Arg Ser Tyr
                85                  90                  95

Asn Asn Tyr Val Phe Gly Gly Gly Thr His Leu Thr Val Leu
                100                 105                 110

<210> SEQ ID NO 122
<211> LENGTH: 110
<212> TYPE: PRT
<213> ORGANISM: Lama glama

<400> SEQUENCE: 122

Asn Phe Met Leu Thr Gln Pro Pro Ser Val Ser Gly Ser Pro Gly Lys
1               5                   10                  15

Thr Val Thr Ile Ser Cys Ala Gly Thr Ser Ser Asp Val Gly Tyr Gly
                20                  25                  30

Asn Tyr Val Ser Trp Tyr Gln Gln Leu Pro Gly Met Ala Pro Lys Leu
            35                  40                  45
```

```
Leu Leu Tyr Asn Ile Asn Lys Arg Ala Ser Gly Ile Ala Asp Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Val Tyr Tyr Cys Ala Ser Tyr Arg Ser Gly
                 85                  90                  95

Asn Asn Tyr Val Phe Gly Gly Gly Thr Glu Leu Thr Val Leu
                100                 105                 110

<210> SEQ ID NO 123
<211> LENGTH: 110
<212> TYPE: PRT
<213> ORGANISM: Lama glama

<400> SEQUENCE: 123

Gln Ser Ala Leu Thr Gln Pro Pro Ser Val Ser Gly Thr Leu Gly Lys
 1               5                  10                  15

Thr Val Thr Ile Ser Cys Ala Gly Thr Asn Ser Asp Ile Gly Asp Tyr
                 20                  25                  30

Asn Phe Val Ser Trp Tyr Gln His Leu Pro Gly Met Ala Pro Lys Leu
             35                  40                  45

Leu Ile Tyr Asp Val Asn Lys Arg Ala Ser Gly Ile Ala Asp Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Ser Ser
                 85                  90                  95

Asn Asn Tyr Val Phe Gly Gly Gly Thr Lys Leu Thr Val Leu
                100                 105                 110

<210> SEQ ID NO 124
<211> LENGTH: 110
<212> TYPE: PRT
<213> ORGANISM: Lama glama

<400> SEQUENCE: 124

Gln Ala Gly Leu Thr Gln Pro Pro Ser Val Ser Gly Ser Leu Gly Lys
 1               5                  10                  15

Thr Ile Thr Ile Ser Cys Ala Gly Thr Arg Asn Asp Ile Gly Gly His
                 20                  25                  30

Gly Tyr Val Ser Trp Tyr Gln Gln Leu Pro Gly Thr Ala Pro Lys Leu
             35                  40                  45

Leu Ile Tyr Lys Ile Asn Thr Arg Ala Ser Gly Ile Pro Asp Arg Phe
         50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Phe Cys Val Ala Asp Ile Asn Gly
                 85                  90                  95

Asp Thr Asn Val Phe Gly Gly Gly Thr His Leu Thr Val Leu
                100                 105                 110

<210> SEQ ID NO 125
<211> LENGTH: 110
<212> TYPE: PRT
<213> ORGANISM: Lama glama

<400> SEQUENCE: 125
```

Ser Ser Glu Leu Thr Gln Pro Pro Ser Val Ser Gly Thr Leu Gly Lys
1               5                   10                  15

Thr Val Thr Ile Ser Cys Ala Gly Thr Ser Asn Asp Ile Gly Ala His
                20                  25                  30

Asn Tyr Val Ser Trp Tyr Gln Gln Leu Pro Gly Thr Ala Pro Lys Leu
            35                  40                  45

Leu Ile Asn Lys Val Ser Thr Arg Ala Ser Gly Ile Pro Asp Arg Phe
        50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ala Tyr Arg Thr Gly
                85                  90                  95

Asp Ala Arg Ile Phe Gly Gly Gly Thr His Leu Thr Val Leu
                100                 105                 110

<210> SEQ ID NO 126
<211> LENGTH: 110
<212> TYPE: PRT
<213> ORGANISM: Lama glama

<400> SEQUENCE: 126

Gln Pro Val Leu Thr Gln Pro Pro Ser Val Ser Gly Ser Pro Gly Lys
1               5                   10                  15

Thr Val Thr Ile Ser Cys Ala Gly Thr Ser Ser Asp Ile Gly Tyr Gly
                20                  25                  30

Asn Tyr Val Ser Trp Tyr Gln Leu Leu Pro Gly Thr Ala Pro Lys Leu
            35                  40                  45

Leu Ile Tyr Asp Val Asn Lys Arg Pro Ser Gly Ile Pro Asp Arg Phe
        50                  55                  60

Ser Gly Ser Lys Ser Gly Asn Gln Ala Tyr Leu Thr Ile Ser Gly Leu
65                  70                  75                  80

Gln Ser Glu Asp Glu Ala Asp Tyr Tyr Cys Val Ser Tyr Arg Glu Pro
                85                  90                  95

Asn Asn Phe Val Ser Gly Gly Gly Thr His Leu Val Val Leu
                100                 105                 110

<210> SEQ ID NO 127
<211> LENGTH: 110
<212> TYPE: PRT
<213> ORGANISM: Lama glama

<400> SEQUENCE: 127

Gln Ser Ala Leu Thr Gln Pro Pro Ser Val Ser Gly Ser Leu Gly Lys
1               5                   10                  15

Thr Val Thr Ile Ser Cys Ala Gly Thr Ile Gly Asp Ile Gly Ala Gly
                20                  25                  30

Asn Tyr Val Ser Trp Tyr Arg Gln Thr Pro Gly Thr Ala Pro Lys Leu
            35                  40                  45

Leu Leu Tyr Glu Val Asn Lys Arg Thr Ser Gly Ile Pro Asp Arg Phe
        50                  55                  60

Ala Gly Ser Arg Ser Gly Asn Thr Ala Ser Leu Ile Ile Ser Gly Leu
65                  70                  75                  80

Gln Ala Glu Asp Glu Ala Asp Tyr Tyr Cys Ala Ser Tyr Arg Ile Gly
                85                  90                  95

Ser Arg Gly Val Phe Gly Gly Thr His Leu Thr Val Leu
                100                 105                 110

<210> SEQ ID NO 128
<211> LENGTH: 110
<212> TYPE: PRT
<213> ORGANISM: Lama glama

<400> SEQUENCE: 128

Gln Pro Val Leu Thr Gln Pro Ser Val Ser Gly Ser Leu Gly Lys
1               5                   10                  15

Thr Val Thr Ile Ser Cys Ala Gly Thr Trp Ser Asp Ile Gly Gly Tyr
            20                  25                  30

Asn Tyr Ile Ser Trp Tyr Arg Gln Leu Pro Gly Thr Ala Pro Arg Leu
        35                  40                  45

Leu Ile Tyr Glu Val Asp Lys Arg Ala Pro Gly Ile Pro Asp Arg Phe
    50                  55                  60

Ser Gly Ser Lys Ser Gly Thr Thr Ala Ser Leu Val Ile Ser Gly Leu
65                  70                  75                  80

Gln Ser Glu Asp Glu Ala Asp Tyr Tyr Cys Ala Ser Tyr Lys Ser Ser
                85                  90                  95

Glu Asn Ala Val Phe Gly Gly Gly Thr His Leu Thr Val Val
            100                 105                 110

<210> SEQ ID NO 129
<211> LENGTH: 99
<212> TYPE: PRT
<213> ORGANISM: Homo Sapiens

<400> SEQUENCE: 129

Gln Ser Ala Leu Thr Gln Pro Ser Ala Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe

<210> SEQ ID NO 130
<211> LENGTH: 110
<212> TYPE: PRT
<213> ORGANISM: Lama glama

<400> SEQUENCE: 130

Gln Ser Val Leu Thr Gln Pro Ser Val Ser Gly Thr Leu Gly Lys
1               5                   10                  15

Thr Leu Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
        35                  40                  45

Leu Ile Tyr Arg Val Ser Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ser Ser Tyr Arg Ser Thr
                85                  90                  95

Gly Thr Ala Val Phe Gly Gly Gly Thr His Leu Ser Val Leu
            100                 105                 110

<210> SEQ ID NO 131
<211> LENGTH: 110
<212> TYPE: PRT
<213> ORGANISM: Lama glama

<400> SEQUENCE: 131

Gln Ser Val Leu Thr Gln Pro Pro Ser Val Ser Gly Thr Leu Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Lys Leu Pro Gly Thr Ala Pro Lys Leu
        35                  40                  45

Leu Ile Tyr Ala Val Ser Tyr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Asp Ser
                85                  90                  95

Asn Asn Ala Val Phe Gly Gly Gly Thr His Leu Thr Ala Leu
            100                 105                 110

<210> SEQ ID NO 132
<211> LENGTH: 110
<212> TYPE: PRT
<213> ORGANISM: Lama glama

<400> SEQUENCE: 132

Leu Pro Val Leu Thr Gln Pro Pro Ser Val Ser Gly Thr Leu Gly Lys
1               5                   10                  15

Ser Leu Thr Ile Ser Cys Ala Gly Thr Ser Ser Asp Val Gly Asn Gly
            20                  25                  30

Asn Tyr Val Ser Trp Tyr Gln Gln Leu Pro Gly Thr Ala Pro Lys Leu
        35                  40                  45

Leu Ile Tyr Arg Val Thr Ser Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Pro Glu Asp Glu Ala Asp Tyr Tyr Cys Ala Ser Tyr Lys Arg Gly
                85                  90                  95

Gly Thr Ser Val Phe Gly Gly Gly Thr His Leu Thr Val Leu
            100                 105                 110

<210> SEQ ID NO 133
<211> LENGTH: 110
<212> TYPE: PRT
<213> ORGANISM: Lama glama

<400> SEQUENCE: 133

Gln Pro Val Leu Thr Gln Pro Pro Ser Val Ser Gly Thr Leu Gly Lys
1               5                   10                  15

Thr Val Thr Ile Ser Cys Ala Gly Thr Ser Thr Asp Ile Gly Gly Tyr
            20                  25                  30

```
Asn Tyr Val Ser Trp Tyr Gln Gln Val Pro Gly Thr Ala Pro Lys Leu
             35                  40                  45

Leu Ile Tyr Glu Val Asn Lys Arg Pro Ser Gly Ile Pro Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Ser Ser
                 85                  90                  95

Asn Asn Val Val Phe Gly Gly Gly Thr His Leu Thr Val Leu
                100                 105                 110

<210> SEQ ID NO 134
<211> LENGTH: 95
<212> TYPE: PRT
<213> ORGANISM: Homo Sapiens

<400> SEQUENCE: 134

Ser Tyr Glu Leu Thr Gln Pro Leu Ser Val Ser Val Ala Leu Gly Gln
 1               5                  10                  15

Thr Ala Arg Ile Thr Cys Gly Gly Asn Asn Ile Gly Ser Lys Asn Val
                 20                  25                  30

His Trp Tyr Gln Gln Lys Pro Gly Gln Ala Pro Val Leu Val Ile Tyr
             35                  40                  45

Arg Asp Ser Asn Arg Pro Ser Gly Ile Pro Glu Arg Phe Ser Gly Ser
 50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Gln Val Trp Asp Ser Ser Thr Ala
                 85                  90                  95

<210> SEQ ID NO 135
<211> LENGTH: 107
<212> TYPE: PRT
<213> ORGANISM: Lama glama

<400> SEQUENCE: 135

Leu Pro Val Leu Thr Gln Pro Ser Ala Leu Ser Val Thr Leu Gly Gln
 1               5                  10                  15

Thr Ala Lys Ile Thr Cys Gln Gly Gly Ser Leu Gly Ser Ser Tyr Ala
                 20                  25                  30

His Trp Tyr Gln Gln Lys Pro Gly Pro Ala Pro Val Leu Val Ile Tyr
             35                  40                  45

Asp Asp Ala Asn Arg Pro Ser Gly Ile Pro Glu Arg Phe Ser Gly Ser
 50                  55                  60

Arg Ser Gly Gly Thr Ala Thr Leu Thr Ile Ser Gly Ala Gln Ala Glu
 65                  70                  75                  80

Asp Glu Gly Asp Tyr Tyr Cys Gln Ser Val Asp Asn Ser Gly Asn Val
                 85                  90                  95

Val Phe Gly Gly Gly Thr His Leu Thr Val Leu
                100                 105

<210> SEQ ID NO 136
<211> LENGTH: 107
<212> TYPE: PRT
<213> ORGANISM: Lama glama

<400> SEQUENCE: 136

Gln Ala Val Leu Thr Gln Pro Ser Ala Val Ser Val Ser Leu Gly Gln
```

```
1               5                   10                  15
Thr Ala Arg Leu Thr Cys Gln Gly Asp Asn Val Glu Thr Ala Gly Thr
            20                  25                  30

Ser Trp Tyr Arg Gln Lys Pro Gly Gln Ala Pro Ser Leu Ile Ile Tyr
            35                  40                  45

Gly Asp Ser Ser Arg Pro Ser Glu Ile Ser Glu Arg Phe Ser Ala Ser
        50                  55                  60

Thr Ser Gly Asn Thr Ala Thr Leu Thr Ile Thr Gly Ala Gln Ala Glu
65                  70                  75                  80

Asp Glu Ala Asp Tyr Tyr Cys Leu Ser Ala Asp Ser Asp Leu Asp Ser
                85                  90                  95

Val Phe Gly Gly Gly Thr Leu Leu Thr Val Leu
                100                 105
```

<210> SEQ ID NO 137
<211> LENGTH: 108
<212> TYPE: PRT
<213> ORGANISM: Lama glama

<400> SEQUENCE: 137

```
Gln Ala Gly Leu Thr Gln Pro Ser Ala Val Ser Val Ser Leu Gly Gln
1               5                   10                  15

Thr Ala Arg Ile Thr Cys Arg Gly Asp Ser Leu Glu Arg Tyr Gly Ala
            20                  25                  30

Asn Trp Tyr Gln Gln Lys Pro Gly Gln Ala Arg Val Gln Val Ile Tyr
            35                  40                  45

Gly Asp Asp Ile Arg Pro Ser Gly Ile Pro Glu Arg Phe Ser Gly Ser
        50                  55                  60

Arg Leu Gly Gly Thr Ala Thr Leu Thr Ile Ser Gly Ala Gln Ala Glu
65                  70                  75                  80

Asp Glu Ala Asp Tyr Tyr Cys Gln Ser Ser Asp Ser Ser Gly Tyr Met
                85                  90                  95

Asn Asp Phe Ser Ser Arg Thr His Leu Thr Val Leu
                100                 105
```

<210> SEQ ID NO 138
<211> LENGTH: 106
<212> TYPE: PRT
<213> ORGANISM: Lama glama

<400> SEQUENCE: 138

```
Gln Ser Ala Leu Thr Gln Pro Ser Ala Val Ser Val Ser Leu Gly Gln
1               5                   10                  15

Thr Ala Glu Ile Thr Cys Arg Gly Arg Asn Phe Glu Ser Gly Phe Pro
            20                  25                  30

His Trp Tyr Arg Gln Lys Pro Gly Gln Ser Pro Glu Leu Val Met Phe
            35                  40                  45

Ile Val Asn Asn Arg Trp Ser Gly Ile Pro Asp Arg Phe Ser Gly Thr
        50                  55                  60

Arg Ser Gly Asp Ala Ala Thr Leu Thr Ile Thr Gly Val Gln Ala Glu
65                  70                  75                  80

Asp Glu Ala Asp Tyr Tyr Cys Gln Met Trp Asp Gly Glu Gly Ala Val
                85                  90                  95

Phe Gly Gly Gly Thr His Leu Thr Val Leu
                100                 105
```

<210> SEQ ID NO 139
<211> LENGTH: 103
<212> TYPE: PRT
<213> ORGANISM: Homo Sapiens

<400> SEQUENCE: 139

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
        35                  40                  45

Lys Val Lys Ser Asp Gly Ser His Ser Lys Gly Asp Gly Ile Pro Asp
50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Val Gly
            100

<210> SEQ ID NO 140
<211> LENGTH: 112
<212> TYPE: PRT
<213> ORGANISM: Lama glama

<400> SEQUENCE: 140

Gln Ser Val Leu Thr Gln Pro Pro Ser Ala Ser Ala Ser Leu Gly Ala
1               5                   10                  15

Ser Ala Lys Leu Thr Cys Thr Leu Ser Ser Gly Tyr Ser Ser Tyr Asn
            20                  25                  30

Val Asp Trp Tyr Gln Gln Val Pro Gly Lys Ser Pro Trp Phe Leu Met
        35                  40                  45

Arg Val Gly Ser Ser Gly Val Gly Ser Lys Gly Ser Gly Val Ser Asp
50                  55                  60

Arg Phe Ser Gly Ser Ser Ser Gly Leu Glu Arg Tyr Leu Thr Ile Gln
65                  70                  75                  80

Asn Val Gln Glu Glu Asp Glu Ala Glu Tyr Ile Cys Gly Ala Asp His
                85                  90                  95

Ala Ser Ser Met Tyr Thr Phe Gly Gly Gly Thr His Leu Thr Val Leu
            100                 105                 110

<210> SEQ ID NO 141
<211> LENGTH: 104
<212> TYPE: PRT
<213> ORGANISM: Homo Sapiens

<400> SEQUENCE: 141

Gln Pro Val Leu Thr Gln Pro Pro Ser Ser Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gly Gln Gly Ser Gly Val
50                  55                  60

Pro Ser Arg Phe Ser Gly Ser Lys Asp Ala Ser Ala Asn Thr Gly Ile
65                  70                  75                  80

```
Leu Leu Ile Ser Gly Leu Gln Ser Glu Asp Glu Ala Asp Tyr Tyr Cys
                85                  90                  95

Met Ile Trp Pro Ser Asn Ala Ser
            100

<210> SEQ ID NO 142
<211> LENGTH: 117
<212> TYPE: PRT
<213> ORGANISM: Lama glama

<400> SEQUENCE: 142

Leu Pro Val Leu Thr Gln Pro Pro Ser Leu Ser Ala Ser Pro Gly Ala
1               5                   10                  15

Ser Ala Arg Leu Thr Cys Ser Leu Asn Ser Gly Thr Ile Val Gly Gly
            20                  25                  30

Tyr His Ile Asn Trp Tyr Gln Gln Lys Ala Gly Ser Pro Pro Arg Tyr
        35                  40                  45

Leu Leu Arg Phe Tyr Ser Asp Ser Asn Lys His Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Val Glu Asp Glu Ala Asp Tyr Tyr Cys
                85                  90                  95

Gly Ile Tyr Asp Ser Asn Thr Gly Thr Tyr Val Phe Gly Gly Gly Thr
            100                 105                 110

Lys Leu Thr Val Leu
        115

<210> SEQ ID NO 143
<211> LENGTH: 117
<212> TYPE: PRT
<213> ORGANISM: Lama glama

<400> SEQUENCE: 143

Leu Pro Val Leu Thr Gln Pro Pro Ser Leu Ser Ala Ser Pro Gly Ala
1               5                   10                  15

Ser Ala Arg Leu Thr Cys Val Leu Ser Ser Gly Thr Val Val Gly Gly
            20                  25                  30

Tyr His Ile Asn Trp Tyr Gln Gln Lys Pro Gly Ser Pro Pro Arg Tyr
        35                  40                  45

Leu Leu Arg Phe Tyr Ser Asp Ser Ser Lys Gln Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Gly Thr Tyr His Ser Asn Thr Gly Thr Tyr Val Phe Gly Gly Gly Thr
            100                 105                 110

Lys Leu Thr Val Leu
        115

<210> SEQ ID NO 144
<211> LENGTH: 117
<212> TYPE: PRT
<213> ORGANISM: Lama glama

<400> SEQUENCE: 144
```

-continued

Leu Pro Val Leu Asn Gln Pro Ser Leu Ser Ala Ser Pro Gly Glu
1               5                   10                  15

Ser Ala Arg Leu Thr Cys Ser Leu Ser Ser Glu Thr Ile Val Gly Gly
            20                  25                  30

Tyr Gln Ile Ala Trp Tyr Gln Gln Thr Ala Gly Ser Pro Pro Arg Tyr
        35                  40                  45

Leu Leu Arg Phe Tyr Ser Asp Ser Asn Lys His Gln Gly Ser Gly Val
    50                  55                  60

Pro Ser Arg Phe Ser Gly Ser Lys Asp Ala Ser Ala Asn Ala Gly Ile
65                  70                  75                  80

Leu Phe Ile Ser Gly Leu Gln Pro Glu Asp Glu Ala Asp Tyr Tyr Cys
                85                  90                  95

Gly Ile Tyr His Tyr Asn Ser Asp Thr Tyr Val Phe Gly Gly Gly Thr
                100                 105                 110

Arg Leu Thr Val Leu
        115

<210> SEQ ID NO 145
<211> LENGTH: 117
<212> TYPE: PRT
<213> ORGANISM: Lama glama

<400> SEQUENCE: 145

Leu Pro Val Leu Thr Gln Pro Ser Leu Ser Ala Ser Pro Gly Ser
1               5                   10                  15

Ser Val Arg Leu Thr Cys Thr Leu Ser Ser Gly Lys Ser Val Gly Met
            20                  25                  30

Tyr Asp Ile Ser Trp Tyr Gln Gln Lys Ala Gly Ser Pro Pro Arg Tyr
        35                  40                  45

Leu Leu Tyr Tyr Tyr Ser Asp Thr Ser Asn His Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Ala Thr Gly Asp Arg Ser Ser Asn Pro His Val Phe Gly Gly Gly Thr
                100                 105                 110

Lys Leu Thr Val Leu
        115

<210> SEQ ID NO 146
<211> LENGTH: 118
<212> TYPE: PRT
<213> ORGANISM: Lama glama

<400> SEQUENCE: 146

Gln Ser Val Leu Thr Gln Pro Ser Leu Ser Ala Ser Pro Gly Ser
1               5                   10                  15

Ser Val Arg Leu Thr Cys Thr Leu Ser Ser Ala Asn Ser Val Asp Asn
            20                  25                  30

Tyr Tyr Ile Ser Trp Tyr Gln Gln Lys Pro Gly Ser Pro Pro Arg Tyr
        35                  40                  45

Leu Leu Tyr Tyr Tyr Ser Asp Ser Tyr Met Gln Arg Asp Ser Gly Leu
    50                  55                  60

Pro Asp Arg Phe Ser Val Ser Lys Asp Ala Ser Thr Asn Ala Gly Leu
65                  70                  75                  80

```
Leu Leu Ile Ser Gly Leu Gln Pro Glu Asp Glu Ala Asp Tyr Tyr Cys
            85                  90                  95

Ala Ser Gly Asp Arg Asn Ser Asn Pro His Ser Val Phe Gly Gly Gly
        100                 105                 110

Thr His Leu Thr Val Leu
        115

<210> SEQ ID NO 147
<211> LENGTH: 98
<212> TYPE: PRT
<213> ORGANISM: Homo Sapiens

<400> SEQUENCE: 147

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala
        35                  40                  45

Leu Ile Tyr Ser Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Gln

<210> SEQ ID NO 148
<211> LENGTH: 109
<212> TYPE: PRT
<213> ORGANISM: Lama glama

<400> SEQUENCE: 148

Gln Ala Val Val Ser Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Ser Thr Ser Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Asp Ile Gly Ser
                85                  90                  95

Tyr Thr Val Phe Gly Gly Gly Thr Lys Leu Thr Val Leu
        100                 105

<210> SEQ ID NO 149
<211> LENGTH: 113
<212> TYPE: PRT
<213> ORGANISM: Lama glama

<400> SEQUENCE: 149

Gln Thr Val Val Thr Gln Glu Pro Ser Leu Ser Val Ser Pro Gly Gly
1               5                   10                  15

Thr Val Thr Leu Thr Cys Gly Leu Thr Ser Gly Ser Val Thr Ala Ser
            20                  25                  30
```

```
Asn Leu Pro Gly Trp Phe Gln Gln Thr Pro Gly Gln Ala Pro Arg Thr
            35                  40                  45

Leu Ile Phe Asp Thr Ile Tyr His His Ser Gly Val Pro Ser Arg Phe
 50                  55                  60

Ser Gly Ser Ile Ala Gly Asn Lys Ala Thr Leu Thr Ile Thr Gly Ala
 65                  70                  75                  80

Gln Pro Glu Asp Glu Gly Asp Tyr Phe Cys Val Leu Trp Met Asp Arg
                 85                  90                  95

Ile Glu Ala Gly Ser Ile Met Phe Gly Gly Thr His Leu Ser Val
                100                 105                 110

Val

<210> SEQ ID NO 150
<211> LENGTH: 95
<212> TYPE: PRT
<213> ORGANISM: Homo Sapiens

<400> SEQUENCE: 150

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                 85                  90                  95

<210> SEQ ID NO 151
<211> LENGTH: 107
<212> TYPE: PRT
<213> ORGANISM: Lama glama

<400> SEQUENCE: 151

Asp Ile Gln Leu Thr Gln Ser Pro Ser Ser Leu Ser Ala Ser Leu Gly
 1               5                  10                  15

Asp Arg Val Thr Ile Thr Cys Gln Ala Ser Gln Ser Ile Ser Thr Glu
                20                  25                  30

Leu Ser Trp Tyr Gln Gln Lys Pro Gly Gln Thr Pro Lys Leu Leu Ile
            35                  40                  45

Tyr Gly Ala Ser Arg Leu Gln Thr Gly Val Pro Ser Arg Phe Ser Gly
 50                  55                  60

Ser Gly Ser Gly Thr Ser Phe Thr Leu Thr Ile Ser Gly Leu Glu Ala
 65                  70                  75                  80

Glu Asp Leu Ala Thr Tyr Tyr Cys Leu Gln Asp Tyr Ser Ser Pro Tyr
                 85                  90                  95

Ser Phe Gly Ser Gly Thr Arg Leu Glu Ile Lys
                100                 105

<210> SEQ ID NO 152
<211> LENGTH: 107
<212> TYPE: PRT
<213> ORGANISM: Lama glama
```

```
<400> SEQUENCE: 152

Asp Ile Gln Leu Thr Gln Ser Pro Ser Leu Ser Ala Ser Leu Gly
1               5                   10                  15

Asp Arg Val Thr Ile Thr Cys Gln Ala Ser Gln Ser Ile Ser Thr Glu
            20                  25                  30

Leu Ser Trp Tyr Gln Gln Lys Pro Gly Gln Thr Pro Lys Leu Leu Ile
        35                  40                  45

Tyr Asp Arg Ser Arg Leu Gln Ile Gly Val Pro Ser Arg Phe Ser Gly
    50                  55                  60

Ser Gly Ser Gly Thr Asp Tyr Thr Leu Thr Ile Ser Asp Leu Glu Ala
65                  70                  75                  80

Glu Asp Leu Ala Thr Tyr Tyr Cys Leu Gln Asp Asp Ser Trp Pro Tyr
                85                  90                  95

Ser Phe Gly Ser Gly Thr Arg Leu Glu Ile Lys
            100                 105

<210> SEQ ID NO 153
<211> LENGTH: 107
<212> TYPE: PRT
<213> ORGANISM: Lama glama

<400> SEQUENCE: 153

Asp Ile Val Met Thr Gln Thr Pro Ser Ser Leu Ser Ala Ser Leu Gly
1               5                   10                  15

Asp Arg Val Thr Ile Thr Cys Gln Ala Ser Gln Ser Ile Asn Thr Glu
            20                  25                  30

Leu Ser Trp Tyr Gln Gln Lys Pro Glu Gln Pro Pro Lys Leu Leu Ile
        35                  40                  45

Tyr Ala Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Asp Ser Asp Trp Pro Leu
                85                  90                  95

Thr Phe Gly Gln Gly Thr Lys Val Glu Leu Lys
            100                 105

<210> SEQ ID NO 154
<211> LENGTH: 107
<212> TYPE: PRT
<213> ORGANISM: Lama glama

<400> SEQUENCE: 154

Asp Ile Val Met Thr Gln Ser Pro Ser Ser Leu Ser Ala Ser Leu Gly
1               5                   10                  15

Asp Arg Val Thr Ile Thr Cys Gln Ala Thr Gln Ser Ile Asn Thr Glu
            20                  25                  30

Leu Ser Trp Tyr Gln Gln Lys Pro Gly Gln Ser Pro Lys Leu Leu Ile
        35                  40                  45

Tyr Glu Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Met Ala Asp Leu Asp Trp Pro Leu
                85                  90                  95

Val Phe Gly Gln Gly Thr Lys Val Glu Leu Lys
```

```
                100                 105

<210> SEQ ID NO 155
<211> LENGTH: 107
<212> TYPE: PRT
<213> ORGANISM: Lama glama

<400> SEQUENCE: 155

Asp Ile Val Met Thr Gln Thr Pro Ser Ser Leu Ser Ala Ser Leu Gly
1               5                   10                  15

Asp Arg Val Thr Ile Thr Cys Gln Ala Ser Gln Ser Ile Ser Thr Glu
            20                  25                  30

Leu Ala Trp Tyr Gln Gln Lys Pro Gly Gln Thr Pro Lys Leu Leu Ile
        35                  40                  45

Tyr Gly Ala Ser Lys Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Gly Tyr Ser Ser Pro Leu
                85                  90                  95

Thr Phe Gly Gln Gly Thr Glu Val Asp Leu Lys
            100                 105

<210> SEQ ID NO 156
<211> LENGTH: 107
<212> TYPE: PRT
<213> ORGANISM: Lama glama

<400> SEQUENCE: 156

Ala Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Thr Glu
            20                  25                  30

Leu Ser Trp Tyr Gln Gln Lys Pro Gly Gln Thr Pro Lys Leu Leu Ile
        35                  40                  45

Tyr Gly Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ser
65                  70                  75                  80

Glu Asp Leu Ala Thr Tyr Tyr Cys Leu Gln Asp Tyr Ser Trp Pro Leu
                85                  90                  95

Thr Phe Gly Gln Gly Thr Lys Val Glu Leu Thr
            100                 105

<210> SEQ ID NO 157
<211> LENGTH: 107
<212> TYPE: PRT
<213> ORGANISM: Lama glama

<400> SEQUENCE: 157

Asp Ile Gln Leu Thr Gln Ser Pro Ser Ser Leu Ser Ala Ser Leu Gly
1               5                   10                  15

Asp Arg Val Thr Ile Thr Cys Gln Ala Ser Gln Ser Ile Ser Thr Glu
            20                  25                  30

Leu Ser Trp Tyr Gln Gln Lys Pro Gly Gln Thr Pro Lys Leu Leu Ile
        35                  40                  45

Tyr Gly Ala Ser Arg Leu Gln Thr Gly Val Pro Ser Arg Phe Ser Gly
    50                  55                  60
```

```
Ser Gly Ser Gly Thr Ser Phe Thr Leu Thr Ile Ser Gly Leu Glu Ala
 65                  70                  75                  80

Glu Asp Leu Ala Thr Tyr Tyr Cys Leu Gln Asp Tyr Ser Trp Pro Arg
                 85                  90                  95

Thr Phe Gly Gln Gly Thr Lys Leu Glu Ile Lys
            100                 105

<210> SEQ ID NO 158
<211> LENGTH: 107
<212> TYPE: PRT
<213> ORGANISM: Lama glama

<400> SEQUENCE: 158

Asp Ile Val Met Thr Gln Thr Pro Ser Leu Ser Ala Ser Leu Gly
 1               5                  10                  15

Asp Arg Val Thr Ile Thr Cys Gln Ala Ser Gln Ser Ile Arg Asn Glu
                 20                  25                  30

Leu Ala Trp Tyr Gln Gln Lys Pro Gly Gln Thr Pro Lys Leu Leu Ile
             35                  40                  45

Tyr Gly Ala Ser Arg Leu Gln Thr Gly Val Pro Ser Arg Phe Ser Gly
 50                  55                  60

Ser Gly Ser Gly Thr Ser Phe Thr Leu Thr Ile Ser Gly Leu Glu Ala
 65                  70                  75                  80

Glu Asp Leu Ala Thr Tyr Tyr Cys Leu Gln Asp Asp Ser Trp Pro Leu
                 85                  90                  95

Thr Phe Gly Gln Gly Thr Lys Val Glu Leu Lys
            100                 105

<210> SEQ ID NO 159
<211> LENGTH: 107
<212> TYPE: PRT
<213> ORGANISM: Lama glama

<400> SEQUENCE: 159

Ala Ile Gln Met Thr Gln Ser Pro Ser Ser Leu Ser Ala Ser Leu Gly
 1               5                  10                  15

Asp Arg Val Thr Ile Thr Cys Gln Ala Ser Gln Ser Ile Ser Ser Tyr
                 20                  25                  30

Leu Ala Trp Tyr Gln Gln Lys Pro Gly Gln Ala Pro Lys Leu Leu Ile
             35                  40                  45

Tyr Gly Ala Ser Thr Leu Gln Thr Gly Val Pro Ser Arg Phe Ser Gly
 50                  55                  60

Ser Gly Ser Gly Thr Ser Phe Thr Leu Thr Ile Ser Gly Leu Glu Ala
 65                  70                  75                  80

Glu Asp Ala Gly Thr Tyr Tyr Cys Gln Gln Tyr Tyr Ser Ile Pro Val
                 85                  90                  95

Thr Phe Gly Gln Gly Thr Lys Val Glu Leu Arg
            100                 105

<210> SEQ ID NO 160
<211> LENGTH: 106
<212> TYPE: PRT
<213> ORGANISM: Lama glama

<400> SEQUENCE: 160

Ala Ile Gln Met Thr Gln Ser Pro Ser Ser Leu Ser Ala Ser Leu Gly
 1               5                  10                  15
```

```
Asp Arg Val Thr Ile Thr Cys Gln Ala Ser Gln Ser Ile Ser Ser Tyr
                20                  25                  30

Leu Ala Trp Tyr Gln Gln Lys Pro Gly Gln Ala Pro Lys Leu Leu Ile
         35                  40                  45

Tyr Gly Ala Ser Arg Leu Gln Thr Gly Val Pro Ser Arg Phe Ser Gly
 50                  55                  60

Ser Gly Ser Gly Thr Ser Phe Thr Leu Thr Ile Ser Gly Leu Glu Ala
 65                  70                  75                  80

Glu Asp Ala Gly Thr Tyr Tyr Cys Gln Leu Tyr Gly Ser Arg Pro Ser
                 85                  90                  95

Phe Gly Gln Gly Thr Lys Val Glu Leu Lys
            100                 105
```

<210> SEQ ID NO 161
<211> LENGTH: 106
<212> TYPE: PRT
<213> ORGANISM: Lama glama

<400> SEQUENCE: 161

```
Val Ile Gln Met Thr Gln Ser Pro Ser Ser Leu Ser Ala Ser Leu Gly
 1               5                  10                  15

Asp Arg Val Thr Ile Thr Cys Gln Ala Ser Gln Ser Ile Ser Asn Tyr
                20                  25                  30

Leu Ala Trp Tyr Gln Gln Lys Pro Gly Gln Ala Pro Lys Leu Val Ile
         35                  40                  45

Tyr Gly Ala Ser Arg Leu Gln Thr Gly Val Pro Ser Arg Phe Ser Gly
 50                  55                  60

Ser Gly Ser Gly Thr Ser Phe Thr Leu Thr Ile Ser Gly Leu Glu Ala
 65                  70                  75                  80

Glu Asp Ala Gly Thr Tyr Tyr Cys Gln Gln Tyr Tyr Ser Thr Tyr Ser
                 85                  90                  95

Phe Gly Ser Gly Thr Arg Leu Glu Ile Lys
            100                 105
```

<210> SEQ ID NO 162
<211> LENGTH: 108
<212> TYPE: PRT
<213> ORGANISM: Lama glama

<400> SEQUENCE: 162

```
Asp Ile Gln Leu Thr Gln Ser Pro Ser Ser Leu Ser Ala Ser Leu Gly
 1               5                  10                  15

Asp Ile Val Thr Ile Thr Cys Gln Ala Ser Gln Ser Ile Thr Thr Glu
                20                  25                  30

Leu Ser Trp Tyr Gln Gln Lys Pro Gly Gln Thr Pro Lys Leu Leu Ile
         35                  40                  45

Tyr Gly Ala Phe Arg Leu Gln Ala Gly Val Pro Ser Arg Phe Ser Gly
 50                  55                  60

Ser Arg Ser Gly Thr Thr Phe Thr Leu Thr Ile Ser Gly Leu Glu Ala
 65                  70                  75                  80

Glu Asp Leu Ala Thr Tyr Tyr Cys Leu Gln Asp Tyr Ser Trp Pro Pro
                 85                  90                  95

Tyr Ser Phe Gly Ser Gly Thr Arg Leu Glu Ile Lys
            100                 105
```

<210> SEQ ID NO 163
<211> LENGTH: 101

```
<212> TYPE: PRT
<213> ORGANISM: Homo Sapiens

<400> SEQUENCE: 163

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 164
<211> LENGTH: 113
<212> TYPE: PRT
<213> ORGANISM: Lama glama

<400> SEQUENCE: 164

Glu Thr Thr Leu Thr Gln Ser Pro Ser Ser Val Thr Ala Ser Val Gly
1               5                   10                  15

Glu Lys Val Thr Ile Asn Cys Lys Ser Ser Gln Asn Val Gly Ser Gly
            20                  25                  30

Ser Asn Gln Lys Ser Ile Leu Asn Trp Ile Gln Gln Arg Pro Gly Gln
        35                  40                  45

Ser Pro Arg Leu Leu Ile Tyr Tyr Ala Ser Thr Arg Asp Ala Gly Ile
    50                  55                  60

Pro Asp Arg Phe Ser Gly Ser Gly Ser Ala Thr Asp Phe Thr Leu Thr
65                  70                  75                  80

Ile Arg Ser Val Gln Pro Glu Asp Ala Ala Val Tyr Tyr Cys Gln Gln
                85                  90                  95

Val Asn Ile Ala Pro Tyr Thr Phe Gly Ser Gly Thr Arg Leu Glu Ile
            100                 105                 110

Arg

<210> SEQ ID NO 165
<211> LENGTH: 113
<212> TYPE: PRT
<213> ORGANISM: Lama glama

<400> SEQUENCE: 165

Glu Ile Val Met Thr Gln Ser Pro Ser Ser Val Thr Ala Ser Ala Gly
1               5                   10                  15

Glu Lys Val Thr Ile Asn Cys Lys Ser Ser Gln Ser Val Phe Gln Ser
            20                  25                  30

Ser Asn Gln Lys Asn Tyr Leu Gly Trp Tyr Gln Gln Arg Ile Gly Gln
        35                  40                  45

Ser Pro Arg Leu Leu Ile Asn Trp Ala Ser Thr Arg Glu Ser Gly Val
    50                  55                  60

Pro Asp Arg Phe Ser Gly Ser Gly Ser Thr Thr Asp Phe Thr Leu Thr
65                  70                  75                  80
```

```
Ile Asn Pro Phe Gln Pro Glu Asp Ala Ala Val Tyr Tyr Cys Gln Gln
                85                  90                  95

Gly Lys Ser Ala Pro Leu Thr Phe Gly Gln Gly Thr Lys Val Glu Leu
            100                 105                 110

Lys

<210> SEQ ID NO 166
<211> LENGTH: 113
<212> TYPE: PRT
<213> ORGANISM: Lama glama

<400> SEQUENCE: 166

Asp Ile Val Met Thr Gln Thr Pro Ser Ser Val Thr Ala Ser Ile Gly
1               5                   10                  15

Glu Lys Val Thr Ile Asn Cys Lys Ser Ser Gln Ser Val Leu Tyr Ser
            20                  25                  30

Ser Asn Gln Lys Asn Tyr Leu Thr Trp Tyr Gln Gln Arg Leu Gly Gln
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Leu Thr Thr Phe Thr Leu Thr
65                  70                  75                  80

Ile Ser Ser Phe Gln Pro Glu Asp Ala Ala Val Tyr Phe Cys Gln Gln
                85                  90                  95

Gly Tyr Ser Val Pro Leu Thr Phe Gly Arg Gly Thr Lys Val Glu Leu
            100                 105                 110

Lys

<210> SEQ ID NO 167
<211> LENGTH: 113
<212> TYPE: PRT
<213> ORGANISM: Lama glama

<400> SEQUENCE: 167

Glu Thr Thr Leu Thr Gln Ser Pro Ser Ser Val Thr Ala Ser Ala Gly
1               5                   10                  15

Glu Lys Val Thr Ile Asn Cys Lys Ser Ser Gln Ser Val Leu Leu Asp
            20                  25                  30

Ser Asn Gln Lys Asn Tyr Leu Ala Trp Tyr Gln Gln Arg Leu Gly Gln
        35                  40                  45

Ser Pro Arg Leu Leu Ile Tyr Trp Ala Ser Thr Arg Gln Ser Gly Val
    50                  55                  60

Pro Asp Arg Phe Ser Gly Ser Gly Ser Thr Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Gly Ile Thr Ile Pro Val Thr Phe Gly Gln Gly Thr Lys Val Glu Leu
            100                 105                 110

Lys

<210> SEQ ID NO 168
<211> LENGTH: 113
<212> TYPE: PRT
<213> ORGANISM: Lama glama

<400> SEQUENCE: 168
```

```
Glu Ile Val Leu Thr Gln Ser Pro Ser Ser Val Thr Ala Ser Ala Gly
1               5                   10                  15

Glu Lys Val Thr Ile Asn Cys Lys Ser Ser Gln Ser Val Leu Tyr Ser
            20                  25                  30

Ser Asp Gln Lys Asn Tyr Leu Ala Trp Tyr Gln Gln Arg Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Gly Tyr Ser Ser Pro His Ser Phe Gly Ser Gly Thr Arg Leu Glu Ile
            100                 105                 110

Lys
```

<210> SEQ ID NO 169
<211> LENGTH: 113
<212> TYPE: PRT
<213> ORGANISM: Lama glama

<400> SEQUENCE: 169

```
Glu Thr Thr Leu Thr Gln Ser Pro Ser Ser Val Thr Ala Ser Ala Gly
1               5                   10                  15

Glu Lys Val Thr Ile Asn Cys Lys Ser Ser Gln Ser Val Leu Tyr Arg
            20                  25                  30

Ser Asp Gln Lys Asn Val Leu Ser Trp Tyr Gln Gln Arg Leu Gly Gln
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Gly Tyr Ser Arg Pro Tyr Ser Phe Gly Asn Gly Thr Arg Leu Glu Ile
            100                 105                 110

Lys
```

<210> SEQ ID NO 170
<211> LENGTH: 113
<212> TYPE: PRT
<213> ORGANISM: Lama glama

<400> SEQUENCE: 170

```
Asp Ile Val Met Thr Gln Thr Pro Ser Ser Val Thr Ala Ser Ala Gly
1               5                   10                  15

Glu Lys Val Thr Ile Asn Cys Lys Ser Ser Gln Ser Val Leu Asn Asn
            20                  25                  30

Ser Asp Gln Lys Ile Tyr Leu Ala Trp Tyr Gln Gln Arg Leu Gly Gln
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Thr Asp Phe Thr Leu Thr
65                  70                  75                  80

Ile Ser Ser Phe Gln Pro Glu Asp Ala Ala Val Tyr Tyr Cys Gln Gln
                85                  90                  95
```

-continued

Glu Tyr Ser Ala Pro Ala Ser Phe Gly Ser Gly Thr Arg Leu Glu Ile
                100                 105                 110

Lys

<210> SEQ ID NO 171
<211> LENGTH: 113
<212> TYPE: PRT
<213> ORGANISM: Lama glama

<400> SEQUENCE: 171

Asp Ile Val Met Thr Gln Ser Pro Gly Ser Val Thr Ala Ser Thr Gly
1               5                   10                  15

Glu Asn Ile Thr Ile Asn Cys Lys Ser Ser Gln Asn Val Leu Leu Ser
            20                  25                  30

Ser Asp Gln Lys Asn Tyr Leu Asn Trp Tyr Gln Arg Leu Gly Gln
        35                  40                  45

Ser Pro Arg Leu Leu Ile Tyr Trp Ala Ser Thr Arg Lys Ser Gly Ile
    50                  55                  60

Pro Asp Arg Phe Ser Gly Arg Gly Ser Thr Thr Asp Phe Thr Leu Thr
65                  70                  75                  80

Ile Asn Ser Phe Gln Pro Glu Asp Ala Ala Val Tyr Tyr Cys Gln Gln
                85                  90                  95

Gly Tyr Ser Ile Pro His Thr Phe Gly Gly Gly Thr Arg Leu Glu Ile
                100                 105                 110

Lys

<210> SEQ ID NO 172
<211> LENGTH: 113
<212> TYPE: PRT
<213> ORGANISM: Lama glama

<400> SEQUENCE: 172

Asp Ile Val Met Thr Gln Thr Pro Thr Ser Val Thr Ala Ser Ala Gly
1               5                   10                  15

Glu Lys Val Thr Ile Asn Cys Lys Ser Ser Gln Ser Leu Leu Tyr Ser
            20                  25                  30

Ala Asn Gln Lys Val Tyr Leu Ala Trp Tyr Gln Gln Arg Leu Gly Gln
        35                  40                  45

Ser Pro Arg Leu Leu Phe Arg Trp Thr Ser Thr Arg Gln Pro Gly Ile
    50                  55                  60

Pro Asp Arg Phe Ser Gly Ser Gly Ser Thr Thr Asp Phe Thr Leu Thr
65                  70                  75                  80

Ile Ser Arg Val Gln Pro Glu Asp Ala Ala Val Tyr Tyr Cys Gln Gln
                85                  90                  95

Ala Tyr Ala Arg Pro His Thr Phe Gly Ser Gly Thr Arg Leu Glu Ile
                100                 105                 110

Lys

<210> SEQ ID NO 173
<211> LENGTH: 113
<212> TYPE: PRT
<213> ORGANISM: Lama glama

<400> SEQUENCE: 173

Asp Ile Val Met Thr Gln Thr Pro Thr Ser Val Thr Ala Ser Ala Gly
1               5                   10                  15

Glu Lys Val Thr Ile Asn Cys Lys Ser Ser Gln Ser Leu Leu Tyr Ser
            20                  25                  30

Ala Asn Gln Lys Val Tyr Leu Ala Trp Tyr Gln Gln Arg Leu Gly Gln
        35                  40                  45

Ser Pro Arg Leu Leu Phe Arg Trp Thr Ser Thr Arg Gln Pro Gly Ile
 50                  55                  60

Pro Asp Arg Phe Ser Val Ser Gly Ser Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ala Arg Pro His Thr Phe Gly Ser Gly Thr Arg Leu Glu Ile
            100                 105                 110

Lys

<210> SEQ ID NO 174
<211> LENGTH: 113
<212> TYPE: PRT
<213> ORGANISM: Lama glama

<400> SEQUENCE: 174

Glu Ile Val Met Thr Gln Ser Pro Thr Ser Val Thr Ala Ser Val Gly
1               5                   10                  15

Glu Lys Val Thr Ile Asn Cys Lys Ser Ser Gln Ser Leu Leu Tyr Ser
            20                  25                  30

Ala Asn Gln Lys Val Tyr Leu Ala Trp Tyr Gln Gln Arg Leu Gly Gln
        35                  40                  45

Ser Pro Arg Leu Leu Phe Tyr Trp Thr Ser Thr Arg Gln Ser Gly Ile
 50                  55                  60

Pro Asp Arg Phe Ser Gly Ser Gly Ser Thr Thr Ser Phe Thr Leu Thr
65                  70                  75                  80

Ile Ser Gly Val Gln Pro Glu Asp Ala Ala Val Tyr Tyr Cys Gln Gln
                85                  90                  95

Ala Tyr Thr Arg Pro His Thr Phe Gly Ser Gly Thr Arg Leu Glu Ile
            100                 105                 110

Arg

<210> SEQ ID NO 175
<211> LENGTH: 113
<212> TYPE: PRT
<213> ORGANISM: Lama glama

<400> SEQUENCE: 175

Glu Ile Val Leu Thr Gln Ser Pro Ser Ser Val Thr Ala Ser Val Gly
1               5                   10                  15

Glu Lys Val Thr Ile Asn Cys Lys Ser Ser Gln Ser Val Lys Ser Gly
            20                  25                  30

Ser Asn Gln Ile Thr Tyr Leu Asn Trp Tyr Gln Gln Thr Pro Gly Gln
        35                  40                  45

Ser Pro Arg Leu Leu Ile Tyr Tyr Ala Ser Thr Gln Glu Leu Gly Ile
 50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Ala Pro Phe Ser Phe Gly Ser Gly Thr Arg Leu Glu Ile
            100                 105                 110

-continued

Lys

<210> SEQ ID NO 176
<211> LENGTH: 113
<212> TYPE: PRT
<213> ORGANISM: Lama glama

<400> SEQUENCE: 176

Glu Thr Thr Leu Thr Gln Ser Pro Ser Ser Val Thr Ala Ser Val Gly
1               5                   10                  15

Glu Lys Val Thr Ile Asn Cys Lys Ser Gln Ser Val Val Ser Gly
            20                  25                  30

Ser Asn Gln Lys Ile Tyr Leu Asn Trp Tyr Gln Gln Arg Pro Gly Gln
        35                  40                  45

Ser Pro Arg Leu Leu Ile Tyr Tyr Ala Ser Thr Gln Glu Ser Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Gly Ala Ser Ala Pro Val Ser Phe Gly Ser Gly Thr Arg Leu Glu Ile
            100                 105                 110

Lys

<210> SEQ ID NO 177
<211> LENGTH: 113
<212> TYPE: PRT
<213> ORGANISM: Lama glama

<400> SEQUENCE: 177

Asp Ile Val Met Thr Gln Thr Pro Ser Ser Val Thr Ala Ser Val Gly
1               5                   10                  15

Glu Thr Val Thr Ile Gly Cys Lys Ser Ser Gln Ser Val Val Ser Gly
            20                  25                  30

Ser Ser Gln Lys Ser Phe Leu Asn Trp Tyr Gln Gln Arg Pro Gly Gln
        35                  40                  45

Ser Pro Arg Leu Leu Ile Tyr Tyr Ala Ser Thr Leu Glu Leu Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Thr Pro Ser Thr Phe Gly Pro Gly Thr Lys Leu Glu Ile
            100                 105                 110

Arg

<210> SEQ ID NO 178
<211> LENGTH: 113
<212> TYPE: PRT
<213> ORGANISM: Lama glama

<400> SEQUENCE: 178

Asp Ile Val Met Thr Gln Thr Pro Arg Ser Val Thr Ala Ser Val Gly
1               5                   10                  15

Glu Lys Val Thr Ile Asn Cys Lys Ser Ser Gln Ser Val Leu Ser Gly
            20                  25                  30

Ser Asn Gln Lys Ser Tyr Leu Asn Trp Tyr Gln Arg Pro Gly Gln
           35                  40                  45

Ser Pro Arg Leu Leu Ile Tyr Tyr Ala Ser Thr Gln Glu Ser Gly Ile
 50                      55                  60

Pro Asp Arg Phe Ser Gly Ser Gly Ser Thr Thr Asp Phe Thr Leu Thr
 65                  70                  75                  80

Ile Ser Gly Val Gln Pro Glu Asp Ala Ala Val Tyr Tyr Cys Gln Gln
                 85                  90                  95

Ala Tyr Ser Ala Pro Ala Thr Phe Gly Gln Gly Thr Val Glu Val
            100                 105                 110

Ile

<210> SEQ ID NO 179
<211> LENGTH: 113
<212> TYPE: PRT
<213> ORGANISM: Lama glama

<400> SEQUENCE: 179

Asp Val Val Met Thr Gln Ser Pro Ser Ser Val Thr Ala Ser Val Gly
 1               5                  10                  15

Glu Lys Val Thr Ile Asn Cys Lys Ser Ser Gln Ser Val Arg Ser Gly
                20                  25                  30

Ser Asn Glu Lys Ser Ser Leu Asn Trp Tyr Gln Gln Arg Pro Gly Gln
           35                  40                  45

Ser Pro Arg Leu Leu Ile Tyr Tyr Ala Ser Gln Glu Ser Gly Ile
 50                      55                  60

Pro Asp Arg Phe Ser Gly Ser Gly Ser Thr Thr Asp Phe Thr Leu Thr
 65                  70                  75                  80

Ile Ser Ser Val Gln Pro Glu Asp Ala Ala Val Tyr Tyr Cys Gln Gln
                 85                  90                  95

Ala Tyr Ser Tyr Pro Ile Thr Phe Gly Gln Gly Thr Lys Val Glu Leu
            100                 105                 110

Lys

<210> SEQ ID NO 180
<211> LENGTH: 113
<212> TYPE: PRT
<213> ORGANISM: Lama glama

<400> SEQUENCE: 180

Asp Val Val Met Thr Gln Ser Pro Ser Ser Val Thr Ala Ser Val Gly
 1               5                  10                  15

Glu Lys Val Thr Ile Asp Cys Lys Ser Ser Gln Ile Leu Val Ser Gly
                20                  25                  30

Ser Asp Gln Lys Ser Tyr Leu Ser Trp Tyr Gln Gln Arg Pro Gly Gln
           35                  40                  45

Ser Pro Arg Leu Leu Ile Tyr Tyr Ala Ser Thr Gln Lys Leu Gly Ile
 50                      55                  60

Pro Asp Arg Phe Ser Gly Ser Gly Ser Thr Thr Asp Phe Thr Leu Thr
 65                  70                  75                  80

Ile Ser Ser Val Gln Pro Glu Asp Ala Ala Val Tyr Tyr Cys Gln Gln
                 85                  90                  95

Thr Tyr Glu Ala Pro Tyr Ser Phe Gly Asn Gly Thr Arg Leu Glu Ile
            100                 105                 110

Lys

<210> SEQ ID NO 181
<211> LENGTH: 113
<212> TYPE: PRT
<213> ORGANISM: Lama glama

<400> SEQUENCE: 181

```
Glu Ile Val Met Thr Gln Thr Pro Ser Ser Val Thr Ala Ser Val Gly
1               5                   10                  15

Glu Lys Val Thr Ile Asn Cys Lys Ser Ser Gln Ser Val Leu Ala
            20                  25                  30

Ser Asn Gln Lys Thr Tyr Leu Asn Trp Tyr Gln Gln Arg Pro Gly Gln
        35                  40                  45

Ser Pro Arg Leu Leu Ile Tyr Tyr Ala Ser Thr Gln Gln Leu Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Leu Ser Ala Pro Tyr Ser Phe Gly Ser Gly Thr Arg Leu Glu Ile
            100                 105                 110

Lys
```

<210> SEQ ID NO 182
<211> LENGTH: 113
<212> TYPE: PRT
<213> ORGANISM: Lama glama

<400> SEQUENCE: 182

```
Asp Val Val Met Thr Gln Ser Pro Ser Ser Val Thr Ala Ser Val Gly
1               5                   10                  15

Glu Lys Val Thr Ile Asn Cys Lys Ser Ser Gln Ser Val Val Ser Gly
            20                  25                  30

Ser Asn Gln Lys Ser Tyr Leu Asn Trp Tyr Gln Gln Arg Pro Gly Gln
        35                  40                  45

Ser Pro Arg Leu Leu Ile Tyr Tyr Ala Ser Thr Gln Glu Leu Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Thr Pro Tyr Ser Phe Gly Ser Gly Thr Arg Leu Glu Ile
            100                 105                 110

Lys
```

<210> SEQ ID NO 183
<211> LENGTH: 112
<212> TYPE: PRT
<213> ORGANISM: Lama glama

<400> SEQUENCE: 183

```
Glu Ile Val Met Thr Gln Ser Pro Ser Thr Val Thr Ala Ser Val Gly
1               5                   10                  15

Glu Lys Val Thr Ile Lys Cys Lys Ser Ser Gln Ser Val Val Ser Gly
            20                  25                  30

Ser Asn Gln Lys Thr Tyr Leu Asn Trp Tyr Gln Gln Arg Pro Glu Gln
        35                  40                  45
```

```
Ser Pro Arg Leu Leu Met Tyr Tyr Ala Ala Thr Pro Glu Leu Gly Ile
    50                  55                  60

Pro Asp Arg Phe Ser Gly Ser Gly Ser Thr Thr Asp Phe Thr Leu Thr
 65                  70                  75                  80

Ile Asn Ser Val Gln Pro Glu Asp Ala Ala Val Tyr Tyr Cys Gln Gln
                 85                  90                  95

Thr Tyr Ser Pro Pro Asn Phe Gly Ser Gly Thr Arg Leu Glu Ile Ala
            100                 105                 110
```

<210> SEQ ID NO 184
<211> LENGTH: 113
<212> TYPE: PRT
<213> ORGANISM: Lama glama

<400> SEQUENCE: 184

```
Asp Val Val Met Thr Gln Ser Pro Ser Ser Val Thr Ala Ser Ala Gly
 1               5                  10                  15

Glu Lys Val Thr Ile Asn Cys Lys Ser Ser Gln Ser Leu Leu Trp Ser
                 20                  25                  30

Asp Asn Lys Lys Asn Tyr Leu Ser Trp Tyr Gln Gln Arg Leu Gly Gln
             35                  40                  45

Ser Pro Arg Leu Leu Ile Tyr Trp Ala Ser Thr Arg Glu Ser Gly Ala
    50                  55                  60

Pro Asp Arg Phe Ser Gly Ser Gly Ser Thr Thr Asp Phe Thr Leu Thr
 65                  70                  75                  80

Ile Ser Asn Phe Gln Pro Glu Asp Ala Ala Val Tyr Tyr Cys Gln Gln
                 85                  90                  95

Gly Tyr Ser Ile Pro Ile Thr Phe Gly Gln Gly Thr Lys Val Glu Leu
            100                 105                 110

Ser
```

<210> SEQ ID NO 185
<211> LENGTH: 113
<212> TYPE: PRT
<213> ORGANISM: Lama glama

<400> SEQUENCE: 185

```
Asp Ile Val Leu Thr Gln Ser Pro Ser Ser Val Thr Ala Ser Ala Gly
 1               5                  10                  15

Glu Lys Val Thr Ile Thr Cys Glu Ser Ser Gln Ser Val Leu Arg Ser
                 20                  25                  30

Ser Asn Gln Arg Asn Tyr Leu Asn Trp Tyr Gln Gln Arg Leu Gly Gln
             35                  40                  45

Ser Pro Arg Leu Ile Ile Tyr Trp Ala Ser Thr Arg Glu Ser Gly Val
    50                  55                  60

Pro Asp Arg Phe Ser Gly Ser Gly Ser Thr Thr Asp Phe Thr Leu Thr
 65                  70                  75                  80

Ile Ser Ser Phe Gln Pro Glu Asp Ala Ala Val Tyr Tyr Cys Gln Gln
                 85                  90                  95

Ala Ser Ser Leu Pro Phe Thr Phe Gly Gln Gly Thr Lys Val Glu Leu
            100                 105                 110

Lys
```

<210> SEQ ID NO 186
<211> LENGTH: 112
<212> TYPE: PRT
<213> ORGANISM: Lama glama

```
<400> SEQUENCE: 186

Glu Ile Val Leu Thr Gln Ser Pro Ser Ser Val Thr Ala Ser Ala Gly
1               5                   10                  15

Glu Lys Val Thr Ile Asn Cys Lys Ser Ser Gln Ser Val Leu Tyr Ser
            20                  25                  30

Ser Asn Gln Lys Asn Tyr Leu Ala Trp Tyr Gln Gln Arg Leu Gly Gln
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Tyr Leu Ser Gly Val Thr Phe Gly Gln Gly Thr Lys Val Glu Leu Lys
            100                 105                 110

<210> SEQ ID NO 187
<211> LENGTH: 98
<212> TYPE: PRT
<213> ORGANISM: Homo Sapiens

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 188
<211> LENGTH: 117
<212> TYPE: PRT
<213> ORGANISM: Lama glama

<400> SEQUENCE: 188

Glu Val Gln Leu Val Gln Ser Gly Ala Glu Leu Arg Asn Pro Gly Ala
1               5                   10                  15

Ser Val Lys Val Ser Cys Lys Ala Ser Gly Tyr Thr Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Asp Thr Lys Tyr Ala Pro Lys Phe
    50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Asp Thr Ala Val Tyr Tyr Cys
                85                  90                  95

Ala Arg Ser Gly Arg Tyr Glu Leu Asp Tyr Trp Gly Leu Gly Thr Gln
```

Val Thr Val Ser Ser
        115

<210> SEQ ID NO 189
<211> LENGTH: 122
<212> TYPE: PRT
<213> ORGANISM: Lama glama

<400> SEQUENCE: 189

Glu Val Gln Leu Val Gln Ser Gly Ala Glu Leu Arg Asn Pro Gly Ala
1               5                   10                  15

Ser Val Lys Val Ser Cys Lys Ala Ser Gly Tyr Thr Phe Thr Ser Tyr
                20                  25                  30

Tyr Ile Glu Trp Val Arg Gln Ala Pro Gly Gln Gly Leu Glu Trp Met
            35                  40                  45

Gly Arg Ile Asp Pro Glu Asp Gly Gly Thr Lys Tyr Ala Gln Lys Phe
50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Asp Thr Ala Val Tyr Phe Cys
                85                  90                  95

Ala Thr Ser Gly Ala Thr Met Ser Asp Leu Asp Ser Phe Gly Ser Trp
            100                 105                 110

Gly Gln Gly Thr Gln Val Thr Val Ser Ser
        115                 120

<210> SEQ ID NO 190
<211> LENGTH: 98
<212> TYPE: PRT
<213> ORGANISM: Homo Sapiens

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 191
<211> LENGTH: 122
<212> TYPE: PRT
<213> ORGANISM: Lama glama

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Thr Thr Ser Gly Phe Thr Phe Glu Asp Tyr
                20                  25                  30

```
Pro Met Asn Trp Val Arg Gln Ala Pro Gly Lys Gly Leu Glu Trp Val
        35                  40                  45

Ser Val Ile Ser Arg Asn Gly Gly Ser Thr Tyr Tyr Ala Glu Ser Met
 50                      55                  60

Lys Gly Arg Phe Thr Ile Ser Arg Asp Asn Ala Lys Asn Thr Leu Tyr
 65                      70                  75                  80

Leu Val Met Asn Ser Leu Thr Ser Glu Asp Thr Ala Val Tyr Tyr Cys
                 85                  90                  95

Thr Lys Pro Ser Thr Ser Trp Ser Thr Asn Tyr Gly Met Asp Tyr Trp
             100                 105                 110

Gly Lys Gly Thr Gln Val Thr Val Ser Ser
         115                 120
```

<210> SEQ ID NO 192
<211> LENGTH: 115
<212> TYPE: PRT
<213> ORGANISM: Lama glama

<400> SEQUENCE: 192

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Asp Asp Tyr
             20                  25                  30

Gly Met Ser Trp Val Arg Gln Ala Pro Gly Lys Gly Leu Glu Trp Val
         35                  40                  45

Ser Gly Ile Thr Trp Asn Gly Gly Thr Thr Asn Tyr Ala Asp Ser Val
 50                      55                  60

Lys Gly Arg Phe Thr Ile Ser Arg Asp Ser Ala Lys Asn Met Val His
 65                      70                  75                  80

Leu Gln Met Asp Ser Leu Lys Ser Glu Asp Thr Ala Val Tyr Tyr Cys
                 85                  90                  95

Ala Lys Ala Tyr Arg Gly Ser Leu Gly Gln Gly Thr Gln Val Thr
             100                 105                 110

Val Ser Ser
        115
```

<210> SEQ ID NO 193
<211> LENGTH: 122
<212> TYPE: PRT
<213> ORGANISM: Lama glama

<400> SEQUENCE: 193

```
Glu Val Gln Leu Val Glu Ser Gly Gly Gly Leu Val Gln Pro Gly Gly
 1               5                   10                  15

Ser Leu Arg Val Ser Cys Ala Ala Ser Gly Phe Thr Phe Ser Thr Tyr
             20                  25                  30

Tyr Met Ser Trp Val Arg Gln Ala Pro Gly Lys Gly Leu Glu Trp Val
         35                  40                  45

Ser Gly Ile Asn Thr Gly Gly Asp Ser Thr Tyr Tyr Ala Asp Ser Val
 50                      55                  60

Met Gly Arg Phe Thr Ile Ser Arg Asp Asn Ala Lys Asn Thr Leu Ser
 65                      70                  75                  80

Leu Gln Met Asn Ser Leu Lys Pro Glu Asp Thr Ala Leu Tyr Tyr Cys
                 85                  90                  95

Ala Arg Asp Leu Arg Asp Tyr Tyr Ser Asp Tyr Thr Phe Val Asn Trp
             100                 105                 110
```

```
Gly Gln Gly Thr Gln Val Thr Val Ser Ser
        115                 120
```

<210> SEQ ID NO 194
<211> LENGTH: 128
<212> TYPE: PRT
<213> ORGANISM: Lama glama

<400> SEQUENCE: 194

```
Glu Val Gln Leu Val Glu Ser Gly Gly Leu Val Gln Pro Gly Gly
1               5                   10                  15

Ser Leu Arg Leu Ser Cys Ser Ala Ser Gly Phe Arg Phe Ser Thr Tyr
            20                  25                  30

Ala Met Thr Trp Val Arg Gln Ala Pro Gly Lys Gly Leu Val Trp Val
            35                  40                  45

Ser Thr Val Asp Ala Ser Gly Ala Thr Thr Ser Tyr Ala Glu Ser Val
        50                  55                  60

Lys Gly Arg Phe Thr Ile Ser Arg Asp Asn Thr Lys Gly Ala Leu Tyr
65                  70                  75                  80

Leu Gln Met Asn Ser Leu Lys Phe Glu Asp Thr Ala Val Tyr Tyr Cys
                85                  90                  95

Gly Thr Arg Ser Gly Thr Trp Trp Arg Gly Ser Tyr Ile Tyr Thr Glu
            100                 105                 110

Ser Glu Glu Asn Gly Trp Gly Gln Gly Thr Gln Val Thr Val Ser Ser
            115                 120                 125
```

<210> SEQ ID NO 195
<211> LENGTH: 125
<212> TYPE: PRT
<213> ORGANISM: Lama glama

<400> SEQUENCE: 195

```
Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Asp Tyr
            20                  25                  30

Ala Met Ile Trp Val Arg Gln Ala Pro Gly Lys Gly Leu Glu Trp Val
            35                  40                  45

Ser Ser Ile Asn Asn Gly Gly Trp Ser Thr Arg Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Glu Gly Tyr Tyr Ser Asp Tyr Ala Ala Val Gly His Ala Tyr
            100                 105                 110

Asp Tyr Trp Gly Gln Gly Thr Gln Val Thr Val Ser Ser
            115                 120                 125
```

<210> SEQ ID NO 196
<211> LENGTH: 124
<212> TYPE: PRT
<213> ORGANISM: Lama glama

<400> SEQUENCE: 196

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
```

```
                    20                  25                  30

Ser Met Ser Trp Val Arg Gln Ala Pro Gly Gln Gly Leu Glu Trp Val
            35                  40                  45

Ser Tyr Ile Asp Ser Asp Gly Ala Thr Thr Tyr Ala Asp Ser Val
        50                  55                  60

Lys Gly Arg Phe Thr Ile Ser Arg Asp Asn Ala Lys Asn Thr Leu Asn
 65                  70                  75                  80

Leu Gln Met Asn Ser Leu Lys Pro Asp Asp Ala Gly Val Tyr Tyr Cys
                85                  90                  95

Ala Ser Phe Gly Ser Ser Ala Tyr Ser Trp Gly Tyr Leu Gly Met Asp
                100                 105                 110

His Trp Gly Lys Gly Ala Leu Val Thr Val Phe Ser
                115                 120

<210> SEQ ID NO 197
<211> LENGTH: 123
<212> TYPE: PRT
<213> ORGANISM: Lama glama

<400> SEQUENCE: 197

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                20                  25                  30

Gly Met Ser Trp Val Arg Gln Ala Pro Gly Lys Gly Leu Glu Trp Val
            35                  40                  45

Ser Val Ile Asn Ser Gly Gly Asp Ser Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Asn Leu Lys Pro Glu Asp Thr Ala Val Tyr Tyr Cys
                85                  90                  95

Ala Lys Gly Gly Val Leu Gly His Ser Asn Tyr Tyr Ala Met Asp Tyr
                100                 105                 110

Trp Gly Lys Gly Thr Leu Val Thr Val Ser Ser
                115                 120

<210> SEQ ID NO 198
<211> LENGTH: 123
<212> TYPE: PRT
<213> ORGANISM: Lama glama

<400> SEQUENCE: 198

Glu Val Gln Leu Val Glu Ser Gly Gly Gly Leu Val Gln Pro Gly Gly
 1               5                  10                  15

Ser Leu Arg Leu Ser Cys Ser Ala Ser Gly Leu Thr Ala Ser Asn Thr
                20                  25                  30

Ala Met Ala Trp Val Arg Gln Val Pro Gly Lys Gln Leu Glu Trp Val
            35                  40                  45

Ser Asp Ile Asn Ser Leu Gly Asn Asn Ile Phe Tyr Ser Lys Ser Val
        50                  55                  60

Lys Gly Arg Phe Thr Ile Ala Arg Asp Lys Lys Asn Thr Leu Val
 65                  70                  75                  80

Leu Ser Met Asn Ser Leu Ser Pro Glu Asp Thr Ala Val Tyr Tyr Cys
                85                  90                  95

Val Ala Asp Ala Ser Ala Leu Ser Trp Ser Arg Pro Ala Leu Glu Val
```

```
                100                 105                 110
Trp Gly Gln Gly Thr Leu Val Thr Val Ser Asp
        115                 120

<210> SEQ ID NO 199
<211> LENGTH: 123
<212> TYPE: PRT
<213> ORGANISM: Lama glama

<400> SEQUENCE: 199

Glu Val Gln Leu Met Gln Ser Gly Gly Gly Leu Ala Gln Pro Gly Gly
1               5                   10                  15

Ser Leu Arg Leu Ser Cys Ala Ala Ser Gly Phe Thr Leu Ser Asn His
            20                  25                  30

Trp Met Tyr Trp Val Arg Gln Ala Pro Gly Lys Gly Leu Glu Trp Val
        35                  40                  45

Ser Ala Ile Ser Ser Gly Ser Ser Thr Tyr Tyr Ile Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ala Glu Asp Lys Gly Val Tyr Tyr Cys
                85                  90                  95

Gly Lys Asp Glu Ser Arg Gly Ile Glu Pro Gly Trp Gly Ser Ile Tyr
            100                 105                 110

Trp Gly Gln Gly Thr Gln Val Thr Val Ser Ser
        115                 120

<210> SEQ ID NO 200
<211> LENGTH: 123
<212> TYPE: PRT
<213> ORGANISM: Lama glama

<400> SEQUENCE: 200

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Ala Phe Ser Ser Ser
            20                  25                  30

Asp Met Ser Trp Val Arg Gln Ala Pro Thr Lys Gly Leu Glu Trp Val
        35                  40                  45

Ser Gly Ile Asn Ser Gly Gly Ser Thr Tyr Tyr Gly Glu Ser Met
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Pro Glu Asp Thr Ala Val Tyr Tyr Cys
                85                  90                  95

Thr Arg Tyr Asp Ser Phe Gly Trp Asn Val Arg Tyr Gly Met Asp Tyr
            100                 105                 110

Trp Gly Lys Gly Thr Leu Val Thr Val Ser Ser
        115                 120

<210> SEQ ID NO 201
<211> LENGTH: 122
<212> TYPE: PRT
<213> ORGANISM: Lama glama

<400> SEQUENCE: 201

Glu Val Gln Leu Val Gln Ser Gly Gly Asp Leu Val Gln Pro Gly Gly
1               5                   10                  15
```

Ser Leu Arg Leu Ser Cys Ala Ala Ser Gly Phe Ala Phe Ser Ser Tyr
            20                  25                  30

His Ile Ser Trp Val Arg Gln Ala Pro Gly Lys Gly Leu Glu Trp Val
            35                  40                  45

Ser Ile Ile Gly Arg Trp Gly Ala Asp Ile Tyr Tyr Ala Asp Ser Val
    50                  55                  60

Lys Gly Arg Leu Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Thr Ala Glu Leu Asn Trp Glu Pro Glu Asn Ala Tyr Ser Asp His Trp
            100                 105                 110

Gly Gln Gly Thr Gln Val Thr Val Ser Ser
            115                 120

<210> SEQ ID NO 202
<211> LENGTH: 122
<212> TYPE: PRT
<213> ORGANISM: Lama glama

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Val Gly Ser Gly Ile Thr Phe Ser Lys Tyr
            20                  25                  30

Ala Met Ser Trp Val Arg Gln Ala Pro Gly Lys Gly Leu Glu Trp Val
            35                  40                  45

Ser Asn Ile Asp Ala Asn Ser Glu Leu Thr Tyr Tyr Glu Asp Thr Val
    50                  55                  60

Lys Gly Arg Phe Thr Ile Ser Arg Asp Asn Val Lys Asn Thr Leu Tyr
65                  70                  75                  80

Leu Gln Met Asn Ser Leu Lys Pro Glu Asp Thr Ala Val Tyr Tyr Cys
                85                  90                  95

Thr Lys Asp Pro Arg Asn Ser Trp Tyr Thr Tyr Gly Met Asp Tyr Gly
            100                 105                 110

Gly Lys Gly Thr Leu Val Val Val Ser Ser
            115                 120

<210> SEQ ID NO 203
<211> LENGTH: 121
<212> TYPE: PRT
<213> ORGANISM: Lama glama

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Pro Pro Gly Lys Gly Leu Glu Trp Leu
            35                  40                  45

Ser Val Ile Ser Ser Ser Gly Asn Thr Lys Tyr Ser Asp Ser Val
    50                  55                  60

Lys Gly Arg Phe Thr Ile Ser Arg Asp Asn Ala Lys Asn Met Val Tyr
65                  70                  75                  80

Leu Gln Met Asn Ser Leu Lys Pro Glu Asp Thr Ala Val Tyr Tyr Cys
                85                  90                  95

```
Ala Lys Arg Ile Glu Gly Gly Met Gly Tyr Gly Met Asp Tyr Trp Gly
            100                 105                 110

Lys Gly Thr Pro Val Thr Val Ser Ser
        115                 120

<210> SEQ ID NO 204
<211> LENGTH: 121
<212> TYPE: PRT
<213> ORGANISM: Lama glama

<400> SEQUENCE: 204

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Lys Thr Trp Val Arg Gln Ala Pro Gly Lys Gly Leu Glu Trp Val
        35                  40                  45

Ser Ser Ile Tyr Ile Phe Val Gly Asn Thr Tyr Tyr Ala Asp Ser Val
    50                  55                  60

Lys Gly Arg Phe Thr Ile Ser Arg Asp Asn Ala Gly Asn Thr Leu Tyr
65                  70                  75                  80

Leu Gln Met Thr Asn Leu Lys Pro Glu Asp Thr Ala Lys Tyr Phe Cys
                85                  90                  95

Val Lys Ser Pro Glu Trp Thr Tyr Tyr Tyr Gly Met Asp Ser Trp Gly
            100                 105                 110

Lys Gly Thr Leu Val Thr Val Ser Ser
        115                 120

<210> SEQ ID NO 205
<211> LENGTH: 121
<212> TYPE: PRT
<213> ORGANISM: Lama glama

<400> SEQUENCE: 205

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ala Ser Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Ser Phe Gly Leu Val Thr Gly Val Tyr Phe Gly Ser Trp Gly
            100                 105                 110

Gln Gly Thr Gln Val Thr Val Ser Ser
        115                 120

<210> SEQ ID NO 206
<211> LENGTH: 121
<212> TYPE: PRT
<213> ORGANISM: Lama glama

<400> SEQUENCE: 206
```

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Ala Phe Ser Asp Tyr
            20                  25                  30

Asp Met Ser Trp Val Arg Gln Ala Pro Gly Lys Gly Leu Glu Trp Val
        35                  40                  45

Ser Ile His Val Ser Gly Asp Gly Arg Ile Phe Tyr Ala Asp Ser Met
    50                  55                  60

Lys Gly Arg Phe Thr Ile Ser Arg Asp Asn Ala Lys Asn Thr Met Tyr
65                  70                  75                  80

Leu Gln Leu Asn Ser Leu Lys Pro Glu Asp Thr Ala Val Tyr Tyr Cys
                85                  90                  95

Ala Ala Asp Ser Tyr His Ala Ala Thr Gly Tyr Leu Glu Gln Trp Gly
            100                 105                 110

Gln Gly Thr Leu Val Thr Val Ser Ser
            115                 120
```

<210> SEQ ID NO 207
<211> LENGTH: 121
<212> TYPE: PRT
<213> ORGANISM: Lama glama

<400> SEQUENCE: 207

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Arg Phe Thr Asp Tyr
            20                  25                  30

Tyr Met Gly Trp Ile Arg Gln Thr Pro Gly Lys Gly Leu Glu Trp Val
        35                  40                  45

Ser Ser Ile Tyr Ser Leu Gly Asp Pro Thr Tyr Tyr Ala Asp Ser Val
    50                  55                  60

Lys Gly Arg Phe Thr Ile Ser Arg Asp Asn Gly Lys Asp Thr Val Tyr
65                  70                  75                  80

Leu Glu Met Asn Ser Leu Lys Ser Asp Asp Thr Gly Leu Tyr Tyr Cys
                85                  90                  95

Ala Arg Asp His Arg Gly Trp Gly Thr Ile Arg Tyr Asp Tyr Trp Gly
            100                 105                 110

Gln Gly Thr Gln Val Thr Val Ser Ser
            115                 120
```

<210> SEQ ID NO 208
<211> LENGTH: 120
<212> TYPE: PRT
<213> ORGANISM: Lama glama

<400> SEQUENCE: 208

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Arg Tyr
            20                  25                  30

Trp Met Tyr Trp Val Arg Gln Ala Pro Gly Lys Gly Leu Glu Trp Val
        35                  40                  45

Ser Gly Met Thr Thr Gly Ser Asp Tyr Ile Tyr Ser Ala Val Ser Val
    50                  55                  60

Lys Gly Arg Phe Thr Ile Ser Arg Asp Asn Ala Lys Asn Thr Leu Tyr
65                  70                  75                  80
```

-continued

```
Leu Gln Met Asn Ser Leu Lys Phe Glu Asp Thr Ala Val Tyr Tyr Cys
                85                  90                  95

Ala Lys Gly Gly Val Ile Asp Ala Asp His Phe Glu Ser Trp Gly Gln
            100                 105                 110

Gly Thr Gln Val Thr Val Ser Ser
        115                 120

<210> SEQ ID NO 209
<211> LENGTH: 120
<212> TYPE: PRT
<213> ORGANISM: Lama glama

<400> SEQUENCE: 209

Glu Val Gln Leu Val Gly Val Trp Gly Arg Leu Gly Ala Pro Gly Gly
1               5                   10                  15

Ser Leu Arg Leu Ser Cys Ala Ala Ser Gly Phe Pro Phe Ser Ile Tyr
            20                  25                  30

Phe Met Ser Trp Phe Arg Gln Arg Pro Glu Lys Gly Ala Arg Met Val
        35                  40                  45

Ser Asp Ile Asp Lys Ser Gly Gly Arg Thr Thr Tyr Ala Pro Ser Val
    50                  55                  60

Lys Gly Arg Phe Thr Ala Ser Arg Asp Asn Ala Lys Asn Thr Leu Tyr
65                  70                  75                  80

Leu Thr Ile Asn Thr Leu Glu Pro Asn Asp Thr Ala Val Tyr Tyr Cys
                85                  90                  95

Ala Lys Pro Thr Ser Ser Met Trp Ser Pro Gly Asp Tyr Trp Gly Gln
            100                 105                 110

Gly Thr Gln Val Thr Val Ala Ser
        115                 120

<210> SEQ ID NO 210
<211> LENGTH: 120
<212> TYPE: PRT
<213> ORGANISM: Lama glama

<400> SEQUENCE: 210

Glu Val Gln Leu Val Gln Ser Gly Gly Asp Leu Val Gln Pro Gly Gly
1               5                   10                  15

Ser Leu Arg Val Ser Cys Ala Val Ser Gly Phe Thr Phe Ile Tyr Tyr
            20                  25                  30

Gly Met Ser Trp Val Arg Gln Ser Pro Gly Lys Gly Leu Glu Trp Ile
        35                  40                  45

Ser Thr Ile Ser Asn Gly Gly Ser Thr Ala Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Glu Met Asn Asp Leu Lys Pro Glu Asp Thr Ala Leu Tyr Tyr Cys
                85                  90                  95

Ala Arg Ile Ser Thr Glu Leu Gly Asn Thr Leu Asp Ala Trp Gly Gln
            100                 105                 110

Gly Ser Leu Val Thr Val Ser Ser
        115                 120

<210> SEQ ID NO 211
<211> LENGTH: 120
<212> TYPE: PRT
<213> ORGANISM: Lama glama
```

-continued

```
<400> SEQUENCE: 211

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Gly Ile Ser Trp Val Arg Gln Ala Pro Gly Lys Gly Leu Glu Trp Val
        35                  40                  45

Ser Ser Val Thr Gly Asp Gly Leu Ser Thr Thr Ala Ile Asp Ser Val
    50                  55                  60

Lys Gly Arg Phe Thr Ile Thr Arg Asp Asn Ala Lys Asn Thr Val Tyr
65                  70                  75                  80

Leu Gln Met Asn Asn Leu Lys Leu Asp Asp Thr Ala Val Tyr Tyr Cys
                85                  90                  95

Ala Lys Leu Asp Val Tyr Val Asp Tyr Gly Met Asp Tyr Trp Gly Lys
            100                 105                 110

Gly Thr Leu Val Thr Val Ser Ser
        115                 120

<210> SEQ ID NO 212
<211> LENGTH: 120
<212> TYPE: PRT
<213> ORGANISM: Lama glama

<400> SEQUENCE: 212

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Tyr Met Asn Trp Val Arg Gln Ala Pro Gly Lys Gly Leu Glu Trp Val
        35                  40                  45

Ser Val Ser Ser Ser Gly Gly Gly Thr Thr Tyr Tyr Ala Asp Ser Val
    50                  55                  60

Lys Gly Arg Phe Thr Ile Ser Arg Asp Asn Ala Gln Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Glu Ser Gly Gly Pro Gly Met Asp Leu Glu Val Trp Gly Gln
            100                 105                 110

Gly Thr Leu Val Thr Val Ser Ser
        115                 120

<210> SEQ ID NO 213
<211> LENGTH: 119
<212> TYPE: PRT
<213> ORGANISM: Lama glama

<400> SEQUENCE: 213

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Asn Ser Gly Gly Gly Ser Thr Tyr Ala Asp Ser Val
    50                  55                  60

Lys Gly Arg Phe Thr Ile Ser Arg Asp Asn Ala Lys Asn Thr Leu Tyr
```

```
                65                  70                  75                  80
Leu Gln Met Asn Ser Leu Lys Pro Glu Asp Thr Ala Val Tyr Tyr Cys
                    85                  90                  95
Ala Lys Trp Glu Val Val Thr Leu Asp Phe Gly Ser Trp Gly Gln Gly
                100                 105                 110
Thr Gln Val Thr Val Ser Ser
115

<210> SEQ ID NO 214
<211> LENGTH: 119
<212> TYPE: PRT
<213> ORGANISM: Lama glama

<400> SEQUENCE: 214

Glu Val Gln Leu Val Glu Ser Gly Gly Gly Leu Val Gln Pro Gly Arg
1               5                   10                  15
Ser Leu Arg Leu Ser Cys Ala Ala Gly Phe Thr Phe Ser Thr Tyr
                20                  25                  30
Trp Met Tyr Trp Ile Arg Gln Ala Pro Gly Lys Gly Leu Glu Trp Val
                35                  40                  45
Ala Thr Ile Thr Ser Leu Gly Gly Ser Gln Trp Tyr Val Asp Ser Val
            50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Pro Glu Asp Met Ala Gln Tyr Tyr Cys
                    85                  90                  95
Val Arg Gly Gly Leu Tyr Gly Tyr Asp Tyr Glu His Trp Gly Gln Gly
                100                 105                 110
Thr Gln Val Thr Val Ser Ser
        115

<210> SEQ ID NO 215
<211> LENGTH: 118
<212> TYPE: PRT
<213> ORGANISM: Lama glama

<400> SEQUENCE: 215

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser Ala
                20                  25                  30
Tyr Met Asn Trp Val Arg Gln Ala Pro Gly Lys Gly Leu Glu Trp Val
                35                  40                  45
Ser Gly Leu Thr Asn Tyr Gly Ser Thr Ser Tyr Ala Asp Ser Val
            50                  55                  60
Lys Gly Arg Phe Thr Ile Ser Arg Asp Asn Thr Val Asn Thr Val Tyr
65                  70                  75                  80
Leu Gln Leu Asn Ser Leu Lys Pro Glu Asp Thr Gly Leu Tyr Tyr Cys
                    85                  90                  95
Ala Arg Val Gly Asn Met Trp Ser Ser Asp Tyr Trp Gly Gln Gly Thr
                100                 105                 110
Gln Val Thr Val Ser Ser
        115

<210> SEQ ID NO 216
<211> LENGTH: 118
<212> TYPE: PRT
```

<213> ORGANISM: Lama glama

<400> SEQUENCE: 216

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Ser Ile Asp Thr Ser Gly Ile Thr Met Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Leu Tyr Tyr Cys
                85                  90                  95

Ala Lys Ala Leu Gly Tyr Asn Ala Phe Asp Ala Trp Gly Arg Gly Thr
            100                 105                 110

Leu Val Thr Val Ser Ser
            115

<210> SEQ ID NO 217
<211> LENGTH: 118
<212> TYPE: PRT
<213> ORGANISM: Lama glama

<400> SEQUENCE: 217

Glu Val Gln Leu Val Glu Ser Gly Gly Gly Leu Val Gln Pro Gly Val
1               5                   10                  15

Ser Leu Arg Leu Ser Cys Thr Thr Ser Gly Phe Thr Phe Ser Thr Gln
            20                  25                  30

Gly Met Asn Trp Val Arg Gln Pro Pro Glu Lys Gly Leu Glu Trp Val
        35                  40                  45

Ser Gly Ile Asp Ser Arg Gly Asn Thr Thr Asn Tyr Ala Asp Ser Val
    50                  55                  60

Lys Gly Arg Phe Thr Ile Ser Arg Asp Asn Ala Lys Asn Ala Leu Tyr
65                  70                  75                  80

Leu Gln Met Asn Asp Leu Arg Pro Asp Asp Thr Ala Met Tyr Tyr Cys
                85                  90                  95

Thr Asn Thr Gly Pro Trp Tyr Thr Tyr Asn Tyr Trp Gly Gln Gly Thr
            100                 105                 110

Gln Val Thr Val Ser Ser
            115

<210> SEQ ID NO 218
<211> LENGTH: 117
<212> TYPE: PRT
<213> ORGANISM: Lama glama

<400> SEQUENCE: 218

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Asp Trp Ile
        35                  40                  45

Ser Gly Ile Ser Val Gly Gly Ala Ser Thr Tyr Tyr Ala Arg Ser Val
    50                  55                  60

```
Gln Asp Arg Phe Thr Ile Ser Arg Asp Asn Thr Lys Asn Thr Leu Tyr
 65                  70                  75                  80

Leu Gln Met Ser Ser Leu Arg Ser Glu Asp Thr Ala Val Tyr Trp Cys
                 85                  90                  95

Thr Arg Gly Gly Asn Thr Pro Tyr Asp Tyr Trp Gly Gln Gly Thr Gln
            100                 105                 110

Val Thr Val Ser Ser
            115
```

<210> SEQ ID NO 219
<211> LENGTH: 114
<212> TYPE: PRT
<213> ORGANISM: Lama glama

<400> SEQUENCE: 219

```
Glu Val Gln Leu Val Gln Ser Gly Gly Gly Leu Val Gln Pro Gly Gly
  1               5                  10                  15

Ser Leu Arg Leu Ser Cys Ala Ala Ser Gly Phe Asn Phe Asp Asp Tyr
             20                  25                  30

Pro Met Thr Trp Ile Arg Gln Ala Pro Gly Lys Gly Leu Glu Trp Val
             35                  40                  45

Ala Ser Ile Tyr Ser Gly Ile Ser Thr Thr Tyr Tyr Pro Asp Ser Val
         50                  55                  60

Lys Gly Arg Phe Thr Ile Ser Thr Asn Asp Ala Lys Asn Thr Val Tyr
 65                  70                  75                  80

Leu Gln Met Asn Asp Leu Lys Ser Asp Asp Thr Ala Val Tyr Tyr Cys
                 85                  90                  95

Ala Asn Pro Arg Arg Asn Tyr Trp Gly Gln Gly Thr His Val Thr Val
            100                 105                 110

Ser Ser
```

<210> SEQ ID NO 220
<211> LENGTH: 97
<212> TYPE: PRT
<213> ORGANISM: Homo Sapiens

<400> SEQUENCE: 220

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Thr Gly Lys Gly Leu Glu Trp Val
             35                  40                  45

Ser Ala Ile Gly Thr Ala Gly Asp Thr Tyr Tyr Pro Gly Ser Val Lys
         50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg
```

<210> SEQ ID NO 221
<211> LENGTH: 121
<212> TYPE: PRT
<213> ORGANISM: Lama glama

<400> SEQUENCE: 221

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Thr Tyr
            20                  25                  30

Ala Met Ser Trp Val Arg Gln Gly Pro Gly Lys Ala Leu Glu Trp Val
            35                  40                  45

Ser Thr Ile Asn Gly Ala Asp Phe Thr Ser Tyr Val Asp Ser Val Lys
        50                  55                  60

Gly Arg Phe Thr Ile Ser Arg Asp Asn Thr Lys Asn Thr Leu Tyr Leu
65                  70                  75                  80

Gln Met Asn Ser Leu Lys Pro Glu Asp Thr Ala Val Tyr Tyr Cys Ala
            85                  90                  95

Lys Gly Leu Ser Gly Leu Asn Trp Tyr Gly Phe Gly Asp Tyr Trp Gly
            100                 105                 110

Gln Gly Thr Gln Val Thr Val Ser Ser
            115                 120

<210> SEQ ID NO 222
<211> LENGTH: 121
<212> TYPE: PRT
<213> ORGANISM: Lama glama

<400> SEQUENCE: 222

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Tyr Trp Val Arg Gln Ala Pro Gly Lys Gly Leu Glu Tyr Val
            35                  40                  45

Gly Ser Ile Asp Asn Asp Gly Phe Thr Tyr Tyr Ser Glu Asp Val Lys
        50                  55                  60

Gly Arg Phe Thr Ile Ser Gly Asp Asn Ala Arg Asn Thr Leu Tyr Leu
65                  70                  75                  80

Gln Ile Asn Ser Val Lys Pro Glu Asp Thr Ala Leu Tyr Tyr Cys Val
            85                  90                  95

Arg Gly Val Tyr Tyr Met Asp Tyr Glu Pro Arg Met Asp Tyr Trp Gly
            100                 105                 110

Lys Gly Thr Leu Val Thr Val Ser Ser
            115                 120

<210> SEQ ID NO 223
<211> LENGTH: 118
<212> TYPE: PRT
<213> ORGANISM: Lama glama

<400> SEQUENCE: 223

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Thr His
            20                  25                  30

Thr Met Ser Trp Val Arg Gln Ala Pro Gly Lys Gly Leu Glu Trp Val
            35                  40                  45

Ser Gly Ile Asn Ser Ala Tyr Gly Thr Ile Tyr Ile Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Asp Asp Thr Ala Val Tyr Tyr Cys Val
                85                  90                  95

Gln Val Val Asp Thr Trp Asp Glu Tyr Asp Tyr Trp Gly Gln Gly Thr
                100                 105                 110

Gln Val Thr Val Ser Ser
        115

<210> SEQ ID NO 224
<211> LENGTH: 114
<212> TYPE: PRT
<213> ORGANISM: Lama glama

<400> SEQUENCE: 224

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Thr Phe Gly Thr Ser
            20                  25                  30

Gly Met Thr Trp Val Arg Gln Ala Pro Gly Lys Gly Leu Glu Trp Val
        35                  40                  45

Ser Thr Ile Asn Ser Gly Gly Leu Thr Thr Ser Ala Asp Ser Val Lys
    50                  55                  60

Gly Arg Phe Thr Ile Ser Arg Asp Asn Gly Lys Asn Thr Leu Tyr Leu
65                  70                  75                  80

Gln Met Asp Ser Leu Lys Pro Asp Asp Thr Ala Val Tyr Tyr Cys Ala
                85                  90                  95

Asn Leu Leu Glu Leu Gly His Trp Gly Arg Gly Thr Gln Val Thr Val
                100                 105                 110

Ser Ser

<210> SEQ ID NO 225
<211> LENGTH: 123
<212> TYPE: PRT
<213> ORGANISM: Lama glama

<400> SEQUENCE: 225

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ser Thr Ile Thr Lys Gly Gly Ser Thr Tyr Tyr Ser Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Ser Glu Asp Thr Ala Val Tyr Tyr Cys Ala
                85                  90                  95

Lys Ser Asn Ser Gly Thr His Trp Tyr Glu Tyr Tyr Gly Met Asp Tyr
                100                 105                 110

Trp Gly Lys Gly Thr Leu Val Thr Val Ser Ser
        115                 120

<210> SEQ ID NO 226
<211> LENGTH: 115
<212> TYPE: PRT
<213> ORGANISM: Lama glama

<400> SEQUENCE: 226

Glu Val Gln Leu Val Glu Ser Gly Gly Leu Val Gln Pro Gly Asp
1               5                   10                  15

Ser Leu Arg Leu Ser Cys Ala Ala Ser Gly Phe Thr Phe Gly Asn Tyr
            20                  25                  30

Asp Met Ser Trp Val Arg Gln Ala Pro Gly Lys Gly Pro Glu Trp Val
        35                  40                  45

Ser Gly Ile Asn Ser Gly Gly Lys Thr Tyr Ser Ala Asp Ser Val Lys
    50                  55                  60

Gly Arg Phe Thr Ile Ser Arg Asp Asn Ala Lys Asn Thr Leu Tyr Leu
65              70                  75                  80

Gln Met Asn Asn Leu Lys Pro Glu Asp Thr Ala Val Tyr Tyr Cys Ile
            85                  90                  95

Leu Gly Ile Val Thr Leu Gly Ser Trp Gly Gln Gly Thr Gln Val Thr
        100                 105                 110

Val Ser Ser
    115

<210> SEQ ID NO 227
<211> LENGTH: 35
<212> TYPE: PRT
<213> ORGANISM: Artificial
<220> FEATURE:
<223> OTHER INFORMATION: PCR Primer

<400> SEQUENCE: 227

Gly Cys Cys Thr Cys Cys Ala Cys Cys Ala Gly Thr Gly Cys Ala Cys
1               5                   10                  15

Ala Gly Thr Cys Thr Gly Thr Gly Tyr Thr Gly Ala Cys Lys Cys Ala
            20                  25                  30

Gly Cys Cys
        35

<210> SEQ ID NO 228
<211> LENGTH: 35
<212> TYPE: PRT
<213> ORGANISM: Artificial
<220> FEATURE:
<223> OTHER INFORMATION: PCR Primer

<400> SEQUENCE: 228

Gly Cys Cys Thr Cys Cys Ala Cys Cys Ala Gly Thr Gly Cys Ala Cys
1               5                   10                  15

Ala Gly Thr Cys Thr Gly Thr Gly Tyr Thr Gly Ala Cys Gly Cys Ala
            20                  25                  30

Gly Cys Cys
        35

<210> SEQ ID NO 229
<211> LENGTH: 35
<212> TYPE: PRT
<213> ORGANISM: Artificial
<220> FEATURE:
<223> OTHER INFORMATION: PCR Primer

<400> SEQUENCE: 229

Gly Cys Cys Thr Cys Cys Ala Cys Cys Ala Gly Thr Gly Cys Ala Cys
1               5                   10                  15

Ala Gly Thr Cys Thr Gly Thr Cys Gly Thr Gly Ala Cys Gly Cys Ala
            20                  25                  30

Gly Cys Cys
        35

<210> SEQ ID NO 230
<211> LENGTH: 35
<212> TYPE: PRT
<213> ORGANISM: Artificial
<220> FEATURE:
<223> OTHER INFORMATION: PCR Primer

<400> SEQUENCE: 230

Gly Cys Cys Thr Cys Cys Ala Cys Cys Ala Gly Thr Gly Cys Ala Cys
1               5                   10                  15

Ala Gly Thr Cys Thr Gly Cys Cys Thr Gly Ala Cys Thr Cys Ala
            20                  25                  30

Gly Cys Cys
        35

<210> SEQ ID NO 231
<211> LENGTH: 38
<212> TYPE: PRT
<213> ORGANISM: Artificial
<220> FEATURE:
<223> OTHER INFORMATION: PCR Primer

<400> SEQUENCE: 231

Gly Cys Cys Thr Cys Cys Ala Cys Cys Ala Gly Thr Gly Cys Ala Cys
1               5                   10                  15

Thr Thr Thr Cys Cys Thr Ala Thr Gly Ala Gly Cys Thr Gly Ala Cys
            20                  25                  30

Trp Cys Ala Gly Cys Cys
        35

<210

<210> SEQ ID NO 234
<211> LENGTH: 35
<212> TYPE: PRT
<213> ORGANISM: Artificial
<220> FEATURE:
<223> OTHER INFORMATION: PCR Primer

<400> SEQUENCE: 234

Gly Cys Cys Thr Cys Cys Ala Cys Cys Ala Gly Thr Gly Cys Ala Cys
1               5                   10                  15

Ala Gly Gly Cys Thr Gly Thr Gly Cys Thr Gly Ala Cys Thr Cys Ala
                20                  25                  30

Gly Cys Cys
        35

<210> SEQ ID NO 235
<211> LENGTH: 38
<212> TYPE: PRT
<213> ORGANISM: Artificial
<220> FEATURE:
<223> OTHER INFORMATION: PCR Primer

<400> SEQUENCE: 235

Gly Cys Cys Thr Cys Cys Ala Cys Ala Gly Thr Gly Cys Ala Cys
1               5                   10                  15

Thr Thr Ala Ala Thr Thr Thr Thr Ala Thr Gly Cys Thr Gly Ala Cys
                20                  25                  30

Thr Cys Ala Gly Cys Cys
        35

<210> SEQ ID NO 236
<211> LENGTH: 35
<212> TYPE: PRT
<213> ORGANISM: Artificial
<220> FEATURE:
<223> OTHER INFORMATION: PCR Primer

<400> SEQUENCE: 236

Gly Cys Cys Thr Cys Cys Ala Cys Ala Gly Thr Gly Cys Ala Cys
1               5                   10                  15

Ala Gly Arg Cys Thr Gly Thr Gly Gly Thr Gly Ala Cys Tyr Cys Ala
                20                  25                  30

Gly Gly Ala
        35

<210> SEQ ID NO 237
<211> LENGTH: 35
<212> TYPE: PRT
<213> ORGANISM: Artificial
<220> FEATURE:
<223> OTHER INFORMATION: PCR Primer

<400> SEQUENCE: 237

Gly Cys Cys Thr Cys Cys Ala Cys Ala Gly Thr Gly Cys Ala Cys
1               5                   10                  15

Trp Gly Cys Cys Thr Gly Thr Gly Cys Thr Gly Ala Cys Thr Cys Ala
                20                  25                  30

Gly Cys Cys
        35

<210> SEQ ID NO 238

-continued

```
<211> LENGTH: 35
<212> TYPE: PRT
<213> ORGANISM: Artificial
<220> FEATURE:
<223> OTHER INFORMATION: PCR Primer

<400> SEQUENCE: 238

Gly Cys Cys Thr Cys Cys Ala Cys Cys Ala Gly Thr Gly Cys Ala Cys
1               5                   10                  15

Ala Gly Gly Cys Ala Gly Gly Cys Thr Gly Ala Cys Thr Cys Ala
            20                  25                  30

Gly Cys Cys
        35

<210> SEQ ID NO 239
<211> LENGTH: 30
<212> TYPE: PRT
<213> ORGANISM: Artificial
<220> FEATURE:
<223> OTHER INFORMATION: PCR Primer

<400> SEQUENCE: 239

Cys Thr Ala Ala Cys Ala Cys Thr Gly Gly Gly Ala Gly Gly Gly
1               5                   10                  15

Gly Ala Cys Ala Cys Cys Gly Thr Cys Thr Thr Cys Thr Cys
            20                  25                  30

<210> SEQ ID NO 240
<211> LENGTH: 30
<212> TYPE: PRT
<213> ORGANISM: Artificial
<220> FEATURE:
<223> OTHER INFORMATION: PCR Primer

<400> SEQUENCE: 240

Cys Thr Ala Ala Cys Ala Cys Thr Gly Gly Gly Ala Gly Gly Gly Asn
1               5                   10                  15

Cys Thr Cys Ala Cys Asn Gly Thr Cys Thr Thr Cys Thr Cys
            20                  25                  30

<210> SEQ ID NO 241
<211> LENGTH: 41
<212> TYPE: PRT
<213> ORGANISM: Artificial
<220> FEATURE:
<223> OTHER INFORMATION: PCR Primer

<400> SEQUENCE: 241

Gly Cys Cys Thr Cys Cys Ala Cys Cys Ala Gly Thr Gly Cys Ala Cys
1               5                   10                  15

Thr Thr Gly Ala Cys Ala Thr Cys Cys Ala Gly Trp Thr Gly Ala Cys
            20                  25                  30

Cys Cys Ala Gly Thr Cys Thr Cys Cys
        35                  40

<210> SEQ ID NO 242
<211> LENGTH: 41
<212> TYPE: PRT
<213> ORGANISM: Artificial
<220> FEATURE:
<223> OTHER INFORMATION: PCR Primer

<400> SEQUENCE: 242

Gly Cys Cys Thr Cys Cys Ala Cys Cys Ala Gly Thr Gly Cys Ala Cys
```

```
1               5                  10                 15
Thr Thr Gly Ala Thr Gly Thr Thr Gly Thr Gly Ala Thr Gly Ala Cys
                20                 25                 30
Thr Cys Ala Gly Thr Cys Thr Cys Cys
                35                 40
```

<210> SEQ ID NO 243
<211> LENGTH: 41
<212> TYPE: PRT
<213> ORGANISM: Artificial
<220> FEATURE:
<223> OTHER INFORMATION: PCR Primer

<400> SEQUENCE: 243

```
Gly Cys Cys Thr Cys Cys Ala Cys Cys Ala Gly Thr Gly Cys Ala Cys
1               5                  10                 15
Thr Thr Gly Ala Ala Ala Thr Thr Gly Thr Gly Trp Thr Gly Ala Cys
                20                 25                 30
Arg Cys Ala Gly Thr Cys Thr Cys Cys
                35                 40
```

<210> SEQ ID NO 244
<211> LENGTH: 41
<212> TYPE: PRT
<213> ORGANISM: Artificial
<220> FEATURE:
<223> OTHER INFORMATION: PCR Primer

<400> SEQUENCE: 244

```
Gly Cys Cys Thr Cys Cys Ala Cys Cys Ala Gly Thr Gly Cys Ala Cys
1               5                  10                 15
Thr Thr Gly Ala Tyr Ala Thr Tyr Gly Thr Gly Ala Thr Gly Ala Cys
                20                 25                 30
Cys Cys Ala Gly Trp Cys Thr Cys Cys
                35                 40
```

<210> SEQ ID NO 245
<211> LENGTH: 41
<212> TYPE: PRT
<213> ORGANISM: Artificial
<220> FEATURE:
<223> OTHER INFORMATION: PCR Primer

<400> SEQUENCE: 245

```
Gly Cys Cys Thr Cys Cys Ala Cys Cys Ala Gly Thr Gly Cys Ala Cys
1               5                  10                 15
Thr Thr Gly Ala Ala Ala Cys Gly Ala Cys Ala Cys Thr Cys Ala Cys
                20                 25                 30
Gly Cys Ala Gly Thr Cys Thr Cys Cys
                35                 40
```

<210> SEQ ID NO 246
<211> LENGTH: 41
<212> TYPE: PRT
<213> ORGANISM: Artificial
<220> FEATURE:
<223> OTHER INFORMATION: PCR Primer

<400> SEQUENCE: 246

```
Gly Cys Cys Thr Cys Cys Ala Cys Cys Ala Gly Thr Gly Cys Ala Cys
1               5                  10                 15
Thr Thr Gly Ala Ala Ala Thr Thr Gly Thr Gly Cys Thr Gly Ala Cys
```

```
                20                  25                  30

Thr Cys Ala Gly Thr Cys Thr Cys Cys
            35                  40

<210> SEQ ID NO 247
<211> LENGTH: 41
<212> TYPE: PRT
<213> ORGANISM: Artificial
<220> FEATURE:
<223> OTHER INFORMATION: PCR Primer

<400> SEQUENCE: 247

Gly Cys Cys Thr Cys Cys Ala Cys Cys Ala Gly Thr Gly Cys Ala Cys
1               5                   10                  15

Thr Thr Gly Ala Thr Ala Thr Thr Gly Thr Gly Ala Thr Gly Ala Cys
                20                  25                  30

Cys Cys Ala Gly Ala Cys Thr Cys Cys
            35                  40

<210> SEQ ID NO 248
<211> LENGTH: 48
<212> TYPE: PRT
<213> ORGANISM: Artificial
<220> FEATURE:
<223> OTHER INFORMATION: PCR Primer

<400> SEQUENCE: 248

Gly Cys Cys Thr Cys Cys Ala Cys Cys Gly Gly Gly Cys Gly Cys Gly
1               5                   10                  15

Cys Cys Thr Thr Ala Thr Thr Ala Gly Cys Ala Gly Thr Gly Thr Cys
                20                  25                  30

Thr Cys Cys Gly Gly Thr Cys Gly Ala Ala Gly Cys Thr Cys Cys Thr
            35                  40                  45

<210> SEQ ID NO 249
<211> LENGTH: 42
<212> TYPE: PRT
<213> ORGANISM: Artificial
<220> FEATURE:
<223> OTHER INFORMATION: PCR Primer

<400> SEQUENCE: 249

Gly Cys Cys Thr Cys Cys Ala Cys Cys Gly Gly Gly Cys Gly Cys Gly
1               5                   10                  15

Cys Cys Thr Thr Ala Thr Thr Ala Arg Cys Ala Arg Thr Gly Tyr Cys
                20                  25                  30

Thr Asn Cys Gly Arg Thr Cys Arg Ala Ala
            35                  40

<210> SEQ ID NO 250
<211> LENGTH: 122
<212> TYPE: PRT
<213> ORGANISM: Lama glama

<400> SEQUENCE: 250

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
            35                  40                  45
```

```
Ser Thr Ile Ser Trp Asn Gly Gly Ala Thr Tyr Tyr Ala Glu Ser Met
    50              55                  60
Lys Gly Arg Phe Thr Ile Ser Arg Asp Asn Ala Lys Asn Thr Leu Tyr
 65              70                  75                  80
Leu Gln Met Asn Ser Leu Lys Ser Glu Asp Thr Ala Val Tyr Tyr Cys
                 85                  90                  95
Ala Lys Pro Tyr Tyr Ser Asp Tyr Val Gly Val Glu Tyr Asp Tyr Trp
             100                 105                 110
Gly Gln Gly Thr Gln Val Thr Val Ser Ser
             115                 120

<210> SEQ ID NO 251
<211> LENGTH: 127
<212> TYPE: PRT
<213> ORGANISM: Lama glama

<400> SEQUENCE: 251

Glu Val Gln Leu Val Glu Ser Gly Gly Leu Val Gln Pro Gly Gly
 1               5                  10                  15
Ser Leu Arg Leu Ser Cys Ala Ala Ser Gly Phe Thr Phe Ser Ser Tyr
             20                  25                  30
Trp Met Tyr Trp Val Arg Gln Ala Pro Gly Lys Gly Leu Glu Trp Val
         35                  40                  45
Ser Ala Ile Asn Thr Gly Gly Gly Arg Thr Tyr Tyr Ala Asp Ser Val
     50                  55                  60
Lys Gly Arg Phe Thr Ile Ser Arg Asp Asn Ala Lys Asn Thr Leu Tyr
 65              70                  75                  80
Leu Gln Met Asn Ser Leu Lys Ser Glu Asp Thr Ala Val Tyr Tyr Cys
                 85                  90                  95
Ala Lys Gly Thr Ser Ala Asp Gly Ser Ser Trp Tyr Val Pro Ala Asp
             100                 105                 110
Pro Tyr Asp Tyr Trp Gly Gln Gly Thr Gln Val Thr Val Ser Ser
             115                 120                 125

<210> SEQ ID NO 252
<211> LENGTH: 117
<212> TYPE: PRT
<213> ORGANISM: Lama glama

<400> SEQUENCE: 252

Glu Val Gln Leu Val Gln Ser Gly Ala Glu Leu Arg Asn Pro Gly Ala
 1               5                  10                  15
Ser Val Lys Val Ser Cys Lys Ala Ser Gly Tyr Thr Phe Thr Ser Tyr
             20                  25                  30
Tyr Ile Asp Trp Val Arg Gln Ala Pro Gly Gln Gly Leu Glu Trp Met
         35                  40                  45
Gly Arg Ile Asp Pro Glu Asp Gly Gly Thr Lys Tyr Ala Gln Lys Phe
     50                  55                  60
Gln Gly Arg Val Thr Phe Thr Ala Asp Thr Ser Thr Ser Thr Ala Tyr
 65              70                  75                  80
Val Glu Leu Ser Ser Leu Arg Ser Glu Asp Thr Ala Val Tyr Tyr Cys
                 85                  90                  95
Ala Arg Ser Gly Arg Tyr Glu Leu Asp Tyr Trp Gly Gln Gly Thr Gln
             100                 105                 110
Val Thr Val Ser Ser
             115
```

-continued

<210> SEQ ID NO 253
<211> LENGTH: 117
<212> TYPE: PRT
<213> ORGANISM: Lama glama

<400> SEQUENCE: 253

Glu Val Gln Leu Val Gln Ser Gly Ala Glu Leu Arg Asn Pro Gly Ala
1               5                   10                  15

Ser Val Lys Val Ser Cys Lys Ala Ser Gly Tyr Thr Phe Thr Ser Tyr
            20                  25                  30

Tyr Thr Asp Trp Val Arg Gln Ala Pro Gly Gln Gly Leu Glu Trp Met
        35                  40                  45

Gly Arg Ile Asp Pro Glu Asp Gly Asp Thr Lys Tyr Ala Gln Lys Phe
50                  55                  60

Gln Gly Arg Val Thr Phe Thr Ala Asp Thr Ser Thr Ser Thr Ala Tyr
65                  70                  75                  80

Val Glu Leu Thr Ser Leu Arg Ser Glu Asp Thr Ala Val Tyr Tyr Cys
                85                  90                  95

Leu Arg Ser Gly Ala Tyr Glu Leu Asp Tyr Trp Gly Gln Gly Thr Gln
            100                 105                 110

Val Thr Val Ser Ser
        115

<210> SEQ ID NO 254
<211> LENGTH: 98
<212> TYPE: PRT
<213> ORGANISM: Homo sapiens

<400> SEQUENCE: 254

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg

<210> SEQ ID NO 255
<211> LENGTH: 116
<212> TYPE: PRT
<213> ORGANISM: Lama glama

<400> SEQUENCE: 255

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Pro Glu Trp Val
        35                  40                  45

Ser Gly Ile Asn Thr Gly Gly Gly Ser Thr Gly Tyr Ala Asp Ser Val
50                  55                  60

```
Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Asp Trp Met Ala Thr Thr Pro Trp Gly Gln Gly Thr Gln Val
            100                 105                 110

Thr Val Ser Ser
        115

<210> SEQ ID NO 256
<211> LENGTH: 116
<212> TYPE: PRT
<213> ORGANISM: Artificial Sequence
<220> FEATURE:
<223> OTHER INFORMATION: Humanized Antibody

<400> SEQUENCE: 256

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
                 20                  25                  30

Ala Met Ser Trp Val Arg Gln Ala Pro Gly Lys Gly Leu Glu Trp Val
             35                  40                  45

Ser Gly Ile Asn Thr Gly Gly Ser Thr Gly Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Trp Met Ala Thr Thr Pro Trp Gly Gln Gly Thr Leu Val
            100                 105                 110

Thr Val Ser Ser
        115

<210> SEQ ID NO 257
<211> LENGTH: 116
<212> TYPE: PRT
<213> ORGANISM: Artificial Sequence
<220> FEATURE:
<223> OTHER INFORMATION: Humanized Antibody

<400> SEQUENCE: 257

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
                 20                  25                  30

Ala Met Ser Trp Val Arg Gln Ala Pro Gly Lys Gly Pro Glu Trp Val
             35                  40                  45

Ser Gly Ile Asn Thr Gly Gly Ser Thr Gly Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Lys Asp Trp Met Ala Thr Thr Pro Trp Gly Gln Gly Thr Gln Val
            100                 105                 110

Thr Val Ser Ser
```

<210> SEQ ID NO 258
<211> LENGTH: 97
<212> TYPE: PRT
<213> ORGANISM: Homo sapiens

<400> SEQUENCE: 258

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```

<210> SEQ ID NO 259
<211> LENGTH: 111
<212> TYPE: PRT
<213> ORGANISM: Lama glama

<400> SEQUENCE: 259

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Ala Ile Asn Ala Ala Gly Ser Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Gln Ser Glu Asp Thr Ala Leu Tyr Tyr Cys Ala
                85                  90                  95

Asn Leu Pro Arg Trp Gly Gln Gly Thr Gln Val Thr Val Ser Ser
            100                 105                 110
```

<210> SEQ ID NO 260
<211> LENGTH: 111
<212> TYPE: PRT
<213> ORGANISM: Artificial Sequence
<220> FEATURE:
<223> OTHER INFORMATION: Humanized Antibody

<400> SEQUENCE: 260

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Ala Ile Asn Ala Ala Gly Ser Thr Tyr Tyr Ala Asp Ser Val Lys
```

```
                    50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                    85                  90                  95

Asn Leu Pro Arg Trp Gly Gln Gly Thr Leu Val Thr Val Ser Ser
                100                 105                 110

<210> SEQ ID NO 261
<211> LENGTH: 111
<212> TYPE: PRT
<213> ORGANISM: Artificial Sequence
<220> FEATURE:
<223> OTHER INFORMATION: Humanized Antibody

<400> SEQUENCE: 261

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                20                  25                  30

Trp Met Tyr Trp Val Arg Gln Ala Pro Gly Lys Gly Leu Glu Trp Val
            35                  40                  45

Ser Ala Ile Asn Ala Ala Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Gln Ser Glu Asp Thr Ala Val Tyr Tyr Cys Ala
                    85                  90                  95

Asn Leu Pro Arg Trp Gly Gln Gly Thr Gln Val Thr Val Ser Ser
                100                 105                 110

<210> SEQ ID NO 262
<211> LENGTH: 98
<212> TYPE: PRT
<213> ORGANISM: Homo sapiens

<400> SEQUENCE: 262

Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Ser
                20                  25                  30

Tyr Tyr Pro Ser Trp Tyr Gln Gln Thr Pro Gly Gln Ala Pro Arg Thr
            35                  40                  45

Leu Thr Tyr Ser Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Ser
                    85                  90                  95

Gly Ile

<210> SEQ ID NO 263
<211> LENGTH: 113
<212> TYPE: PRT
<213> ORGANISM: Lama glama

<400> SEQUENCE: 263

Gln Ala Val Val Thr Gln Glu Pro Ser Leu Ser Val Ser Pro Gly Gly
```

```
                1               5                  10                  15
            Thr Val Thr Leu Thr Cys Gly Leu Ser Ser Gly Ser Val Thr Thr Asn
                            20                  25                  30

Asn Tyr Pro Gly Trp Phe Gln Gln Thr Pro Gly Gln Ala Pro Arg Thr
                        35                  40                  45

Leu Ile Tyr Asn Thr Asn Arg His Ser Gly Val Pro Ser Arg Phe
                    50                  55                  60

Ser Gly Ser Ile Ser Gly Asn Lys Ala Ala Leu Thr Ile Thr Gly Ala
            65                  70                  75                  80

Gln Pro Glu Asp Glu Ala Asp Tyr Tyr Cys Ala Leu Tyr Met Ser Ser
                            85                  90                  95

Gly Ser Asn Asn Ala Val Phe Gly Gly Gly Thr His Leu Thr Val Leu
                        100                 105                 110

Gly

<210> SEQ ID NO 264
<211> LENGTH: 113
<212> TYPE: PRT
<213> ORGANISM: Artificial Sequence
<220> FEATURE:
<223> OTHER INFORMATION: Humanized Antibody

<400> SEQUENCE: 264

Gln Thr Val Val Thr Gln Glu Pro Ser Phe Ser Val Ser Pro Gly Gly
            1               5                  10                  15

Thr Val Thr Leu Thr Cys Gly Leu Ser Ser Gly Ser Val Thr Thr Asn
                            20                  25                  30

Asn Tyr Pro Gly Trp Tyr Gln Gln Thr Pro Gly Gln Ala Pro Arg Thr
                        35                  40                  45

Leu Ile Tyr Asn Thr Asn Arg Ser Ser Gly Val Pro Asp Arg Phe
                    50                  55                  60

Ser Gly Ser Ile Leu Gly Asn Lys Ala Ala Leu Thr Ile Thr Gly Ala
            65                  70                  75                  80

Gln Ala Asp Asp Glu Ser Asp Tyr Tyr Cys Ala Leu Tyr Met Ser Ser
                            85                  90                  95

Gly Ser Asn Asn Ala Val Phe Gly Gly Gly Thr Lys Leu Thr Val Leu
                        100                 105                 110

Gly

<210> SEQ ID NO 265
<211> LENGTH: 113
<212> TYPE: PRT
<213> ORGANISM: Artificial Sequence
<220> FEATURE:
<223> OTHER INFORMATION: Humanized Antibody

<400> SEQUENCE: 265

Gln Thr Val Val Thr Gln Glu Pro Ser Phe Ser Val Ser Pro Gly Gly
            1               5                  10                  15

Thr Val Thr Leu Thr Cys Gly Leu Ser Ser Gly Ser Val Thr Thr Asn
                            20                  25                  30

Asn Tyr Pro Gly Trp Phe Gln Gln Thr Pro Gly Gln Ala Pro Arg Thr
                        35                  40                  45

Leu Ile Tyr Asn Thr Asn Arg His Ser Gly Val Pro Ser Arg Phe
                    50                  55                  60

Ser Gly Ser Ile Leu Gly Asn Lys Ala Ala Leu Thr Ile Thr Gly Ala
            65                  70                  75                  80
```

-continued

Gln Ala Asp Asp Glu Ser Asp Tyr Tyr Cys Ala Leu Tyr Met Ser Ser
                85                  90                  95

Gly Ser Asn Asn Ala Val Phe Gly Gly Gly Thr Lys Leu Thr Val Leu
            100                 105                 110

Gly

<210> SEQ ID NO 266
<211> LENGTH: 113
<212> TYPE: PRT
<213> ORGANISM: Lama glama

<400> SEQUENCE: 266

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Gly
            20                  25                  30

Asn Tyr Pro Gly Trp Tyr Gln Gln Lys Pro Gly Gln Ala Pro Arg Thr
        35                  40                  45

Leu Ile Tyr Asn Thr Asn Ser Arg Tyr Ser Gly Val Pro Asn Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Val Tyr Ile Gly Ser
                85                  90                  95

Ser Ser Tyr Pro Val Val Phe Gly Gly Gly Thr His Leu Thr Val Leu
            100                 105                 110

Gly

<210> SEQ ID NO 267
<211> LENGTH: 113
<212> TYPE: PRT
<213> ORGANISM: Artificial Sequence
<220> FEATURE:
<223> OTHER INFORMATION: Humanized Antibody

<400> SEQUENCE: 267

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ser Gly
            20                  25                  30

Asn Tyr Pro Gly Trp Tyr Gln Gln Thr Pro Gly Gln Ala Pro Arg Thr
        35                  40                  45

Leu Ile Tyr Asn Thr Asn Ser Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Val Tyr Ile Gly Ser
                85                  90                  95

Ser Ser Tyr Pro Val Val Phe Gly Gly Gly Thr Lys Leu Thr Val Leu
            100                 105                 110

Gly

<210> SEQ ID NO 268
<211> LENGTH: 113
<212> TYPE: PRT
<213> ORGANISM: Artificial Sequence
<220> FEATURE:

<223> OTHER INFORMATION: Humanized Antibody

<400> SEQUENCE: 268

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Ser Gly
            20                  25                  30

Asn Tyr Pro Gly Trp Tyr Gln Gln Lys Pro Gly Gln Ala Pro Arg Thr
        35                  40                  45

Leu Ile Tyr Asn Thr Asn Ser Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Pro Asp Asp Glu Ser Asp Tyr Tyr Cys Ala Val Tyr Ile Gly Ser
                85                  90                  95

Ser Ser Tyr Pro Val Val Phe Gly Gly Gly Thr His Leu Thr Val Leu
            100                 105                 110

Gly

<210> SEQ ID NO 269
<211> LENGTH: 96
<212> TYPE: PRT
<213> ORGANISM: Homo Sapiens

<400> SEQUENCE: 269

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

<210> SEQ ID NO 270
<211> LENGTH: 96
<212> TYPE: PRT
<213> ORGANISM: Lama pacos

<400> SEQUENCE: 270

Glu Val Gln Leu Val Gln Pro Gly Ala Glu Leu Arg Asn Pro Gly Ala
1               5                   10                  15

Ser Val Lys Val Ser Cys Lys Ala Ser Gly Tyr Thr Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
    50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Gly Thr Ala Val Tyr Tyr Cys
                85                  90                  95

<210> SEQ ID NO 271
<211> LENGTH: 96
<212> TYPE: PRT
<213> ORGANISM: Lama pacos

<400> SEQUENCE: 271

Glu Val Gln Leu Val Gln Pro Gly Ala Glu Leu Arg Lys Pro Gly Ala
1               5                   10                  15

Ser Val Lys Val Ser Cys Lys Ala Ser Gly Tyr Thr Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Gly Thr Pro Val Tyr Tyr Cys
                85                  90                  95

<210> SEQ ID NO 272
<211> LENGTH: 96
<212> TYPE: PRT
<213> ORGANISM: Lama pacos

<400> SEQUENCE: 272

Glu Val Gln Leu Val Gln Pro Gly Ala Glu Leu Arg Lys Pro Gly Ala
1               5                   10                  15

Ser Leu Lys Val Ser Cys Lys Ala Ser Gly Tyr Thr Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
50                  55                  60

Gln Gly Arg Val Thr Phe Thr Ala Asp Thr Ser Thr Arg Thr Ala Tyr
65                  70                  75                  80

Val Glu Leu Ser Ser Leu Arg Ser Glu Gly Thr Ala Val Tyr Tyr Cys
                85                  90                  95

<210> SEQ ID NO 273
<211> LENGTH: 96
<212> TYPE: PRT
<213> ORGANISM: Lama pacos

<400> SEQUENCE: 273

Glu Val Gln Leu Val Gln Pro Gly Ala Glu Leu Arg Lys Pro Gly Ala
1               5                   10                  15

Ser Leu Lys Val Ser Cys Lys Ala Ser Gly Tyr Thr Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Gly Thr Ala Val Tyr Tyr Cys
                85                  90                  95

<210> SEQ ID NO 274
<211> LENGTH: 96
<212> TYPE: PRT
<213> ORGANISM: Lama pacos
<220> FEATURE:
<221> NAME/KEY: MISC_FEATURE
<222> LOCATION: (38)..(38)
<223> OTHER INFORMATION: Unknown amino acid

<400> SEQUENCE: 274

Glu Val Gln Leu Val Gln Pro Gly Ala Glu Leu Arg Lys Pro Gly Ala
1               5                   10                  15

Ser Val Lys Val Ser Cys Lys Ala Ser Gly Tyr Thr Phe Thr Ser Tyr
                20                  25                  30

Tyr Ile Asp Trp Val Xaa Gln Ala Pro Gly Gln Gly Leu Glu Trp Met
            35                  40                  45

Gly Arg Ile Asp Pro Glu Asp Gly Gly Thr Asn Tyr Ala Gln Lys Phe
    50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Gly Thr Ala Val Tyr Tyr Cys
                85                  90                  95

<210> SEQ ID NO 275
<211> LENGTH: 96
<212> TYPE: PRT
<213> ORGANISM: Homo Sapiens

<400> SEQUENCE: 275

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

<210> SEQ ID NO 276
<211> LENGTH: 96
<212> TYPE: PRT
<213> ORGANISM: Lama pacos

<400> SEQUENCE: 276

Glu Val Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Ala Met Ser Trp Val Arg Gln Ala Pro Gly Lys Gly Leu Glu Trp Val
            35                  40                  45

Ser Ala Ile Ser Trp Asn Gly Ser Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Gly Thr Ala Val Tyr Tyr Cys

<210> SEQ ID NO 277
<211> LENGTH: 96
<212> TYPE: PRT
<213> ORGANISM: Lama pacos

<400> SEQUENCE: 277

Gln Leu Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asp Asp Tyr
            20                  25                  30
Gly Met Ser Trp Val Arg His Ser Pro Gly Lys Gly Leu Glu Trp Val
        35                  40                  45
Ser Ala Ile Ser Trp Asn Gly Gly Ser Thr Tyr Tyr Ala Glu Ser Met
    50                  55                  60
Lys Gly Arg Phe Thr Ile Ser Arg Asp Asn Ala Lys Asn Thr Val Tyr
65                  70                  75                  80
Leu Gln Met Asn Ser Leu Lys Pro Glu Gly Thr Ala Val Tyr Tyr Cys
                85                  90                  95

<210> SEQ ID NO 278
<211> LENGTH: 96
<212> TYPE: PRT
<213> ORGANISM: Lama pacos

<400> SEQUENCE: 278

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Pro Glu Trp Val
        35                  40                  45
Ser Ala Ile Asn Ser Gly Gly Gly Ser Thr Tyr Tyr Ala Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Pro Glu Gly Thr Ala Val Tyr Tyr Cys
                85                  90                  95

<210> SEQ ID NO 279
<211> LENGTH: 96
<212> TYPE: PRT
<213> ORGANISM: Lama pacos

<400> SEQUENCE: 279

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Gly Ser Tyr
            20                  25                  30
Asp Met Ser Trp Val Arg Gln Ala Pro Gly Lys Gly Pro Glu Trp Val
        35                  40                  45
Ser Ala Ile Asn Ser Gly Gly Gly Ser Thr Tyr Tyr Ala Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Lys Pro Glu Gly Thr Ala Val Tyr Tyr Cys
                85                  90                  95

<210> SEQ ID NO 280
<211> LENGTH: 96
<212> TYPE: PRT
<213> ORGANISM: Lama pacos

<400> SEQUENCE: 280

Gln Val Gln Leu Val Glu Ser Gly Gly Gly Leu Val Gln Ala Gly Gly
1               5                   10                  15

Ser Leu Lys His Ser Cys Ala Ala Ser Gly Leu Thr Phe Gly Ser Tyr
            20                  25                  30

Asp Met Ser Trp Val Arg Gln Ala Pro Gly Lys Gly Pro Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 281
<211> LENGTH: 96
<212> TYPE: PRT
<213> ORGANISM: Lama pacos

<400> SEQUENCE: 281

Gln Leu Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Asn Thr Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 282
<211> LENGTH: 96
<212> TYPE: PRT
<213> ORGANISM: Lama pacos

<400> SEQUENCE: 282

Gln Leu Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Asn Thr Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 283
<211> LENGTH: 96
<212> TYPE: PRT
<213> ORGANISM: Lama pacos

<400> SEQUENCE: 283

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

<210> SEQ ID NO 284
<211> LENGTH: 96
<212> TYPE: PRT
<213> ORGANISM: Lama pacos

<400> SEQUENCE: 284

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 285
<211> LENGTH: 96
<212> TYPE: PRT
<213> ORGANISM: Lama pacos

<400> SEQUENCE: 285

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 286
<211> LENGTH: 96
<212> TYPE: PRT
<213> ORGANISM: Lama pacos

<400> SEQUENCE: 286

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg His Ser Pro Gly Lys Gly Leu Glu Trp Val
        35                  40                  45

Ser Ala Ile Asn Ser Gly Gly Ser Thr Ser Tyr Ala Asp Ser Met
    50                  55                  60

Lys Gly Gln Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 287
<211> LENGTH: 96
<212> TYPE: PRT
<213> ORGANISM: Lama pacos

<400> SEQUENCE: 287

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Gly Gly Asp Gly Ser Thr Ser Tyr Ala Asp Ser Val
    50                  55                  60

Lys Gly Arg Ser Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 288
<211> LENGTH: 96
<212> TYPE: PRT
<213> ORGANISM: Homo Sapiens

<400> SEQUENCE: 288

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

<210> SEQ ID NO 289

-continued

```
<211> LENGTH: 96
<212> TYPE: PRT
<213> ORGANISM: Lama pacos

<400> SEQUENCE: 289

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Ser Ile Tyr Ser Tyr Ser Ser Asn Thr Tyr Tyr Ala Asp Ser Val
    50                  55                  60

Lys Gly Arg Phe Thr Ile Ser Thr Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

<210> SEQ ID NO 290
<211> LENGTH: 96
<212> TYPE: PRT
<213> ORGANISM: Lama pacos

<400> SEQUENCE: 290

Glu Val Arg Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Arg Val Arg Gln Val Pro Gly Lys Gly Leu Glu Trp Val
        35                  40                  45

Ser Ser Ile Tyr Ser Tyr Ser Ser Asn Thr Tyr Tyr Ala Asp Ser Val
    50                  55                  60

Lys Gly Arg Phe Thr Ile Ser Thr Asp Asn Ala Lys Asn Thr Leu Tyr
65                  70                  75                  80

Leu Gln Met Asn Ser Leu Lys Ser Glu Gly Thr Ala Val Tyr Tyr Cys
                85                  90                  95

<210> SEQ ID NO 291
<211> LENGTH: 96
<212> TYPE: PRT
<213> ORGANISM: Lama pacos

<400> SEQUENCE: 291

Gln Val Gln Leu Val Glu Ser Val Gly Gly Leu Val Gln Asp Gly Gly
1               5                   10                  15

Ser Leu Arg Leu Ser Cys Ala Ala Ser Gly Arg Thr Phe Ser Ser Ser
            20                  25                  30

Ala Met Ser Trp Val Arg Gln Ala Pro Gly Lys Gly Leu Glu Trp Val
        35                  40                  45

Ser Ser Ile Tyr Ser Tyr Ser Ser Asn Thr Tyr Asn Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 292
<211> LENGTH: 96
```

<212> TYPE: PRT
<213> ORGANISM: Lama pacos

<400> SEQUENCE: 292

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Ala Met Ser Trp Val Arg Gln Ala Pro Gly Lys Gly Leu Glu Ser Val
        35                  40                  45

Ser Thr Ile Asn Ser Asp Gly Ser Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Asp Gly Thr Ala Val Tyr Tyr Cys
                85                  90                  95
```

<210> SEQ ID NO 293
<211> LENGTH: 96
<212> TYPE: PRT
<213> ORGANISM: Lama pacos

<400> SEQUENCE: 293

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Tyr Met Ser Trp Val Arg Gln Ala Pro Gly Lys Gly Leu Glu Trp Val
        35                  40                  45

Ser Gly Ile Tyr Ser Asp Gly Ser Asp Thr Tyr Tyr Ala Asp Ser Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95
```

<210> SEQ ID NO 294
<211> LENGTH: 96
<212> TYPE: PRT
<213> ORGANISM: Lama pacos

<400> SEQUENCE: 294

```
Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Gly Ile Tyr Ser Asp Gly Ser Asp Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95
```

<210> SEQ ID NO 295
<211> LENGTH: 95
<212> TYPE: PRT

<213> ORGANISM: Lama pacos

<400> SEQUENCE: 295

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Ala Arg Gln Val Pro Gly Lys Gly Leu Glu Trp Val
        35                  40                  45

Ser Gly Ile Tyr Ser Asp Gly Ser Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Ser Glu Gly Thr Ala Val Tyr Tyr Cys
                85                  90                  95

<210> SEQ ID NO 296
<211> LENGTH: 95
<212> TYPE: PRT
<213> ORGANISM: Lama pacos

<400> SEQUENCE: 296

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Ala Arg Gln Val Pro Gly Lys Gly Leu Glu Trp Val
        35                  40                  45

Ser Gly Ile Tyr Ser Asp Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Gly Thr Ala Val Tyr Tyr Cys
                85                  90                  95

<210> SEQ ID NO 297
<211> LENGTH: 95
<212> TYPE: PRT
<213> ORGANISM: Lama pacos

<400> SEQUENCE: 297

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Gly Ile Tyr Ser Asp Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Gly Thr Ala Val Tyr Tyr Cys
                85                  90                  95

<210> SEQ ID NO 298
<211> LENGTH: 96
<212> TYPE: PRT
<213> ORGANISM: Lama pacos

<400> SEQUENCE: 298

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Ser Val
        35                  40                  45

Ser Ser Ile Tyr Ser Tyr Ser Ser Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Met Ala Val Tyr Tyr Cys
                85                  90                  95

<210> SEQ ID NO 299
<211> LENGTH: 96
<212> TYPE: PRT
<213> ORGANISM: Lama pacos

<400> SEQUENCE: 299

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Ser Val
        35                  40                  45

Ser Ser Ile Tyr Ser Tyr Ser Ser Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Gly Thr Ala Val Tyr Tyr Cys
                85                  90                  95

<210> SEQ ID NO 300
<211> LENGTH: 96
<212> TYPE: PRT
<213> ORGANISM: Lama pacos

<400> SEQUENCE: 300

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Tyr Met Ser Trp Val Arg Gln Ala Pro Gly Lys Gly Leu Glu Ser Val
        35                  40                  45

Ser Thr Ile Tyr Ser Tyr Gly Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 301
<211> LENGTH: 96
<212> TYPE: PRT
<213> ORGANISM: Lama pacos

<400> SEQUENCE: 301

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Pro Glu Trp Val
        35                  40                  45

Ser Asp Ile Asn Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 302
<211> LENGTH: 96
<212> TYPE: PRT
<213> ORGANISM: Lama pacos

<400> SEQUENCE: 302

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Gly Ser Tyr
            20                  25                  30

Asp Met Ser Trp Val Arg Gln Ala Pro Gly Lys Gly Pro Glu Trp Val
        35                  40                  45

Ser Cys Ile Asn Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Gly Thr Ala Val Tyr Tyr Cys
                85                  90                  95

<210> SEQ ID NO 303
<211> LENGTH: 96
<212> TYPE: PRT
<213> ORGANISM: Lama pacos

<400> SEQUENCE: 303

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Asp Met Ser Trp Val Arg Arg Ala Pro Gly Lys Gly Leu Glu Trp Val
        35                  40                  45

Ser Tyr Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Gly Thr Ala Val Tyr Tyr Cys
                85                  90                  95

<210> SEQ ID NO 304
<211> LENGTH: 96
<212> TYPE: PRT
<213> ORGANISM: Lama pacos

<400> SEQUENCE: 304

Glu Val Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

<210> SEQ ID NO 305
<211> LENGTH: 96
<212> TYPE: PRT
<213> ORGANISM: Lama pacos

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

Ala Met Ser Trp Val Arg Gln Ala Pro Gly Lys Gly Leu Glu Trp Val
        35                  40                  45

Ser Tyr Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Gly Thr Ala Val Tyr Tyr Cys
                85                  90                  95

<210> SEQ ID NO 306
<211> LENGTH: 96
<212> TYPE: PRT
<213> ORGANISM: Lama pacos

<400> SEQUENCE: 306

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Arg Ala Pro Gly Lys Gly Leu Glu Trp Val
        35                  40                  45

Ser Tyr Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 307
<211> LENGTH: 96
<212> TYPE: PRT
<213> ORGANISM: Lama pacos

<400> SEQUENCE: 307

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Asn Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
            85                  90                  95

<210> SEQ ID NO 308
<211> LENGTH: 96
<212> TYPE: PRT
<213> ORGANISM: Homo Sapiens

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
            85                  90                  95

<210> SEQ ID NO 309
<211> LENGTH: 96
<212> TYPE: PRT
<213> ORGANISM: Lama pacos

<400> SEQUENCE: 309

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Gly Ile Tyr Ser Asp Gly Ser Asp Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
            85                  90                  95

<210> SEQ ID NO 310
<211> LENGTH: 96
<212> TYPE: PRT
<213> ORGANISM: Lama pacos

<400> SEQUENCE: 310

Gln Val Gln Leu Val Glu Ser Gly Gly Gly Leu Val Gln Pro Gly Gly

```
1               5                  10                 15
Ser Leu Arg Leu Ser Cys Ala Ala Ser Gly Phe Thr Phe Ser Ser Tyr
            20                  25                 30

Trp Met Asn Trp Val Arg Gln Ala Pro Gly Lys Gly Leu Glu Trp Val
            35                  40                 45

Ser Ala Ile Asn Ser Gly Gly Ser Thr Ser Tyr Ala Asp Ser Met
            50              55                  60

Lys Gly Gln Phe Thr Ile Ser Arg Asp Asn Ala Lys Asn Thr Leu Tyr
65                      70                  75                 80

Leu Gln Met Asn Ser Leu Lys Pro Glu Gly Thr Ala Val Tyr Tyr Cys
                    85                  90                  95
```

<210> SEQ ID NO 311
<211> LENGTH: 96
<212> TYPE: PRT
<213> ORGANISM: Lama pacos

<400> SEQUENCE: 311

```
Gln Leu Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Gly Ser Tyr
            20                  25                 30

Trp Met Tyr Trp Val Arg Gln Ala Pro Gly Lys Gly Leu Glu Trp Val
            35                  40                 45

Ser Ala Ile Asn Ser Gly Gly Gly Ser Thr Ser Tyr Ala Asp Ser Met
            50                  55                  60

Lys Gly Gln Phe Thr Ile Ser Ser Asp Asn Ala Arg Asn Thr Leu Tyr
65                      70                  75                 80

Leu Gln Met Asn Ser Leu Lys Pro Glu Gly Thr Ala Val Tyr Tyr Cys
                    85                  90                  95
```

<210> SEQ ID NO 312
<211> LENGTH: 96
<212> TYPE: PRT
<213> ORGANISM: Lama pacos

<400> SEQUENCE: 312

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Thr Phe Gly Ser Tyr
            20                  25                 30

Val Leu Ser Trp Val Cys His Ser Pro Gly Lys Gly Leu Glu Trp Val
            35                  40                 45

Ser Ala Ile Asn Ser Cys Gly Gly Ser Thr Ser Tyr Ala Asp Ser Val
            50                  55                  60

Lys Gly Arg Phe Thr Ile Ser Arg Asp Asn Ala Lys Asn Thr Val Tyr
65                      70                  75                 80

Leu Gln Met Asn Ser Leu Lys Pro Glu Gly Thr Ala Val Tyr Tyr Cys
                    85                  90                  95
```

<210> SEQ ID NO 313
<211> LENGTH: 96
<212> TYPE: PRT
<213> ORGANISM: Lama pacos

<400> SEQUENCE: 313

```
Gln Leu Gln Leu Val Glu Ser Gly Gly Gly Leu Val Gln Pro Gly Gly
1               5                  10                 15
```

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
            35                  40                  45

Ser Ala Ile Asn Ser Gly Gly Gly Ser Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Gly Thr Ala Val Tyr Tyr Cys
                85                  90                  95

<210> SEQ ID NO 314
<211> LENGTH: 97
<212> TYPE: PRT
<213> ORGANISM: Homo Sapiens

<400> SEQUENCE: 314

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
            50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys

<210> SEQ ID NO 315
<211> LENGTH: 96
<212> TYPE: PRT
<213> ORGANISM: Lama pacos

<400> SEQUENCE: 315

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Ile Thr Thr Ser
            20                  25                  30

Cys Tyr Ala Trp Ser Cys Ile Cys Gln Pro Pro Glu Lys Gly Leu Glu
            35                  40                  45

Trp Met Ala Ala Ile Tyr Ser Gly Ser Thr Tyr Tyr Ser Pro Ser Leu
            50                  55                  60

Lys Ser His Thr Ser Ile Ser Arg Asp Thr Ser Lys Asn Gln Phe Ser
65                  70                  75                  80

Leu Gln Leu Ser Ser Val Thr Pro Glu Gly Thr Ala Val Tyr Tyr Cys
                85                  90                  95

<210> SEQ ID NO 316
<211> LENGTH: 97
<212> TYPE: PRT
<213> ORGANISM: Homo Sapiens

<400> SEQUENCE: 316

Gln Val Gln Leu Gln Glu Ser Gly Pro Gly Leu Val Lys Pro Ser Gln

```
1               5                   10                  15
Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
            35                  40                  45

Trp Ile Gly Tyr Ile Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys

<210> SEQ ID NO 317
<211> LENGTH: 97
<212> TYPE: PRT
<213> ORGANISM: Lama pacos

<400> SEQUENCE: 317

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Tyr Tyr Ala Trp Ser Trp Ile Arg Gln Pro Pro Gly Lys Gly Leu Glu
            35                  40                  45

Trp Met Gly Ala Ile Ala Tyr Ser Gly Ser Thr Tyr Tyr Ser Pro Ser
    50                  55                  60

Leu Lys Ser Arg Thr Ser Ile Ser Arg Asp Thr Ser Asn Asn Gln Phe
65                  70                  75                  80

Ser Leu Gln Leu Ser Ser Val Thr Pro Glu Gly Thr Ala Val Tyr Tyr
                85                  90                  95

Cys

<210> SEQ ID NO 318
<211> LENGTH: 97
<212> TYPE: PRT
<213> ORGANISM: Lama pacos

<400> SEQUENCE: 318

Glu Val Gln Val Gln Glu Ser Gly Pro Gly Leu Val Lys Pro Ser Gln
1               5                   10                  15

Ala Leu Ser Leu Thr Cys Thr Ala Ser Gly Gly Ser Asn Thr Thr Ser
            20                  25                  30

Tyr Tyr Ala Trp Ser Trp Ile Arg Gln Pro Pro Gly Lys Gly Leu Glu
            35                  40                  45

Trp Met Gly Ala Ile Ala Tyr Ser Gly Ser Thr Tyr Tyr Ser Pro Ser
    50                  55                  60

Leu Lys Ser Arg Thr Ser Ile Ser Arg Asp Thr Ser Asn Asn Gln Phe
65                  70                  75                  80

Ser Leu Gln Leu Ser Ser Val Thr Pro Glu Gly Thr Ala Val Tyr Tyr
                85                  90                  95

Cys

<210> SEQ ID NO 319
<211> LENGTH: 97
<212> TYPE: PRT
```

<210> SEQ ID NO 319
<211> LENGTH: 97
<212> TYPE: PRT
<213> ORGANISM: Lama pacos

<400> SEQUENCE: 319

Gln Val Gln Arg Gln Glu Ser Gly Pro Gly Leu Val Lys Pro Ser Gln
1               5                   10                  15

Met Leu Ser Leu Thr Cys Thr Ala Ser Gly Gly Ser Asn Thr Thr Ser
            20                  25                  30

Tyr Tyr Ala Trp Ser Trp Ile Arg Gln Pro Pro Gly Lys Gly Leu Glu
        35                  40                  45

Trp Met Gly Ala Ile Ala Tyr Asp Gly Ser Thr Tyr Tyr Ser Pro Ser
    50                  55                  60

Leu Lys Ser His Thr Ser Ile Ser Arg Asp Thr Ser Lys Asn Gln Phe
65                  70                  75                  80

Ser Leu Gln Leu Ser Ser Val Thr Pro Glu Gly Thr Ala Val Tyr Tyr
                85                  90                  95

Cys

<210> SEQ ID NO 320
<211> LENGTH: 97
<212> TYPE: PRT
<213> ORGANISM: Lama pacos

<400> SEQUENCE: 320

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Tyr Tyr Tyr Trp Ser Trp Ile Arg Gln Pro Pro Gly Lys Gly Leu Glu
        35                  40                  45

Trp Met Gly Ala Ile Ala Tyr Asp Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu Gln Leu Ser Ser Val Thr Pro Glu Gly Thr Ala Val Tyr Tyr
                85                  90                  95

Cys

<210> SEQ ID NO 321
<211> LENGTH: 97
<212> TYPE: PRT
<213> ORGANISM: Lama pacos

<400> SEQUENCE: 321

Glu Val Gln Leu Gln Glu Ser Gly Pro Gly Leu Leu Lys Pro Ser Gln
1               5                   10                  15

Thr Leu Ser Leu Thr Cys Ala Val Tyr Gly Gly Ser Ile Thr Thr Ser
            20                  25                  30

Tyr Tyr Tyr Trp Ser Trp Ile Arg Gln Pro Pro Gly Lys Gly Leu Glu
        35                  40                  45

Trp Met Gly Ala Ile Ala Tyr Asp Gly Ser Thr Tyr Tyr Ser Pro Ser
    50                  55                  60

Leu Lys Ser His Thr Ser Ile Ser Arg Asp Thr Ser Lys Asn Gln Phe
65                  70                  75                  80

Ser Leu Gln Leu Ser Ser Val Thr Pro Glu Gly Thr Ala Val Tyr Tyr
                85                  90                  95

Cys

<210> SEQ ID NO 322
<211> LENGTH: 96
<212> TYPE: PRT
<213> ORGANISM: Lama pacos
<220> FEATURE:
<221> NAME/KEY: MISC_FEATURE
<222> LOCATION: (49)..(49)
<223> OTHER INFORMATION: Unknown amino acid

<400> SEQUENCE: 322

Gln Val Gln Leu Gln Glu Ser Gly Pro Asp Leu Val Lys Pro Ser Gln
1               5                   10                  15

Met Leu Ser Leu Thr Cys Thr Val Ser Gly Gly Ser Asn Thr Thr Ser
            20                  25                  30

Tyr Tyr Ala Trp Ser Trp Ile Arg Gln Pro Pro Gly Lys Gly Leu Glu
        35                  40                  45

Xaa Met Gly Ala Ile Tyr Ser Gly Ser Thr Tyr Tyr Ser Pro Ser Leu
50                  55                  60

Lys Ser Arg Thr Ser Ile Ser Arg Asp Thr Ser Lys Asn Gln Phe Ser
65                  70                  75                  80

Leu Gln Leu Ser Ser Val Thr Pro Glu Gly Thr Ala Val Tyr Tyr Cys
                85                  90                  95

<210> SEQ ID NO 323
<211> LENGTH: 96
<212> TYPE: PRT
<213> ORGANISM: Lama pacos

<400> SEQUENCE: 323

Gln Val Gln Leu Gln Glu Ser Gly Pro Gly Leu Val Lys Pro Ser Gln
1               5                   10                  15

Thr Leu Ser Leu Thr Cys Thr Ala Ser Gly Gly Ser Asn Thr Thr Ser
            20                  25                  30

Tyr Tyr Ala Trp Ser Trp Ile Arg Gln Pro Pro Gly Lys Gly Leu Glu
        35                  40                  45

Trp Met Gly Ala Ile Tyr Ser Gly Ser Thr Tyr Tyr Ser Pro Ser Leu
50                  55                  60

Lys Ser Arg Thr Ser Ile Ser Arg Asp Thr Ser Asn Asn Gln Phe Ser
65                  70                  75                  80

Leu Gln Leu Ser Ser Val Thr Pro Glu Gly Thr Cys Val Tyr Tyr Cys
                85                  90                  95

<210> SEQ ID NO 324
<211> LENGTH: 95
<212> TYPE: PRT
<213> ORGANISM: Lama pacos
<220> FEATURE:
<221> NAME/KEY: MISC_FEATURE
<222> LOCATION: (48)..(48)
<223> OTHER INFORMATION: Unknown amino acid

<400> SEQUENCE: 324

Gln Val Gln Leu Glu Ser Gly Pro Gly Leu Val Lys Pro Ser Gln Thr
1               5                   10                  15

Leu Ser Leu Thr Cys Thr Val Ser Gly Gly Ser Ile Thr Thr Ser Cys
            20                  25                  30

Tyr Ala Trp Ser Trp Ile His Gln Pro Pro Gly Lys Gly Leu Glu Xaa
        35                  40                  45

Met Gly Ala Ile Tyr Ser Gly Ser Thr Tyr Tyr Ser Pro Ser Leu Lys

```
                 50                  55                  60
Ser His Thr Ser Ile Ser Arg Asp Thr Ser Lys Asn Gln Phe Ser Leu
 65                  70                  75                  80

Gln Leu Ser Ser Val Thr Pro Glu Gly Thr Ala Val Tyr Tyr Cys
                 85                  90                  95
```

<210> SEQ ID NO 325
<211> LENGTH: 96
<212> TYPE: PRT
<213> ORGANISM: Lama pacos

<400> SEQUENCE: 325

```
Glu Val Gln Leu Gln Glu Ser Gly Pro Gly Leu Val Lys Pro Ser Gln
  1               5                  10                  15

Met Leu Ser Leu Thr Cys Thr Leu Ser Gly Asp Ser Ile Thr Thr Ser
                 20                  25                  30

Cys Tyr Ala Trp Ser Trp Ile Arg Gln Pro Pro Gly Lys Gly Leu Glu
                 35                  40                  45

Trp Met Gly Ala Ile Tyr Ser Gly Ser Thr Tyr Tyr Ser Pro Ser Leu
                 50                  55                  60

Lys Ser Arg Thr Ser Ile Ser Arg Asp Thr Ser Lys Asn Gln Phe Ser
 65                  70                  75                  80

Leu Gln Leu Ser Ser Val Thr Pro Glu Gly Thr Ala Val Tyr Tyr Cys
                 85                  90                  95
```

<210> SEQ ID NO 326
<211> LENGTH: 98
<212> TYPE: PRT
<213> ORGANISM: Homo sapiens

<400> SEQUENCE: 326

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
                 35                  40                  45

Ser Ala Ile Ser Gly Ser Gly Gly Ser Thr Tyr Tyr Ala Asp Ser Val
                 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys
```

<210> SEQ ID NO 327
<211> LENGTH: 107
<212> TYPE: PRT
<213> ORGANISM: Lama glama

<400> SEQUENCE: 327

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Gly Arg Tyr
                 20                  25                  30

Ala Met Ser Trp Val Arg Gln Ala Pro Gly Lys Gly Pro Glu Trp Val
                 35                  40                  45
```

```
Ser Ala Ile Ser Trp Asn Ser Gly Arg Ile Tyr Asp Ala Glu Ser Met
         50                  55                  60
Lys Gly Arg Phe Thr Val Ser Arg Asp Asn Lys Asn Thr Leu Tyr
 65                  70                  75                  80
Leu Gln Met Asn Ala Leu Lys Thr Asp Thr Ala Val Tyr Tyr Cys
                 85                  90                  95
Ala Arg Ser Thr Ala Glu Ser Asn Trp Ile Pro
                100                 105

<210> SEQ ID NO 328
<211> LENGTH: 102
<212> TYPE: PRT
<213> ORGANISM: Lama glama

<400> SEQUENCE: 328

Glu Val Gln Leu Val Gln Ser Gly Gly Gly Leu Val Gln His Gly Gly
 1               5                  10                  15
Ser Leu Arg Leu Ser Cys Ala Ala Ser Gly Phe Ala Phe Ser Ser Ala
                20                  25                  30
Gly Met Ser Trp Val Arg Gln Ala Pro Gly Lys Gly Leu Glu Gly Val
             35                  40                  45
Ser Ala Ile Asn Thr Arg Ser Gly Thr Thr Tyr Tyr Ala Asp Phe Thr
         50                  55                  60
Lys Gly Arg Phe Thr Ile Ser Arg Asp Asn Ala Lys Asn Thr Val Tyr
 65                  70                  75                  80
Leu Gln Met Asn Ser Leu Lys Pro Glu Asp Thr Ala Val Tyr Tyr Cys
                 85                  90                  95
Asn Ala Gly Phe Pro Ser
                100

<210> SEQ ID NO 329
<211> LENGTH: 107
<212> TYPE: PRT
<213> ORGANISM: Lama glama

<400> SEQUENCE: 329

Glu Glu Gln Leu Val Ser Gly Gly Gly Leu Val Gln Pro Gly Gly
 1               5                  10                  15
Ser Leu Arg Leu Ser Cys Ala Ala Ser Gly Phe Thr Phe Gly Ser Tyr
                20                  25                  30
Asp Met Tyr Trp Val Arg Gln Ala Pro Gly Lys Gly Pro Glu Trp Val
             35                  40                  45
Ser Ala Ile Arg Ser Gly Gly Ser Thr Tyr Tyr Ala Asp Ser Val
         50                  55                  60
Lys Gly Arg Phe Thr Ile Ser Arg Asp Asn Ala Lys Asn Thr Leu Tyr
 65                  70                  75                  80
Leu Gln Met Asn Ser Leu Lys Pro Glu Asp Thr Ala Val Tyr Tyr Cys
                 85                  90                  95
Ala Lys Pro Ser Thr Ile Ala Thr Ile Leu Phe
                100                 105

<210> SEQ ID NO 330
<211> LENGTH: 111
<212> TYPE: PRT
<213> ORGANISM: Lama glama

<400> SEQUENCE: 330

Glu Val Gln Leu Val Glu Ser Gly Gly Gly Leu Val Gln Pro Gly Gly
 1               5                  10                  15
```

```
1               5                   10                  15
Ser Leu Arg Leu Ser Cys Ala Ala Ser Gly Phe Thr Phe Ser Ser Tyr
                20                  25                  30

Tyr Met Ser Trp Val Arg Gln Ala Pro Gly Lys Gly Leu Glu Trp Val
                35                  40                  45

Ser Ser Ile Tyr Ser Asp Gly Ser Tyr Thr Tyr Ala Asp Ser Val
                50                  55                  60

Lys Gly Arg Phe Thr Ile Ser Arg Asp Asn Ala Lys Asn Thr Leu Tyr
 65                 70                  75                  80

Leu Gln Met Asn Ser Leu Lys Ser Glu Asp Thr Ala Val Tyr Tyr Cys
                85                  90                  95

Ala Asn Trp Asp Tyr Ser Gly Ser Tyr Tyr Ala Pro Ala Thr Phe
                100                 105                 110

<210> SEQ ID NO 331
<211> LENGTH: 101
<212> TYPE: PRT
<213> ORGANISM: Lama glama

<400> SEQUENCE: 331

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Ala
                20                  25                  30

Val Met Ser Trp Val Arg Gln Ala Pro Gly Lys Gly Leu Glu Trp Val
                35                  40                  45

Ser Gly Ile Gly Ser Gly Ser Thr Thr Ser Tyr Ala Asp Ser Val
                50                  55                  60

Lys Gly Arg Phe Thr Ile Ser Arg Asp Asn Ala Lys Asn Thr Leu Tyr
 65                 70                  75                  80

Leu Gln Met Asn Ser Leu Lys Pro Glu Asp Thr Ala Val Tyr Tyr Cys
                85                  90                  95

Thr Gly Arg Gly Phe
                100

<210> SEQ ID NO 332
<211> LENGTH: 101
<212> TYPE: PRT
<213> ORGANISM: Lama glama

<400> SEQUENCE: 332

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Ala
                20                  25                  30

Val Met Ser Trp Val Arg Gln Ala Pro Gly Lys Gly Leu Glu Trp Val
                35                  40                  45

Ser Thr Ile Gly Ala Ala Gly Ser Thr Thr Ser Tyr Ala Asp Ser Val
                50                  55                  60

Lys Gly Arg Phe Thr Ile Ser Arg Asp Asn Ala Lys Asn Thr Leu Tyr
 65                 70                  75                  80

Leu Gln Met Asn Ser Leu Lys Pro Glu Asp Thr Ala Val Tyr Tyr Cys
                85                  90                  95

Thr Gly Arg Gly Phe
                100
```

-continued

<210> SEQ ID NO 333
<211> LENGTH: 96
<212> TYPE: PRT
<213> ORGANISM: Homo sapiens

<400> SEQUENCE: 333

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

<210> SEQ ID NO 334
<211> LENGTH: 107
<212> TYPE: PRT
<213> ORGANISM: Lama glama

<400> SEQUENCE: 334

Asn Phe Met Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Arg Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Val Phe Gly Gly Gly Thr His Leu Thr Val Leu
            100                 105

<210> SEQ ID NO 335
<211> LENGTH: 104
<212> TYPE: PRT
<213> ORGANISM: Homo sapiens

<400> SEQUENCE: 335

Gln Pro Val Leu Thr Gln Pro Pro Ser Ser Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
        35                  40                  45

Leu Leu Tyr Tyr Tyr Ser Asp Ser Asp Lys Gly Gln Gly Ser Gly Val
    50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

```
Met Ile Trp Pro Ser Asn Ala Ser
            100

<210> SEQ ID NO 336
<211> LENGTH: 117
<212> TYPE: PRT
<213> ORGANISM: Lama glama

<400> SEQUENCE: 336

Gln Ala Val Leu Thr Gln Pro Pro Ser Leu Ser Ala Ser Pro Gly Ser
1               5                   10                  15

Ser Val Arg Leu Thr Cys Thr Leu Ser Ser Gly Asn Ser Val Gly Ser
            20                  25                  30

Tyr Asp Ile Ser Trp Tyr Gln Gln Lys Ala Gly Ser Pro Pro Arg Tyr
        35                  40                  45

Leu Leu Tyr Tyr Tyr Ser Asp Ser Phe Asn His Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Ser Ala Tyr Lys Ser Gly Ser Tyr Asn Pro Thr Phe Gly Gly Gly Thr
            100                 105                 110

Lys Leu Thr Val Leu
        115

<210> SEQ ID NO 337
<211> LENGTH: 98
<212> TYPE: PRT
<213> ORGANISM: Homo sapiens

<400> SEQUENCE: 337

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile

<210> SEQ ID NO 338
<211> LENGTH: 112
<212> TYPE: PRT
<213> ORGANISM: Lama glama

<400> SEQUENCE: 338

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Gly Trp Tyr Gln Gln Lys Pro Gly Gln Ala Pro Arg Thr
```

```
                35                  40                  45

Leu Ile Tyr Asn Thr Asn Ser Arg Tyr Ser Gly Val Pro Asn Arg Phe
    50                  55                  60

Ser Gly Ser Ile Ser Gly Asn Lys Ala Val Leu Thr Ile Thr Gly Ala
65                  70                  75                  80

Gln Pro Glu Asp Glu Ala Asp Tyr Tyr Cys Ala Val Tyr Thr Gly Ser
                85                  90                  95

Ser Asn Tyr Pro Ala Val Phe Gly Gly Gly Thr His Leu Thr Val Leu
            100                 105                 110

<210> SEQ ID NO 339
<211> LENGTH: 110
<212> TYPE: PRT
<213> ORGANISM: Lama glama

<400> SEQUENCE: 339

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Ala Ala Trp Phe Gln Gln Ala Pro Gly Gln Ala Pro Arg Thr
        35                  40                  45

Leu Ile Tyr Lys Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ser Leu Tyr Pro Gly Ser
                85                  90                  95

Asp Ile Ser Val Phe Gly Gly Gly Thr His Leu Thr Val Leu
            100                 105                 110

<210> SEQ ID NO 340
<211> LENGTH: 112
<212> TYPE: PRT
<213> ORGANISM: Lama glama

<400> SEQUENCE: 340

Ser Ser Glu Leu Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Gly Trp Tyr Gln Gln Lys Pro Gly Gln Ala Pro Arg Thr
        35                  40                  45

Leu Ile Tyr Asn Thr Asn Ser Arg Tyr Ser Gly Val Pro Asn Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Val Tyr Ile Gly Ser
                85                  90                  95

Gly Gly Tyr Pro Pro Val Phe Gly Gly Gly Thr Lys Leu Thr Val Leu
            100                 105                 110

<210> SEQ ID NO 341
<211> LENGTH: 110
<212> TYPE: PRT
<213> ORGANISM: Lama glama

<400> SEQUENCE: 341
```

Ser Tyr Glu Leu Thr Gln Asp Pro Ser Leu Ser Val Ser Pro Gly Glu
1               5                   10                  15

Thr Val Thr Leu Thr Cys Gly Leu Asn Ser Gly Ser Val Thr Ser His
            20                  25                  30

Asn Tyr Pro Ala Trp Tyr Gln Gln Lys Pro Gly Gln Ala Pro Arg Thr
        35                  40                  45

Leu Met Tyr Asn Thr Asn Ser Arg Tyr Pro Met Val Pro Pro Arg Phe
    50                  55                  60

Ser Gly Ser Ile Phe Gly Asn Lys Ala Ala Leu Thr Ile Thr Gly Ala
65              70                  75                  80

Gln Ala Glu Asp Glu Ala Asp Tyr Tyr Cys Ala Val Tyr Ile Arg Ser
                85                  90                  95

Arg Thr Leu Glu Phe Gly Gly Gly Thr His Leu Thr Val Leu
            100                 105                 110

<210> SEQ ID NO 342
<211> LENGTH: 100
<212> TYPE: PRT
<213> ORGANISM: Homo sapiens

<400> SEQUENCE: 342

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 343
<211> LENGTH: 111
<212> TYPE: PRT
<213> ORGANISM: Lama glama

<400> SEQUENCE: 343

Asp Ile Val Met Thr Gln Thr Pro Gly Ser Leu Ser Val Val Pro Gly
1               5                   10                  15

Glu Ser Ala Ser Ile Ser Cys Lys Ala Ser Gln Ser Leu Val His Ser
            20                  25                  30

Asp Gly Lys Thr Tyr Leu Tyr Trp Leu Leu Gln Lys Pro Gly Gln Ser
        35                  40                  45

Pro Gln Arg Leu Ile Tyr Gln Val Ser Asn Arg Gly Ser Gly Val Pro
    50                  55                  60

Asp Arg Phe Thr Gly Ser Gly Ser Gly Thr Asp Phe Thr Leu Lys Ile
65              70                  75                  80

Ser Gly Val Lys Ala Glu Asp Ala Gly Val Tyr Tyr Cys Ala Gln Ala
                85                  90                  95

Thr Tyr Tyr Val Thr Phe Gly Gln Gly Thr Lys Val Glu Leu Lys
            100                 105                 110

<210> SEQ ID NO 344
<211> LENGTH: 113
<212> TYPE: PRT
<213> ORGANISM: Lama glama

<400> SEQUENCE: 344

Asp Ile Val Met Thr Gln Thr Pro Gly Ser Leu Ser Val Val Pro Gly
1               5                   10                  15
Glu Ser Ala Ser Ile Ser Cys Lys Ala Ser Gln Ser Leu Val His Ser
            20                  25                  30
Asp Gly Lys Thr Tyr Leu Tyr Trp Leu Leu Gln Lys Pro Gly Gln Ser
        35                  40                  45
Pro Gln Arg Leu Ile Tyr Gln Val Ser Asn Arg Gly Ser Gly Val Pro
    50                  55                  60
Asp Arg Phe Thr Gly Ser Gly Ser Gly Thr Asp Phe Thr Leu Lys Ile
65                  70                  75                  80
Ser Gly Val Lys Ala Glu Asp Ala Gly Val Tyr Tyr Cys Ala Gln Ala
                85                  90                  95
Ser Tyr Tyr Pro Pro Leu Thr Phe Gly Gln Gly Thr Lys Val Glu Leu
            100                 105                 110
Lys

<210> SEQ ID NO 345
<211> LENGTH: 111
<212> TYPE: PRT
<213> ORGANISM: Lama glama

<400> SEQUENCE: 345

Asp Ile Val Met Thr Gln Thr Pro Gly Ser Leu Ser Val Val Pro Gly
1               5                   10                  15
Glu Ser Ala Ser Ile Ser Cys Lys Ala Ser Gln Ser Leu Val Leu Ser
            20                  25                  30
Gly Gly Lys Thr Tyr Leu Tyr Trp Leu Leu Gln Lys Pro Gly Gln Ser
        35                  40                  45
Pro Gln Arg Leu Ile Tyr Gln Val Ser Asn Arg Gly Ser Gly Val Pro
    50                  55                  60
Asp Arg Phe Thr Gly Ser Gly Ser Gly Thr Asp Phe Thr Leu Lys Ile
65                  70                  75                  80
Ser Gly Val Lys Ala Glu Asp Ala Gly Val Tyr Tyr Cys Thr Gln Ala
                85                  90                  95
Thr Tyr Tyr Ile Thr Phe Gly Lys Gly Thr Arg Leu Glu Ile Lys
            100                 105                 110

<210> SEQ ID NO 346
<211> LENGTH: 109
<212> TYPE: PRT
<213> ORGANISM: Lama glama

<400> SEQUENCE: 346

Glu Ile Val Leu Thr Thr Pro Gly Ser Leu Ser Val Val Pro Gly Glu
1               5                   10                  15
Ser Ala Ser Ile Ser Cys Lys Ala Ser Gln Ser Leu Val Arg Ser Asp
            20                  25                  30
Gly Lys Thr Tyr Leu Tyr Trp Leu Leu Gln Lys Pro Gly Gln Ser Pro
        35                  40                  45
Gln Arg Leu Ile Tyr Gln Val Ser Asn Arg Gly Ser Gly Val Pro Arg

```
                50                  55                  60
Phe Thr Gly Ser Gly Ser Gly Thr Asp Phe Thr Leu Lys Ile Ser Gly
 65                  70                  75                  80

Val Lys Ala Glu Asp Ala Gly Val Tyr Tyr Cys Ala Gln Ala Thr Tyr
                 85                  90                  95

Tyr Val Thr Phe Gly Gln Gly Thr Lys Val Glu Leu Lys
                100                 105

<210> SEQ ID NO 347
<211> LENGTH: 23
<212> TYPE: PRT
<213> ORGANISM: Artificial Sequence
<220> FEATURE:
<223> OTHER INFORMATION: PCR Primer

<400> SEQUENCE: 347

Cys Ala Gly Gly Thr Lys Cys Ala Gly Cys Thr Gly Thr Gly Thr Cys
 1               5                  10                  15

Ala Gly Thr Cys Thr Gly Gly
             20

<210> SEQ ID NO 348
<211> LENGTH: 23
<212> TYPE: PRT
<213> ORGANISM: Artificial Sequence
<220> FEATURE:
<223> OTHER INFORMATION: PCR Primer

<400> SEQUENCE: 348

Gly Ala Arg Gly Thr Gly Cys Ala Gly Cys Thr Gly Thr Gly Thr Cys
 1               5                  10                  15

Ala Gly Thr Cys Thr Gly Gly
             20

<210> SEQ ID NO 349
<211> LENGTH: 23
<212> TYPE: PRT
<213> ORGANISM: Artificial Sequence
<220> FEATURE:
<223> OTHER INFORMATION: PCR Primer

<400> SEQUENCE: 349

Cys Ala Gly Ser Thr Gly Cys Ala Gly Cys Thr Gly Cys Ala Gly Gly
 1               5                  10                  15

Ala Gly Thr Cys Thr Gly Gly
             20

<210> SEQ ID NO 350
<211> LENGTH: 23
<212> TYPE: PRT
<213> ORGANISM: Artificial Sequence
<220> FEATURE:
<223> OTHER INFORMATION: PCR Primer

<400> SEQUENCE: 350

Cys Ala Gly Gly Thr Gly Cys Ala Gly Cys Thr Ala Cys Ala Gly Cys
 1               5                  10                  15

Ala Gly Thr Cys Thr Gly Gly
             20

<210> SEQ ID NO 351
<211> LENGTH: 23
<212> TYPE: PRT
```

<213> ORGANISM: Artificial Sequence
<220> FEATURE:
<223> OTHER INFORMATION: PCR Primer

<400> SEQUENCE: 351

Cys Ala Gly Gly Thr Cys Ala Cys Cys Thr Thr Gly Ala Arg Gly Gly
1               5                   10                  15

Ala Gly Thr Cys Thr Gly Gly
            20

<210> SEQ ID NO 352
<211> LENGTH: 53
<212> TYPE: PRT
<213> ORGANISM: Artificial Sequence
<220> FEATURE:
<223> OTHER INFORMATION: PCR Primer

<400> SEQUENCE: 352

Cys Thr Cys Gly Cys Ala Ala Cys Thr Gly Cys Gly Gly Cys Cys Cys
1               5                   10                  15

Ala Gly Cys Cys Gly Gly Cys Cys Ala Thr Gly Gly Cys Cys Cys Ala
            20                  25                  30

Gly Gly Thr Lys Cys Ala Gly Cys Thr Gly Gly Thr Gly Cys Ala Gly
        35                  40                  45

Thr Cys Thr Gly Gly
    50

<210> SEQ ID NO 353
<211> LENGTH: 53
<212> TYPE: PRT
<213> ORGANISM: Artificial Sequence
<220> FEATURE:
<223> OTHER INFORMATION: PCR Primer

<400> SEQUENCE: 353

Cys Thr Cys Gly Cys Ala Ala Cys Thr Gly Cys Gly Gly Cys Cys Cys
1               5                   10                  15

Ala Gly Cys Cys Gly Gly Cys Cys Ala Thr Gly Gly Cys Cys Gly Ala
            20                  25                  30

Arg Gly Thr Gly Cys Ala Gly Cys Thr Gly Gly Thr Gly Cys Ala Gly
        35                  40                  45

Thr Cys Thr Gly Gly
    50

<210> SEQ ID NO 354
<211> LENGTH: 53
<212> TYPE: PRT
<213> ORGANISM: Artificial Sequence
<220> FEATURE:
<223> OTHER INFORMATION: PCR Primer

<400> SEQUENCE: 354

Cys Thr Cys Gly Cys Ala Ala Cys Thr Gly Cys Gly Gly Cys Cys Cys
1               5                   10                  15

Ala Gly Cys Cys Gly Gly Cys Cys Ala Thr Gly Gly Cys Cys Cys Ala
            20                  25                  30

Gly Ser Thr Gly Cys Ala Gly Cys Thr Gly Cys Ala Gly Gly Ala Gly
        35                  40                  45

Thr Cys Thr Gly Gly
    50

-continued

```
<210> SEQ ID NO 355
<211> LENGTH: 53
<212> TYPE: PRT
<213> ORGANISM: Artificial Sequence
<220> FEATURE:
<223> OTHER INFORMATION: PCR Primer

<400> SEQUENCE: 355

Cys Thr Cys Gly Cys Ala Ala Cys Thr Gly Cys Gly Gly Cys Cys Cys
1               5                   10                  15

Ala Gly Cys Cys Gly Gly Cys Cys Ala Thr Gly Gly Cys Cys Cys Ala
            20                  25                  30

Gly Gly Thr Gly Cys Ala Gly Cys Thr Ala Cys Ala Gly Cys Ala Gly
        35                  40                  45

Thr Cys Thr Gly Gly
    50

<210> SEQ ID NO 356
<211> LENGTH: 53
<212> TYPE: PRT
<213> ORGANISM: Artificial Sequence
<220> FEATURE:
<223> OTHER INFORMATION: PCR Primer

<400> SEQUENCE: 356

Cys Thr Cys Gly Cys Ala Ala Cys Thr Gly Cys Gly Gly Cys Cys Cys
1               5                   10                  15

Ala Gly Cys Cys Gly Gly Cys Cys Ala Thr Gly Gly Cys Cys Cys Ala
            20                  25                  30

Gly Gly Thr Cys Ala Cys Cys Thr Thr Gly Ala Arg Gly Gly Ala Gly
        35                  40                  45

Thr Cys Thr Gly Gly
    50
```

ANTIGEN BINDING POLYPEPTIDES

RELATED APPLICATIONS

This application is a Divisional of U.S. patent application Ser. No. 13/233,345, filed Sep. 15, 2011, which is a Divisional of U.S. patent application Ser. No. 12/497,239, filed Jul. 2, 2009, issued as U.S. Pat. No. 8,444,976 on May 21, 2013, which claims the benefit of priority of U.S. Provisional Application Ser. No. 61/077,730, filed Jul. 2, 2008, and U.S. Provisional Application Ser. No. 61/110,161, each of which is incorporated by reference in its entirety. This application also claims the benefit of foreign priority to GB 0812120.4, filed Jul. 2, 2008, which is incorporated by reference in its entirety.

FIELD OF THE INVENTION

The invention relates to a novel platform for generation of antigen binding polypeptides, including monoclonal antibodies, which share a high degree of sequence and structural homology with the variable domains of human antibodies.

BACKGROUND TO THE INVENTION

Monoclonal antibodies have many applications as research tools and, increasingly, as therapeutic or diagnostic agents. Currently more than 20 different monoclonal antibodies have received regulatory approval to treat a variety of different diseases, including cancer, inflammation, auto-immune disorders, infectious disease, asthma, cardiovascular diseases and transplant rejection and the number of monoclonal antibody drugs in the development pipeline is increasing year-on-year.

The utility of rodent (specifically murine) monoclonal antibodies in human therapy is limited because of problems associated with their non-human origin, in particular their immunogenicity in a human host. In order to minimize the human immune response against therapeutic antibody drugs, monoclonal antibody technology has evolved from full mouse antibodies to chimeric antibodies (mouse variable domains grafted on a human IgG backbone), to humanized antibodies (mouse CDRs grafted on a human IgG backbone), to "fully human" antibodies derived from synthetic libraries or immunized transgenic mice expressing part of the human IgG repertoire.

A number of technology platforms have been developed which allow production of fully human or "humanized" monoclonal antibodies against target antigens of therapeutic interest. Each of these platforms has its own particular characteristics and potential shortcomings.

Humanisation of mouse monoclonal antibodies was initially achieved by combining mouse variable domains with human constant domains, creating so called chimeric antibodies having about 70% of human content. A further degree of humanization was subsequently achieved by grafting the complementarity-determining regions (CDRs) of mouse monoclonal antibodies onto human framework regions of the variable antibody domains of human antibodies. In addition, several amino acid residues present in those framework regions were identified as interacting with the CDRs or antigen and were back mutated in the humanized antibody to improve binding. (Almagro et al. Frontiers in Bioscience. 13: 1619-1633 (2008)). Monoclonal antibodies engineered using this approach have a relatively high degree of primary sequence homology to human VH and VL domain sequences after humanisation, but a drawback is the possibility of ending up with hypervariable loops not having human-like structure, because not all mouse-encoded CDRs use canonical folds, and canonical fold combinations, which are not found in human antibodies (Almagro et al., Mol. Immunol. 34:1199-1214 (1997); Almagro et al., Immunogen. 47:355-63 (1998)). A further drawback is the large number of mutations typically required to humanise such antibodies (the procedure for which is complex and time-consuming), with the consequent risk of losing affinity and potency as a result of the number of changes needed for humanisation and, the fact that VKappa domains are mainly used in the murine repertoire, whereas approximately half of all human antibodies possess VLambda domains.

As a potential improvement on humanised mouse monoclonal antibodies, "fully human" monoclonal antibodies can be produced by two very different approaches. The first approach is selection from a fully synthetic human combinatorial antibody library (for example HuCAL®, MorphoSys). The potential drawback of this approach is that the synthetic library only approximates the functional diversity naturally present in the human germline, thus the diversity is somewhat limited. Also, antibodies generated using this approach are not derived from in vivo selection of CDRs via active immunisation, and typically affinity maturation has to be done in order to improve affinity for the target antigen. Affinity maturation is a lengthy process which may add considerable time to the antibody discovery process. Also, in the process of affinity maturation certain amino acid residues may be changed which may negatively affect the binding specificity or stability of the resulting antibody (Wu et al., J. Mol. Biol. 368: 652-65 (2007)).

Alternative "fully human" platforms are based on transgenic mice which have been engineered to replace the murine immunoglobulin encoding region with antibody-encoding sequences from the human germline (for example HuMab, Medarex). These systems have the advantage that antibodies are raised by active immunisation, with the target antigen, i.e. they have a high starting affinity for the antigen, and that no or only minimal antibody engineering of the original antibodies is required in order to make them more human-like. However, the transgenic mouse strains are by definition highly inbred and this has adverse consequences for the strength and diversity of the antibody response. Another drawback with this platform may be impaired B cell maturation due to human Fc/mouse Fc receptor interaction in some transgenic mouse systems.

A further platform is based on immunisation of non-human primates, specifically cynomologous monkeys. Due to the high degree of amino acid sequence identity between monkey and human immunoglobulins it is postulated that antibodies raised in monkeys will require little or no additional "humanisation" in the variable domains in order to render them useful as human therapeutics (see WO 93/02108).

SUMMARY OF THE INVENTION

The present inventors have recognised the need for a "humanised" monoclonal antibody (antigen binding polypeptide) platform which avoids some or all of the shortcomings they have observed with prior art humanised or fully human antibody platforms and which enables the production of antibodies of high specificity and affinity against a broad range of target antigens of therapeutic importance whilst minimising immunogenicity in a human host.

The present inventors have observed that both the VH and the VL domains of conventional antibodies from the family Camelidae exhibit a high degree of amino acid sequence identity with the VH and VL domains of human antibodies over the framework regions. In fact, the degree of sequence identity between camelid conventional VH domains and human VH domains, and between camelid conventional VL domains and human VL domains can approach that observed between humans and other primate species, e.g. cynomologous monkeys, and is much higher than might be expected given the phylogenetic distance between humans and camelids. This finding is surprising given that the variable domains of heavy-chain camelid antibodies (VHH) do not show this high degree of sequence homology with human variable domains.

In addition, the inventors have observed that the hypervariable loops (H1, H2, L1, L2 and L3) of camelid VH and VL domains often exhibit a high degree of structural homology with the hypervariable loops of human VH and VL domains, which is again unexpected given the evolutionary distance between humans and camelids. The high degree of structural homology between camelid conventional antibodies (or rather the hypervariable loops of such antibodies) and human antibodies is also surprising since the hypervariable loops of heavy-chain camelid antibodies have been reported to vary substantially in conformation and length from the corresponding loops in human and mouse VH (see review De Genst et al., Develop Comp. Immunol. 30:187-98 (2006)).

The high degree of primary amino acid sequence homology with the framework regions of human antibodies, coupled with the high degree of structural homology of the antigen binding sites comprising the hypervariable loops with the binding sites of human antibodies, plus the fact that Camelidae conventional antibodies can be raised by active immunisation of an outbred animal population, which are phylogenetically quite distant from humans, has led the present inventors to surmise that conventional antibodies from the family Camelidae are an attractive starting point for engineering monoclonal antibodies having potential utility as human therapeutics.

Therefore, in accordance with a first aspect of the invention there is provided an antigen binding polypeptide comprising a VH domain and a VL domain, wherein at least one hypervariable loop or complementarity determining region (CDR) in the VH domain or the VL domain is obtained from a VH or VL domain of a species in the family Camelidae.

In one embodiment the antigen binding polypeptide of the invention may be immunoreactive with a target antigen. In another embodiment the antigen binding polypeptide may bind specifically to a target antigen.

In a non-limiting embodiment the antigen binding polypeptide of the invention may be a recombinant polypeptide.

In a non-limiting embodiment the antigen binding polypeptide of the invention may be a chimeric polypeptide.

In a non-limiting embodiment the antigen binding polypeptide of the invention may be a monoclonal antibody.

In a non-limiting embodiment the antigen binding polypeptide of the invention may be a recombinantly expressed chimeric monoclonal antibody.

In a non-limiting embodiment the antigen binding polypeptide according to the invention may comprise hypervariable loops or complementarity determining regions which have been obtained by active immunisation of a species in the family Camelidae.

In a second aspect the invention provides a process for preparing an antigen binding polypeptide immunoreactive with a target antigen, said process comprising:

(a) determining the nucleotide sequence encoding at least one hypervariable loop or complementarity determining region (CDR) of the VH and/or the VL domain of a Camelidae conventional antibody immunoreactive with said target antigen; and (b) expressing an antigen binding polypeptide immunoreactive with said target antigen, said antigen binding polypeptide comprising a VH and a VL domain, wherein at least one hypervariable loop or complementarity determining region (CDR) of the VH domain or the VL domain has an amino acid sequence encoded by the nucleotide sequence determined in part (a).

In a third aspect the invention provides a process for preparing a recombinant antigen binding polypeptide that is immunoreactive with (or specifically binds to) a target antigen, said antigen binding polypeptide comprising a VH domain and a VL domain, wherein at least one hypervariable loop or complementarity determining region (CDR) in the VH domain or the VL domain is obtained from a species in the family Camelidae, said process comprising the steps of:

(a) isolating Camelidae nucleic acid encoding at least one hypervariable loop or complementarity determining region (CDR) of the VH and/or the VL domain of a Camelidae conventional antibody immunoreactive with said target antigen;

(b) preparing a polynucleotide comprising a nucleotide sequence encoding hypervariable loop(s) or complementarity determining region(s) having amino acid sequence identical to the hypervariable loop(s) or complementarity determining region(s) encoded by the nucleic acid isolated in step (a), which polynucleotide encodes an antigen binding polypeptide comprising a VH domain and a VL domain that is immunoreactive with (or specifically binds to) said target antigen; and (c) expressing said antigen binding polypeptide from the recombinant polynucleotide of step (b).

The polynucleotide prepared in step (b) is preferably recombinant.

The invention further provides a polynucleotide comprising a nucleotide sequence which encodes an antigen binding polypeptide according to the first aspect of the invention, or which encodes a fragment of said antigen binding polypeptide, which fragment comprises at least one hypervariable loop or complementarity determining region (CDR) obtained from a VH or VL domain of a species in the family Camelidae.

The invention also provides an expression vector comprising the polynucleotide defined above operably linked to regulatory sequences which permit expression of the antigen binding polypeptide in a host cell or cell-free expression system, a host cell or cell-free expression system containing the expression vector, and a method of producing a recombinant antigen binding polypeptide which comprises culturing the host cell or cell free expression system under conditions which permit expression of the antigen binding polypeptide and recovering the expressed antigen binding polypeptide.

Still further, the invention provides a test kit comprising an antigen binding polypeptide according to the first aspect of the invention and a pharmaceutical formulation comprising an antigen binding polypeptide according to the first aspect of the invention and at least one pharmaceutically acceptable diluent, excipient or carrier.

BRIEF DESCRIPTION OF THE DRAWINGS

FIG. 2—illustrates the amino acid sequences of "humanized" variants of two Fabs immunoreactive with IL-1 Beta, coded 1E2 and 1F2. Based on the alignment against the closest human germlines, mutations in the VH and Vλ framework regions of 1E2 and 1F2 were proposed. Besides the fully humanized (hum) and the wild type (wt) V regions, also a "safe variant" with only three wild type residues remaining was proposed (safe).

FIG. 4—shows the results of phage ELISA in which phage displaying humanized variants of Fabs 1E2 and 1F2 were tested for binding to IL-1 Beta.

FIG. 5—shows the results of ELISA in which chimeric 1E2 was tested for binding to IL-1 Beta.

DETAILED DESCRIPTION OF THE INVENTION

The invention relates to a new platform technology for production of antigen binding polypeptides having specificity for a desired target antigen which is based on the conventional antibody repertoire of species in the family Camelidae, and to antigen binding polypeptides obtained using this technology platform.

Thus, in a first aspect the invention provides an antigen binding polypeptide comprising a VH domain and a VL domain, wherein at least one hypervariable loop or complementarity determining region (CDR) in the VH domain or the VL domain is obtained from a VH or VL domain of a species in the family Camelidae.

In the following passages different aspects of the invention are defined in more detail. Each aspect so-defined may be combined with any other aspect or aspects unless clearly indicated to the contrary. In particular, any feature indicated as being preferred or advantageous may be combined with any other feature or features indicated as being preferred or advantageous.

DEFINITIONS

The term "antigen binding polypeptide" refers to any polypeptide comprising a VH domain and a VL domain which is immunoreactive with, exhibits specific binding to, a target antigen. Exemplary antigen binding polypeptides include antibodies and immunoglobulins, and also antibody fragments, as discussed elsewhere herein.

The term "antigen", when referring to the "target antigen" against which the antigen binding polypeptide is immunoreactive, takes its normal meaning to a person of ordinary skill in the art, and includes, inter alia, polypeptide, peptide, polysaccharide, glycoprotein, polynucleotide (e.g. DNA), or synthetic chemical antigens.

The term "antigen" can also be used to describe the material employed in the immunisation of animals (e.g. camelids) during the manufacture of antigen binding polypeptides of the invention. In this context the term "antigen" may take a wider meaning, and could encompass purified forms of the antigen, and also crude or semi-purified preparations of the antigen, such as for example cells, cell lysates or supernatants, cell fractions, e.g. cell membranes, etc., plus haptens conjugated with an appropriate carrier protein. The "antigen" used in an immunisation protocol is not necessarily structurally identical to the "target antigen" with which the resulting antigen binding polypeptide is to immunoreact. Typically the "antigen" used for immunisation may be a truncated form of the "target antigen", e.g. a fragment containing an immunogenic epitope. Further characteristics of "antigens" used for active immunisation are described elsewhere herein, and would be generally known to a person skilled in the art.

"Specific binding" between and antigen binding polypeptide and a target antigen refers to immunological specificity. An antigen binding polypeptide binds "specifically" to its target antigen if it binds an epitope on the target antigen in preference to other epitopes.

"Specific binding" does not exclude cross-reactivity with other antigens bearing similar antigenic epitopes.

"Antibodies" (Abs) and "immunoglobulins" (Igs) are glycoproteins which exhibit binding specificity to a (target) antigen.

The camelid species are known to possess two different types of antibodies; the classical or "conventional" antibodies and also the heavy-chain antibodies.

As used herein, the term "conventional antibody" refers to antibodies of any isotype, including IgA, IgG, IgD, IgE or IgM. Native or naturally occurring "conventional" camelid antibodies are usually heterotetrameric glycoproteins, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end (N-terminal) a variable domain (VH) followed by a number of constant domains. Each light chain has a variable domain (VL) at one end (N-terminal) and a constant domain (CL) at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "heavy-chain antibody" refers to the second type of antibodies known to occur naturally in camelid species, such antibodies being naturally devoid of light chains (Hamers-Casterman, et al. Nature. 1993; 363; 446-8). The heavy-chain antibodies (abbreviated to HCAb) are composed of two heavy chains linked by a covalent disulphide bond. Each heavy chain in the HCAb has a variable domain at one end. The variable domains of HCAbs are referred to as "VHH" in order to distinguish them from the variable domains of the heavy chains of "conventional" camelid antibodies (VH). The VHH domains and VH domains are entirely distinct and are encoded by different gene segments in the camelid genome.

The VL domains in the polypeptide of the invention may be of the VLambda type or the Vkappa type. The term "VL domain" therefore refers to both VKappa and VLambda isotypes from Camelidae, and engineered variants thereof which contain one or more amino acid substitutions, insertions or deletions relative to a Camelidae VL domain.

The term "VH domain" refers to a VH domain of any known heavy chain isotype of Camelidae, including γ, ε, δ, α or μ isotypes, as well as engineered variants thereof which contain one or more amino acid substitutions, insertions or deletions relative to a Camelidae VH domain. The term "VH domain" refers only to VH domains of camelid conventional antibodies and does not encompass camelid VHH domains.

The term "variable" refers to the fact that certain portions of the variable domains VH and VL differ extensively in sequence among antibodies and are used in the binding and specificity of each particular antibody for its target antigen.

Figure 1:
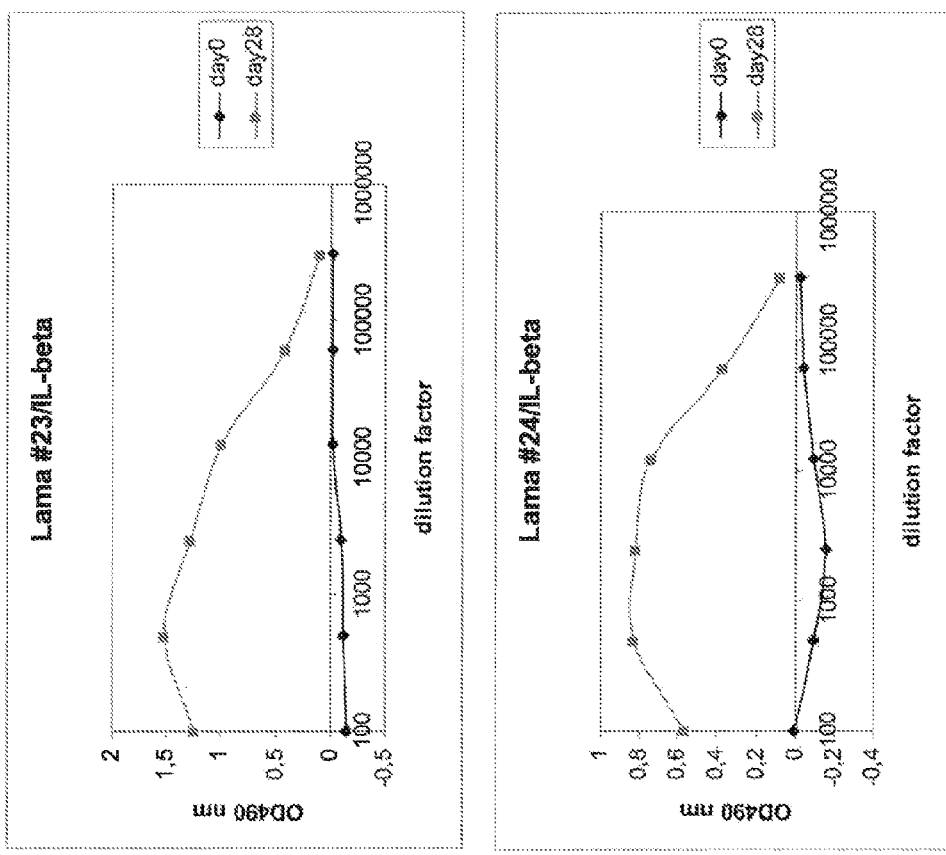
FIG. 1—shows the results of an ELISA in which sera from llamas immunised with IL1-Beta were tested for the presence of antibodies against IL1-Beta, on day 0 and day 28 following immunisation.

However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1(λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20:267-279 (2000)). The first, second and third hypervariable loops of the VKappa light chain domain are referred to herein as UM, L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes from Camelidae. The terms H1, H2 and H3 respectively refer to the first, second and third hypervariable loops of the VH domain, and encompass hypervariable loops obtained from any of the known heavy chain isotypes from Camelidae, including γ, ε, δ, α or μ.

The hypervariable loops L1, L2, L3, H1, H2 and H3 may each comprise part of a "complementarity determining region" or "CDR". The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains.

The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR). The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

The constant domains are not involved directly in binding of an antibody to an antigen, but exhibit various effector functions, such as participation of the antibody in antibody-dependent cellular toxicity (ADCC) or complement-dependent cytotoxicity (CDC).

In all aspects and embodiments of the invention, the Camelidae (or camelid) species (from which the hypervariable loops or CDRs of the antigen binding polypeptide of the invention are obtained) can be camel, llama, dromedary, vicunia, guanaco or alpaca and any crossings thereof. Llama (*Lama glama*) and alpaca (*Lama pacos*) are the preferred Camelidae species for all aspects of the invention.

The antigen binding polypeptides of the invention are characterised in that they contain at least one hypervariable loop or complementarity determining region which is obtained from a VH domain or a VL domain of a species in the family Camelidae. For the avoidance of doubt, the terms "VH domain" "VL domain" refer to domains derived from camelid conventional antibodies. This definition excludes the camelid heavy chain only VHH antibodies, and recombinant constructs containing solely HVs or CDRs of camelid VHH domains, which are not encompassed within the scope of the present invention.

By "hypervariable loop or complementarity determining region obtained from a VH domain or a VL domain of a species in the family Camelidae" is meant that that hypervariable loop (HV) or CDR has an amino acid sequence which is identical, or substantially identical, to the amino acid sequence of a hypervariable loop or CDR which is encoded by a Camelidae immunoglobulin gene. In this context "immunoglobulin gene" includes germline genes, immunoglobulin genes which have undergone rearrangement, and also somatically mutated genes. Thus, the amino acid sequence of the HV or CDR obtained from a VH or VL domain of a Camelidae species may be identical to the amino acid sequence of a HV or CDR present in a mature Camelidae conventional antibody. The term "obtained from" in this context implies a structural relationship, in the sense that the HVs or CDRs of the antigen binding polypeptide of the invention embody an amino acid sequence (or minor variants thereof) which was originally encoded by a Camelidae immunoglobulin gene. However, this does not necessarily imply a particular relationship in terms of the production process used to prepare the antigen binding polypeptide of the invention. As will be discussed below, there are several processes which may be used to prepare antigen binding polypeptides comprising HVs or CDRs with amino acid sequences identical to (or substantially identical to) sequences originally encoded by a Camelidae immunoglobulin gene.

For the avoidance of doubt, the terms "VH domain of a conventional antibody of a camelid" and "VH domain obtained from a species of Camelidae" are used synonymously and encompass VH domains which are the products of synthetic or engineered recombinant genes (including codon-optimised synthetic genes), which VH domains have an amino acid sequence identical to (or substantially identical to) the amino acid sequence of a VH domain encoded by a Camelidae immunoglobulin gene (germline, rearranged or somatically mutated). Similarly, the terms "VL domain of a conventional antibody of a camelid" and "VL domain obtained from a species of Camelidae" are used synonymously and encompass VL domains which are the products of synthetic or engineered recombinant genes (including codon-optimised synthetic genes), which VL domains have an amino acid sequence identical to (or substantially identical to) the amino acid sequence of a VL domain encoded by a Camelidae immunoglobulin gene (germline, rearranged or somatically mutated).

The antigen binding polypeptides of the invention are typically recombinantly expressed polypeptides, and may be chimeric polypeptides. The term "chimeric polypeptide" refers to an artificial (non-naturally occurring) polypeptide which is created by juxtaposition of two or more peptide fragments which do not otherwise occur contiguously. Included within this definition are "species" chimeric polypeptides created by juxtaposition of peptide fragments encoded by two or more species, e.g. camelid and human.

The antigen binding polypeptides of the invention are not naturally occurring human antibodies, specifically human autoantibodies, due to the requirement for at least one hypervariable loop (or CDR) from camelid. By "naturally occurring" human antibody is meant an antibody which is naturally expressed within a human subject. Antigen binding polypeptides having an amino acid sequence which is 100% identical to the amino acid sequence of a naturally occurring human antibody, or a fragment thereof, which natural antibody or fragment is not chimeric and has not been subject to any engineered changes in amino acid sequence (excluding somatic mutations) are excluded from the scope of the invention.

The antigen binding polypeptides according to the invention comprise both a heavy chain variable (VH) domain and a light chain variable (VL) domain, and are characterised in that at least one hypervariable loop or complementarity determining region in either the VH domain or the VL domain is obtained from a species in the family Camelidae.

In alternative embodiments, either H1 or H2, or both H1 and H2 in the VH domain may be obtained from a species in the family Camelidae, and independently either L1 or L2 or both L1 and L2 in the VL domain may be obtained from a species in the family Camelidae. In further embodiments H3 in the VH domain or L3 in the VL domain may also be obtained from a species in the family Camelidae. All possible permutations of the foregoing are permitted.

In one specific embodiment each of the hypervariable loops H1, H2, H3, L1, L2 and L3 in both the VH domain and the VL domain may be obtained from a species in the family Camelidae.

In one embodiment the entire VH domain and/or the entire VL domain may be obtained from a species in the family Camelidae. The Camelidae VH domain and/or the Camelidae VL domain may then be subject to protein engineering, in which one or more amino acid substitutions, insertions or deletions are introduced into the Camelidae sequence. These engineered changes preferably include amino acid substitutions relative to the Camelidae sequence. Such changes include "humanisation" or "germlining" wherein one or more amino acid residues in a camelid-encoded VH or VL domain are replaced with equivalent residues from a homologous human-encoded VH or VL domain.

In certain embodiments, Camelidae hypervariable loops (or CDRs) may be obtained by active immunisation of a species in the family Camelidae with a desired target antigen.

As discussed and exemplified in detail herein, following immunisation of Camelidae (either the native animal or a transgenic animal engineered to express the immunoglobulin repertoire of a camelid species) with the target antigen, B cells producing (conventional Camelidae) antibodies having specificity for the desired antigen can be identified and polynucleotide encoding the VH and VL domains of such antibodies can be isolated using known techniques.

Thus, in a specific embodiment, the invention provides a recombinant antigen binding polypeptide immunoreactive with a target antigen, the polypeptide comprising a VH domain and a VL domain, wherein at least one hypervariable loop or complementarity determining region in the VH domain or the VL domain is obtained from a VH or VL domain of a species in the family Camelidae, which antigen binding polypeptide is obtainable by a process comprising the steps of:

(a) immunising a species in the family Camelidae with a target antigen or with a polynucleotide encoding said target antigen and raising an antibody to said target antigen;

(b) determining the nucleotide sequence encoding at least one hypervariable loop or complementarity determining region (CDR) of the VH and/or the VL domain of a Camelidae conventional antibody immunoreactive with said target antigen; and (c) expressing an antigen binding polypeptide immunoreactive with said target antigen, said antigen binding polypeptide comprising a VH and a VL domain, wherein at least one hypervariable loop or complementarity determining region (CDR) of the VH domain or the VL domain has an amino acid sequence encoded by the nucleotide sequence determined in part (a).

Isolated Camelidae VH and VL domains obtained by active immunisation can be used as a basis for engineering antigen binding polypeptides according to the invention. Starting from intact Camelidae VH and VL domains, it is possible to engineer one or more amino acid substitutions, insertions or deletions which depart from the starting Camelidae sequence. In certain embodiments, such substitutions, insertions or deletions may be present in the framework regions of the VH domain and/or the VL domain. The purpose of such changes in primary amino acid sequence may be to reduce presumably unfavourable properties (e.g. immunogenicity in a human host (so-called humanization), sites of potential product heterogeneity and or instability (glycosylation, deamidation, isomerisation, etc.) or to enhance some other favourable property of the molecule (e.g. solubility, stability, bioavailability, etc.). In other embodiments, changes in primary amino acid sequence can be engineered in one or more of the hypervariable loops (or CDRs) of a Camelidae VH and/or VL domain obtained by active immunisation. Such changes may be introduced in order to enhance antigen binding affinity and/or specificity, or to reduce presumably unfavourable properties, e.g. immunogenicity in a human host (so-called humanization), sites of potential product heterogeneity and or instability, glycosylation, deamidation, isomerisation, etc., or to enhance some other favourable property of the molecule, e.g. solubility, stability, bioavailability, etc.

Thus, in one embodiment, the invention provides a recombinant antigen binding polypeptide which contains at least one amino acid substitution in at least one framework or CDR region of either the VH domain or the VL domain in comparison to a Camelidae VH or VL domain obtained by active immunisation of a species in the family Camelidae with a target antigen. This particular embodiment excludes antigen binding polypeptides containing native Camelidae VH and VL domains produced by active immunisation As an alternative to "active immunisation" with a target antigen (or a composition comprising the target antigen or a polynucleotide encoding it) it is also possible to make use of immune responses in diseased Camelidae animals or naturally occurring immune responses within Camelidae species as a source of VH and/or VL domains which can be used as components of antigen binding polypeptides with the desired antigen-binding properties. Such VH/VL domains may also be used as the starting point for engineering antigen-binding polypeptides in an analogous manner to VH/VL domains obtained by active immunisation. The invention still further encompasses the use of non-immune libraries, and to antigen-binding polypeptides obtained/derived therefrom.

In other embodiments, the invention encompasses "chimeric" antibody molecules comprising VH and VL domains from Camelidae (or engineered variants thereof) and one or more constant domains from a non-camelid antibody, for example human-encoded constant domains (or engineered variants thereof). The invention also extends to chimeric antigen binding polypeptides (e.g. antibody molecules) wherein one of the VH or the VL domain is camelid-encoded, and the other variable domain is non-camelid (e.g. human). In such embodiments it is preferred that both the VH domain and the VL domain are obtained from the same species of camelid, for example both VH and VL may be from *Lama glama* or both VH and VL may be from *Lama pacos* (prior to introduction of engineered amino acid sequence variation). In such embodiments both the VH and the VL domain may be derived from a single animal, particularly a single animal which has been actively immunised.

As an alternative to engineering changes in the primary amino acid sequence of Camelidae VH and/or VL domains, individual Camelidae hypervariable loops or CDRs, or combinations thereof, can be isolated from Camelidae VH/VL domains and transferred to an alternative (i.e. non-Camelidae) framework, e.g. a human VH/VL framework, by CDR grafting.

Sequence Identity/Homology with Human Variable Domains

The present inventors have observed that Camelidae germline and somatically mutated DNA sequences encoding both the VH and the VL domains of conventional antibodies from species in the family Camelidae exhibit a high degree of sequence identity/sequence homology with the human germline DNA sequences which encode VH and VL domains of human antibodies, over the framework regions.

Thus, the antigen binding polypeptides of the invention are characterised in that they exhibit a high degree of amino acid sequence homology with VH and VL domains of human antibodies.

In one embodiment the VH domain of the antigen binding polypeptide according to the invention may exhibit an amino acid sequence identity or sequence homology of 80% or greater with one or more human VH domains across the framework regions FR1, FR2, FR3 and FR4. In other embodiments the amino acid sequence identity or sequence homology between the VH domain of the polypeptide of the invention and one or more human VH domains may be 85% or greater, 90% or greater, 95% or greater, 97% or greater, or up to 99% or even 100%, of course with the proviso that at least one hypervariable loop or CDR is obtained from Camelidae, i.e. has an amino acid sequence which is identical (or substantially identical) to the amino acid sequence of a hypervariable loop or CDR encoded by a Camelidae VH or VL gene.

In one embodiment the VH domain of the polypeptide of the invention may contain one or more amino acid sequence mis-matches across the framework regions FR1, FR2, FR3 and FR4, in comparison to the closest matched human VH sequence. This latter embodiment would expressly exclude polypeptides comprising a VH domain, or both VH and VL domains, in which the framework region has entirely human sequence.

In another embodiment the VL domain of the antigen binding polypeptide according to the invention may exhibit a sequence identity or sequence homology of 80% or greater with one or more human VL domains across the framework regions FR1, FR2, FR3 and FR4. In other embodiments the amino acid sequence identity or sequence homology between the VL domain of the polypeptide of the invention and one or more human VL domains may be 80% or greater 90% or greater, 95% or greater, 97% or greater, or up to 99% or even 100%.

In one embodiment the VL domain of the polypeptide of the invention may contain one or more amino acid sequence mis-matches across the framework regions FR1, FR2, FR3 and FR4, in comparison to the closest matched human VL sequence. This latter embodiment would expressly exclude polypeptides comprising VL domain, or both VL and VH domains in which the framework region has entirely human sequence.

The antigen binding polypeptide of the invention may comprise a "fully human" VH or VL domain, provided that only one fully human variable domain is present, and then in combination with a variable domain comprising hypervariable loop(s) or CDR(s) obtained from Camelidae.

Representative alignments of Camelidae and human germline sequences included in the accompanying examples reveal that the conventional camelid VH and VL domains exhibit a remarkably high sequence homology to their human counterparts. From these examples it can be concluded that typically less than 8, and often only as few as 5 amino acid residues present in the framework regions of a VH or VL domain differ in a given position from the closest human germline-encoded sequences. Given that there are no structural limitations associated with those positions, humanization by site directed mutagenesis is expected to be straightforward.

Therefore, in a particular embodiment, the antigen binding polypeptides of the invention may comprise VH and/or VL domains of conventional Camelidae antibodies, for example conventional Camelidae antibodies obtained (obtainable) by active immunisation of camelidae with a target antigen (or polynucleotide encoding the target antigen), wherein said VH and VL domains have been (independently) engineered to introduce a total of between 1 and 10, i.e. 1, 2, 3, 4, 5, 6, 7, 8, 9 or 10 amino acid substitutions across the framework regions FR1, FR2, FR3 and FR4 in either one or both of the VH domain and the VL domain. Such amino acid substitutions may include (but are not limited to) substitutions which result in "humanisation", by replacing mis-matched amino acid residues in a starting Camelidae VH or VL domain with the equivalent residue found in a human germline-encoded VH or VL domain. It is also possible to independently make amino acid substitutions in the hypervariable loops (CDRs) of said camelid-derived VH and VL domains, and such variants may form part of the present invention. References herein to "amino acid substitutions" include substitutions in which a naturally occurring amino acid is replaced with a non-natural amino acid, or an amino acid subjected to post-translational modification.

Before analyzing the percentage sequence identity between Camelidae and human germline VH and VL, the canonical folds may be determined, which allows the identification of the family of human germline segments with the identical combination of canonical folds for H1 and H2 or L1 and L2 (and L3). Subsequently the human germline family member that has the highest degree of sequence homology with the Camelidae variable region of interest is chosen for scoring the sequence homology. The determination of Chothia canonical classes of hypervariable loops L1, L2, L3, H1 and H2 was performed with the bioinformatics tools publicly available on webpage www.bioinf.org.uk/abs/chothia.html.page. The output of the program shows the key residue requirements in a datafile. In these datafiles, the key residue positions are shown with the allowed amino acids at each position. The sequence of the variable region of the antibody is given as input and is first aligned with a consensus antibody sequence to assign the Kabat numbering scheme. The analysis of the canonical folds uses a set of key residue templates derived by an automated method developed by Martin and Thornton (Martin et al., J. Mol. Biol. 263:800-815 (1996)).

With the particular human germline V segment known, which uses the same combination of canonical folds for H1 and H2 or L1 and L2 (and L3), the best matching family member in terms of sequence homology was determined. With bioinformatics tools the percentage sequence identity between Camelidae VH and VL domain framework amino acid sequences and corresponding sequences encoded by the human germline can be determined, but actually manual aligning of the sequences can be applied as well. Human immunoglobulin sequences can be identified from several protein data bases, such as VBase (http://vbase.mrc-cpe.cam.ac.ukl) or the Pluckthun/Honegger database (http://www-.bioc.unizh.ch/antibody/Sequences/Germlines. To compare the human sequences to the V regions of Camelidae VH or VL domains a sequence alignment algorithm such as available via websites like wwwexpasy.ch/tools/#align can be used, but also manual alignment with the limited set of sequences can be performed. Human germline light and heavy chain sequences of the families with the same combinations of canonical folds and with the highest degree of homology with the framework regions 1, 2, and 3 of each chain are selected and compared with the Camelidae variable region of interest; also the FR4 is checked against the human germline JH and JK or JL regions.

Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences). However, for the purposes of humanization, residues in framework regions identical to members of other human germline families, which do not have the same combination of canonical folds, can be considered "human", despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et la., Clin. Cancer Res. 5:3095-3100 (1999)) and Ono and colleagues (Ono et al., Mol. Immunol. 36:387-395 (1999)).

The boundaries of the individual framework regions may be assigned using the IMGT numbering scheme, which is an adaptation of the numbering scheme of Chothia (Lefranc et al., NAR 27: 209-212 (1999); http://imgt.cines.fr).

Despite the unexpectedly high sequence homology between Camelidae and human across the framework regions of the VH and VL domains, it is nevertheless possible to distinguish camelid-encoded hypervariable loops (CDRs) from human-encoded hypervariable loops (CDRs) by straightforward sequence comparison with camelid and human germline VH and VL sequences.

Structural Homology with Human-Encoded VH and VL Domains

A preferred embodiment is also to use Camelid hypervariable loops or CDRs having human or human-like canonical folds, as discussed in detail below.

Thus, in one embodiment at least one hypervariable loop or CDR in either the VH domain or the VL domain of the antigen binding polypeptide of the invention is obtained from a VH or VL domain obtained from a species of Camelidae, yet exhibits a predicted or actual canonical fold structure which is substantially identical to a canonical fold structure which occurs in human antibodies.

It is well established in the art that although the primary amino acid sequences of hypervariable loops present in both VH domains and VL domains encoded by the human germline are, by definition, highly variable, all hypervariable loops, except CDR H3 of the VH domain, adopt only a few distinct structural conformations, termed canonical folds (Chothia et al., J. Mol. Biol. 196:901-917 (1987); Tramontano et al. Proteins 6:382-94 (1989)), which depend on both the length of the hypervariable loop and presence of the so-called canonical amino acid residues (Chothia et al., J. Mol. Biol. 196:901-917 (1987)). Actual canonical structures of the hypervariable loops in intact VH or VL domains can be determined by structural analysis (e.g. X-ray crystallography), but it is also possible to predict canonical structure on the basis of key amino acid residues which are characteristic of a particular structure (discussed further below). In essence, the specific pattern of residues that determines each canonical structure forms a "signature" which enables the canonical structure to be recognised in hypervariable loops of a VH or VL domain of unknown structure; canonical structures can therefore be predicted on the basis of primary amino acid sequence alone.

Based on analysis of germline and somatically mutated VH and VL sequences, the present inventors predict that the hypervariable loops of Camelidae VH and VL domains (with the exception of H3 in the VH domain and sometimes also L3 in the VL domain) also adopt canonical fold structures which are substantially identical to canonical fold structures adopted by the hypervariable loops of human antibodies.

The predicted canonical fold structures for the hypervariable loops of any given VH or VL sequence in an antigen binding polypeptide can be analysed using algorithms which are publicly available from www.bioinf.org.uk/abs/chothia.html, www.biochem.ucl.ac.uk/~martin/antibodies.html and www.bioc.unizh.ch/antibody/Sequences/Germlines/Vbase_hVk.html. These tools permit query VH or VL sequences to be aligned against human VH or VL domain sequences of known canonical structure, and a prediction of canonical structure made for the hypervariable loops of the query sequence.

In the case of the VH domain, H1 and H2 loops derived from Camelidae may be scored as having a canonical fold structure "substantially identical" to a canonical fold structure known to occur in human antibodies if at least the first, and preferable both, of the following criteria are fulfilled:

1. An identical length, determined by the number of residues, to the closest matching human canonical structural class.

2. At least 33% identity, preferably at least 50% identity with the key amino acid residues described for the corresponding human H1 and H2 canonical structural classes. (note for the purposes of the foregoing analysis the H1 and H2 loops are treated separately and each compared against its closest matching human canonical structural class)

The foregoing analysis relies on prediction of the canonical structure of the Camelidae H1 and H2 loops. If the actual structure of the H1 and H2 loops is known, for example based on X-ray crystallography, then the H1 and H2 loops derived from Camelidae may also be scored as having a canonical fold structure "substantially identical" to a canonical fold structure known to occur in human antibodies if the length of the loop differs from that of the closest matching human canonical structural class (typically by ±1 or ±2 amino acids) but the actual structure of the Camelidae H1 and H2 loops matches the structure of a human canonical fold.

Key amino acid residues found in the human canonical structural classes for the first and second hypervariable loops of human VH domains (H1 and H2) are described by Chothia et al., J. Mol. Biol. 227:799-817 (1992), the contents of which are incorporated herein in their entirety by reference. In particular, Table 3 on page 802 of Chothia et al., which is specifically incorporated herein by reference, lists preferred amino acid residues at key sites for H1 canonical structures found in the human germline, whereas Table 4 on page 803, also specifically incorporated by reference, lists preferred amino acid residues at key sites for CDR H2 canonical structures found in the human germline.

The accompanying examples contain an analysis of germline VH sequences from Camelidae species (specifically llama and dromedary) comparing the actual amino acid residues found in Camelidae versus the amino acid residues in the closest human germline VH sequence, for each of the positions in H1 and H2, and underlying framework regions, considered to be key for the canonical fold structure according to the criteria of Chothia et al., J Mol Biol. 227:799-817 (1992). It is observed that the number of identical key residues between camelid and human is most often above 33%, and typically in the range of from 50 to 100%.

In one embodiment, both H1 and H2 in the VH domain of the antigen binding polypeptide of the invention are obtained from a VH domain of a Camelidae species, yet exhibit a predicted or actual canonical fold structure which is substantially identical to a canonical fold structure which occurs in human antibodies.

The inventors surmise that it is important not only for the hypervariable loops, specifically H1 and H2 in the VH domain, individually to have canonical structures of a type which occurs naturally in human antibodies, it is also important for H1 and H2 in any given VH domain to form a combination of canonical fold structures which is identical to a combination of canonical structures known to occur in at least one human germline VH domain. It has been observed that only certain combinations of canonical fold structures at H1 and H2 actually occur in VH domains encoded by the human germline. The present inventors were surprised to discover that every available Camelidae germline or somatically mutated VH sequence which could be analysed exhibited not only individual canonical fold structures at H1 and H2 substantially identical to those used in human antibodies, but also the correct combinations of structures at H1 and H2 to match combinations found in human antibodies. This represents a distinct advantage over other platforms for production of antibodies for potential therapeutic use in humans which may produce antibodies having "correct" human-like canonical fold structures at H1 and H2 but in a combination which does not occur in human antibodies. By way of example, the inventors' own analysis of the structure of antibodies derived from non-human primates (Biogen IDEC's galiximab (anti-CD80) an lumiliximab (anti-CD23) and the non-human primate mAb against Anthrax Toxin from Pelat et al., J. Mol. Biol. 384:1400-7 (2008)) indicates that structurally they are not consistently very close to the human antibody structure, particularly having regard to the combination of canonical folds. The absence of a correct combination of canonical folds at H1 and H2 could lead to a given antigen binding polypeptide (which is "humanised" in the framework regions) being immunogenic in a human host.

Thus, in a further embodiment H1 and H2 in the VH domain of the antigen binding polypeptide of the invention are obtained from a VH domain of a Camelidae species, yet form a combination of predicted or actual canonical fold structures which is identical to a combination of canonical fold structures known to occur in a human germline or somatically mutated VH domain.

In non-limiting embodiments H1 and H2 in the VH domain of the antigen binding polypeptide of the invention are obtained from a VH domain of a Camelidae species, and form one of the following canonical fold combinations: 1-1, 1-2, 1-3, 1-6, 1-4, 2-1, 3-1 and 3-5.

It is preferred that the VH domain of the antigen binding polypeptide of the invention exhibit both high sequence identity/sequence homology with human VH, and also that the hypervariable loops in the VH domain exhibit structural homology with human VH.

It may be advantageous for the canonical folds present at H1 and H2 in the VH domain of the antigen binding polypeptide according to the invention, and the combination thereof, to be "correct" for the human VH germline sequence which represents the closest match with the VH domain of the antigen binding polypeptide of the invention in terms of overall primary amino acid sequence identity. By way of example, if the closest sequence match is with a human germline VH3 domain, then it may be advantageous for H1 and H2 (obtained from Camelidae) to form a combination of canonical folds which also occurs naturally in a human VH3 domain.

Thus, in one embodiment the VH domain of the antigen binding polypeptide of the invention may exhibit a sequence identity or sequence homology of 80% or greater, 85% or greater, 90% or greater, 95% or greater, 97% or greater, or up to 99% or even 100% with a human VH domain across the framework regions FR1, FR2, FR3 and FR4, and in addition H1 and H2 in the same antigen binding polypeptide are obtained from a VH domain of a Camelidae species, but form a combination of predicted or actual canonical fold structures which is the same as a canonical fold combination known to occur naturally in the same human VH domain.

In other embodiments, L1 and L2 in the VL domain of the antigen binding polypeptide of the invention are each obtained from a VL domain of a Camelidae species, and each exhibit a predicted or actual canonical fold structure which is substantially identical to a canonical fold structure which occurs in human antibodies.

As with the VH domains, the hypervariable loops of VL domains of both VLambda and VKappa types can adopt a limited number of conformations or canonical structures, determined in part by length and also by the presence of key amino acid residues at certain canonical positions.

L1, L2 and L3 loops obtained from a VL domain of a Camelidae species, yet may be scored as having a canonical fold structure "substantially identical" to a canonical fold structure known to occur in human antibodies if at least the first, and preferable both, of the following criteria are fulfilled:

1. An identical length, determined by the number of residues, to the closest matching human structural class.
2. At least 33% identity, preferably at least 50% identity with the key amino acid residues described for the corresponding human L1 or L2 canonical structural classes, from either the VLambda or the VKappa repertoire.

(note for the purposes of the foregoing analysis the L1 and L2 loops are treated separately and each compared against its closest matching human canonical structural class)

The foregoing analysis relies on prediction of the canonical structure of the Camelidae L1, L2 and L3 loops. If the actual structure of the L1, L2 and L3 loops is known, for example based on X-ray crystallography, then L1, L2 or L3 loops derived from Camelidae may also be scored as having a canonical fold structure "substantially identical" to a canonical fold structure known to occur in human antibodies if the length of the loop differs from that of the closest matching human canonical structural class (typically by ±1 or ±2 amino acids) but the actual structure of the Camelidae loops matches a human canonical fold.

Key amino acid residues found in the human canonical structural classes for the CDRs of human VLambda and VKappa domains are described by Morea et al. Methods, 20: 267-279 (2000) and Martin et al., J. Mol. Biol., 263:800-815 (1996). The structural repertoire of the human VKappa domain is also described by Tomlinson et al. EMBO J. 14:4628-4638 (1995), and that of the VLambda domain by Williams et al. J. Mol. Biol., 264:220-232 (1996). The contents of all these documents are to be incorporated herein by reference.

The accompanying examples contain an analysis of germline VL sequences or both kappa and lambda type from Camelidae species (specifically llama and dromedary), comparing the actual amino acid residues found in Camelidae versus the amino acid residues in the closest human germline VLambda or VKappa sequence, for each of the positions in L1 and L2 considered to be key for the canonical fold structure. It is observed that the number of identical key residues between camelid and human is typically in the range of from 33 to 100%, more often between 50 to 100%, typically closer to 100%.

L1 and L2 in the VL domain may form a combination of predicted or actual canonical fold structures which is identical to a combination of canonical fold structures known to occur in a human germline VL domain.

In non-limiting embodiments L1 and L2 in the VLambda domain may form one of the following canonical fold combinations: 11-7, 13-7(A,B,C), 14-7(A,B), 12-11, 14-11 and 12-12 (as defined in Williams et al. J. Mol. Biol. 264:220-32 (1996) and as shown on http://www.bioc.uzh.ch/antibody/Sequences/Germlines/VBase_hVL.html). In non-limiting embodiments L1 and L2 in the Vkappa domain may form one of the following canonical fold combinations: 2-1, 3-1, 4-1 and 6-1 (as defined in Tomlinson et al. EMBO J. 14:4628-38 (1995) and as shown on http://www.bioc.uzh.ch/antibody/Sequences/Germlines/VBase_hVK.html).

In a further embodiment, all three of L1, L2 and L3 in the VL domain may exhibit a substantially human structure. Most human Vκ germline segments encode also a single conformation of the L3 loop (type 1), which is stabilized by the conserved cis-proline on position 95, but other conformations in rearranged sequences are possible due to the process of V-J joining and the potential loss of this proline residue.

The publicly available somatically mutated dromedary Vκ sequences have a type 1 canonical fold for L3(κ) like is found in human kappa germline sequences, and Proline on position 95 occurs in six out of seven dromedary Vκ domains. Therefore, where the antigen binding polypeptide contains a Vκ domain, this domain may possess the conserved Proline residue on position 95.

The structural repertoire of the human VL germline sequences was analyzed by Williams and colleagues (Williams et al., J. Mol. Biol. 264:220-232 (1996)). The three families analyzed here encode identical conformations of the L2 loop. The L3 loop conformation is thought to be more highly variable, as there is some length variation and no cis-proline residue. Indeed the available somatically mutated dromedary Vλ sequences show a high variability in the length of L3. Most of these have a canonical fold for L3 (f.i. VLambda 3-1 family members CamvI19 (10A) and CamvI20 (1/9A), VLambda 2-18 family members CamvI5, 17, 30, 36 and 52 (all 10B) and VLambda 1-40 family member CamvI44 (5/11A)).

It is preferred that the VL domain of the antigen binding polypeptide of the invention exhibit both high sequence identity/sequence homology with human VL, and also that the hypervariable loops in the VL domain exhibit structural homology with human VL.

In one embodiment, the VL domain of the antigen binding polypeptide of the invention may exhibit a sequence identity of 80% or greater, 85% or greater, 90% or greater, 95% or greater, 97% or greater, or up to 99% or even 100% with a human VL domain across the framework regions FR1, FR2, FR3 and FR4, and in addition hypervariable loop L1 and hypervariable loop L2 may form a combination of predicted or actual canonical fold structures which is the same as a canonical fold combination known to occur naturally in the same human VL domain.

It is, of course, envisaged that VH domains exhibiting high sequence identity/sequence homology with human VH, and also structural homology with hypervariable loops of human VH will be combined with VL domains exhibiting high sequence identity/sequence homology with human VL, and also structural homology with hypervariable loops of human VL to provide antigen binding polypeptides containing (camelid-derived) VH/VL pairings with maximal sequence and structural homology to human-encoded VH/VL pairings. A particular advantage of the camelid platform provided by the invention is that both the VH domain and the VL domain exhibit high sequence and structural homology with the variable domains of human antibodies.

Structure of the Antigen Binding Polypeptide

The antigen binding polypeptide of the invention can take various different embodiments, provided that both a VH domain and a VL domain are present. Thus, in non-limiting embodiments the antigen binding polypeptide may be an immunoglobulin, an antibody or antibody fragment. The term "antibody" herein is used in the broadest sense and encompasses, but is not limited to, monoclonal antibodies (including full length monoclonal antibodies), polyclonal antibodies, multispecific antibodies (e.g., bispecific antibodies), so long as they exhibit the appropriate specificity for a target antigen. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes) on the antigen, each monoclonal antibody is directed against a single determinant or epitope on the antigen.

"Antibody fragments" comprise a portion of a full length antibody, generally the antigen binding or variable domain thereof. Examples of antibody fragments include Fab, Fab', F(ab')2, bi-specific Fab's, and Fv fragments, diabodies, linear antibodies, single-chain antibody molecules, a single chain variable fragment (scFv) and multispecific antibodies formed from antibody fragments (see Holliger and Hudson, Nature Biotechnol. 23:1126-36 (2005), the contents of which are incorporated herein by reference).

In non-limiting embodiments, antibodies and antibody fragments according to the invention may comprise CH1 domains and/or CL domains, the amino acid sequence of which is fully or substantially human. Where the antigen binding polypeptide of the invention is an antibody intended for human therapeutic use, it is typical for the entire constant region of the antibody, or at least a part thereof, to have fully or substantially human amino acid sequence. Therefore, an antibody of the invention must comprise VH and VL domains, at least one of which includes at least one hypervariable loop derived from Camelidae, but one or more or any combination of the CH1 domain, hinge region, CH2 domain, CH3 domain and CL domain (and CH4 domain if present) may be fully or substantially human with respect to its amino acid sequence.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence.

As discussed elsewhere herein, it is contemplated that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the antibody, it may be desirable to modify the antibody of the invention with respect to its binding properties to Fc receptors, for example to modulate effector function. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp. Med. 176:1191-1195 (1992) and Shopes, B. J. Immunol. 148:2918-2922 (1992). Alternatively, an antibody can be engineered which has dual Fc regions and may thereby have enhanced complement lysis and ADCC capabilities. See Stevenson et al., Anti-Cancer Drug Design 3:219-230 (1989). The invention also contemplates immunoconjugates comprising an antibody as described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension.

The invention can, in certain embodiments, encompass chimeric Camelidae/human antibodies, and in particular chimeric antibodies in which the VH and VL domains are of fully camelid sequence (e.g. Llama or alpaca) and the remainder of the antibody is of fully human sequence. In preferred embodiments the invention also encompasses "humanised" or "germlined" Camelidae antibodies, and Camelidae/human chimeric antibodies, in which the VH and VL domains contain one or more amino acid substitutions in the framework regions in comparison to Camelidae VH and VL domains obtained by active immunisation. Such "humanisation" increases the % sequence identity with human germline VH or VL domains by replacing mis-matched amino acid residues in a starting Camelidae VH or VL domain with the equivalent residue found in a human germline-encoded VH or VL domain.

The invention still further encompasses CDR-grafted antibodies in which CDRs (or hypervariable loops) derived from a Camelidae antibody, for example an Camelidae antibody raised by active immunisation with a target antigen, or otherwise encoded by a camelid gene, are grafted onto a human VH and VL framework, with the remainder of the antibody also being of fully human origin. However, given the high degree of amino acid sequence homology and structural homology they have observed between Camelidae and human immunoglobulins, the inventors anticipate that in the majority of cases it will be possible to achieve the levels of human homology required for in vivo therapeutic use via "humanisation" of the framework regions of camelid-derived VH and VL domains without the need for CDR grafting or via CDR grafting on to limited number of backbone sequences without the need for veneering (also see Almagro et al, Frontiers in Bioscience 13: 1619-1633 (2008), the contents of which are incorporated herein by reference).

Humanised, chimeric and CDR-grafted antibodies according to the invention, particularly antibodies comprising hypervariable loops derived from active immunisation of Camelidae with a target antigen, can be readily produced using conventional recombinant DNA manipulation and expression techniques, making use of prokaryotic and eukaryotic host cells engineered to produce the polypeptide of interest and including but not limited to bacterial cells, yeast cells, mammalian cells, insect cells, plant cells, some of them as described herein and illustrated in the accompanying examples.

The invention also encompasses antigen binding polypeptides wherein either one or other of the VH or VL domain is obtained from Camelidae, or contains at least one CDR or hypervariable region derived from Camelidae, and the "other" variable domain has non-camelid, e.g. human, amino acid sequence. Thus, it is contemplated to pair a camelid VH domain with a human VL domain, or to pair a human VH domain with a camelid VL domain. Such pairings may increase the available antigen-binding repertoire from which to select high affinity binders with the desired antigen binding properties.

The invention still further extends to antigen binding polypeptides wherein the hypervariable loop(s) or CDR(s) of the VH domain and/or the VL domain are obtained from Camelidae, but wherein at least one of said (camelid-derived) hypervariable loops or CDRS has been engineered to include one or more amino acid substitutions, additions or deletions relative to the camelid-encoded sequence. Such changes include "humanisation" of the hypervariable loops/CDRs. Camelid-derived HVs/CDRs which have been engineered in this manner may still exhibit an amino acid sequence which is "substantially identical" to the amino acid sequence of a camelid-encoded HV/CDR. In this context, "substantial identity" may permit no more than one, or no more than two amino acid sequence mis-matches with the camelid-encoded HV/CDR.

Antibodies according to the invention may be of any isotype. Antibodies intended for human therapeutic use will typically be of the IgA, IgD, IgE IgG, IgM type, often of the IgG type, in which case they can belong to any of the four sub-classes IgG1, IgG2a and b, IgG3 or IgG4. Within each of these sub-classes it is permitted to make one or more amino acid substitutions, insertions or deletions within the Fc portion, or to make other structural modifications, for example to enhance or reduce Fc-dependent functionalities.

Antigen binding polypeptides according to the invention may be useful in a wide range of applications, both in research and in the diagnosis and/or treatment of diseases. Because of the high degree of amino acid sequence identity with the VH and VL domains of natural human antibodies, and the high degree of structural homology (specifically the correct combinations of canonical folds as are found in human antibodies) the antigen binding polypeptides of the invention, particularly in the form of monoclonal antibodies, will find particular utility as human therapeutic agents.

The invention provides a platform for production of antigen binding polypeptides, and specifically monoclonal antibodies, against a wide range of antigens and in its broadest aspect the invention is not intended to be limited with respect to the exact identity of the target antigen, nor indeed the specificity or affinity of binding to the target antigen. However, in particular, non-limiting, embodiments the target antigen may be a non-camelid antigen, a bacterial antigen, a viral antigen or a human antigen. In a preferred embodiment the target antigen may be an antigen of particular therapeutic importance. The term "target of therapeutic importance" refers to a target involved in formation, onset, progression, mediation of human or animal diseases or of the effects related to the respective disease. Included within this definition are targets wherein the expression levels and/or activity of the target are modulated by antibody binding (e.g. receptors whose activity may be modulated by binding of agonist or antagonist antibodies), and targets wherein the activity and/or expression of the target has a direct or indirect impact on a disease.

By way of example, "human antigens" may include naturally occurring human polypeptides (proteins) which function as receptors, receptor ligands, cell-signalling molecules, hormones, cytokines or cytokine receptors, neurotransmitters, etc. By "naturally occurring" is meant that the polypeptide is expressed within the human body, at any stage if its development, including polypeptides expressed by the human body during the course of a disease.

Non-limiting embodiments of the antigen binding polypeptide of the invention include the following:

A chimeric antigen binding polypeptide comprising a VH domain and a VL domain, wherein at least one hypervariable loop or complementarity determining region (CDR) in the VH domain or the VL domain is obtained from a VH or VL domain of a species in the family Camelidae. In a particular embodiment both the VH domain and the VL domain are obtained from Llama (*Lama glama*).

A recombinantly expressed antigen binding polypeptide comprising a VH domain and a VL domain, wherein at least one hypervariable loop or complementarity determining region (CDR) in the VH domain or the VL domain is obtained from a VH or VL domain of a species in the family Camelidae. In a particular embodiment both the VH domain and the VL domain are obtained from Llama (*Lama glama*).

A monoclonal antibody comprising a VH domain and a VL domain, wherein at least one hypervariable loop or complementarity determining region (CDR) in the VH domain or the VL domain is obtained from a VH or VL domain of a species in the family Camelidae. In a particular embodiment both the VH domain and the VL domain are obtained from Llama (*Lama glama*).

An antigen binding polypeptide comprising a VH domain and a VL domain, wherein at least one hypervariable loop or complementarity determining region (CDR) in the VH domain or the VL domain is obtained from a VH or VL domain of a species in the family Camelidae and wherein said antigen binding polypeptide is immunoreactive with a target antigen of therapeutic or diagnostic importance. In a particular embodiment both the VH domain and the VL domain are obtained from Llama (*Lama glama*).

A chimeric antigen binding polypeptide comprising or consisting of a VH domain of a conventional antibody of a camelid (in particular Llama or alpaca), a VL domain of a conventional antibody of a camelid (in particular Llama or alpaca) and one or more constant domains of a human antibody. In a particular embodiment both the VH domain and the VL domain are obtained from Llama (*Lama glama*).

A chimeric antigen binding polypeptide immunoreactive with a target antigen of therapeutic or diagnostic importance, which antigen binding polypeptide comprises or consists of a VH domain of a conventional antibody of a camelid (in particular Llama or alpaca), a VL domain of a conventional antibody of a camelid (in particular Llama or alpaca) and one or more constant domains of a human antibody. In a particular embodiment both the VH domain and the VL domain are obtained from Llama (*Lama glama*).

A chimeric antibody comprising or consisting of a VH domain of a conventional antibody of a camelid (in particular Llama or alpaca), a VL domain of a conventional antibody of a camelid (in particular Llama or alpaca) and the constant domains of a human antibody of an isotype selected from the group consisting of: IgG, IgM, IgD, IgE and IgA. In a particular embodiment both the VH domain and the VL domain are obtained from Llama (*Lama glama*).

A chimeric antigen binding polypeptide immunoreactive with a target antigen of therapeutic or diagnostic importance, which antigen binding polypeptide comprises or consists of a VH domain of a conventional antibody of a camelid (in particular Llama or alpaca), a VL domain of a conventional antibody of a camelid (in particular Llama or alpaca) and the constant domains of a human antibody of an isotype selected from the group consisting of: IgG, IgM, IgD, IgE, IgA. In a particular embodiment both the VH domain and the VL domain are obtained from Llama (*Lama glama*).

In particular embodiments of the foregoing, both the VH and the VL domain may be from the same species of camelid (in particular Llama or alpaca), and may even be from the same animal within this species, for example a single animal which has been actively immunised. In particular, both the VH domain and the VL domain may be obtained from a single actively immunised Llama. However, it is not excluded that the VH and VL domain may be obtained from different animals, or non-immune libraries.

In the foregoing embodiments, the terms "VH domain of a conventional antibody of a camelid" and "VL domain of a conventional antibody of a camelid" are intended to encompass variants which have been engineered to introduce one or more changes in amino acid sequence, such as variants which have been "humanised" or "germlined" in one or more framework regions, as described elsewhere herein, and also encompass the products of synthetic (e.g. codon-optimised) genes, as described elsewhere herein.

Polynucleotides, Vectors and Recombinant Expression

The invention also provides a polynucleotide molecule encoding the antigen binding polypeptide of the invention, an expression vector containing a nucleotide sequence encoding the antigen binding polypeptide of the invention operably linked to regulatory sequences which permit expression of the antigen binding polypeptide in a host cell or cell-free expression system, and a host cell or cell-free expression system containing this expression vector.

Polynucleotide molecules encoding the antigen binding polypeptide of the invention include, for example, recombinant DNA molecules.

The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of an antigen binding polypeptide according to the invention, a recombinant polynucleotide encoding it may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); mouse myeloma cells SP2/0-AG14 (ATCC CRL 1581; ATCC CRL 8287) or NS0 (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antigen binding polypeptide according to the invention has been introduced are explicitly excluded from the scope of the invention.

In an important aspect, the invention also provides a method of producing a recombinant antigen binding polypeptide which comprises culturing a host cell (or cell free expression system) containing polynucleotide (e.g. an expression vector) encoding the recombinant antigen binding polypeptide under conditions which permit expression of the antigen binding polypeptide, and recovering the expressed antigen binding polypeptide. This recombinant expression process can be used for large scale production of antigen binding polypeptides according to the invention, including monoclonal antibodies intended for human therapeutic use. Suitable vectors, cell lines and production processes for large scale manufacture of recombinant antibodies suitable for in vivo therapeutic use are generally available in the art and will be well known to the skilled person.

Further aspects of the invention relate to test kits, including diagnostic kits etc. comprising an antigen binding polypeptide according to the invention, and also pharmaceutical formulations comprising an antigen binding polypeptide according to the invention.

Where the antigen binding polypeptide is intended for diagnostic use, for example where the antigen binding polypeptide is specific for an antigen which is a biomarker of a disease state or a disease susceptibility, then it may be convenient to supply the antigen binding polypeptide as a component of a test kit. Diagnostic tests typically take the form of standard immunoassays, such as ELISA, radioimmunoassay, Elispot, etc. The components of such a test kit may vary depending on the nature of the test or assay it is intended to carry out using the antigen binding polypeptide of the invention, but will typically include additional reagents required to carry out an immunoassay using the antigen binding polypeptide of the invention. Antigen binding polypeptides for use as diagnostic reagents may carry a revealing label, such as for example a fluorescent moiety, enzymatic label, or radiolabel.

Antigen binding polypeptides intended for in vivo therapeutic use are typically formulated into pharmaceutical dosage forms, together with one or more pharmaceutically acceptable diluents, carriers or excipients (Remington's Pharmaceutical Sciences, 16th edition., Osol, A. Ed. 1980). Antigen binding polypeptides according to the invention are typically formulated as sterile aqueous solutions, to be administered intravenously, or by intramuscular, intraperitoneal, intra-cerebrospinal, intratumoral, oral, peritumoral, subcutaneous, intra-synovial, intrathecal, topical, sublingual or inhalation routes, to a mammalian subject, typically a human patient, in need thereof. For the prevention or treatment of disease, the appropriate dosage of antigen binding polypeptide will depend on the type of disease to be treated, the severity and clinical course of the disease, plus the patient's age, weight and clinical history, and will be determined by the judgement of the attending physician.

Processes for the Production of Antigen Binding Polypeptides

A key aspect of the present invention relates to processes for the production of high affinity antigen binding polypeptides, and specifically monoclonal antibodies, against a target antigen of interest.

Accordingly, the invention provides a process for preparing an antigen binding polypeptide immunoreactive with a target antigen, said process comprising:
  (a) determining the nucleotide sequence encoding at least one hypervariable loop or complementarity determining region (CDR) of the VH and/or the VL domain of a Camelidae conventional antibody immunoreactive with said target antigen; and
  (b) expressing an antigen binding polypeptide immunoreactive with said target antigen, said antigen binding polypeptide comprising a VH and a VL domain, wherein at least one hypervariable loop or complementarity determining region (CDR) of the VH domain or the VL domain has an amino acid sequence encoded by the nucleotide sequence determined in part (a).

In one embodiment, the antigen binding polypeptide expressed in part (b) is not identical to the Camelidae conventional antibody of part (a).

In one non-limiting embodiment, the invention provides a process for preparing a recombinant antigen binding polypeptide that is immunoreactive with (or specifically binds to) a target antigen, said an antigen binding polypeptide comprising a VH domain and a VL domain, wherein at least one hypervariable loop or complementarity determining region (CDR) in the VH domain or the VL domain is obtained from a species in the family Camelidae, said process comprising the steps of:
  (a) isolating Camelidae nucleic acid encoding at least one hypervariable loop or complementarity determining region (CDR) of the VH and/or the VL domain of a Camelidae conventional antibody immunoreactive with said target antigen;
  (b) preparing a recombinant polynucleotide comprising a nucleotide sequence encoding hypervariable loop(s) or complementarity determining region(s) having amino acid sequence identical to the hypervariable loop(s) or complementarity determining region(s) encoded by the nucleic acid isolated in step (a), which recombinant polynucleotide encodes an antigen binding polypeptide comprising a VH domain and a VL domain that is immunoreactive with (or specifically binds to) said target antigen; and
  (c) expressing said antigen binding polypeptide from the recombinant polynucleotide of step (b).

In one embodiment, the antigen binding polypeptide expressed in part (c) is not identical to the Camelidae conventional antibody of part (a).

The foregoing methods may be referred to herein as "general processes" for preparing antigen binding polypeptides.

The first step of either process may involve active immunisation of a species in the family Camelidae in order to elicit an immune response against the target antigen, thereby raising camelid conventional antibodies immunoreactive with the target antigen. Protocols for immunisation of camelids are described in the accompanying examples. The antigen preparation used for immunisation may be a purified form of the target antigen, for example recombinantly expressed polypeptide, or an immunogenic fragment thereof. However, it is also possible to immunise with crude preparations of the antigen, such as like isolated cells or tissue preparations expressing or encoding the target antigen, cell lysates, cell supernatants or fractions such as cell membranes, etc., or with a polynucleotide encoding said target antigen (a DNA immunisation).

The process will typically involve immunisation of animals of a Camelidae species (including, but limited to, llamas and alpacas), and advantageously these animals will belong to an outbred population. However, it is also contemplated to use transgenic animals (e.g. transgenic mice) containing the Camelid conventional Ig locus, or at least a portion thereof.

A topic of increasing interest seems to be the difference between the complementarity determining regions (CDRs) of in vivo and in vitro generated antibodies. The inventors surmise that the in vivo selection has a favourable impact on the immunogenicity, functionality, stability and therefore improved manufacturability of the resulting antibodies, whilst synthetic CDRs generated and selected in vitro may have a disadvantage from this point of view. This is important since a given therapeutic antibody risks to be neutralized by the so called anti-idiotypic antibody response from the patient (Lonberg, Nature Biotechnology, 23: 1117-1125, (2005)).

A key advantage of processes according to the invention based on active immunisation of camelids stems from the fact that all species of Camelidae can be maintained in large outbred populations where the individual animals have a different genetic background. It is therefore possible to use active immunisation to elicit a strong and diverse immune response against the antigen of interest from which a diverse pool of potential antigen binding molecules can be obtained. As illustrated in the accompanying examples, the present inventors have observed that active immunisation of camelids can generate Fab fragments binding to a target antigen with a high degree of immunodiversity. Without wishing to be bound by theory, the inventors surmise that the phylogenetic distance between humans and camelids may be important for production of a diverse immune response against a given target antigen. In contrast, the non-human primates are phylogenetically close to humans, thus targets with high homology between non-human primates and humans may elicit only a limited immune response in terms of strength and diversity in non-human primates.

The ability to use active immunisation in an outbred population which is phylogenetically distant from human would not be particularly advantageous if the antibodies so-produced were to exhibit a low sequence and structural homology with human antibodies such that substantial "protein engineering" would be required to create a candidate antibody with therapeutic potential. It is therefore extremely important that the inventors have shown that the Camelidae germline (and somatically mutated sequences) encodes both VH and VL domains with a very high degree of sequence and structural homology with human VH and VL domains (as explained above). This high degree of homology in combination with the availability of large outbred populations results in a very powerful platform for development of monoclonal antibodies for use as human therapeutics.

Following active immunisation with the target antigen, peripheral blood lymphocytes or biopsies such as lymph nodes or spleen biopsies may be isolated from the immunised animal and screened for production of conventional camelid antibodies against the target antigen. Techniques such as enrichment using panning or FACS sorting may be used at this stage to reduce the complexity of the B cell repertoire to be screened, as illustrated in the examples. Antigen-specific B cells are then selected and used for total RNA extraction and subsequent cDNA synthesis. Nucleic acid encoding the native camelid VH and VL domains (specific for the target antigen) can be isolated by PCR.

It is not essential to use active immunisation in order to identify camelid convention antibodies immunoreactive with a target of interest. In other embodiments it may be possible to make use of the camelid's own immune response, either the immunodiversity naturally present in the animal, or for example a diseased animal or animal which has been naturally exposed to a particular pathogen, e.g. by normal infection routes. In this regard, the invention encompasses the use of non-immune libraries. If "natural" immune responses within the camelid already give rise to antibodies which bind the target antigen of interest, then it is possible to make use of the genetic engineering techniques described herein, and other standard techniques known in the art, in order to culture and isolate B cells producing such antibodies, or produce monoclonal cultures of such antibodies, and/or to determine the nucleotide sequence of the camelid gene segments encoding the VH and/or VL domains of such antibodies. Armed with this sequence information, it is then possible to engineer recombinant DNA constructs encoding antigen binding polypeptides which embody the camelid derived VH and/or VL, or the hypervariable loops (or CDRs) thereof.

Nucleic acid encoding camelid VH and VL domains (whether obtained by active immunisation or by other means) may be cloned directly into an expression vector for the production of an antigen binding polypeptide according to the invention. In particular, these sequences could be cloned into an expression vector which also encodes a human antibody constant region, or a portion thereof, in order to produce a chimeric antibody. However, it is typical to carry out further manipulations on the isolated camelid VH and VL sequences before cloning and expression with human constant region sequences.

As a first step, candidate camelid VH and VL sequences (including sequences isolated following the active immunisation) may be used to prepare a camelid libraries (e.g. Fab libraries, as described in the accompanying examples). The library may then be screened (e.g. using phage display) for binding to the target antigen. Promising lead candidates can be further tested for target antigen binding, for example using Biacore or a suitable bioassay. Finally, the sequences encoding the VH and VL domains of the most promising leads can be cloned as an in-frame fusion with sequences encoding a human antibody constant region.

It is not essential that the polynucleotide sequence used to encode the (camelid-derived) HVs/CDRs (e.g. for recombinant expression of the antigen binding polypeptide of the invention) is identical to the native polynucleotide sequence which naturally encodes the HVs/CDRs in the camelid. Therefore, the invention encompasses/permits codon optimisation, and other changes in polynucleotide sequence related to cloning and/or expression, which do not alter the encoded amino acid sequence.

In certain embodiments, "chain shuffling" may be performed in which a particular variable domain known to bind the antigen of interest is paired with each of a set of variable domains of the opposite type (i.e. VH paired with VL library or vice versa), to create libraries, and the resulting "promiscuous" combinations of VH/VL tested for antigen binding affinity and/or specificity. Alternatively, a library of VH domains could be paired with a library of VL domains, either randomly or in a hierarchical manner, and the resulting combinations tested (see Clackson et al., Nature., Vol. 352. pp 624-638, 1991). In this process, the libraries may be libraries of rearranged VH and VL (Vκ or Vλ) from camelids which display immunity to the antigen of interest (including animals which have been actively immunised). The chain shuffling process can increase immunodiversity and produce pairings with significantly enhanced affinity.

The invention also contemplates performing epitope imprinted selection (so-called "guided selection") starting from a camelid VH or VL domain, wherein the other variable domain is taken from a non-camelid species, e.g. human. Thus, in one embodiment a camelid VH domain may be "shuffled" with a library of human-encoded VL domains, to replace the native camelid-encoded VL domain, resulting in camelid VH/human VL pairings. One or more of these pairings may then be subjected a second chain shuffling step in which the human VL domain is shuffled against a library of VH domains, which may be human-encoded. This second step may produce human-encoded VH/VL combinations which have the epitope imprint of the original camelid-encoded VH/VL combination.

Also included within the scope of the invention is the reverse "chain shuffling" process, starting with non-camelid (preferably human)-encoded VH/VL domain combination which binds to an antigen of interest. This could be, for example, a fully human therapeutic antibody against a validated disease target. Starting from this VH/VL combination, it is possible to carry out a first round of selection in which the VH domain is "shuffled" with a library of camelid-encoded VL domains (or vice versa), and the pairings tested for antigen binding. Selected non-camelid (e.g. human) VH/camelid VL pairings may then be subjected to a second round of selection in which the camelid-encoded VL is shuffled against a library of camelid-encoded VH, and the resulting pairings tested for antigen binding. As a result, it may be possible to produce a camelid VH/camelid VL combination which carries the epitope imprint of the starting VH/VL combination. This camelid VH/VL combination could be further engineered/modified and combined with human-encoded constant domains as required, using any of the processes described herein.

In the processes of the invention, "native" camelid-derived VH and VL domains may be subject to protein engineering in which one or more selective amino acid substitutions are introduced, typically in the framework regions. The reasons for introducing such substitutions into the "wild type" camelid sequence can be (i) humanisation of the framework region, (ii) improvement in stability, bioavailability, product uniformity, tissue penetration, etc., or (iii) optimisation of target antigen binding.

"Humanisation" of camelid-derived VH and VL domains by selective replacement of one or more amino acid residues in the framework regions may be carried out according to well-established principles (as illustrated in the accompanying examples, and reviewed by Almagro et al. Frontiers in Bioscience 13:1619-1633 (2008), the contents of which are specifically incorporated herein by reference). It will be appreciated that the precise identity of the amino acid changes made to achieve acceptable "humanisation" of any given VH domain, VL domain or combination thereof will vary on a case-by-case basis, since this will depend upon the sequence of the framework regions derived from Camelidae and the starting homology between these framework regions and the closest aligning human germline (or somatically mutated) framework region, and possible also on the sequence and conformation of the hypervariable loops which form the antigen binding site.

The overall aim of humanisation is to produce a molecule in which the VH and VL domains exhibit minimal immunogenicity when introduced into a human subject, whilst retaining the specificity and affinity of the antigen binding site formed by the parental VH and VL domains encoded by Camelidae (e.g. camelid VH/VL obtained by active immunisation). There are a number of established approaches to humanisation which can be used to achieve this aim. Techniques can be generally classified as either rational approaches or empirical approaches. Rational approaches include CDR-grafting, resurfacing or veneering, superhumanization and human string content optimisation. Empirical approaches include the FR library approach, guided selection, FR shuffling and humaneering. All of these techniques are reviewed in Almagro, Frontiers in Bioscience 2008, ibid. and any of these techniques, or combinations or modifications thereof, can be used to prepare "humanised" antigen binding polypeptides according to the invention.

Methods of Library Construction

In a related aspect, the invention also encompasses a method of producing a library of expression vectors encoding VH and/or VL domains of camelid conventional antibodies, said method comprising the steps:

a) amplifying regions of nucleic acid molecules encoding VH and/or VL domains of camelid conventional antibodies to obtain amplified gene segments, each gene segment containing a sequence of nucleotides encoding a VH domain or a sequence of nucleotides encoding a VL domain of a camelid conventional antibody, and b) cloning the gene segments obtained in a) into expression vectors, such that each expression vector contains at least a gene segment encoding a VH domain and/or a gene segment encoding a VL domain, whereby a library of expression vectors is obtained.

The above methods of "library construction" may also form part of the general process for production of antigen binding polypeptides of the invention, described above. Hence, any feature described as being preferred or advantageous in relation to this aspect of the invention may also be taken as preferred or advantageous in relation to the general process, and vice versa, unless otherwise stated.

In one embodiment, the nucleic acid amplified in step a) comprises cDNA or genomic DNA prepared from lymphoid tissue of a camelid, said lymphoid tissue comprising one or more B cells, lymph nodes, spleen cells, bone marrow cells, or a combination thereof. Circulating B cells are particularly preferred. The present inventors have surprisingly found that peripheral blood lymphocytes (PBLs) can be used as a source of nucleic acid encoding VH and VL domains of conventional camelid antibodies, i.e. there is sufficient quantity of plasma cells (expressing antibodies) present in a sample of PBLs to enable direct amplification. This is advantageous because PBLs can be prepared from a whole blood sample taken from the animal (camelid). This avoids the need to use invasive procedures to obtain tissue biopsies (e.g. from spleen or lymph node), and means that the sampling procedure can be repeated as often as necessary, with minimal impact on the animal. For example, it is possible to actively immunise the camelid, remove a first blood sample from the animal and prepare PBLs, then immunise the same animal a second time, either with a "boosting" dose of the same antigen or with a different antigen, then remove a second blood sample and prepare PBLs.

Accordingly, a particular embodiment of this method of the invention may involve: preparing a sample containing PBLs from a camelid, preparing cDNA or genomic DNA from the PBLs and using this cDNA or genomic DNA as a template for amplification of gene segments encoding VH or VL domains of camelid conventional antibodies.

In one embodiment the lymphoid tissue (e.g. circulating B cells) is obtained from a camelid which has been actively immunised, as described elsewhere herein. However, this embodiment is non-limiting and it is also contemplated to prepare non-immune libraries and libraries derived from lymphoid tissue of diseased camelids, also described elsewhere herein.

Conveniently, total RNA (or mRNA) can be prepared from the lymphoid tissue sample (e.g. peripheral blood cells or tissue biopsy) and converted to cDNA by standard techniques. It is also possible to use genomic DNA as a starting material.

This aspect of the invention encompasses both a diverse library approach, and a B cell selection approach for construction of the library. In a diverse library approach, repertoires of VH and VL-encoding gene segments may be amplified from nucleic acid prepared from lymphoid tissue without any prior selection of B cells. In a B cell selection approach, B cells displaying antibodies with desired antigen-binding characteristics may be selected, prior to nucleic acid extraction and amplification of VH and VL-encoding gene segments.

Various conventional methods may be used to select camelid B cells expressing antibodies with desired antigen-binding characteristics. For example, B cells can be stained for cell surface display of conventional IgG with fluorescently labelled monoclonal antibody (mAb, specifically recognizing conventional antibodies from llama or other camelids) and with target antigen labelled with another fluorescent dye. Individual double positive B cells may then be isolated by FACS, and total RNA (or genomic DNA) extracted from individual cells. Alternatively cells can be subjected to in vitro proliferation and culture supernatants with secreted IgG can be screened, and total RNA (or genomic DNA) extracted from positive cells. In a still further approach, individual B cells may be transformed with specific genes or fused with tumor cell lines to generate cell lines, which can be grown "at will", and total RNA (or genomic DNA) subsequently prepared from these cells.

Instead of sorting by FACS, target specific B cells expressing conventional IgG can be "panned" on immobilized monoclonal antibodies (directed against camelid conventional antibodies) and subsequently on immobilized target antigen. RNA (or genomic DNA) can be extracted from pools of antigen specific B cells or these pools can be transformed and individual cells cloned out by limited dilution or FACS.

B cell selection methods may involve positive selection, or negative selection.

Whether using a diverse library approach without any B cell selection, or a B cell selection approach, nucleic acid (cDNA or genomic DNA) prepared from the lymphoid tissue is subject to an amplification step in order to amplify gene segments encoding individual VH domains or VL domains.

Total RNA extracted from the lymphoid tissue (e.g. peripheral B cells or tissue biopsy) may be converted into random primed cDNA or oligo dT primer can be used for cDNA synthesis, alternatively Ig specific oligonucleotide primers can be applied for cDNA synthesis, or mRNA (i.e. poly A RNA) can be purified from total RNA with oligo dT cellulose prior to cDNA synthesis. Genomic DNA isolated from B cells can be used for PCR.

PCR amplification of heavy chain and light chain (kappa and lambda) gene segments encoding at least VH or VL can be performed with FR1 primers annealing to the 5' end of the variable region in combination with primers annealing to the 3' end of CH1 or Ckappa/Clambda region with the advantage that for these constant region primers only one primer is needed for each type. This approach enables camelid Fabs to be cloned. Alternatively sets of FR4 primers annealing to the 3' end of the variable regions can be used, again for cloning as Fabs (fused to vector encoded constant regions) or as scFv (single chain Fv, in which the heavy and light chain variable regions are linked via a flexible linker sequence); alternatively the variable regions can be cloned in expression vectors allowing the production of full length IgG molecules displayed on mammalian cells.

In general the amplification is performed in two steps; in the first step with non-tagged primers using a large amount of cDNA (to maintain diversity) and in the second step the amplicons are re-amplified in only a few cycles with tagged primers, which are extended primers with restriction sites introduced at the 5' for cloning. Amplicons produced in the first amplification step (non-tagged primers) may be gel-purified to remove excess primers, prior to the second amplification step. Alternatively, promoter sequences may be introduced, which allow transcription into RNA for ribosome display. Instead of restriction sites recombination sites can be introduced, like the Cre-Lox or TOPO sites, that permit the site directed insertion into appropriate vectors.

Amplified gene segments encoding camelid conventional VH and VL domains may then be cloned into vectors suitable for expression of VH/VL combinations as functional antigen binding polypeptides. By way of example, amplified VHCH1/VKCK/VLCL gene segments from pools of B cells (or other lymphoid tissue not subject to any B cell selection) may be first cloned separately as individual libraries (primary libraries), then in a second step Fab or scFV libraries may be assembled by cutting out the light chain fragments and ligating these into vectors encoding the heavy chain fragments. The two step procedure supports the generation of large libraries, because the cloning of PCR products is relatively inefficient (due to suboptimal digestion with restriction enzymes). scFv encoding DNA fragments can be generated by splicing-by-overlap extension PCR (SOE) based on a small overlap in sequence in amplicons; by mixing VH and VL encoding amplicons with a small DNA fragment encoding the linker in a PCR a single DNA fragment is formed due to the overlapping sequences.

Amplicons comprising VH and VL-encoding gene segments can be cloned in phage or phagemid vectors, allowing selection of target specific antibody fragments by using phage display based selection methods. Alternatively amplicons can be cloned into expression vectors which permit display on yeast cells (as Fab, scFv or full length IgG) or mammalian cells (as IgG).

In other embodiments, cloning can be avoided by using the amplicons for ribosome display, in which a T7 (or other) promoter sequence and ribosome binding site is included in the primers for amplification. After selection for binding to target antigen, pools are cloned and individual clones are analyzed. In theory, larger immune repertoires can be sampled using this approach as opposed to a phage display library approach, because cloning of libraries and selection with phage is limited to $10^{10}$ to $10^{12}$ clones.

When applying B cell sorting, amplicons contain VH or VL-encoding gene segments of individual target specific B cells can be cloned directly into bacterial or mammalian expression vectors for the production of antibody fragments (scFVs or Fabs) or even full length IgG.

In a particular, non-limiting, embodiment of the "library construction" process, the invention provides a method of producing a library of expression vectors encoding VH and VL domains of camelid conventional antibodies, said method comprising the steps:

a) actively immunising a camelid, thereby raising conventional camelid antibodies against a target antigen;

b) preparing cDNA or genomic DNA from a sample comprising lymphoid tissue (e.g. circulating B cells) from said immunised camelid (including, but not limited to, Llama or alpaca);

c) amplifying regions of said cDNA or genomic DNA to obtain amplified gene segments, each gene segment comprising a sequence of nucleotides encoding a VH domain or a sequence of nucleotides encoding a VL domain of a camelid conventional antibody; and d) cloning the gene segments obtained in c) into expression vectors, such that each expression vector contains a gene segment encoding a VH domain and a gene segment encoding a VL domain and directs expression of an antigen binding polypeptide comprising said VH domain and said VL domain, whereby a library of expression vectors is obtained.

The foregoing methods may be used to prepare libraries of camelid-encoded VH and VL domains (in particular Llama and alpaca VH and VL domains), suitable for expression of VH/VL combinations as functional antigen-binding polypeptides, e.g. in the form of scFVs, Fabs or full-length antibodies.

Libraries of expression vectors prepared according to the foregoing process, and encoding camelid (including but not limited to Llama or alpaca) VH and VL domains, also form part of the subject-matter of the present invention.

In a particular embodiment the invention provides a library of phage vectors encoding Fab or scFV molecules, wherein each Fab or scFV encoded in the library comprises a VH domain of a camelid conventional antibody and a VL domain of a camelid conventional antibody.

In one embodiment the library is a "diverse" library, in which the majority of clones in the library encode VH domains of unique amino acid sequence, and/or VL domains of unique amino acid sequence, including diverse libraries of camelid VH domains and camelid VL domains. Therefore, the majority (e.g. >90%) of clones in a diverse library encode a VH/VL pairing which differs from any other VH/VL pairing encoded in the same library with respect to amino acid sequence of the VH domain and/or the VL domain.

The invention also encompasses expression vectors containing VH and VL-encoding gene segments isolated from a single selected B cell of a camelid (e.g. Llama or alpaca).

In a further aspect, the present invention also provides a method of selecting an expression vector encoding an antigen binding polypeptide immunoreactive with a target antigen, the method comprising steps of:

i) providing a library of expression vectors, wherein each vector in said library comprises a gene segment encoding a VH domain and a gene segment encoding a VL domain, wherein at least one of said VH domain or said VL domain is from a camelid conventional antibody, and wherein each vector in said library directs expression of an antigen binding polypeptide comprising said VH domain and VL domain;

ii) screening antigen binding polypeptides encoded by said library for immunoreactivity with said target antigen, and thereby selecting an expression vector encoding an antigen binding polypeptide immunoreactive with said target antigen.

This method of the invention encompasses screening/selection of clones immunoreactive with target antigen, from a library of clones encoding VH/VL pairings. The method may also encompass library construction, which may be carried out using the library construction method described above. Optional downstream processing/optimisation steps may be carried out on selected clones, as described below. This method of selection and screening, may also form part of the general process for production of antigen binding polypeptides of the invention, described above. Hence, any feature described as being preferred or advantageous in relation to Screening and Selection of Clones Immunoreactive with Target Antigen Screening/selection typically involves contacting expression products encoded by clones in the library (i.e. VH/VL pairings in the form of antigen binding polypeptides, e.g. Fabs, scFVs or antibodies) with a target antigen, and selecting one or more clones which encode a VH/VL pairings exhibiting the desired antigen binding characteristics.

Phage display libraries may be selected on immobilized target antigen or on soluble (often biotinylated) target antigen. The Fab format allows affinity driven selection due to its monomeric appearance and its monovalent display on phage, which is not possible for scFv (as a consequence of aggregation and multivalent display on phage) and IgG (bivalent format). Two to three rounds of selections are typically needed to get sufficient enrichment of target specific binders.

Affinity driven selections can be performed by lowering the amount of target antigen in subsequent rounds of selection, whereas extended washes with non-biotinylated target enables the identification of binders with extremely good affinities.

The selection procedure allows the user to home in on certain epitopes; whereas the classical method for elution of phage clones from the immobilized target is based on a pH shock, which denatures the antibody fragment and/or target, competition with a reference mAb against the target antigen or soluble receptor or cytokine leads to the elution of phage displaying antibody fragments binding to the relevant epitope of the target (this is of course applicable to other display systems as well, including the B cells selection method).

Individual clones taken from the selection outputs may be used for small scale production of antigen-binding polypeptides (e.g. antibody fragments) using periplasmic fractions prepared from the cells or the culture supernatants, into which the fragments "leaked" from the cells. Expression may be driven by an inducible promoter (e.g. the lac promoter), meaning that upon addition of the inducer (IPTG) production of the fragment is initiated. A leader sequence ensures the transport of the fragment into the periplasm, where it is properly folded and the intramolecular disulphide bridges are formed.

The resulting crude protein fractions may be used in target binding assays, such as ELISA. For binding studies, phage prepared from individual clones can be used to circumvent the low expression yields of Fabs, which in general give very low binding signals. These protein fractions can also be screened using in vitro receptor—ligand binding assays to identify antagonistic antibodies; ELISA based receptor—ligand binding assays can be used, also high throughput assays like Alphascreen are possible. Screening may be performed in radiolabelled ligand binding assays, in which membrane fractions of receptor overexpressing cell lines are immobilized; the latter assay is extremely sensitive, since only picomolar amounts of radioactive cytokine are needed, meaning that minute amounts of antagonistic Fabs present in the crude protein fraction will give a positive read-out. Alternatively, FACS can be applied to screen for antibodies, which inhibit binding of a fluorescently labelled cytokine to its receptor as expressed on cells, while FMAT is the high throughput variant of this.

Fabs present in periplasmic fractions or partially purified by IMAC on its hexahistidine tag or by protein G (known to bind to the CH1 domain of Fabs) can be directly used in bioassays using cells, which are not sensitive to bacterial impurities; alternatively, Fabs from individual E. coli cells can be recloned in mammalian systems for the expression of Fabs or IgG and subsequently screened in bioassays.

Following identification of positive expression vector clones, i.e. clones encoding a functional VH/VL combination which binds to the desired target antigen, it is a matter of routine to determine the nucleotide sequences of the variable regions, and hence deduce the amino acid sequences of the encoded VH and VL domains.

If desired, the Fab (or scFV) encoding region may be recloned into an alternative expression platform, e.g. a bacterial expression vector (identical to the phagemid vector, but without the gene 3 necessary for display on phage), which allows larger amounts of the encoded fragment to be produced and purified.

The affinity of target binding may be determined for the purified Fab (or scFV) by surface plasmon resonance (e.g. Biacore) or via other methods, and the neutralizing potency tested using in vitro receptor—ligand binding assays and cell based assays.

Families of antigen-binding, and especially antagonistic Fabs (or scFVs) may be identified on the basis of sequence analysis (mainly of VH, in particular the length and amino acid sequence of CDR3 of the VH domain).

Potency Optimisation

Clones identified by screening/selection as encoding a VH/VL combination with affinity for the desired target antigen may, if desired, be subject to downstream steps in which the affinity and/or neutralising potency is optimised.

Potency optimization of the best performing member of each VH family can be achieved via light chain shuffling, heavy chain shuffling or a combination thereof, thereby selecting the affinity variants naturally occurring in the animal. This is particularly advantageous in embodiments where the original camelid VH/VL domains were selected from an actively immunised camelid, since it is possible to perform chain shuffling using the original library prepared from the same immunised animal, thereby screening affinity variants arising in the same immunised animal.

For light chain shuffling the gene segment encoding the VH region (or VHCH1) of VH/VL pairing with desirable antigen binding characteristics (e.g. an antagonistic Fab) may be used to construct a library in which this single VH-encoding gene segment is combined with the light chain repertoire of the library from which the clone was originally selected. For example, if the VH-encoding segment was selected from a library (e.g. Fab library) prepared from a camelid animal actively immunised to elicit an immune response against a target antigen, then the "chain shuffling" library may be constructed by combining this VH-encoding segment with the light chain (VL) repertoire of the same immunised camelid. The resulting library may then be subject to selection of the target antigen, but under stringent conditions (low concentrations of target, extensive washing with non-biotinylated target in solution) to ensure the isolation of the best affinity variant. Off-rate screening of periplasmic fractions may also assist in the identification of improved clones. After sequence analysis and recloning into a bacterial production vector, purified selected Fabs may be tested for affinity (e.g. by surface plasmon resonance) and potency (e.g. by bioassay).

Heavy chain shuffling can be performed by cloning back the gene segment encoding the light chain (VL) of a clone selected after light-chain shuffling into the original heavy chain library from the same animal (from which the original VH/VL-encoding clone was selected). Alternatively a CDR3 specific oligonucleotide primer can be used for the amplification of the family of VH regions, which can be cloned as a repertoire in combination with the light chain of the antagonistic Fab. Affinity driven selections and off-rate screening then allow the identification of the best performing VH within the family.

It will be appreciated that the light chain shuffling and heavy chain shuffling steps may, in practice, be performed in either order, i.e. light chain shuffling may be performed first and followed by heavy chain shuffling, or heavy chain shuffling may be performed first and followed by light chain shuffling. Both possibilities are encompassed within the scope of the invention.

From light chains or heavy chains of VH/VL pairings (e.g. Fabs) with improved affinity and potency the sequences of, in particular, the CDRs can be used to generate engineered variants in which mutations of the individual Fabs are combined. It is known that often mutations can be additive, meaning that combining these mutations may lead to an even more increased affinity.

Germlining and Formatting for Human Therapeutic Use

The VH and VL-encoding gene segments of selected expression clones encoding VH/VL pairings exhibiting desirable antigen-binding characteristics (e.g. phage clones encoding scFVs or Fabs) may be subjected to downstream processing steps and recloned into alternative expression platforms, such as vectors encoding antigen binding polypeptide formats suitable for human therapeutic use (e.g. full length antibodies with fully human constant domains).

Promising "lead" selected clones may be engineered to introduce one or more changes in the nucleotide sequence encoding the VH domain and/or the VL domain, which changes may or may not alter the encoded amino acid sequence of the VH domain and/or the VL domain. Such changes in sequence of the VH or VL domain may be engineered for any of the purposes described elsewhere herein, including germlining or humanisation, codon optimisation, enhanced stability, optimal affinity etc.

The general principles germlining or humanisation described herein apply equally in this embodiment of the invention. By way of example, lead selected clones containing camelid-encoded VH and VL domains may be germlined/humanised in their framework regions (FRs) by applying a library approach. After alignment against the closest human germline (for VH and VL) and other human germlines with the identical canonical folds of CDR1 and CDR2, the residues to be changed in the FRs are identified and the preferred human residue selected, as described elsewhere herein in detail. Whilst germlining may involve replacement of camelid-encoded residues with an equivalent residue from the closest matching human germline this is not essential, and residues from other human germlines could also be used.

The germlining of a VH domain having an amino acid sequence homologous to a member of the human VH3 family will often involve replacement/substitution of a number of residues, which already deviate in publically known *Lama glama, Lama pacos* or *Camelus dromedarius* derived germline sequences. Permitted amino acid substitutions for germlining/humanisation of a VH3 domain of *Lama glama, Lama pacos* or *Camelus dromedarius*, and in particular *Lama glama* include, but are not limited to, amino acid replacements at any one or any combination of positions 71, 83 and 84 in the framework region (using Kabat numbering). Such replacement(s) will involve substitution of the camelid-encoded residue(s) at these positions with a different amino acid, which may be a natural or non-natural amino acid, and is preferably an amino acid known to occur at the equivalent position in a human-encoded VH3 domain. For example, Alanine at position 71 might be replaced with serine or alanine, Lysine at position 83 might be replaced with Arginine and Proline at position 84 might be replaced with Alanine. Accordingly, particular non-limiting embodiments of the antigen binding polypeptide of the invention include variants comprising a camelid (and more specifically llama, alpaca or dromedary) VH domain exhibiting sequence homology to a human VH3 domain, which VH domain includes amino acid substitutions (versus the camelid-encoded sequence) at one or more or all of positions 71, 83 and 84 (using Kabat numbering). In particular, variants with one or more or any combination of the following substitutions are permitted: A changed to S at position 71, K changed to R at position 83 or P changed to A at position 84.

Once the amino acid sequences of the lead VH and VL domains (following potency optimisation, as appropriate) are known, synthetic genes of VH and VL can be designed, in which residues deviating from the human germline are replaced with the preferred human residue (from the closest matching human germline, or with residues occurring in other human germlines, or even the camelid wild type residue). At this stage the gene segments encoding the variable domains may be re-cloned into expression vectors in which they are fused to human constant regions of the Fab, either during gene synthesis or by cloning in an appropriate display vector.

The resulting VH and VL synthetic genes can be recombined into a Fab library or the germlined VH can be recombined with the wild type VL (and vice versa, referred to as "hybrid" libraries). Affinity-driven selections will allow the isolation of the best performing germlined version, in case of the "hybrid" libraries, the best performing germlined VH can be recombined with the best performing germlined VL.

Amino acid and nucleotide sequence information for the germlined Fabs can be used to generate codon-optimized synthetic genes for the production of full length human IgG of the preferred isotype (IgG1 for ADCC and CDC, IgG2 for limited effector functions, IgG4 as for IgG2, but when monovalent binding is required). For non-chronic applications and acute indications bacterially or mammalian cell produced human Fab can produced as well.

Combining steps of the above-described processes, in a particular non-limiting embodiment the present invention provides a method of producing an expression vector encoding a chimeric antigen binding polypeptide immunoreactive with a target antigen, said method comprising the steps of:

a) actively immunising a camelid (including but not limited to Llama or alpaca), thereby raising conventional camelid antibodies against a target antigen;

b) preparing cDNA or genomic DNA from a sample comprising lymphoid tissue (e.g. circulating B cells) from said immunised camelid;

c) amplifying regions of said cDNA or genomic DNA to obtain amplified gene segments, each gene segment comprising a sequence of nucleotides encoding a VH domain or a sequence of nucleotides encoding a VL domain of a camelid conventional antibody;

d) cloning the gene segments obtained in c) into expression vectors, such that each expression vector contains a gene segment encoding a VH domain and a gene segment encoding a VL domain and directs expression of an antigen binding polypeptide comprising said VH domain and said VL domain, thereby producing a library of expression vectors;

e) screening antigen binding polypeptides encoded by the library obtained in step d) for immunoreactivity with said target antigen, and thereby selecting an expression vector encoding an antigen binding polypeptide immunoreactive with said target antigen;

f) optionally performing a light chain shuffling step and/or a heavy chain shuffling step to select an expression vector encoding a potency-optimised antigen binding polypeptide immunoreactive with said target antigen;

g) optionally subjecting the gene segment encoding the VH domain of the vector selected in step e) or step f) and/or the gene segment encoding the VL domain of the vector selected in step e) or step f) to germlining and/or codon optimisation; and h) cloning the gene segment encoding the VH domain of the vector selected in part e) or f) or the germlined and/or codon optimised VH gene segment produced in step g) and the gene segment encoding the VL domain of the vector selected in part e) or f) or the germlined and/or codon optimised VL gene segment produced in step g) into a further expression vector, in operable linkage with a sequence of nucleotides encoding one or more constant domains of a human antibody, thereby producing an expression vector encoding a chimeric antigen binding polypeptide comprising the VH and VL domains fused to one or more constant domains of a human antibody.

The invention also extends to expression vectors prepared according to the above-described processes, and to a method of producing an antigen binding polypeptide immunoreactive with a target antigen, the method comprising steps of:

a) preparing expression vector encoding an antigen binding polypeptide immunoreactive with a target antigen using the method described above;

b) introducing said expression vector into host cell or cell-free expression system under conditions which permit expression of the encoded antigen binding polypeptide; and c) recovering the expressed antigen binding polypeptide.

In one embodiment, the latter process encompasses bulk production-scale manufacture of the antigen-binding polypeptide of the invention, particularly bulk-scale manufacture of therapeutic antibodies intended for use as pharmaceutically active agents, by recombinant expression. In such embodiments, the expression vector prepared in step a) and the host cell/expression system used in step b) are selected to be suitable for large-scale production of recombinant antibodies intended for administration to human patients. The general characteristics of suitable vectors and expression systems for this purpose are well known in the art.

The invention will be further understood with reference to the following non-limiting experimental examples.

Examples 1 to 9 illustrate the process of raising an antibody against an example antigen denoted "cytokine x", starting from immunization of llamas. The same general protocol can be adapted for any target antigen in any camelid species, hence the precise identity of "cytokine x" is not material. The process is also illustrated for preparation of Fabs binding IL-1 Beta (Example 15 onwards).

Various publications are cited in the foregoing description and throughout the following examples, each of which is incorporated by reference herein in its entirety.

General Protocol

Example 1

Immunization of Llamas

Immunizations of llamas (*Lama glama*) and harvesting of peripheral blood lymphocytes as well as the subsequent extraction of RNA and amplification of antibody gene fragments were performed as described by De Haard and colleagues (De Haard et al., J. Bact. 187: 4531-4541 (2005)).

One llama was immunized intramuscularly with recombinant human Cytokine x using Freund's complete adjuvant or an appropriate animal-friendly adjuvant Stimune (Cedi Diagnostics BV, The Netherlands). Cytokine x (recombinantly expressed in engineered human cell line) was purchased. Prior to immunization the lyophilized cytokine x was reconstituted in PBS (Dulbecco) at a concentration of 250 μg/ml. The llama received 6 injections at weekly intervals, the first two injections with 100 μg of cytokine per injection, the four last injections with 50 μg for each boost. Four days after the last immunization a blood sample (PBL1) of 150 ml was collected from the animal and serum was prepared. Ten days after the last immunization a second blood sample (PBL2) of 150 ml was taken and serum was prepared. Peripheral blood lymphocytes (PBLs), as the genetic source of the llama immunoglobulins, were isolated from the blood sample using a Ficoll-Paque gradient (Amersham Biosciences) yielding between 1 and $5\times10^8$ PBLs. The maximal diversity of antibodies is expected to be equal to the number of sampled B-lymphocytes, which is about 10% (between 9.2-23.2% (De Genst et al., Dev. Comp. Immunol. 30:187-98 (2006)) of the number of PBLs ($1-5\times10^7$). The fraction of conventional antibodies in llama serum is up to 80% of the amount of total immunoglobulin, which might be extrapolated to a similar fraction of B-lymphocytes that produce the conventional antibodies. Therefore, the maximal diversity of conventional antibodies in the 150 ml blood sample is calculated as $0.8-4\times10^7$ different molecules. Total RNA was isolated from PBLs according to the method of Chomczynski et al. Anal. Biochem. 162:156-159 (1987)).

Example 2

Enrichment of Antigen Reactive B Cells by Panning or FACS Sorting (Optional)

In order to reduce the complexity of the sampled B cell repertoire enabling the efficient cloning of the recombinatorial Fab phage display library, antigen reactive B cells were enriched by a FACS sorting (Weitkamp et al., J. Immunol. Meth. (2003) 275: 223-237) using fluorescently labelled antigen and a mAb recognizing camelid conventional antibody specifically (as B cell marker) or by a panning procedure on immobilized antigen (Lightwood et al., J. Immunol. Meth. 316:133-143 (2006)).

PBLs from immunized animals were isolated via a density centrifugation on Ficoll-Paque as described above. Optionally co-purified red blood cells were lysed by resuspending the PBL pellet in 20 ml of lysis buffer (8.29 g/L NH4Cl, 1.09 g/L KHCO3 and 37 mg/L EDTA) at room temperature followed by centrifugation for 10 minutes at 200×g. Optional was also the depletion of monocytes by adhering these to the plastic surface of TI50 culture flask. To achieve this cells were resuspended in 70 ml RPMI (Invitrogen) supplemented with 10% foetal calf serum, Glutamax, 25 mM Hepes, penicillin-streptomycin (Invitrogen) and 0.38% sodium citrate and incubated for 2 hours at 37° C. and 5% CO2 in the flasks. The supernatant fraction containing the B selected was recovered and cells were counted.

Bulk sorting in FACS of (living) B cells displaying target specific conventional antibodies was performed by simultaneous staining with the fluorescently labeled mAb specifically recognizing camelid conventional antibodies and target antigen, labeled with yet another fluorescent dye. Between 1,000 and 100,000 antigen specific cells were sorted and used for RNA extraction by applying the protocol of Gough and colleagues (Gough, Anal. Biochem. 173:93-95 (1988)) or by using the TRIzol kit (Invitrogen). Total RNA was converted into random primed cDNA as template for the amplification of the antibody heavy and light chain variable genes (see Example 3 and further).

Example 3

Amplification and Cloning of Variable Region Genes

Random primed cDNA was prepared from 80 μg of PBL RNA using the superscript III First-Strand Synthesis System for RT-PCR (Invitrogen). RNA was heat-denatured for 5 min at 65° C. in the presence of 2.5 μM of random hexanucleotide primer and 500 μM dNTPs in 8 independent reaction of 20 ul reaction. Subsequently, buffer and dithiothreitol were added according to the suppliers instructions, as well as 640 units of RNasOUT (40 units/μl, Invitrogen), and 3200 units of SuperscriptIII reverse transcriptase (200 units/μl; Invitrogen) in a total final volume of 8×40 μl. After 50 min at 50° C., 5 min at 85° C. and 1 min at 1° C. RNAse H was added (~4U) and incubated for 20 min at 37° C. The pooled cDNA was cleanup using QIAquick PCR Purification Kit according to supplier's recommendation and used for PCR.

Primers annealing to the 3' end of CH1 and 5' and 3' end of VH were designed on the basis of germline sequences from llama and dromedary, for which the deposited sequences could be retrieved from IMGT and other databases following the citations from De Genst and colleagues (De Genst et al, Dev. Comp. Immunol. 30:187-198 (2006)). For design of oligonucleotides for amplification of the light chain the rearranged and somatically mutated dromedary sequences were used that were published in a thesis study (I. Legssyer, Free University Brussels).

All primary PCRs were carried out with separate BACK primers annealing to the 5' end of the variable region and combined with FOR primers annealing to the 3' end of CH1, on relatively large amounts of random primed cDNA as template (up to 2.5 μl corresponding to 6 μg of total RNA) to maintain maximal diversity. The heavy chain derived amplicons can be reamplified with a combination of JHFOR primers, annealing to the 3' end of VH and containing a naturally occurring BstEII site, and SfiI-tagged VHBACK primers annealing to the 5' end of the VH gene, and subsequently cloned as VH fragments. The light chain V-genes were obtained by PCR with a set of CKFOR or CLFOR primer annealing to the 3' end of the constant domain and BACK primers priming at the 5' end of the V-regions. The amplicons from the first PCR reactions were reamplified with extended CH1FOR (containing a NotI site) or CKFOR and CLFOR primers (containing an AscI site) and subsequently cloned as llama Fab fragments. Alternatively, the DNA segments can be reamplified with primers tagged with restriction sites (FOR primers with AscI site and FR4 based BACK primers with XhoI site) and cloned as VL fragments thus creating chimeric Fab's containing llama derived V regions combined with human C regions.

PCR was performed in a volume of 50 μl reactions using Phusion polymerase (Finnzymes) and 500 pM of each primer for 28 cycles (1 min at 96° C., 1 min at 60° C., and 1 min at 72° C. All products were purified from agarose gel with the QIAex-II extraction kit (Qiagen). As input for reamplification to introduce restriction sites, 100-200 ng of purified DNA fragment was used as template in a 100-μl reaction volume. The large amount of input, ensuring the maintenance of variability, was checked by analysis of 4 μl of the "unamplified" PCR mixture on agarose gel.

Example 4

Construction of the Primary and Secondary Camelid Fab Repertoires

For the construction of the primary heavy chain and the two primary light chain repertoires, the PCR products, appended with restriction sites, were gel-purified prior to digestion and the different VH, VK, and VL families combined into three groups. The VHCH1 fragments were digested with SfiI and NotI and the VKCK and VLCL fragments were digested with ApaLI and AscI, and cloned into the phagemid vector pCB3 (similar to vector pCES1 with adapted multiple cloning site). The digested fragment (1 to 2 μg) were ligated to digested and purified PCB3 (2 to 4 μg) using T4-DNA ligase (Fermentas) at room temperature for several hours and then at 37° C. for 1-2 hours. The desalted ligation mixture for light or heavy chain pools was used for electroporation of the *E. coli* strain TG1, to create the one-chain libraries.

Alternatively, the VH fragments, 1.5 μg in total, may be digested with SfiI and BstEII (present in the VH) and ligated in a 100-200-μl reaction mixture with 9 units of T4-DNA ligase at room temperature to 4 μg, gel-purified vector PCB4 (similar to vector PCB3, but with the pIII gene deleted). In addition, the VH gene segments may be cloned via SfiI and BstEII and the VK/VL gene segments via ApaLI and XhoI, yielding the chimeric Fd and VKCK and VLCL.

The Fab library was obtained by cloning of light chain fragments, digested from plasmid DNA prepared from the light chain repertoires, into the plasmid collection containing the heavy chain repertoires. Plasmid DNA, isolated from at least 3×10$^9$ bacteria of the VL library (the donor vector), was digested with ApaLI and AscI for cloning of the gel purified DNA fragments in the acceptor vector that already contained the heavy chain libraries, thus creating a separate Fab library with kappa light chains and another library consisting of Fabs with a lambda light chain with a size of 1-10×10$^9$ clones. Similarly, the VLCL or VKCK from the single chain library can be extracted from agarose gel using ApaLI/AscI and cloned into the VHCH library vector using the same restriction site.

Example 5

Selection of the Library

The rescue of phagemid particles with helper phage M13-KO7 or VCSM-13 was performed on 2-liter scale, using representative numbers of bacteria from the library for inoculation, to ensure the presence of at least 10 bacteria from each clone in the start inoculum. For selections, 10$^{13}$ colony-forming units were used with antigens immobilized in immunotubes (Maxisorp tubes, Nunc) or in 96 wells microtiterplates (Maxisorp, Nunc) or with soluble biotinylated antigens. The amount of the immobilized antigens was reduced 10-100 fold during subsequent selection rounds, starting at 10 μg/ml at round 1. Antigens were biotinylated at a ratio of 3 to 10 molecules of NHS-Biotin (Pierce) per molecule of antigen according to the suppliers recommendations and tested for their bioactivity in a bioassay. Unless stated otherwise, the antigens were used for selection at concentrations of 1 to 10 nM during round 1 and 10 pM to 1 nM during subsequent rounds.

Example 6

Screening for Antagonistic Cytokine x Specific Fab's

Soluble Fab was produced from individual clones as described in Marks et al. (Marks et al., J. Mol. Biol. 222:581-

597 (1991)), but preferably as monoclonal phage (Lee et al., Blood 108:3103-3111 (2006)) to boost the sensitivity. Culture supernatants containing soluble Fab or Fab displaying phage were tested in ELISA with directly coated antigen or captured via immobilized streptavidin. Recombinant human cytokine x and streptavidin were coated at 10 µg/ml in 0.1 M NaHCO$_3$, pH 9.6, for 16 h at 4° C. Following 3 washes with PBS, 0.1% (v/v) Tween 20, biotinylated antigen was added for 30 to 60 minutes at room temperature at a concentration of 0.5 µg/ml. The plates were blocked during 30 min at room temperature with 2% (w/v) semi-skim milk powder (Marvel) in PBS or with 1% casein solution (in PBS). The culture supernatant was diluted 1- or 5-fold in 2% (w/v) Marvel/PBS and incubated 2 h; bound Fab was detected with anti-myc antibody 9E10 (5 µg/ml) recognizing the myc-peptide tag at the carboxyl terminus of the heavy Fd chain, and rabbit anti-mouse-HRP conjugate (Dako). Following the last incubation, staining was performed with tetramethylbenzidine and H$_2$O$_2$ as substrate and stopped by adding 0.5 volume of 1M H$_2$SO$_4$; the optical density was measured at 450 nm. Clones giving a positive signal in ELISA (over 2 times background), were analyzed by BstNI or HinfI fingerprinting of the PCR products obtained by amplification with the oligonucleotide primers M13-reverse and geneIII-forward (4) or of the separate Fd and VKCK or VLCL amplicons.

Screening for the Fab's capacity to interfere with binding of cytokine x to its receptor was performed in an appropriate receptor—ligand binding ELISA. For this, low amounts of biotinylated cytokine x were incubated with Fab in culture supernatant on cytokine x—Receptor coated plates and bound cytokine x was subsequently detected with streptavidin-HRP conjugate. Positive hits were sequenced and Fab purified for determining their potency (IC50) in the in vitro receptor—ligand assay and to assess their affinity in BIAcore on immobilized cytokine x.

Large scale induction of soluble Fab fragments from individual clones was performed on a 50-ml or 250-ml scale in 2×TY containing 100 µg/ml carbenicillin and 2% glucose. After growth at 37° C. to an OD600 of 0.9, the cells were pelleted (10 min at 2,934×g) and resuspended in 2×TY with carbenicillin and 1 mM isopropyl-1-thio-D-galactopyranoside (IPTG). Alternative the De Bellis procedure (De Bellis and Schwartz, NAR (1990) 18(5): 1311) was followed using 0.2% in stead of 2% glucose, thus permitting the direct addition of IPTG to the medium of the late log phase cells. Bacteria were harvested after 3.5 h of growth at 30° C. by centrifugation (as before); periplasmic fractions were prepared by resuspending the cell pellet in 1 ml of ice-cold PBS. After 2-16 h of rotating head-over-head at 4° C., the spheroplasts were removed by two centrifugation steps; after spinning during 10 min at 3,400×g, the supernatant was clarified by an additional centrifugation step during 10 min at 13,000×g in an Eppendorf centrifuge. The periplasmic fraction obtained was directly used in the different functional assays (target binding ELISA, in vitro receptor—ligand binding assays and Biacore).

For sequencing, plasmid DNA was prepared from 5-ml cultures grown at 30° C. in LB-medium, containing 100 µg/ml carbenicillin and 2% glucose, using the Qiagen Mini-kit (Qiagen) or on amplicons with vector primers M13-reverse and geneIII-forward, which anneal at the borders of the Fab insert.

Example 7

Large Scale Production and Purification of Lead Fab's

Fab inserts from 3 to 6 different leads were recloned via ApaLI-NotI in an expression vector (coded pCB5) identical to pCB3 including the hexahistidine and C-MYC tags fused to the carboxyterminus of the Fd, but lacking the bacteriophage M13 gene3. In parallel the V regions were recloned with the appropriate combination of restriction enzymes and sequentially cloned in gene3 deleted vectors containing human CH1 and CK or CL for the expression of chimeric Fabs. After fingerprint analysis, individual clones obtained after recloning were grown on 50-ml or 250-ml scale and periplasmic fractions were prepared as described above. Fab fragment was IMAC purified and the correctly formed Fab was further purified via Size Exclusion Chromatography using a Superdex 75HR column (Amersham Pharmacia Biotech). Depending on the cell based assay endotoxin was removed by passage over an anion exchange column (Source30Q, GE Healthcare), which was sensitized overnight in 1 M NaOH and subsequently equilibrated in D-PBS. The yield was determined by measuring the optical density at 280 nm using a molar extinction coefficient of 13 for Fabs.

The purified Fab's were tested in the in vitro receptor—ligand binding assay and Biacore to confirm the observations made with the Fab fragment as produced by the gene3 containing pCB3 vector. Finally the potency of the Fab was determined in the bioassay.

Example 8

In this example the llama derived lead Fabs against cytokine x were humanized by using a soft randomization procedure targeting a small set of framework residues and by monovalent display of the resulting Fab library on the surface of filamentous phage in order to identify high affinity framework sequences via affinity based selection (US2003/0190317 A1, incorporated herein by reference). For instance, for dromedary derived germline VH (IGHV1S20) a small library was generated for positions 5 (Val, Leu), 55 (Gly, Ala), 83 (Ala, Ser), 95 (Lys, Arg), 96 (Ser, Ala) and 101 (Met, Val) maintaining 70% of the wild type residues (IMGT numbering). Amino acids in the hypervariable loops could be addressed in a similar way.

Site-directed mutagenesis to correct PCR errors or to introduce additional specific single codon changes was performed essentially as described by Kunkel et al. Curr. Protoc. Mol. Biol. CH8U8.1 (2001) or alternatively Synthetic genes encoding the variants ordered from GeneArt. The template for site-directed experiments was single-stranded DNA from a humanized Fab clone.

Site directed mutagenesis was also used to directly change a limited number of amino acid codons for humanization or modification purposes in the DNA encoding the wild type or humanized Fabs.

After selection the individual leads were tested on affinity and potency and the best leads were chosen for reformatting into human Fab/IgGs.

Example 9

Expression of Human Fab Fragments and Human Monoclonal Antibodies

Starting from the humanized VH and VL regions expression of humanized Fabs was performed as described in Rauchenberger et al. J. Biol. Chem. 278:38194-204 (2003). For the expression of human monoclonal antibodies two separate expressions vectors, one for the light chain and one for the heavy chain construct were constructed based on the pcDNA 3.1 vector. The expression vector for the light chain contained either the human C kappa or human C lambda sequence downstream of a CMV promoter as well as restriction sites allowing the cloning of the light chain construct as KPN1 BsmB1 fragments downstream of the CMV promoter and in frame with the light chain constant domain. The expression vector for the heavy chain contained then human CH1-hinge-CH2-CH3 sequence downstream of a CMV promoter as well as restriction sites allowing the cloning of the VH construct as KPN1 BsmB1 fragments downstream of the CMV promoter and in frame with the heavy chain constant domains.

The VL and VH fragments were cloned into the appropriate expression vectors as KPN1 BsmB1 fragments containing the Kozak sequence followed by the mouse IgG kappa leader sequences in frame with the respective VL or VH sequence. These sequences were obtained by gene synthesis and optimized for expression in mammalian cells (Geneart).

For full length IgG production VH and VL expression vectors constructs were co-transfected into mammalian cells (HEK-293 (transient) or CHO(stable)). Supernatant from transiently transfected cells or from stably transfected cells was purified via protein A chromatography.

Monoclonal antibodies or Fabs were tested in receptor binding assays and in bioassays and the best leads were selected for further development.

Example 10

Camelid Vs Human Homology Analysis

Methodology

Sequences of germline llama and dromedary J regions, which encode for FR4 were compared with human sequences and were completely identical (10 out of 10 residues match); the only exception is IGHJ4, which contains Glutamine (instead of Leucine or Methionine) on position 6 in FR4 (alignments shown below). For somatically mutated VLambda FR4 from dromedary 9 out of 10 residues match (90% homology), since most of the available sequences have Histidine in stead of Lysine or Glutamate or Glutamine on position 6 (alignment shown below). Finally there is again 90% identity (9 out of 10 residues) in FR4 of the set of six available somatically mutated dromedary VKappa sequences, because position 3 residue Serine deviates from what is found in the human germline JK segments, i.e. Glutamine, Proline and Glycine (alignment shown below).

For VH, VLambda and VKappa the analysis is supported by alignments (see below). Sequence alignment was done with closest human germline sequence, having identical H1 and H2 canonical folds.

Residues which don't align, but which appear in another family member (or subclass) of the same germline are considered as homologous, based on the assumption that it is feasible to mutate them back to said closest human germline sequence.

Canonical structures are compared using the following programs: http://www.bioinf.org.uk/abs/chothia/html and http://www.bioc.unizh.ch/antibody/Sequences/Germlines/VBase_hVK.html. Residues of analyzed camelid antibodies (or from other species) which do not fit exactly the canonical fold algorithm are checked for their appearance in the sequence of members of the matching human germline family with the same combination of canonical folds, or mentioned residues allowing the folds are checked for their appearance within the family of camelid antibodies to which the analyzed antibody belongs.

Results are presented in the following sections:
10.1—Dromedary VH
10.2—*Lama glama* VH
10.3—VL 1-40
10.4—VL 2-18
10.5—VL 3-1
10.6—VL 3-12
10.7—VKappa 2-40
10.8—J(H) region comparisons of llama and human
10.9—Comparison of light chain J regions
10.10—*Lama pacos* VH germline homology
10.11—*Lama glama* derived VH homology analysis
10.12—*Lama glama* derived VL analysis

| IGHV gene | FR1-IMGT (1-26) | CDR1-IMGT (27-38) | FR2-IMGT (39-55) | CDR2-IMGT (56-65) | FR3-IMGT (66-104) | CDR3-IMGT (105-115) |
|---|---|---|---|---|---|---|
| | | | 10.1 Dromedary VH | | | |
| M99679, IGHV3-53 | EVQLVESGG.GLIQPGGSLRLSCAAS | GFTVSSYY... | MSWVRQAPGKGLEWVSV | IYSGGST... | YYADSVK.GRFTISRDNSKNTLYLQMNSLRAEDTAVYYC | AR......... |
| AF000603, IGHV1S1 | EVQLVESGG.GLVQPGGSLRLSCAAS | GFTFSSYY... | MSWVRQAPGKGLEWVSG | IYSDGST... | YYGDSVK.GRFTISRDNAKNMLYLQMNSLKPEDTAVYYC | AG......... |
| AJ245151, IGHV1S2 | QVQLVESGG.GLVQPGGSLRLSCAAS | GFTFSSYY... | MSWVRQAPGKGLEWVSG | IYSDGST... | YYGDSVK.GRFTISRDNAKNMLYLQMNSLKPEDTAMYYC | |
| AJ245152, IGHV1S3 | EVQLVESGG.GLVQPGGSLRLSCAAS | GFTFSSYY... | MSWARQAPGKGLEWVSG | IYSDGST... | YYGDSVK.GRFTISRDNAKNMLYLQMNSLKPEDTAMYYC | |
| AJ245153, IGHV1S4 | EVQLVESGG.GLVQPGGSLRLSCAAS | GFTFSSYY... | MSWVRQAPGKGLEWVSG | IYSDGST... | YYGDSVK.GRFTISRDNAKNTLYLQMNSLKPEDTAVYYC | |
| AJ245154, IGHV1S5 | EVQLVESGG.GLVQPGGSLRLSCAAS | GFTFSSYY... | MSWVRQAPGKGLEWVSG | IYSDGST... | YYGDSVK.GRFTISRDNAKNMLYLQVNSLKPEDTAVYYC | |
| AJ245155, IGHV1S6 | EVQLVESGG.GLVQPGGSLRLSCAAS | GFTFSSYY... | MSWVRQAPGKGLEWVSG | IYSDGST... | YYGDSVK.GRFTISRDKAKNMLYLQMNSLKPEDTAMYYC | |
| AJ245157, IGHV1S7 | EVQLVESGG.GLVQPGGSLRLSCAAS | GFTFSSYD... | MSWVRKAQGKGLEWVSG | IYSDGST... | YYGDSVK.GRFTISRDKAKNMLYLQMNSLKPEDTAMYYC | |
| AJ245158, IGHV1S8 | EVQLVESGG.GLVQPGGSLRLSCAAS | GFTFSSYY... | MSWVRQAPGKGLEWVSG | NTSDGST... | YYGDSVR.GRFTISRDKAKNMLYLQMNSLMPEDTAMCYC | |
| AJ245159, IGHV1S9 | EVQLVESGG.GLVQPGGSLRLSCAAS | GFTFSGYY... | MSWVRQAPGRGLEWVSG | IYSDGST... | YYGDSVK.GRFTISRDKAKNMLYLQMNSLKPEDTSMYYC | |
| AJ245160, IGHV1S10 | AVQLVESGG.GLVQPGGSLRLSCAAS | GFTFSSYY... | MSWVRQAPGKGLEWVSG | IYSDGST... | YYGDSVK.GRFTISRDKAKNMLYLQMNSLKPEDTAMYYC | |
| AJ245164, IGHV1S11 | QVQLVESGG.GSVQAGGSLRLSCAAS | GFTFSSYY... | MSWVRQAPGKGLEWVSG | IYSDGST... | YYGDSVK.GRFTISRDNAKNMLYLQMNSLKPEDTAMYYC | |
| AJ245165, IGHV1S12 | AVQLVESGG.GSVQAGGSLRLSCAAS | GFTFSSYY... | MYWVRQAPGKGLEWVSG | IYSDGST... | YYGDSVK.GRFTISRDNAKNMLYLQMNSLKPEDTAMYYC | |
| AJ245167, IGHV1S13 | EVQLVESGG.GLVQPGGSLRLSCAAS | GFTFSSYW... | MYWVRQAPGKP1EWVSG | IYSDGST... | YYGDSVK.GRFTISRDKAKNMLYLQMNSLKPEDTAMYYC | |
| AJ245168, IGHV1S14 | QVQLVESGG.GLVQPGGSLRLSCAAS | GFTFSSYD... | MSWVRQAPGKGLEWVSA | INSDGST... | NYADSVK.GRFTISRDNAKNMLYLQMNSLKPEDTAMYYC | |
| AJ245170, IGHV1S15 | EVQLVESGG.GLVQPGGSLRLSCAAS | GFTFSSYA... | MSWVRQAPGKGLEWVSA | INSRGST... | HYADSMK.GRFTISRDNAKNVLYLQMNSLKPEDTAMYYC | |
| AJ245171, IGHV1S16 | EVQLVESGG.GLVQPGGSLRLSCAAS | GFTFSSYY... | MSWVRQAPGKGLEWVSG | IYSDGST... | YYGDSVK.GRFTISQDNAKNTVYLQMNSLKPEDTAMYYC | |

A) Sequence comparisons
Sequences in comparison to human IGHV3-23 and other human germlines:
55 G/S/A can be considered more variable/beginning of CDR2

-continued 10.1 Dromedary VH

| 68 | G | also human A exist in the same context (IGHV1S17/18) -> should be replaceable by A |
| 83 | A | present in many other human VH3 class germlines |
| 86 | M/V | also human T exist in the same context -> should be replaceable by T |
| 95 | K | also in human germlines 3-15/49/72/73 |
| 96 | P | also in human germline 3-19 |
| 101 | M | not found in human IGHV3 class |

Sequence homology: 26/26 (FR1) + 17/17 (FR2) + 38/39 (FR3) = 81/82 = 99%

B) Canonical folds analysis CDR H1 and H2
1) Analysis of germline Dromedary VH sequences IGHV1S1 to IGHV1S19 reveals a canonical fold 1 for CDR1 and fold 1 for CDR2, so identical to the folds of human germline VH3-13 and HV3-53, confirming the data published by Nguyen and colleagues (EMBO J (2000), 19(15), p 921-930). The analysis for dromedary IGHV1S1 and human IGHV3-53 are shown below as examples using auto-generated SDR templates:

IGHV1S1
CDR H1 Class ?
! Similar to class 1/10A, but:
! H94 (Chothia Numbering) is deleted.
CDR H2 Class 1/9A [1gig]

IGHV3-53
CDR H1 Class ?
! Similar to class 1, but:
! H94 (Kabat Numbering) is deleted.
CDR H2 Class 1 chothia:human [1gig]

| IGHV gene | FR1-IMGT (1-26) | CDR1-IMGT (27-38) | FR2-IMGT (39-55) | CDR2-IMGT (56-65) | FR3-IMGT (66-104) | CDR3-IMGT (105-115) |
|---|---|---|---|---|---|---|
| M99660, IGHV3-23 | EVQLLESGG.GLVQPGGSLRLSCAAS | GFTFSSYA... | MSWVRQAPGKGLEWVSG | ISGSGGST.. | YYADSVK.GRFTISRDNSKNTLYLQMNSLRAEDTAVYYC | AK........ |
| AJ245177, IGHV1S20 | EVQLVESGG.GLVQPGGSLRLSCAAS | GFTFSSYY... | MSWVRQAPGKGLEWVSG | INSDGSNT.. | YYADSVK.GRFTISRDNAKNTLYLQMNSLKPEDTAMYYC | |
| AJ245178, IGHV1S21 | AVQLVESGG.GLVQPGGSLRLSCAAS | GFTFSSYY... | MSWVRQAPGKGLEWVSG | IYTGGGST.. | YYADSVK.GRFTISRDNAKNVLYLKLSSLKPEDTAMYYC | |
| AJ245183, IGHV1S22 | EVQLVESGG.GLVQPGGSLRLSCAAS | GFTFSSYY... | MSWVRQAPGKGLEWVST | INSGGGST.. | YYADSVK.GRFTISRDNAKNMLYLQMNSLKPEDTAMYYC | |
| AJ245185, IGHV1S23 | EVQLVESGG.GLVQPGGSLRLSCAAS | GFTFSSYW... | MYWVRQAPGKGLEWVST | INSGGGST.. | YYADSVK.GRFTISRDNAKNMLYLQMNSLKPEDTAMYYC | |
| AJ245186, IGHV1S24 | EVQLVESGG.GLVQPGGSLRLSCAAS | GFTFSSYW... | MYWVRQAPGKGPEWVST | INSGGGST.. | YYADSVK.GRFTISRDNAKNMLYLQMNSLKPEDTAMYYC | |
| AJ245187, IGHV1S25 | EVQLVESGG.GLVQPGGSLRLSCAAS | GFTFSSYW... | MYWVRQAPRKGLEWVST | INSAGGST.. | YYADSVK.GRFTISRDNAKNTVLQMNSLKPEDTAMYYC | |

-continued 10.1 Dromedary VH

| | | | | |
|---|---|---|---|---|
| AJ245189, IGHV1S26 | EVQLVESGG.GLVQPGGSLRLSCAAS | GFTFSSYW... | MYNVRQAPGKGLEWVST | INSAGGST.. YYADSVK.GRFTISRDNAKNTVYLQMNSLKPEDTAMYYC |
| AJ245191, IGHV1S27 | EVQLVESGG.GLVQPGGSLRLSCAAS | GFTFSSYD... | MSWVRQAPGKGLEWVSA | INSGGGST.. YYADSVK.GRFTISRDNAKNTLYLQMNSLKPEDTAMYYC |
| AJ245192, IGHV1S28 | EVQLVESGG.GLVQPGGSLRLSCAAS | GFTFSSYD... | MSWVRQAPGKGLEWVSA | INSGGGST.. YYADSVK.GQFTISRDNAKNTLYLQMNSLKPEDTAMYYC |
| AJ245193, IGHV1S29 | EVQLVESGG.GLVQPGGSLRLSCAAS | GFTFSSYA... | ISWVRQAPGKGLEWVSA | INSGGGST.. YYADSVK.GRFTISRDNAKNTVYLQLNSLKPEDTAMYYC |
| AJ245194, IGHV1S30 | EVQLVESGG.GLVQPGGSLRLSCAAS | GFTFSSYA... | MSWVRQAPGKGLEWVSA | INSGGGST.. YYADSVK.GRFTISRDNAKNTLYLQLNSLKTEDTAMYYC |
| AJ245195, IGHV1S31 | AVQLVESGG.GLVQPGGSLRLSCAAS | GFTFSSYA... | ISWVRQAPGKGLEWVSA | INSGGGST.. YYADSVK.GRFTISRDNAKNTVYLQLNSLKPEDTAMYYC |
| AJ245179, IGHV1S32 | EVQLVESGG.GLVQPGGSLRLSCAAS | GFTFSSYW... | VYWVRQAPGKGLEWVSS | IYTGGGST.. YYADSVK.GRFTISKDNAKNTLYLYLQMNSLKPEDTAMYYC |
| AJ245180, IGHV1S33 | EVQLVESGG.GLVQPGGSLRLSCAAS | GFTFSSYW... | MYWVRQAPGKGLEWVSS | IYTGGGST.. YYADSVK.GRFTISKDNAKNTLYLYLQMNSLKPEDTAMYYC |
| AJ245182, IGHV1S34 | EVQLVESGG.GLVQPGGSLRLSCAAS | GFTFSSYW... | MYWVRQAPGKALQWVSS | IYTGGGST.. YYADSVK.GPLTISKDNAKNTLYLQMNSLKPEDTAMYYC |
| AJ245190, IGHV1S35 | EVQLVESGG.GLVQPGGSLRLSCAAS | GFTFSSYW... | MYWVRQAPGKGLEWVSA | INSGGGST.. YYADSVK.GRFTISQDNAKNTRYLQMNSLKPEDTAMYYC |
| AJ245196, IGHV1S36 | EVQLVESGG.GLVQPGGSLRLSCAAS | GFTFSSYA... | MSWVRQAPGKGLEWVSA | IYTGGGST.. YYADSVK.GRFTISKDNAKNMLYLQMNSLKPEDTAMYYC |
| AJ245197, IGHV1S37 | EVQLVESGG.GSVQAGGSLRLSCAAS | GFTFSSYD... | MSWVRQAPGKGLEWVSA | INSGGGST.. YYADSVK.GRFTISKDNAKNTLYLQMNSLKPEDTAMYYC |
| AJ245181, IGHV1S38 | EVQLVESGG.GLVQPGGSLRLSCAAS | GFTSSSYW... | MYWVRQAPGKGFEWVSA | IYTGGGST.. YYADSVK.GRFTISQDNAKNTLYLQMNSLKPEDTAMYYC |
| AJ245198, IGHV1S39 | EVQLVESGG.GLVQPGGSLRLSCAAS | AFTYSSCC... | MYWVRQAPGKGLEWVSA | INSGGGST.. YYADSVK.GRFTISQDNAKNTRYLQMNSLKPEDTAMYYC |
| AJ245199, IGHV1S40P | EVQLVESGG.GLVQPGGSLRLSCAAS | *FTFSSYA... | ISWVRQAPGKGLEWVSA | INSGGGST.. YYADSVK.GRFTISQDNAKNTRYLQMNSLKPEDTAMYYC |

A) Sequence comparisons
Sequences in comparison to human IGHV3-23 and other human germlines:
  5 V        exist in all other VH3 germlines
 55 G/T/S    can be considered more variable/beginning of CDR2
 83 A        present in many other human VH3 germlines
 86 M/V      majority is human T in the same context -> should be replaceable by T
 95 K        also in human germlines 3-15/49/72/73
 96 P        also in human germline 3-19
101 M        not found in human IGHV3 class
Sequence homology: 26/26 (FR1) + 17/17 (FR2) + 38/39 (FR3) = 81//82 = 99%

B) Canonical folds analysis CDR H1 and H2
2) Analysis of the germline Dromedary VH sequences IGHV1S20 and IGH1S22 to IGH1S24 shows the presence of canonical fold 1 for CDR1 and fold 3 for CDR2, so identical to the canonical folds found in human germline VH3-23, confirming the data published by Nguyen and colleagues (EMBO J (2000), 19(5), p 921-930). The analysis for dromedary IGHV1S20 and human -continued 10.1 Dromedary VH IGHV are shown below as examples, where it should be mentioned that residue H57 Asparagine is found back in VH3-21 that also have a class 3 fold for CDR2 in combination with class 1 fold of CDR1 (deletions are D- and/or J-region encoded):

IGHV1S20:
CDR H1 Class ?
! Similar to class 1/10A, but:
!    H94 (Chothia Numbering) is deleted.
!    H102 (Chothia Numbering) = - (allows: YHVISDG)

CDR H2 Class ?
! Similar to class 3/10B, but:
!    H52 (Chothia Numbering) = N (allows: SFWH)

IGHV3-21
CDR H1 Class ?
! Similar to class 1, but:
!    H94 (Chothia Numbering) is deleted.

CDR H2 Class 3 chothia:human (1igc)
3) Germline Dromedary VH sequences IGH1S21 and IGHV1S25 to IGHV1S39 have canonical fold 1 for CDR1 and fold 2 for CDR2, identical to the folds of human germline VH5, thereby confirming the data published by Nguyen and colleagues (EMBO J (2000), 19(5), p 921-930). The analysis for IGHV1S32 is shown below as an example using auto-generated SDR templates. Serine (S) in position H55 is not found nor Lysine (K) in human germline VH with fold 2 of CDR2:

IGHV1S32:
CDR H1 Class ?
! Similar to class 1/10A, but:
!    H94 (Chothia Numbering) is deleted.
!    H102 (Chothia Numbering) = - (allows: YHVISDG)

CDR H2 Class ?
! Similar to class 2/10A, but:
!    H50 (Chothia Numbering) = S (allows: REWYGQVLNKA)
!    H71 (Chothia Numbering) = K (allows: VAL)

-continued 10.1 Dromedary VH

Compared to results for IGHV3-23:
CDR H1 Class ?
! Similar to class 1/10A, but:
! H94 (Chothia Numbering) is deleted.
! H102 (Chothia Numbering) = K (allows: YHVISDG)

CDR H2 Class ?
! Similar to class 2/10A, but:
! H71 (Chothia Numbering) = R (allows: VAL)

Conclusions:
Canonical fold 1 for CDR1 and fold 1 for CDR2 were predicted for a large group of germline dromedary VH human germline VH3-13), another large group used canonical fold 1 for CDR1 and fold 3 VH3-21) and another group used canonical fold 1 for CDR2 (as found in human germline VH3-21)
Note:
Residues 50, 52, 71, 94, 102 according to Chothia numbering compare with residues 55, 57, 80, 107, 117 in IMGT numbering system, respectively.

```
                              10.2 Llama VH

IGHV         FR1-IMGT                CDR1-IMGT      FR2-IMGT           CDR2-IMGT     FR3-IMGT                                              CDR3-IMGT
  gene         (1-26)                  (27-38)        (39-55)            (56-65)       (66-104)                                              (105-115)
                 1        10        20      30           40       50        60        70        80        90       100       110
                 |         |         |       |            |        |         |         |         |         |         |         |
                 ........|.........|. ........|. .......|........|. ........|. .......|........|........|........|. .....|....

M99660, IGHV3-23    EVQLLESGG.GLVQPGGSLRLSCAAS GFTFSSYA.... MSWVRQAPGKGLEWVSA ISGSGGST.. YYADSVK.GRFTISRDNSKNTLYLQMNSLRAEDTAVYYC AK........
AF305949, IGHV1S6   EVQLVESGG.GLVQPGGSLRLSCAAS GFTFSSSA.... MSWVRQAPGKGLEMVSS IYSYSSNT.. YYADSVK.SRFTISTDNAKNTLYLQMNSLKPEDTAVYYC AA........

A) Sequence comparisons:
Sequences in comparison to human IGHV3-23 and other human germlines:
  5 V    exist in all other VH3 germlines
 55 S    in 3-21/38; can be considered more variable/beginning of CDR2
 74 S    not in human gemline class 3 but in 4 and 6
 80 T    not present in any other human VH3 germlines
 83 A    in many other human class 3 germlines
 95 L    not present in any other human VH germlines
 96 P    not present in class 3 but in 2 and 6
sequence homology: 26/26 (FR1) + 17/17 (FR2) + 35/39 (FR3) = 78/82 = 95%

B) Canonical folds analysis:
M99660, IGHV3-23 Results using auto-generated SDR templates:
CDR H1 Class ?
! Similar to class 1/10A, but:
!    H94 (Chothia Numbering) is deleted.
!    H102 (Chothia Numbering) = K (allows: YHVISDG)

CDR H2 Class ?
! Similar to class 2/10A, but:
!    H71 (Chothia Numbering) = R (allows: VAL)

AF305949 ,IGHV1S6 Results using auto-generated SDR templates:
```

-continued

| 10.2 Llama VH |
|---|
| CDR H1 Class ? |
| ! Similar to class 1/10A, but: |
| ! H32 (Chothia Numbering) = S (allows: IHYFTNCED) |
| ! H94 (Chothia Numbering) is deleted. |
| ! H102 (Chothia Numbering) = A (allows: YHVISDG) |
| CDR H2 Class ? |
| ! Similar to class 2/10A, but: |
| ! H50 (Chothia Numbering) = S (allows: REWYGQVLNKA) |
| ! H56 (Chothia Numbering) = N (allows: YREDGVSA) |
| ! H71 (Chothia Numbering) = T (allows: VAL) |
| (B) Canonical folds CDR H1 and H2 |
| Analysis of the only available germline Llama VH sequence aligning to human germline IGHV3-23 reveals a canonical fold 1 for CDR1 and fold 2 for CDR2 identical to the folds of CDR1 and 2 of some human germline VH2 members and all VH5 and VH7 members. The analysis for IGHV1S6 is shown below: |
| Discussion analysis: |
| 1) Position 32 Serine is also found in human germline VH2-8, VH3-20 and VH3-22, which all have a canonical fold 1 for CDR1 |
| 2) Position 94 is deleted, position 102 is A; these residues are encoded by the D and/or J region |
| 3) Position 50 Serine (S) for canonical fold 2 for CDR2 is not found in human germline VH with the same fold |
| 4) Position 56 Asparagine (N) is found in VH2-9 and VH2-10 that share canonical fold 2 for CDR2 |
| 5) Position 71 Threonine (T) is found in almost all human germline VH with canonical fold 2 for CDR2 |

Conclusion:
Llama germline sequence IGHV1S6 is most likely adopting canonical folds 1/10A for CDR1 and 2/10A for CDR2 just as found for the human IGHV3-23 germline sequence.
Note:
Chothia numbering 32, 50, 56, 71, 94 and 102 compare to numbers 33, 55, 62, 77, 107 and 115 in IMGT numbering scheme, respectively.

```
                                        10.3 VL 1-40

IGLV         FR1-IMGT          CDR1-IMGT       FR2-IMGT       CDR2-IMGT       FR3-IMGT                                CDR3-IMGT         FR4
gene          (1-26)            (27-38)         (39-55)        (56-65)        (66-104)                                (105-115)

1         10        20       30        40        50        60        70        80        90        100       110
          |.........|.........|.....   ..|.........|.........|   .........|.........|.........|.........|   .........|.........|....

M94116, IGLV1-40  QSVLTQPPS.VSGAPGQRVTISCTGS SSNIGAGYD... VHWYQQLPGTAPKLLIY GNS......  NRPSGVP.DRFSGSK..SGTSASLAITGLQAEDEADYYC QSYDSSLSG...
Camv144           QSVLTQPPS.MSGSLGQRVTISCTGS SSNIGGGSG... VQWFQQLPGTAPKLLIY GNS......  NRASIGP.DRFSESK..SGSSASLTITGLQADDEADYYC ASYDNRLSG--PVFGGGTKLTVLG A) Sequence comparisons:
 11 M:    not found in any human sequence 14 S:    not in human VL1 sequences but in almost all other VL types 15 L:    not in human VL1 but in VL 3, 4 9, 10 classes 40 Q:    not in human VL1 but in VL6-57

42 F:    in 3-27 and V17 but in not in class 1

68 A:    not in any human VL

78 E:    not in any human VL

85 S:    not in any human VL

90 T:    not in human VL1 but in classes 2-4 and 6-8

97 D:    not in VL1 but in 4-3 and 8-61
Sequence homology: 23/26 (FR1) + 15/17 (FR2) + 34/39 (FR3) = 72/82 = 88% homology B) Canonical folds analysis:
M94116, IGLV1-40: Results using auto-generated SDR templates
CDR L1 Class ?
! Similar to class 6/14A, but:

!  L31 (Chothia Numbering) = Y (allows: H)

!  L32 (Chothia Numbering) = D (allows: N)

!  L93 (Chothia Numbering) = S (allows: R)
```

-continued 10.3 VL 1-40

CDR L2 Class 1/7A [11mk]

Camvl44: Results using auto-generated SDR templates
CDR L1 Class ?
! Similar to class 6/14A, but:

! L31 (Chothia Numbering) = S (allows: H)
! L32 (Chothia Numbering) = G (allows: N)
! L93 (Chothia Numbering) = N (allows: R)

CDR L2 Class 1/7A [11mk]

CDR L2 gives a perfect match for canonical fold 1/7A, while for CDR L1 three key residues are questionable for giving a perfect match with canonical fold 6/14A, which now will be discussed individually.
1) Position L31 Serine (S, in CDR1) and L32 Glycine (G, in CDR1) should be Histidine (H) and Asparagine (N), respectively; both residues were not found in sequences with a canonical fold 14A; no other camelid lambda sequences, which align with human germline VL1 family, were identified, therefore making the analysis rather difficult 2) Position L93 Asparagine (N, in CDR3) should be Arginine (R), but Asparagine (N) also occurs in two human germline VL4 family members, which share the canonical fold 14A with human germline VL1-2

Conclusions:
1) Canonical fold 1/7(A) for CDR2 expected and probably fold number 6/14A for CDR1, i.e. identical to what is found in human germline VL1 member 1-40.
NOTE:
Positions 31, 32 and 93 (Chothia) compare to 34, 35, and 109 in IMGT nomenclature used for the sequence comparison.

10.4 VL 2-18

| IGLV gene | leader | FR1-IMGT (1-26) | CDR1-IMGT (27-38) | FR2-IMGT (39-55) |
|---|---|---|---|---|

```
                            1         10        20            30            40        50
                            .........|.........|......   ...|......... .|........

Z73642,            QSALTQPPS.VSGSPGQSVTISCTGT SSDVGSYNR... VSWYQQPPGTAPKLMIY EVS....
IGLV2-18

Camvl17   MAWALLLLTLLTQGTGSWA QSALTQPSS.VSGTPGQTVTISCTGT SNDVGGYNY... VSWYQQLPGTAPKLLIY Camvl33   MAWALLLLTLLTQGTGSWA QSALTQPSS.VSGTPGQTVTITCTGT RDDVGGYNY... VSWYQQLPGTAPKLLIY Camvl36   MAWALLLLTLLTQGTGSWA QSALTQPSS.VSGTPGQTVTISCTGT SNDVGGYNY... VSRYQQLPGTAPKLLIY Camvl59   MAWALLLLTLLTQGTGSWA QSALTQPSS.VSGTPGQTVTISCTGT SNDVGRYNY... VSWYQQLPGTAPKFLIY Camvl30   MAWALLLLTLLTQGTGSWA QSALTQPSS.VSGTPGQTVTISCTGT SNDVGRYNY... VSWYQQFPGTAPKLLIY Camvl32   MAWALLLLTLLTQGTGSWA QSALTQPSS.VSGTPGQTVTISCTGT SNGVGGYNY... VSWYRQLPGTAPKLLIY Camvl57   MAWALLLLTLLTQGTGSWA QSALTQPSS.VSGTPGQTVTISCTGT SNDVGGYNY... VSWYQQLPGTAPKLLIY Camvl5    MAWALLLLTLLTQGTGSWA QSALTQPSS.VSGTPGQTVTISCTGT SNDVGRYNY... VSWYQQLPETAPKLLIY Camvl65                       QAVLTQPSS.VSGTPGQTVTISCTGT SNDVGKYNY... VSWYQQFPGTAPKLLIY Camvl51   MAWALLLLTLLTQGTGSWA QSALTQPSS.VSGTPGQTVTISCTGT SNDVGGYNY... VSWHQQVPGTAPKLILY Camvl31   MAWALLLLTLLTQGTGSWA QSALTQPSS.VSGTPGQTVTISCTGT SDDVGAYNY... VSWYQQLPGTAPKLLIY Camvl60   MAWALLLLTLLTQGTGSWA QSALTQPSS.VSGTPGQTVTISCTGT RDDVGKYNY... VSWYQQLPGTAPKLLIY Camvl52   MAWALLLLTLLTQGTGSWA QSALTQPSS.VSGTPGQTVTISCTGT SNDVGRYNY... VSWYQHLPGTAPKLLIY
```

| IGLV gene | CDR2-IMGT (56-65) | FR3-IMGT (66-104) | CDR3-IMGT (105-115) | FR4 |
|---|---|---|---|---|

```
                   60        70        80        90       100           110
                 .|.... ....|......... ....|......... .........|.........|.... .....|......

Z73642,    ... NRPSGVP.DRFSGSK..SGNTASLTISGLQAEDEADYYC SLYTSSSTF...
IGLV2-18

Camvl17    QDS...... KRNSGIP.DRFSGSK..SDNTASMTISGLQSADEADYYC ASYRSTYH---SL FGGGTHLTVLG Camvl33    QIN...... KRLSGIP.DRFSGSK..SGNTASMTISGLQSADEADYYC ASYRDLNT---LV FGGGTHLTVLG Camvl36    QIN...... KRASGIP.DRFSGSK..SGNTASMTISGLQSADEADYYC ASYRATNS---IV FGGGTHLTVLG Camvl59    QVN...... KRASGIP.DRFSGSK..SGNTASMTISGLQSADEADYYC ASLRSSGN---AV FGGGTHLTVLG Camvl30    QVN...... KRASGIP.DRFSGSK..SGNTASMTISGLQSADEADYYC ASYRNWAN---LP FGGGTHLTVLG Camvl32    QVN...... KRASGIP.DRFSGSK..SGNTASMTISGLQSADEADYYC ASYRNGNN---AV FGGGTHLTVLG Camvl57    QVN...... KRASGIP.DRFSGSK..SDNTASMTISGLQSADEADYYC ASYRSRDN---AV FGGGTHLTVLG Camvl5     DVD...... KRASGIP.DRFSGSK..SGNTASMTISGLQSADEADYYC ASYRSGDN---AA FGGGTRLTVLG Camvl65    QVN...... KRGSGIP.DRFSGSK..SGNTASMTISGLQSADEADYYC ASLSSGNN---AV FGGGTHLTVLG Camvl51    QVK...... ERPSGIP.DRFSGSK..FGDTASMTISGLQSADEADYYC ASYSSPNN---VL FGGGTHLTVLG Camvl31    QVN...... KRPSGIP.DRFSGSK..SGNTVSLTISGLQSADEADYTC ASYKHTYN---AV FGGGTHLTVLG Camvl60    QVN...... KRASGIP.DRFSGSK..SGNTASMTISGLQSADEADYYC ASVRDYDNNEFVV FGGGTHLTVLG Camvl52    QVN...... KRASGIP.DRFSGSK..SGNTASMTTSGLQSADEADYYC SAYRSNDGP---V FGGGTHLTVLG
```

A) Sequence comparisons:

8 S     not in class 2 but also in 3-27 and 4-60, 5-52

14 T     not in class 2 but also in 1-44/47

13 T     not in class 2 but in many other germlines of class 3 and in many other germline classes as well

| 10.4 VL 2-18 |
| --- |

```
45 L        not in class 2, only in class 1

53 L        in 2-23, as well as in classes 1, 4, 5, 7, 8, 10

66 K        in classes 1, 2, 3

68 N/L/A/G     somatic mutation and also human residue P is found in Camvl51 and Camvl31

71 I        in other class 2 members and in class 1-41/51 and classes 3, 4, 9, 10

89 M        somatic mutation (?) as also human residue L is found in Camvl31

96 S        in classes 1, 2, 4, 5

97 A        not found in human germline
Sequence homology: 23/26 (FR1) + 16/17 (FR2) + 38/39 (FR3) = 78/82 = 94% homology B) Canonical folds analysis:
Z73642, IGLV2-18: Results using auto-generated SDR templates
CDR L1 Class ?
! Similar to class ?/14C, but:

!    L32 (Chothia Numbering) = R (allows: Y)

!    L90 (Chothia Numbering) = L (allows: S)

!    L93 (Chothia Numbering) = S (allows: G)
CDR L2 Class 1/7A [1lmk]

Camvl59 Results using auto-generated SDR templates
CDR L1 Class ?
! Similar to class ?/14C, but:

!    L28 (Chothia Numbering) = N (allows: S)

!    L93 (Chothia Numbering) = S (allows: G)
CDR L2 Class 1/7A [1lmk]

Analysis of the camelid lambda light chain variable sequences aligning to human germline
IGLV2-18 reveals a canonical fold 2/14 for CDR1 and fold 1/7A for CDR2, so identical to
the folds of CDR1 and 2 of human germline VL2 family. The analysis for Camvl59 is shown
as an example:
CDR L2 gives a perfect match for canonical fold 1/7A, while for CDR L1 only two key
residues are questionable for giving a perfect match with canonical fold 2/14C, which now
will be discussed individually.
1)        Position L28 Asparagine (N, in CDR1) should be Serine (S), but Aspartate (D)
found in Camvl33 is the most often found residue in human germline VL2 sequences 2)        Position L93 Serine (S, in CDR3) should be Glycine (G), but Serine present
in three of the 8 aligned camelid VLs is the most often found residue in human germline
VL2, as in the human IGLV2-18 used for comparison
```

NOTE:
Position 93 (Chothia) compares to 109 in IMGT nomenclature used for the sequence comparison.
Conclusions:
Canonical for number 2/14 for CDR1 expected and fold 1/7(A) for CDR2, i.e. identical to what is found in human germline VL2.

| 10.5 VL-3-1 | | | | |
| --- | --- | --- | --- | --- |
| IGLV gene | FR1-IMGT (1-26) | CDR1-IMGT (27-38) | FR2-IMGT (39-55) | CDR2-IMGT (56-65) |
| | 1        10        20 | 30 | 40        50 | 60 |
| X57826, IGLV3-1 | SYELTQPPS.VSVSPGQTASITCSGD | KLGDKY...... | ACWYQQKPGQSPVLVIY | QDS....... KRP |
| Camvl19 | QSVLTQPSA.VSVSLGETARITCQGG | NFGSYY...... | ANWYQQKPGQAPVLVLY | KDS....... ARP |
| Camvl20 | QSVLTQPSA.VSVPLGETARITCQGG | DFGDYY...... | VSWYQQKPGQSPVLVIY | KDT....... LRP |
| Camvl8 | TALTQPSA.VSVSLGETARITCQGG | NFGSYY...... | TSWYQQKPEEAPVVVIY | KDT....... ERP |
| Camvl18 | QAVLSQPSA.VSVSLGETARITCQGD | NFGSYY...... | FSWYQQKPGQAPVLVIY | RNS....... NRP |

| 10.5 VL-3-1 |
| --- |

```
Camv123         QSVLTQPSA.VSVSLGQTARITCQGG ILGSKK...... TNWYQQKPGQAPVLVIY GDD....... SRP
```

|  | FR3-IMGT<br>(66-104) | CDR3-IMGT<br>(105-115) |
| --- | --- | --- |

```
                          70        80        90       100          110
                         .|.........|.........|.........|....  .....|......

X57826, IGLV3-1  SGIP.ERFSGSN..SGNTATLTISGTQAMDEADYC  QAWDSSTA....

Camvl19  SGIP ERFSGSS  SGGTATLTISGAQAEDEADYC  QSGSSSA-SA--V FGGGTHLTVLG

Camvl20  SGIP ERFTGSS  SGGAATLTISGAQAEDEADYC  QSETSSA-T---V FGGGTHLTVLG

Camvl8  SGIP ERFSASS  SGDTATLTISGAQAEDEADYC  QSGSSSA-NAP-V FGGGTKLTVLG

Camvl18  SGIP ERFSASS  SGGTATLTISGAQAEDEADYC  QSADSSGRNAR-A FGGGTKLTVLG

Camvl23  SGIP ERFSGSR  SGGTATLTISGAQAEDEADYC  QLLDSTDSSSYWV FGGGTHLTVLG
```

C) Sequence comparisons:
1 Q             primer encoded

2 S/T           primer encoded

3 V/A           primer encoded

5 S             primer encoded

8 S             also in 3-27 and 4-60

9 A             also in 3-19/32

15 L            in 3-9/16/19/32

17 E            not in human class 3 but human Q exists in Camvl23 in same context 20 R            in all other human class 3 sequences and others 24 Q            in 3-19/32

26 G            somatic mutation/part of CDR; human D exists in Camvl18 in same context 39 V/T/F        somatic mutation/part of CDR 40 N/S          somatic mutation/part of CDR 49 A            in many other class 3

66 A/L/N/S      somatic mutation/part of CDR

80 S            in 3-16/19/10/25/27

85 G            not in class 3 but in classes 6 and 7

94 A            in 3-19/10/9

97 E            in 3-10/16/19

Sequence homology: 26/26 (FR1) + 17/17 (FR2) + 38/39 (FR3) = 81/82 = 99% homology D) Canonical folds analysis:
Analysis of the above listed camelid lambda light chain variable sequences on the UCL webpage http://www.bioinf.org.uk/abs/chothia.html shows that CDR-L1 adopts canonical fold 11, while CDR-L2 has canonical fold 7. This corresponds with the canonical folds found in all human germline IGLV3 family members (see Pluckthun homepage http://www.bioc.unizh.ch/antibody/Sequences/Germlines/VBase_hVK.html). The canonical fold is determined by the length of the CDRs and certain key residues within and outside of the CDR. The analysis of e.g. Camvl20 is shown below:
CDR L1 Class ?
! Similar to class 2/11A, but:

!       L2 (Chothia Numbering = S (allows: I)

!       L25 (Chothia Numbering = G (allows: A)

!       L26 (Chothia Numbering = G (allows: S)

10.5 VL-3-1

! L28 (Chothia Numbering = F (allows: NSDE)

! L29 (Chothia Numbering = G (allows: IV)

! L51 (Chothia Numbering = D (allows: ATGV)

! L71 (Chothia Numbering = A (allows: YF)

! L90 (Chothia Numbering = S (allows: HQ)

CDR L2 Class 1/7A [1lmk]
CDR L2 gives a perfect match for canonical fold 1/7A, while for CDR L1 certain key residues are questionable for giving a perfect match with canonical fold 2/11A, which now will be discussed individually.

1) Position L2 Serine (S) should be Isoleucine (I), but human IGLV3-5 (which also has fold 11) has Serine (S) residue found in these camelid VLs.

2) L25 Glycine (G) is found in all human VL3 family members

3) L26 Glycine (G) should be Serine (S), but Aspartate (D) found in Camv118 is most often used in human VL3 members 4) L28 Phenylalanine (F, in CDR1) should be Asparagine (N), Serine (S), Aspartate (D) or Glutamate (E), but Leucine (L) found in Camv123 is the most often used residue in human VL3

5) L29 Glycine (G, in CDR1) is found in 4 of the 9 human VL3 germlines

6) L51 Aspartate (D, in CDR2) is most often used in human VL3

7) L71 Alanine (A, FR3) is most often used in human VL3

8) L90 Serine (S, CDR3) is most used residue in human VL3

Conclusions:
2) Canonical fold number 11 for CDR1 is expected and fold 7 for CDR2, i.e. identical to what is found in human germline VL3
Note:
Chothia Numbering 51, 71, and 90 compares to IMGT numbering 57, 87, and 106

10.6 VL 3-12

| IGLV gene | leader | FR1-IMGT (1-26) | CDR1-IMGT (27-38) | FR2-IMGT (39-55) |
|---|---|---|---|---|
| | | 1        10        20 | 30 | 40        50 |
| Z73658, IGLV3-12 | | SYELTQPHS.VSVATAQMARITCGGN | NIGSKA...... | VHWYQQKPGQDPVLVIY SDS. |
| Camvl11 | | QSVLTQPST.ASMSLGQTAKITCQGS | SLRNYA...... | AHWYQQKPGAAPVLVIY NDN. |

| IGLV gene | CDR2-IMGT (56-65) | FR3-IMGT (66-104) | CDR3-IMGT (105-115) | FR4 |
|---|---|---|---|---|
| | 60        70 | 80        90        100 | 110 | |
| Z73658, IGLV3-12 | ......  NRPSGIP. | ERFSGSN..PGNTTTLTISRIEAGDEADYYC | QVWDSSSH... | |
| Camvl11 | ......  NRPSGIP. | ERFSGSN..SGGTATLTISRTKAEDEADYYC | LSRDMSDSN-RVV | FGGGTHLTVLG |

A) Sequence comparisons:
 1 Q    primer encoded

2 S    primer encoded

10.6 VL 3-12

| | | |
|---|---|---|
| 3 V | primer encoded | |
| 5 S | primer encoded | |
| 8 S | also in 3-27 and 4, 5 | |
| 9 T | not in any human germline | |
| 11 A | not in class 3 but in classes 1, 2, 4, and 9 | |
| 13 M | not in other human germline | |
| 14 S | in many other germlines of class 3 and in many other germline classes as well | |
| 15 L | in 3-16/19/32 and in many other classes | |
| 16 G | almost everywhere other than in this particular germline | |
| 18 T | in many other germlines of class 3 and in many other germline classes as well | |
| 20 K | not in human class 3 sequences but in class 4 | |
| 24 Q | in 3-19/32 | |
| 26 G | somatic mutation/part of CDR | |
| 39 A | in many other germlines of class 3 | |
| 48 A | not in any human germline | |
| 49 A | in many other germlines of class 3 and in many other germline classes as well | |
| 80 K | in 3-32 and many other germline classes | |
| 85 G | not in class 3 but in class 7 | |
| 87 A | in many other germlines of class 3 and in many other germline classes as well | |
| 94 T | in 3-1 | |
| 95 K | not class 3 but in 2-33 and 6-57 | |
| 97 E | in 3-10/16/19 and in many other germline classes | |

Sequence homology: 22/26 (FR1) + 16/17 (FR2) + 37/39 (FR3) = 75/82 = 91% homology
Most likely homology underestimated due to somatic mutations and because only one family member is found.

B) Canonical folds analysis:
Z73658, IGLV3-12: Results using auto-generated SDR templates
CDR L1 Class ?
! Similar to class 2/11A, but:

!    L2 (Chothia Numbering) = Y (allows: I)

!    L25 (Chothia Numbering) = G (allows: A)

!    L26 (Chothia Numbering) = N (allows: S)

!    L28 (Chothia Numbering) = I (allows: NSDE)

!    L29 (Chothia Numbering) = G (allows: IV)

!    L51 (Chothia Numbering) = D (allows: ATGV)

| 10.6 VL 3-12 |
|---|

```
!    L71 (Chothia Numbering) = T (allows: YF)

!    L90 (Chothia Numbering) = V (allows: HQ)
CDR L2 Class 1/7A [1lmk]

Camvl11: Results using auto-generated SDR templates
CDR L1 Class ?
! Similar to class ?/11B, but:

!    L25 (Chothia Numbering) = G (allows: A)

!    L26 (Chothia Numbering) = G (allows: N)

!    L29 (Chothia Numbering) = R (allows: P)

!    L34 (Chothia Numbering) = H (allows: Y)

!    L46 (Chothia Numbering) = L (allows: M)

!    L71 (Chothia Numbering) = A (allows: V)

!    L90 (Chothia Numbering) = S (allows: A)

!    L93 (Chothia Numbering) = M (allows: N)
CDR L2 Class 1/7A [1lmk]
```

Remarks:
more difficult to align, especially FR1. These are somatically mutated sequences, meaning that variations in FR can be expected as well. Deviations from canonical fold analyis are very comparable in IGLV3-12, so most likely adopts comparable canonical folds. For CDR L2 fold 1-7A shows a perfect match, CDR L2 will adopt fold 2-11 just as in human counterpart.
Conclusion:
Adopts canonical fold 2/11 for CDR1 and fold 1/7A for CDR2, so identical to human germline VL3. Only one family member found, which is somatically mutated and therefore it is difficult to draw conclusions.

10.7 VKappa 2-40

```
IGKV gene           FR1-IMGT                    CDR1-IMGT        FR2-IMGT              CDR2-IMGT   FR3-IMGT                                    CDR3-IMGT
                    (1-26)                      (27-38)          (39-55)               (56-65)     (66-104)                                    (105-115)
                    1        10        20       30               40        50          60          70        80        90        100           110
                    |........|.........|......  |.........|..    |.........|.......    |.....      |.........|.........|.........|..          |.......|

X59314, IGKV2-40    DIVMTQTPLSLPVTPGEPASISCRSS  QSLLDSDDGNTY     LDWYLQKPGQSPQLLIY     TLS.....    YRASGVP.DRFSGSG..SGTDFTLKISRVEAEDVGVYYC      MQRIEFP....
Kp6                 DIVMTQSPSSVTASVGEKVIINCKSS  QSVFDTSRQKSF     LNWHRQRPGQSPRELIY     YAS.....    TRQSGVP.DRFSGSG..STTDFTLTISSVQPEDAAVYYC     QQAFNVQPS  FGSGTRLEIKR
Kp48                DIVMTQSPSSVTASVGEKVTINCKSS  QSVRSSSSQKSL     LDWHQQRPGQSPRRLIY     YAS.....    ARASGVP.DRFSGSG..STTDFTLTISSVQPEDAAVYYC     QQYSGSPPT  FGSGTRLEIKR
Kp3                 DIVMTQSPSSVTASVGEKVTINCKSS  QHVISVSNQKSY     LNWYQQRPGQSPRLLIY     YAS.....    TRESGIP.DRFSGSG..STTDFALTISSVQPEDAAVYYC     QQAYSTPYS  FGSGTRLEIKR
Kp20                DIVMTQSPSSVTASVGEKVTINCKSS  QSVLSSSNQKSY     LNWYQQRPGQSPRLLIY     YAS.....    TRESGIP.DRFSGSG..STTDFTLTISSVQPEDAAVYYC     QQAYSAPYS  FGSGTRLEIKR
Kp7                 DIVMTQSPSSVLASVGEKVTINCKSS  QSVLSSSNQKSY     LNWYQQRPGQSPRLLIT     YAS.....    TRESGVP.DRFSGSG..STTDFTLTISSVQPEDAVVYYC     QQAYSKPYN  FGNGTRLEIKR
Kp10                DIVMTQSPTSVTASVGEKVTINCKSS  QSVFASSSSQKBQ    LAWRQQRPGQSPRRLIY     YAS.....    TRESGVP.DRFSGSG..STTDFTLTISSVQPEDAAVYYC     QHLYSAPYS  FGSGTRLEIKR
Kp1                 DIVMTQSPSSVTASVGEKVTINCKSS  QNLVSDSNQRSL     LAWHQQRPGQSPRKLIY     YAS.....    TRTSGTP.DRFSGSG..STTDFTLTISSVQPEDAAVYYC     QQGKKDPLS  FGSGTRLEIKR
```

A) Sequence comparisons:

| | | |
|---|---|---|
| 7 | S | primer encoded |
| 9 | S | only in human kappa 1 not kappa 2 family |
| 11 | V | only in human kappa 1-12 not kappa 2 family |
| 12 | T/L | not in human kappa germline |
| 13 | A | not in class 2 but in class 1 and 5 |
| 14 | S | not in class 2 but in class 1, 3, 4, 7 |
| 15 | V | only in class 1 |
| 19 | V | not in class 2 but in class 1, 5, 6 |
| 20 | T | not in class 2 but in class 1, 3, 4, 6, 7 |
| 22 | N | not in class 2 but in class 4 |
| 24 | K | in classes 2, 4, 5 |
| 40 | N/A | somatic mutation, human D also exists in KP48 |
| 42 | H | somatic mutation, human Y also exists in KP3/20/7 |
| 43 | Q/R | Q also found in classes 1, 2, 3, 4, 5, 6 and 7; R is somatic mutation |
| 51 | R | in 2-24 and 2-30 as well as is class 3 |
| 52 | R/K | R in 2-30 and 1-17; human L also exists |
| 66 | T/A | in classes 1, 3, 4 but not in 2; somatic mutation/part of CDR |
| 68 | Q/E | somatic mutation, human A also exists in KP48 |
| 71 | I | somatic mutation; human V also exists in same context in various dromedary kappa chains |
| 84 | T | not in any human kappa germline |
| 90 | T | not in class 2 but in classes 1, 3, 4, 5, 6, 7 |
| 93 | S | not in class 2 but in classes 1, 3, 4, 6 |
| 95 | Q | not in class 2 but in classes 1, 3, 4 |
| 96 | P | not in class 2 but in classes 1, 3 |

-continued 10.7 VKappa 2-40

99 A         not in class 2 but in classes 5, 6
100 A/V      not in class 2 but in classes 1, 3, 4, 5, 6, 7

Sequence homology: 17/26 (FR1) + 17/17 (FR2) + 31/39 (FR3) = 66/82 = 80% homology
Most likely homology underestimated due to somatic mutations and because all sequences seem to belong to the same class.

B) Canonical folds analysis:
X59314, IGKV2-40 Results using auto-generated SDR templates CDR L1 Class ?
! Similar to class 3/17A, but:
! L90 (Chothia Numbering) = Q (allows: N)
! L93 (Chothia Numbering) = E (allows: NS)
CDR L2 Class 1/7A [11mk]

Kp6 Results using auto-generated SDR templates

CDR L1 Class ?
! Similar to class 3/17A, but:
! L29 (Chothia Numbering) = V (allows: L)
! L90 (Chothia Numbering) = Q (allows: N)
CDR L2 Class 1/7A [11mk]

Analysis of the camelid kappa light chain variable sequences aligning to human germline IGLV2-40 reveals a canonical fold 3/17A for CDR1 and fold 1/7A for CDR2, so identical to the folds of CDR1 and 2 of human germline IGKV2-40. Dromedary Kp6 was analyzed as an example. CDR2 gives a perfect match for canonical fold 1, while for CDR1 a number of residues are questionable for giving a perfect match with canonical fold 3/17A, which now will be discussed individually.
1) Position L29 Valine (V, in CDR1) should be Leucine (L) for having canonical fold 3 for CDR1, but this residue is present in dromedary Kp1 sequence
2) Position L90 Glutamine (Q, in CDR3) occurs as well in human germline VBase_VK4_1, which also has canonical folds 3 for CDR1 (in combination with fold 1 for CDR2)

Conclusions:
Canonical fold 1 for CDR2 expected and most probably fold number 3/17A for CDR1 and fold 1 for CDR2, i.e. identical to what is found in human germline.

NOTE: Positions 90 (Chothia) compares to position 107 in IMGT nomenclature used for the sequence comparison.

10.8 J(H) Region Comparisons of Human and Llama

| 10.8 J(H) region comparisons of human and llama |  |
|---|---|
| Human |  |
| IGHJ Genes | ---CDR3--- ----FR4----<br>1          10         20<br>.........|.........| |
| J00256, IGHJ1 | ...AEYFQH WGQGTLVTVSS |
| J00256, IGHJ2 | ...YWYFDL WGRGTLVTVSS |
| J00256, IGHJ3 | .....AFDV WGQGTMVTVSS |
| J00256, IGHJ4 | .....YFDY WGQGTLVTVSS |
| J00256, IGHJ5 | ....NWFDS WGQGTLVTVSS |
| J00256, IGHJ6 | YYYYYGMDV WGQGTTVTVSS |
| Llama: |  |

| 10.8 J(H) region comparisons of human and llama |  |
|---|---|
| IGHJ Genes | --CDR3--- ----FR4----<br>1        10<br>..........|........ |
| AF305952, IGHJ2 | GYRYLEV WGQGTLVTVSS |
| AF305952, IGHJ3 | NALDA WGQGTLVTVSS |
| AF305952, IGHJ4 | EYDY WGQGTQVTVSS |
| AF305952, IGHJ5 | PQFEY WGQGTLVTVS |
| AF305952, IGHJ6 (1) | DFGS WGQGTLVTVS |

Sequence analysis:
The J(H) regions derived from llama show a perfect homology to their human counterparts. There is a 100% sequence identity. The only exception is the 6$^{th}$ residue of FR4 in llama IGHJ4 being Gln (Q). This residue is not found in human J(H) regions at this position.

10.9 Comparison of Light Chain J Regions

Lambda J:

| 10.9 Comparison of light chain J regions |  |
|---|---|
| Lambda J: |  |
| Kabat numbering | ..97 98......108<br>-- CDR3 -- ---FR4----<br>-J-lamba-<br>.. ..........|
| X04457, IGLJ1 | YV FGTGTKVTVL |
| M15641, IGLJ2 | VV FGGGTKLTVL |
| M15642, IGLJ3 | VV FGGGTKLTVL |
| X51755, IGL34 | FV FGGGTQLIIL |
| X51755, IGLJ5 | WV FGEGTELTVL |
| M18338, IGLJ6 | NV FGSGTKVTVL |
| X51755, IGLJ7 | AV FGGGTQLTVL |
| Camv119 etc. | .. FGGGTHLTVLG (38/44 anaylzed sequences) |
| Camv18/18/4 | .. FGGGTKLTVLG (3/44 analyzed sequences) |
| Camv158/28/5 | .. FGGGTPLTVLG (3/44 analyzed sequences) |

Sequence analysis:
The first 2 residues of the human germline J are considered part of the CDR3. They are often changed during the joining process. The best match of dromedary J-lambda regions is with IGLJ2 and 3. 9/10 amino acids are identical: 90% sequence identity. Only His or Arg in position 103 (Kabat) do not match. Arg is positively charged (as Lys) and even His can be considered somewhat positively charged. Therefore exchange to the human Lys should be possible.

| Kappa J: |  |
|---|---|
| Kabat numbering | ..97 98......108<br>-- CDR3 -- ---FR4----<br>Kappa<br>.. ..........|
| J00242, IGKJ1 | WT FGQGTKVEIK |
| J00242, IGKJ2 | YT FGQGTKLEIK |

| 10.9 Comparison of light chain J regions | | |
|---|---|---|
| J00242, IGKJ3 | FT | FGPGTKVDIK |
| J00242, IGKJ4 | LT | FGGGTKVEIK |
| J00242, IGKJ5 | IT | FGQGTRLEIK |
| Kp6/48/3/20/10/1 | | FGSGTRLEIKR (6/7 analyzed sequences) |
| Kp7 | | FGNGTRLEIKR (1/7 analyzed sequences) |

Sequence analysis:
The first 2 residues of the human germline J regions are considered part of the CDR3. They are often changed during the joining process. Best match of dromedary J-kappa is with human IGKJ5. 9/10 amino acids match: 90% sequence identity.

10.10 Lama pacos VH germline analysis

| Name | % Ident | % Homol | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | FR1 | |
| X92343\|IGHV1-46*01 | | | Q | V | Q | L | V | Q | S | G | A | E | V | K | K | P | G | A | S | V | K | V | S | C | K | A | S | G | Y | T | F | T |
| LpVH1-s6 (AM939701) | 89.2% | 91.9% | E | V | Q | L | V | Q | S | G | A | E | L | R | K | P | G | A | S | V | K | V | S | C | K | A | S | G | Y | T | F | T |
| LpVH1-s2 (AM939697) | 89.2% | 91.9% | E | V | Q | L | V | Q | P | G | A | E | L | R | K | P | G | A | S | V | K | V | S | C | K | A | S | G | Y | T | F | T |
| LpVH1-s3 (AM939698) | 87.8% | 90.5% | E | V | Q | L | V | Q | P | G | A | E | L | R | K | P | G | A | S | L | K | V | S | C | K | A | S | G | Y | T | F | T |
| LpVH1-s4 (AM939699) | 89.2% | 91.9% | E | V | Q | L | V | Q | P | G | A | E | L | R | K | P | G | A | S | L | K | V | S | C | K | A | S | G | Y | T | F | T |
| LpVH1-s5Ps (AM939700) | 89.2% | 91.9% | E | V | Q | L | V | Q | P | G | A | E | L | R | K | P | G | A | S | V | K | V | S | C | K | A | S | G | Y | T | F | T |
| M99660\|IGHV3-23*01 | | | E | V | Q | L | L | E | S | G | G | G | L | V | Q | P | G | G | S | L | R | L | S | C | A | A | S | G | F | T | F | S |
| AM939712 | 94.6% | 98.6% | E | V | Q | L | V | E | S | G | G | G | L | V | Q | P | G | G | S | L | R | L | S | C | A | A | S | G | F | T | F | S |
| AM939713 | 89.2% | 94.6% | Q | L | R | V | E | S | G | G | G | L | V | Q | P | G | G | S | L | R | L | S | C | A | A | S | G | F | T | F | D |
| AM939730 | 93.2% | 95.9% | E | V | Q | L | V | E | S | G | G | V | L | V | Q | P | G | G | S | L | R | L | S | C | A | A | S | G | R | T | F | D |
| AM939731 | 91.9% | 97.3% | E | V | Q | L | V | E | S | G | G | G | L | V | Q | P | G | G | S | L | R | L | S | C | A | A | S | G | F | T | F | G |
| AM939744 | 86.5% | 93.2% | E | L | Q | L | V | E | S | G | G | G | L | V | Q | A | G | G | S | L | R | H | S | C | A | A | S | G | F | T | F | S |
| AM939726 | 93.2% | 97.3% | E | V | Q | L | V | E | S | G | G | G | L | V | Q | P | G | G | S | L | K | L | S | C | A | A | S | G | L | T | F | S |
| AM939727 | 97.3% | 97.3% | E | V | Q | L | V | E | S | G | G | G | L | V | Q | P | G | G | S | L | R | V | S | C | A | A | S | G | F | T | F | S |
| AM939739 | 97.3% | 97.3% | E | L | Q | L | V | E | S | G | G | G | L | V | Q | P | G | G | S | L | R | L | S | C | A | A | S | G | F | T | F | S |
| AM939740 | 94.6% | 98.6% | Q | V | Q | L | V | E | S | G | G | G | L | V | Q | P | G | G | S | L | R | L | S | C | A | A | S | G | F | T | F | S |
| AM939741 | 94.6% | 97.3% | E | V | Q | L | V | E | S | G | G | G | L | V | Q | P | G | G | S | L | R | L | S | C | A | A | S | G | F | T | F | G |
| AM939742 | 90.5% | 95.9% | E | V | L | L | V | E | S | G | G | G | L | V | Q | P | G | G | S | L | R | L | S | C | A | A | S | G | F | T | F | S |
| AM939743 | 93.2% | 97.3% | E | V | Q | L | V | E | S | G | G | G | L | V | Q | P | G | G | S | L | R | L | S | C | A | A | S | G | F | T | F | S |
| U29481\|IGHV3-23*03 | | | E | V | Q | L | L | E | S | G | G | G | L | V | Q | P | G | G | S | L | R | L | S | C | A | A | S | G | F | T | F | S |
| AM939716 | 94.6% | 97.3% | E | V | Q | L | V | E | S | G | G | G | L | V | Q | P | G | G | S | L | R | L | S | C | A | A | S | G | F | T | F | S |
| AM939728 | 90.5% | 94.6% | E | V | L | V | E | S | G | G | G | L | V | Q | P | G | G | S | L | R | L | S | C | A | A | S | G | F | T | F | S |  |
| AM939738 | 91.9% | 95.9% | E | V | Q | L | V | E | S | G | G | G | L | V | Q | P | G | G | S | L | R | L | S | C | A | A | S | G | F | T | F | S |
| AM939710 | 89.2% | 93.2% | Q | V | Q | L | V | E | S | G | G | G | L | V | Q | P | G | G | S | L | R | L | S | C | A | A | S | G | F | T | F | S |
| AM939748 | 93.2% | 97.3% | Q | V | Q | L | V | E | S | G | G | G | L | V | Q | A | G | G | S | L | R | L | S | C | A | A | S | G | F | T | F | S |
| AM939750 | 94.6% | 98.6% | Q | V | Q | L | V | E | S | G | G | G | L | V | Q | P | G | G | S | L | R | L | S | C | A | A | S | G | F | T | F | S |
| AM939751 | 91.9% | 95.9% | E | L | Q | L | V | E | S | G | G | G | L | V | Q | P | G | G | S | L | K | L | S | C | A | A | S | G | F | T | F | S |
| AM939767 | 90.5% | 94.6% | Q | V | Q | L | V | E | S | G | G | G | L | V | Q | P | G | G | S | L | R | L | S | C | A | A | S | G | L | T | L | G |
| AM939768 | 93.2% | 97.3% | Q | V | Q | L | V | E | S | G | G | G | L | V | Q | P | G | G | S | L | R | L | S | C | A | A | S | G | L | T | L | G |
| AM939707 | 93.2% | 97.3% | Q | L | Q | L | V | E | S | G | G | G | L | V | Q | P | G | G | S | L | R | L | S | C | A | A | S | G | F | T | F | S |
| AM939708 | 93.2% | 97.3% | Q | V | Q | L | V | E | S | G | G | G | L | V | Q | P | G | G | S | L | R | L | S | C | A | A | S | G | F | T | F | G |
| AM939709 | 91.9% | 97.3% | Q | L | Q | L | V | E | S | G | G | G | L | V | Q | P | G | G | S | L | R | L | S | C | A | A | S | G | F | T | F | G |
| AM939732 | 93.2% | 95.9% | Q | V | Q | L | V | E | S | G | G | G | L | V | Q | P | G | G | S | L | R | L | S | C | A | A | S | G | F | T | F | S |
| AM939733 | 89.2% | 94.6% | Q | V | Q | L | V | E | S | G | G | G | L | V | Q | P | G | G | S | L | R | L | S | C | A | A | S | G | F | T | F | S |
| AM939717 | 90.5% | 95.9% | E | V | Q | L | V | E | S | G | G | G | L | V | Q | P | G | G | S | L | R | L | S | C | A | A | S | G | F | T | F | G |
| AM939734 | 93.2% | 97.3% | Q | V | Q | L | V | E | T | G | G | G | L | V | Q | P | G | G | S | L | R | L | S | C | A | A | S | G | F | T | F | G |
| AM939735 | 91.9% | 97.3% | Q | V | Q | L | V | E | S | G | G | G | L | V | Q | P | G | G | S | L | R | L | S | C | A | A | S | G | L | T | F | S |
| AM939736 | 93.2% | 97.3% | Q | L | Q | L | V | E | S | G | G | G | L | V | Q | P | G | G | S | L | R | L | S | C | A | A | S | G | L | T | F | D |
| AM939737 | 94.6% | 98.6% | Q | V | Q | L | V | E | S | G | G | G | L | V | Q | P | G | G | S | L | R | L | S | C | A | A | S | G | F | T | F | S |

-continued 10.10 Lama pacos VH germline analysis

| Name | % Ident | % Homol | Sequence |
|------|---------|---------|----------|
| L33851\|IGHV3-74*01 | | | |
| AM939749 | 94.6% | 98.6% | E V L Q L V E S G G G L V Q P G G S L R L S C A A S G F T F S |
| AM939724 | 93.2% | 98.6% | Q V Q L V E S G G G L V Q P G G S L R L S C A A S G F T F S |
| AM939725 | 89.2% | 95.9% | Q V Q L V E S G G G L V Q P G G S L R L S C A A S G F T F S |
| AM939745 | 87.8% | 93.2% | E L Q L V E S G G G L V Q P G G S L R L S C A A S G F T F S |
| AM939723 | 93.2% | 97.3% | Q V Q L V E S G G G L V Q P G G S L R L S C A A S G F T F T |
| X92229\|IGHV4-30-2*03 | | | |
| LpVH2-s7 (AM939704) | 78.4% | 81.1% | Q L Q L Q Q S G P G L V K P S Q T L S L T C A V S G H S I S |
| Z14238\|IGHV4-30-4*01 | | | |
| LpVH2-s2 (AM939769) | 86.5% | 86.5% | Q V Q L Q E S G P G L V K P S Q T L S L T C T V S G G S I S |
| LpVH2-s3 (AM939770) | 82.4% | 82.4% | E V Q L Q E S G P G L V K P S Q T L S L T C T V S G G S I S |
| LpVH2-s4 (AM939771) | 82.4% | 82.4% | Q V Q L Q E S G P G L V K P S Q T L S L T C T V S G A S I S |
| LpVH2-s5 (AM939772) | 87.8% | 87.8% | E V Q L Q E S G P G L V K P S Q T L S L T C T V S G G S I S |
| LpVH2-s6 (AM939773) | 82.4% | 86.5% | Q V Q L Q E S G P G L V K P S Q M L S L T C A V S G Y S I S |
| LpVH2-s11Ps (AM939703) | 82.4% | 82.4% | Q V R L Q E S G P D L V K P S Q T L S L V C T V S G G S I S |
| LpVH2-s8 (AM939705) | 82.4% | 82.4% | E V Q L Q E S G P G L V K P S Q T L S L T C A V S G A S I S |
| LpVH2-s9Ps (AM939706) | 83.8% | 83.8% | Q V * L * Q S G P G L V K P S Q T L S L T C T V S G Y S I H |
| LpVH2-s10 (AM939702) | 83.8% | 83.8% | E V Q L Q E S G P G L L K P S Q M L S L T C L V S G Y S I S |

|  |  |  | CDR1 | | | | | | | | FR2 | | | | | | | | | | | | |
|---|---|---|---|---|---|---|---|---|---|---|---|---|---|---|---|---|---|---|---|---|---|---|---|
| Name | % Ident | % Homol | 31 | 32 | 33 | 34 | 35 | 35a | 35b | 35c | 36 | 37 | 38 | 39 | 40 | 41 | 42 | 43 | 44 | 45 | 46 | 47 | 48 | 49 |
| X92343\|IGHV1-46*01 | | | S | Y | Y | M | H | | | | W | V | R | Q | A | P | G | Q | G | L | E | W | M | G |
| LpVH1-s6 (AM939701) | 89.2% | 91.9% | S | Y | Y | I | D | | | | W | V | R | Q | A | P | G | Q | G | L | E | W | M | G |
| LpVH1-s2 (AM939697) | 89.2% | 90.5% | S | Y | Y | I | D | | | | W | V | R | Q | A | P | G | Q | G | L | E | W | M | G |
| LpVH1-s3 (AM939698) | 87.8% | 91.9% | S | Y | Y | I | D | | | | W | V | R | Q | A | P | G | Q | G | L | E | W | M | G |
| LpVH1-s4 (AM939699) | 89.2% | 91.9% | S | Y | Y | I | | | | | W | V | * | Q | A | P | G | K | G | L | E | W | M | G |
| LpVH1-s5Ps (AM939700) | 89.2% | 91.9% | S | Y | Y | I | | | | | W | V | R | Q | A | P | G | K | G | L | E | W | V | S |
| M99660\|IGHV3-23*01 | | | S | Y | A | M | S | | | | W | V | R | Q | A | P | G | K | G | L | E | W | V | S |

-continued 10.10 Lama pacos VH germline analysis

| ID | % | | | | | | | | | | | | | | | | | | | | |
|---|---|---|---|---|---|---|---|---|---|---|---|---|---|---|---|---|---|---|---|---|---|
| AM939712 | 94.6% | D | Y | A | M | S | | | W | V | R | Q | A | P | G | K | G | L | E | W | V | S |
| AM939713 | 89.2% | D | Y | G | M | S | | | W | V | R | H | A | P | G | K | G | L | E | W | V | S |
| AM939730 | 93.2% | S | Y | A | M | S | | | W | V | R | Q | S | P | G | K | G | L | P | W | V | S |
| AM939731 | 91.9% | S | Y | D | M | S | | | W | V | R | Q | A | P | G | K | G | L | P | W | V | S |
| AM939744 | 86.5% | S | Y | D | M | S | | | W | V | R | Q | A | P | G | K | G | L | P | W | V | S |
| AM939726 | 93.2% | S | Y | Y | M | S | | | W | V | R | Q | A | P | G | K | G | L | L | W | V | S |
| AM939727 | 97.3% | S | Y | Y | M | S | | | W | V | R | Q | A | P | G | K | G | L | L | W | V | S |
| AM939739 | 97.3% | S | Y | D | M | S | | | W | V | R | Q | A | P | G | K | G | L | L | W | V | S |
| AM939740 | 94.6% | S | Y | A | M | S | | | W | V | R | Q | A | P | G | K | G | L | L | W | V | S |
| AM939741 | 98.6% | S | Y | A | M | S | | | W | V | R | Q | A | P | G | K | G | L | L | W | V | S |
| AM939742 | 95.9% | S | Y | A | M | S | | | W | V | R | Q | S | P | G | K | G | L | L | W | V | S |
| AM939743 | 97.3% | S | Y | A | M | S | | | W | V | R | Q | A | P | G | K | G | L | L | W | V | S |
| U29481\|IGHV3-23*03 | | | | | | | | | | | | | | | | | | | | | | |
| AM939716 | 94.6% | S | Y | A | M | S | | | W | V | R | Q | A | P | G | K | G | L | E | W | V | S |
| AM939728 | 90.5% | S | Y | A | M | S | | | W | V | R | Q | A | P | G | K | G | L | L | W | V | S |
| AM939738 | 94.6% | S | Y | A | M | S | | | W | V | R | Q | A | P | G | K | G | L | L | W | V | S |
| AM939710 | 95.9% | S | Y | A | M | S | | | R | A | R | Q | V | P | G | K | G | L | L | W | V | S |
| AM939748 | 91.9% | S | Y | A | M | S | | | W | V | R | Q | A | P | G | K | G | L | L | W | V | S |
| AM939750 | 89.2% | S | Y | A | M | S | | | W | V | R | Q | V | P | G | K | G | L | L | W | V | S |
| AM939751 | 94.6% | S | Y | A | M | S | | | W | V | R | Q | A | P | G | K | G | L | L | W | V | S |
| AM939767 | 95.9% | S | Y | A | M | S | | | W | V | R | Q | A | P | G | K | G | L | L | W | V | S |
| AM939707 | 90.5% | S | Y | D | M | S | | | W | V | R | Q | V | P | G | K | G | L | L | W | S | S |
| AM939708 | 93.2% | S | Y | D | M | S | | | W | V | R | Q | A | P | G | K | G | L | L | W | V | S |
| AM939709 | 91.9% | S | Y | D | M | H | | | W | V | R | Q | A | P | G | K | G | L | L | W | V | S |
| AM939732 | 93.2% | S | Y | D | M | N | | | W | V | R | Q | A | P | G | K | G | L | L | W | V | S |
| AM939733 | 89.2% | S | Y | D | L | Y | | | W | A | R | R | V | P | G | K | G | L | L | W | S | S |
| AM939717 | 87.8% | S | Y | V | M | S | | | W | V | R | C | A | P | G | K | G | L | L | W | V | S |
| AM939734 | 95.9% | S | Y | V | M | S | | | W | V | R | Q | A | P | G | K | G | L | L | W | V | S |
| AM939735 | 94.6% | S | Y | W | M | S | | | W | V | R | Q | V | P | G | K | G | L | L | W | V | S |
| AM939736 | 91.9% | N | Y | A | M | S | | | W | V | R | Q | A | P | G | K | G | L | L | W | V | S |
| AM939737 | 93.2% | S | Y | A | M | S | | | W | V | R | Q | A | P | G | K | G | L | L | W | V | S |
| L33851\|IGHV3-74*01 | 94.6% | S | Y | A | M | S | | | W | V | R | Q | A | P | G | K | G | L | L | W | V | S |
| AM939749 | 93.2% | S | Y | A | M | S | | | W | V | R | Q | A | P | G | K | G | L | L | W | V | S |
| AM939724 | 89.2% | S | Y | A | M | S | | | W | V | R | Q | A | P | E | K | G | L | L | W | V | S |
| AM939725 | 95.9% | S | Y | A | M | S | | | W | V | R | Q | A | P | G | K | G | L | L | W | V | S |
| AM939745 | 93.2% | S | Y | A | M | S | | | W | V | R | Q | A | P | G | K | G | L | L | W | V | S |
| AM939723 | 87.8% | S | Y | A | M | S | | | W | V | R | Q | A | P | G | K | G | L | L | W | V | S |
| X92229\|IGHV2-2*03 LpVH2-s7 (AM939704) | 78.4% 81.1% | T | S | C | Y | Y | S | W | C | I | R | Q | P | G | K | G | L | V | W | I | G |
| Z14238\|IGHV4-30-4*01 LpVH2-s2 (AM939769) | 86.5% 86.5% | S | G | D | Y | Y | W | S | W | I | R | Q | P | G | K | G | L | E | W | I | G |
| | | T | S | Y | Y | A | W | S | W | I | R | Q | P | E | K | G | L | L | W | M | A |
| | | | S | Y | Y | Y | W | S | W | I | R | Q | P | G | K | G | L | E | W | M | G |

-continued 10.10 Lama pacos VH germline analysis

| Name | % Ident | % Homol | 50 | 51 | 52 | 52a | 52b | 52c | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|
| LpVH2-s3 (AM939770) | | 82.4% | 82.4% | T | S | Y | A | | | W | I | R | Q | P | S | K | G | L | E | W | M | G |
| LpVH2-s4 (AM939771) | | 82.4% | 82.4% | T | S | Y | A | | | W | I | R | Q | P | K | K | G | L | E | W | M | G |
| LpVH2-s5 (AM939772) | | 87.8% | 87.8% | T | S | Y | Y | | | W | I | R | Q | P | G | K | G | L | E | W | M | G |
| LpVH2-s6 (AM939773) | | 82.4% | 86.5% | T | S | Y | Y | | | W | I | R | Q | P | G | K | G | L | E | W | M | G |
| LpVH2-s11Ps | | 82.4% | 82.4% | T | S | Y | A | | | W | I | R | Q | P | G | K | G | L | E | * | M | G |
| LpVH2-s8 (AM939705) | | 82.4% | 82.4% | T | S | Y | A | | | W | I | R | Q | P | G | K | G | L | E | W | M | G |
| LpVH2-s9PS (AM939706) | | 83.8% | 83.8% | T | S | C | A | | | W | I | H | Q | P | G | K | G | L | E | * | M | G |
| LpVH2-s10 (AM939702) | | 83.8% | 83.8% | T | S | C | Y | | | W | I | R | Q | P | G | K | G | L | E | W | M | G |

|  |  |  |  |  |  |  |  |  | CDR2 |  |  |  |  |  |  |  |  |  |  |  |  |

| Name | % Ident | % Homol | 50 | 51 | 52 | 52a | 52b | 52c | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|
| X92343\|IGHV1-46*01 | | | *I* | *I* | *N* | *P* | | | *S* | *G* | *G* | *S* | *T* | *S* | *Y* | *A* | *Q* | *K* | *F* | *Q* | *G* |
| LpVH1-s6 | 89.2% | 91.9% | R | I | D | P | | | E | D | G | G | T | K | Y | A | E | S | F | Q | G |
| LpVH1-s2 | 89.2% | 94.6% | R | I | D | P | | | E | D | G | G | T | K | Y | A | E | S | F | Q | G |
| LpVH1-s3 | 93.2% | 97.3% | R | I | D | P | | | E | D | G | G | T | N | Y | A | E | S | M | Q | G |
| LpVH1-s4 | 91.9% | 97.3% | R | I | D | P | | | E | D | G | G | T | N | Y | A | E | S | M | Q | G |
| LpVH1-s5P | 89.2% | 91.9% | R | I | D | P | | | E | D | G | G | T | N | Y | A | E | S | F | Q | G |
| M99660\|IGHV3-23*01 | | | *A* | *I* | *S* | *G* | | | *S* | *G* | *G* | *S* | *T* | *Y* | *Y* | *A* | *D* | *S* | *V* | *K* | *G* |
| AM939712 | 94.6% | 98.6% | A | I | S | W | | | N | G | G | S | T | Y | Y | A | D | S | M | K | G |
| AM939713 | 89.2% | 94.6% | A | I | N | S | | | N | G | G | S | T | Y | Y | A | D | S | M | K | G |
| AM939730 | 93.2% | 97.3% | A | I | N | S | | | G | G | G | S | T | Y | Y | A | E | S | V | K | G |
| AM939731 | 91.9% | 97.3% | A | I | N | T | | | G | G | G | S | T | Y | Y | A | D | S | V | K | G |
| AM939744 | 86.5% | 93.2% | A | I | N | T | | | G | G | G | S | T | Y | Y | A | D | S | V | K | G |
| AM939726 | 93.2% | 97.3% | A | I | N | S | | | G | G | G | S | T | Y | Y | A | D | S | V | K | G |
| AM939727 | 94.6% | 98.6% | A | I | N | S | | | G | G | G | S | T | S | Y | A | D | S | V | K | G |
| AM939739 | 94.6% | 97.3% | A | I | N | S | | | G | G | G | S | T | Y | Y | A | D | S | V | K | G |
| AM939740 | 94.6% | 98.6% | A | I | N | S | | | G | D | G | S | T | S | Y | A | D | S | M | K | G |
| AM939741 | 94.6% | 98.6% | A | I | N | S | | | G | G | G | S | T | Y | Y | A | D | S | V | K | G |
| AM939742 | 90.5% | 95.9% | A | I | N | G | | | G | G | G | S | T | Y | Y | A | D | S | V | K | G |
| AM939743 | 93.2% | 97.3% | A | I | N | S | | | G | D | G | S | T | Y | Y | A | D | S | M | K | G |
| U29481\|IGHV3-23*03 | | | *V* | *I* | *Y* | *S* | | | *G* | *G* | *S* | *S* | *T* | *Y* | *Y* | *A* | *D* | *S* | *V* | *K* | *G* |
| AM939716 | 94.6% | 97.3% | S | I | Y | S | | | Y | S | S | N | T | Y | Y | A | D | S | V | K | G |
| AM939728 | 90.5% | 94.6% | S | I | Y | S | | | Y | G | S | N | T | Y | Y | A | D | S | V | K | G |
| AM939738 | 91.9% | 95.9% | T | I | Y | S | | | D | G | S | D | T | Y | Y | A | D | S | V | K | G |
| AM939710 | 93.2% | 95.9% | G | I | Y | S | | | D | G | S | D | T | Y | Y | A | D | S | V | K | G |
| AM939748 | 89.2% | 93.2% | G | I | Y | S | | | D | G | S | D | T | Y | Y | A | D | S | M | K | G |
| AM939751 | 94.6% | 98.6% | G | I | Y | S | | | D | G | S | D | T | Y | Y | A | D | S | V | K | G |
| AM939767 | 91.9% | 95.9% | G | I | Y | S | | | D | G | S | - | T | Y | Y | A | D | S | V | K | G |
| AM939767 | 90.5% | 94.6% | G | I | Y | S | | | D | G | S | - | T | Y | Y | A | D | S | V | K | G |

-continued 10.10 Lama pacos VH germline analysis

| Name | % Ident | % Homol | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 |
|---|---|---|---|---|---|---|---|---|---|---|---|---|---|---|---|---|---|---|---|---|---|---|---|---|---|---|---|---|---|---|---|---|
| AM939768 | 93.2% | 97.3% | G | | I | | Y | | S | | | | | | | D | G | | S | | | | | T | Y | A | | D | | S | V | K | G |
| AM939707 | 93.2% | 97.3% | S | | I | | Y | | S | | | | | | | Y | S | | S | | | N | | T | Y | A | | D | | S | V | K | G |
| AM939708 | 93.2% | 97.3% | S | | I | | Y | | S | | | | | | | Y | G | | S | | | N | | T | Y | A | | D | | S | V | K | G |
| AM939709 | 91.9% | 95.9% | T | | I | | N | | S | | | | | | | Y | G | | S | | | N | | T | Y | A | | D | | S | V | K | G |
| AM939732 | 93.2% | 94.6% | D | | I | | N | | S | | | | | | | Y | G | | S | | | S | | T | Y | A | | D | | S | V | K | G |
| AM939733 | 89.2% | 95.9% | C | | I | | N | | S | | | | | | | Y | G | | S | | | S | | T | Y | A | | D | | S | V | K | G |
| AM939717 | 90.5% | 95.9% | Y | | I | | Y | | S | | | | | | | Y | G | | S | | | S | | T | Y | A | | D | | S | V | K | G |
| AM939734 | 94.6% | 97.3% | Y | | I | | Y | | S | | | | | | | Y | G | | S | | | S | | T | Y | A | | D | | S | V | K | G |
| AM939735 | 91.9% | 97.3% | Y | | I | | N | | S | | | | | | | Y | G | | S | | | S | | T | Y | A | | D | | S | V | K | G |
| AM939736 | 93.2% | 97.3% | Y | | I | | N | | S | | | | | | | Y | G | | S | | | S | | T | Y | A | | D | | S | V | K | G |
| AM939737 | 94.6% | 98.6% | D | | I | | Y | | S | | | | | | | Y | G | | S | | | S | | T | Y | A | | D | | S | V | K | G |
| L33851\|IGHV3-74*01 | | | | | | | | | | | | | | | | | | | | | | | | | | | | | | | | | |
| AM939749 | 94.6% | 98.6% | R | | I | | N | | S | | | | | | | D | G | | S | | | S | | T | S | Y | | D | | S | V | K | G |
| AM939724 | 93.2% | 86.5% | G | | I | | Y | | S | | | | | | | D | G | | G | | | D | | T | S | A | | D | | S | V | K | G |
| AM939725 | 89.2% | 82.4% | A | | I | | N | | S | | | | | | | G | G | | G | | | N | | T | S | A | | D | | S | M | K | G |
| AM939745 | 87.8% | 95.9% | A | | I | | N | | S | | | | | | | C | G | | G | | | S | | T | S | A | | D | | S | V | K | G |
| AM939723 | 93.2% | 93.2% | A | | I | | N | | S | | | | | | | G | G | | G | | | S | | T | Y | A | | D | | S | V | K | G |
| X92229\|IGHV4-30-2*03 | | 97.3% | | | | | | | | | | | | | | | | | | | | | | | | | | | | | | | |
| LpVH2-s7 (AM939704) | 78.4% | 81.1% | S | | I | | Y | | | | | | | | | Y | S | | S | | | S | | T | Y | N | | P | | S | L | K | S |
| Z14238\|IGHV4-30-4*01 | | | | | | | | | | | | | | | | | | | | | | | | | | | | | | | | | |
| LpVH2-s2 (AM939769) | 86.5% | 86.5% | A | | I | | - | | | | | | | | | Y | S | | S | | | S | | T | Y | N | | P | | S | L | K | S |
| LpVH2-s3 (AM939770) | 82.4% | 82.4% | A | | I | | Y | | | | | | | | | Y | S | | S | | | S | | T | Y | S | | P | | S | L | K | S |
| LpVH2-s4 (AM939771) | 82.4% | 82.4% | A | | I | | A | | | | | | | | | Y | S | | S | | | S | | T | Y | S | | P | | S | L | K | S |
| LpVH2-s5 (AM939772) | 87.8% | 87.8% | A | | I | | A | | | | | | | | | Y | D | | S | | | S | | T | Y | S | | P | | S | L | K | S |
| LpVH2-s6 (AM939773) | 82.4% | 86.5% | A | | I | | A | | | | | | | | | Y | D | | S | | | S | | T | Y | S | | P | | S | L | K | S |
| LpVH2-s11Ps (AM939703) | 82.4% | 82.4% | A | | I | | A | | | | | | | | | Y | D | | S | | | S | | T | Y | S | | P | | S | L | K | S |
| LpVH2-s8 (AM939705) | 82.4% | 82.4% | A | | I | | - | | | | | | | | | Y | S | | S | | | S | | T | Y | S | | P | | S | L | K | S |
| LpVH2-s9Ps (AM939706) | 83.8% | 83.8% | A | | I | | - | | | | | | | | | Y | S | | S | | | S | | T | Y | S | | P | | S | L | K | S |
| LpVH2-s10 (AM939702) | 83.8% | 83.8% | A | | I | | - | | | | | | | | | Y | S | | S | | | S | | T | Y | S | | P | | S | L | K | S |

| Name | % Ident | % Homol | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 |
|---|---|---|---|---|---|---|---|---|---|---|---|---|---|---|---|---|---|---|---|---|---|---|---|---|---|---|---|---|---|---|---|---|
| | | | R | V | T | M | T | R | D | T | S | T | S | T | V | Y | M | E | L | S | S | L | R | S | E | D | T | A | V | Y | Y | C |
| X92343\|IGHV1-46*01 LpVH1-s6 | 89.2% | 91.9% | R | V | T | F | T | A | D | T | S | T | S | T | A | Y | V | E | L | S | S | L | R | S | G | T | A | V | Y | Y | C |

FR3

-continued 10.10 Lama pacos VH germline analysis

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| LpVH1-s2 | 89.2% | R | V | T | F | A | D | T | S | T | A | Y | L | E | L | S | S | L | R | S | E | G | T | A | V | Y | C |
| LpVH1-s3 | 87.8% | R | V | T | F | A | D | T | T | T | A | Y | V | E | L | S | S | L | R | S | E | G | T | A | V | Y | C |
| LpVH1-s4 | 89.2% | R | V | T | F | A | D | T | R | T | A | Y | V | E | L | S | S | L | R | S | E | G | T | A | V | Y | C |
| LpVH1-s5Ps | 89.2% | R | V | T | F | A | D | T | S | T | A | Y | V | E | L | S | S | L | R | S | E | G | T | A | V | Y | C |
| M99660\|IGHV3-23*01 | 94.6% | R | F | T | H | S | R | N | K | T | L | Y | L | Q | M | N | S | L | R | A | E | D | T | A | V | Y | C |
| AM939712 | 98.6% | R | F | T | H | S | R | N | K | T | L | Y | L | Q | M | N | S | L | K | S | E | G | T | A | V | Y | C |
| AM939713 | 94.6% | R | F | T | H | S | R | N | K | T | L | Y | L | Q | M | N | S | L | K | P | E | G | T | A | V | Y | C |
| AM939730 | 97.3% | R | F | T | H | S | R | N | K | T | L | Y | L | Q | M | N | S | L | K | P | E | G | T | A | V | Y | C |
| AM939731 | 97.3% | R | F | T | H | S | R | N | K | T | L | Y | L | Q | M | N | S | L | K | P | E | G | T | A | V | Y | C |
| AM939744 | 93.2% | R | F | T | H | S | R | N | K | T | V | Y | L | Q | M | N | S | L | K | P | E | G | T | A | V | Y | C |
| AM939726 | 86.5% | R | F | T | H | S | R | N | K | T | L | Y | L | Q | M | N | S | L | K | P | E | G | T | A | V | Y | C |
| AM939727 | 93.2% | R | F | T | H | S | R | N | K | T | L | Y | L | Q | M | N | S | L | K | P | E | G | T | A | V | Y | C |
| AM939739 | 97.3% | R | F | T | H | S | R | N | K | T | L | Y | L | Q | M | N | S | L | K | P | E | G | T | A | V | Y | C |
| AM939740 | 94.6% | R | F | T | H | S | R | N | K | T | L | Y | L | Q | M | N | S | L | K | P | E | G | T | A | V | Y | C |
| AM939741 | 98.6% | R | F | T | H | S | R | N | K | T | L | Y | L | Q | M | N | S | L | K | P | E | G | T | A | V | Y | C |
| AM939742 | 95.9% | R | F | T | H | S | R | N | K | T | L | Y | L | Q | M | N | S | L | K | P | E | G | T | A | V | Y | C |
| AM939743 | 97.3% | Q | F | T | H | S | R | N | K | T | L | Y | L | Q | M | N | S | L | K | P | E | G | T | A | V | Y | C |
| U29481\|IGHV3-23*03 | 94.6% | R | F | T | H | S | R | N | K | T | L | Y | L | Q | M | N | S | L | R | A | E | D | T | A | V | Y | C |
| AM939716 | 97.3% | R | F | T | H | S | R | N | K | T | T | Y | L | Q | M | N | S | L | K | S | E | G | T | A | V | Y | C |
| AM939728 | 90.5% | R | F | T | H | S | T | N | K | T | L | Y | L | Q | M | N | S | L | K | P | E | G | T | A | V | Y | C |
| AM939738 | 95.9% | R | F | T | H | S | T | N | K | T | L | Y | L | Q | M | N | S | L | K | P | E | G | T | A | V | Y | C |
| AM939710 | 91.9% | R | F | T | H | S | R | N | K | T | L | Y | L | Q | M | N | S | L | K | P | E | G | T | A | V | Y | C |
| AM939748 | 89.2% | R | F | T | H | S | R | N | K | T | L | Y | L | Q | M | N | S | L | K | P | E | G | T | A | V | Y | C |
| AM939750 | 98.6% | R | F | T | H | S | R | N | K | T | L | Y | L | Q | M | N | S | L | K | P | E | G | T | A | V | Y | C |
| AM939751 | 91.9% | R | F | T | H | S | R | N | K | T | L | Y | L | Q | M | N | S | L | K | P | E | G | T | A | V | Y | C |
| AM939767 | 90.5% | R | F | T | H | S | R | N | K | T | L | Y | L | Q | M | N | S | L | K | P | E | G | T | A | V | Y | C |
| AM939768 | 94.6% | R | F | T | H | S | R | N | K | T | V | Y | L | Q | M | N | S | L | K | P | E | G | T | A | V | Y | C |
| AM939707 | 97.3% | R | F | T | H | S | R | N | K | T | L | Y | L | Q | M | N | S | L | K | P | E | G | T | A | V | Y | C |
| AM939708 | 97.3% | R | F | T | H | S | R | N | K | T | V | Y | L | Q | M | N | S | L | K | P | E | G | T | A | V | Y | C |
| AM939709 | 95.9% | R | F | T | H | S | R | N | K | T | V | Y | L | Q | M | N | S | L | K | P | E | G | T | A | V | Y | C |
| AM939732 | 91.9% | R | F | T | H | S | R | N | K | T | L | Y | L | Q | M | N | S | L | K | P | E | G | T | A | V | Y | C |
| AM939733 | 93.2% | R | F | T | H | S | R | N | K | T | L | Y | L | Q | M | N | S | L | K | P | E | G | T | A | V | Y | C |
| AM939717 | 89.2% | Q | F | T | H | S | R | N | R | T | V | Y | L | Q | M | N | S | L | K | P | E | G | T | A | V | Y | C |
| AM939734 | 90.5% | Q | F | T | H | S | R | N | K | T | V | Y | L | Q | M | N | S | L | K | P | E | G | T | A | V | Y | C |
| AM939735 | 94.6% | R | F | T | H | S | R | N | K | T | L | Y | L | Q | M | N | S | L | K | P | E | G | T | A | V | Y | C |
| AM939736 | 91.9% | R | F | T | H | S | R | N | K | T | L | Y | L | Q | M | N | S | L | K | P | E | G | T | A | V | Y | C |
| AM939737 | 93.2% | R | F | T | H | S | R | N | K | T | L | Y | L | Q | M | N | S | L | K | P | E | G | T | A | V | Y | C |
| L33851\|IGHV3-74*01 | 94.6% | R | F | T | H | S | R | D | K | A | L | Y | L | Q | M | N | S | L | R | A | E | D | T | A | V | Y | C |
| AM939749 | 98.6% | R | F | T | H | S | R | D | K | A | L | Y | L | Q | M | N | S | L | K | S | E | G | T | A | V | Y | C |
| AM939724 | 98.6% | R | F | T | H | S | R | D | K | A | L | Y | L | Q | M | N | S | L | K | P | E | G | T | A | V | Y | C |
| AM939725 | 89.2% | Q | F | T | H | S | R | D | K | A | V | Y | L | Q | M | N | S | L | K | P | E | G | T | A | V | Y | C |
| AM939745 | 87.8% | Q | F | T | H | S | R | D | K | A | V | Y | L | Q | M | N | S | L | K | P | E | G | T | A | V | Y | C |
| AM939723 | 93.2% | R | F | T | H | S | R | D | K | A | L | Y | L | Q | M | N | S | L | K | P | E | G | T | A | V | Y | C |
| X92229\|IGHV4-30-2*03 | 78.4% | R | V | T | I | S | V | D | T | S | K | N | Q | F | S | L | K | L | S | S | V | T | A | A | D | T | A | V | Y | Y | C |
| LpVH2-s7 (AM939704) | 81.1% | H | T | S | H | S | R | D | T | S | K | N | Q | L | L | Q | L | T | T | P | E | G | T | A | V | Y | C |

-continued 10.10 Lama pacos VH germlne analysis

| | % | | R | V | T | I | S | V | D | T | S | K | N | Q | F | S | L | K | L | S | S | V | T | A | A | D | T | A | V | Y | C |
|---|---|---|---|---|---|---|---|---|---|---|---|---|---|---|---|---|---|---|---|---|---|---|---|---|---|---|---|---|---|---|---|
| Z14238\|IGHV4-30-4*01 | 86.5% | 86.5% | | | | | | | | | | | | | | | | | | | | | | | | | | | | | |
| LpVH2-s2 (AM939769) | 82.4% | 82.4% | R | T | S | I | S | R | D | T | S | N | N | Q | F | S | L | Q | L | S | S | V | T | P | E | G | T | A | V | Y | C |
| LpVH2-s3 (AM939770) | 82.4% | 82.4% | R | T | S | I | S | R | D | T | S | N | N | Q | F | S | L | Q | L | S | S | V | T | P | E | G | T | A | V | Y | C |
| LpVH2-s4 (AM939771) | 87.8% | 87.8% | H | T | S | I | S | R | D | T | S | K | N | Q | F | S | L | Q | L | S | S | V | T | P | E | G | T | A | V | Y | C |
| LpVH2-s5 (AM939772) | 82.4% | 86.5% | R | T | S | I | S | R | D | T | S | K | N | Q | F | S | L | Q | L | S | S | V | T | P | E | G | T | A | V | Y | C |
| LpVH2-s6 (AM939773) | 82.4% | 82.4% | H | T | S | I | S | R | D | T | S | N | N | Q | F | S | L | Q | L | S | S | V | T | P | E | G | T | A | V | Y | C |
| LpVH2-s11Ps (AM939703) | 82.4% | 82.4% | R | T | S | I | S | R | D | T | S | K | N | Q | F | S | L | Q | L | S | S | V | T | P | E | G | T | A | V | Y | C |
| LpVH2-s8 (AM939705) | 82.4% | 82.4% | H | T | S | I | S | R | D | T | S | N | N | Q | F | S | L | Q | L | S | S | V | T | P | E | G | T | A | V | Y | C |
| LpVH2-s9Ps (AM939706) | 83.8% | 83.8% | R | T | S | I | S | R | D | T | S | K | N | Q | F | S | L | Q | L | S | S | V | T | P | E | G | T | A | V | Y | C |
| LpVH2-s10 (AM939702) | 83.8% | 83.8% | R | T | S | I | S | R | D | T | S | K | N | Q | F | S | L | Q | L | S | S | V | T | P | E | G | T | A | V | Y | C |

Color codes
Residue found in closest matching germline
Residue found in other germlines of the same subclass (VH3, VK4, . . .)
Residue found in other germlines of the same subclass (VH, VK or VL)
Residue not found in any germlines of the same class (VH, VK or VL)
Primer-encoded residue
Scores
% Identity: fraction of framework residues which is found in the closest matching germline
% Homology: fraction of framework residues which is found in the closest matching germline or other germlines of the same subclass 10.11 *Lama glama* Derived VH Analysis

| \multicolumn{17}{c}{10.11 *Lama glama* derived VH analysis} |
|---|

| Name | % Ident | % Homol | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| AJ879486\|IGHV3-23*04 | | | E | V | Q | L | V | E | S | G | G | G | L | V | Q | P |
| S-VH1 | 88.5% | 93.1% | E | V | Q | L | V | E | S | G | G | G | L | V | Q | P |
| S-VH3 | 87.4% | 90.8% | E | V | Q | L | V | Q | S | G | G | G | L | V | Q | H |
| S-VH4 | 92.0% | 96.6% | E | E | Q | L | V | E | S | G | G | G | L | V | Q | P |
| L33851\|IGHV3-74*01 | | | E | V | Q | L | V | E | S | G | G | G | L | V | Q | P |
| S-VH2 | 93.2% | 95.5% | E | V | Q | L | V | E | S | G | G | G | L | V | Q | P |
| S-VH6 | 93.1% | 96.6% | E | V | Q | L | V | E | S | G | G | G | L | V | Q | P |
| S-VH5 | 93.1% | 96.6% | E | V | Q | L | V | E | S | G | G | G | L | V | Q | P |

| Name | % Ident | % Homol | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|
| AJ879486\|IGHV3-23*04 | | | G | G | S | L | R | L | S | C | A | A | S | G | F | T |
| S-VH1 | 88.5% | 93.1% | G | G | S | L | R | L | S | C | A | A | S | G | F | T |
| S-VH3 | 87.4% | 90.8% | G | G | S | L | R | L | S | C | A | A | S | G | F | A |
| S-VH4 | 92.0% | 96.6% | G | G | S | L | R | L | S | C | A | A | S | G | F | T |
| L33851\|IGHV3-74*01 | | | G | G | S | L | R | L | S | C | A | A | S | G | F | T |
| S-VH2 | 93.2% | 95.5% | G | G | S | L | R | L | S | C | A | A | S | G | F | T |
| S-VH6 | 93.1% | 96.6% | G | G | S | L | R | L | S | C | A | A | S | G | F | T |
| S-VH5 | 93.1% | 96.6% | G | G | S | L | R | L | S | C | A | A | S | G | F | T |

| Name | % Ident | % Homol | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|
| AJ879486\|IGHV3-23*04 | | | F | S | *S* | *Y* | *A* | *M* | *S* | W | V | R | Q | A | P | G |
| S-VH1 | 88.5% | 93.1% | F | S | *R* | *Y* | *A* | *M* | *S* | W | V | R | Q | A | P | G |
| S-VH3 | 87.4% | 90.8% | F | S | *S* | *A* | *G* | *M* | *S* | W | V | R | Q | A | P | G |
| S-VH4 | 92.0% | 96.6% | F | G | *S* | *Y* | *D* | *M* | *Y* | W | V | R | Q | A | P | G |
| L33851\|IGHV3-74*01 | | | F | S | *S* | *Y* | *W* | *M* | *H* | W | V | R | Q | A | P | G |
| S-VH2 | 93.2% | 95.5% | F | S | *S* | *Y* | *Y* | *M* | *S* | W | V | R | Q | A | P | G |
| S-VH6 | 93.1% | 96.6% | F | S | *S* | *A* | *V* | *M* | *S* | W | V | R | Q | A | P | G |
| S-VH5 | 93.1% | 96.6% | F | S | *S* | *A* | *V* | *M* | *S* | W | V | R | Q | A | P | G |

| Name | % Ident | % Homol | 43 | 44 | 45 | 46 | 47 | 48 | 49 | 50 | 51 | 52 | 52a | 53 | 54 | 55 |
|---|---|---|---|---|---|---|---|---|---|---|---|---|---|---|---|---|
| AJ879486\|IGHV3-23*04 | | | K | G | L | E | W | V | S | *A* | *I* | *S* | *G* | *S* | *G* | *G* |
| S-VH1 | 88.5% | 93.1% | K | G | P | E | W | V | S | A | I | S | W | N | S | G |
| S-VH3 | 87.4% | 90.8% | K | G | L | E | G | V | S | A | I | N | T | R | S | G |
| S-VH4 | 92.0% | 96.6% | K | G | P | E | W | V | S | A | I | R | S | G | G | G |
| L33851\|IGHV3-74*01 | | | K | G | L | V | W | V | S | *R* | *I* | *N* | *S* | *D* | *G* | *S* |
| S-VH2 | 93.2% | 95.5% | K | G | L | E | W | V | S | S | I | Y | S | D | G | S |
| S-VH6 | 93.1% | 96.6% | K | G | L | E | W | V | S | G | I | G | S | G | G | S |
| S-VH5 | 93.1% | 96.6% | K | G | L | E | W | V | S | T | I | G | A | A | G | S |

| Name | % Ident | % Homol | 56 | 57 | 58 | 59 | 60 | 61 | 62 | 63 | 64 | 65 | 66 | 67 | 68 | 69 |
|---|---|---|---|---|---|---|---|---|---|---|---|---|---|---|---|---|
| AJ879486\|IGHV3-23*04 | | | *S* | *T* | *Y* | *Y* | *A* | *D* | *S* | *V* | *K* | *G* | R | F | T | I |
| S-VH1 | 88.5% | 93.1% | R | I | Y | D | A | E | S | M | K | G | R | F | T | V |
| S-VH3 | 87.4% | 90.8% | T | T | Y | Y | A | D | F | T | K | G | R | F | T | I |
| S-VH4 | 92.0% | 96.6% | S | T | Y | Y | A | D | S | V | K | G | R | F | T | I |
| L33851\|IGHV3-74*01 | | | *S* | *T* | *S* | *Y* | *A* | *D* | *S* | *V* | *K* | *G* | R | F | T | I |
| S-VH2 | 93.2% | 95.5% | Y | T | Y | Y | A | D | S | V | K | G | R | F | T | I |
| S-VH6 | 93.1% | 96.6% | T | T | S | Y | A | D | S | V | K | G | R | F | T | I |
| S-VH5 | 93.1% | 96.6% | T | T | S | Y | A | D | S | V | K | G | R | F | T | I |

| Name | % Ident | % Homol | 70 | 71 | 72 | 73 | 74 | 75 | 76 | 77 | 78 | 79 | 80 | 81 | 82 | 82a |
|---|---|---|---|---|---|---|---|---|---|---|---|---|---|---|---|---|
| AJ879486\|IGHV3-23*04 | | | S | R | D | N | S | K | N | T | L | Y | L | Q | M | N |
| S-VH1 | 88.5% | 93.1% | S | R | D | N | T | K | N | T | I | Y | I | Q | M | N |
| S-VH3 | 87.4% | 90.8% | S | R | D | N | A | K | N | T | V | Y | L | Q | M | N |
| S-VH4 | 92.0% | 96.6% | S | R | D | N | A | K | N | T | L | Y | L | Q | M | N |
| L33851\|IGHV3-74*01 | | | S | R | D | N | A | K | N | T | L | Y | L | Q | M | N |
| S-VH2 | 93.2% | 95.5% | S | R | D | N | A | K | N | T | L | Y | L | Q | M | N |
| S-VH6 | 93.1% | 96.6% | S | R | D | N | A | K | N | T | L | Y | L | Q | M | N |
| S-VH5 | 93.1% | 96.6% | S | R | D | N | A | K | N | T | L | Y | L | Q | M | N |

| Name | % Ident | % Homol | 82b | 82c | 83 | 84 | 85 | 86 | 87 | 88 | 89 | 90 | 91 | 92 | 93 | 94 |
|---|---|---|---|---|---|---|---|---|---|---|---|---|---|---|---|---|
| AJ879486\|IGHV3-23*04 | | | S | L | R | A | E | D | T | A | V | Y | Y | C | A | K |
| S-VH1 | 88.5% | 93.1% | A | I | K | T | D | D | T | A | V | Y | Y | C | A | R |
| S-VH3 | 87.4% | 90.8% | S | L | K | P | E | D | T | A | V | Y | Y | C | N | A |
| S-VH4 | 92.0% | 96.6% | S | L | K | P | E | D | T | A | V | Y | Y | C | A | K |
| L33851\|IGHV3-74*01 | | | S | L | R | A | E | D | T | A | V | Y | Y | C | A | R |
| S-VH2 | 93.2% | 95.5% | S | L | K | S | E | D | T | A | V | Y | Y | C | A | N |
| S-VH6 | 93.1% | 96.6% | S | L | K | P | E | D | T | A | V | Y | Y | C | T | G |
| S-VH5 | 93.1% | 96.6% | S | L | K | P | E | D | T | A | V | Y | Y | C | T | G |

-continued

| 10.11 *Lama glama* derived VH analysis |||||||||||||||||||||||
|---|---|---|---|---|---|---|---|---|---|---|---|---|---|---|---|---|---|---|---|---|---|---|
| Name | % Ident | % Homol | 95 | 96 | 97 | 98 | 99 | 100 | 100a | 100b | 100c | 100d | 100e | 100f | 100g | 101 | 102 | 103 | 104 | 105 | 106 | 107 | 108 | 109 | 110 | 111 | 112 | 113 |
| AJ879486\|IGHV3-23*04 | | | | | | | | | | | | | | | | | | | | | | | | | | | | |
| S-VH1 | 88.5% | 93.1% | S | T | A | F | S | N | W | I | P | | | | | I | D | W | G | Q | G | T | Q | V | T | V | S | S |
| S-VH3 | 87.4% | 90.8% | G | F | P | S | | | | | | | | | | R | Y | W | G | Q | G | T | Q | V | T | V | S | S |
| S-VH4 | 92.0% | 96.6% | P | S | T | I | A | T | I | L | F | | | | | T | S | W | G | Q | G | T | Q | V | T | V | S | S |
| L33851\|IGHV3-74*01 | | | | | | | | | | | | | | | | | | | | | | | | | | | | |
| S-VH2 | 93.2% | 95.5% | W | D | Y | S | G | S | Y | Y | A | P | A | T | F | G | S | W | G | Q | G | T | R | V | T | V | S | S |
| S-VH6 | 93.1% | 96.6% | R | G | F | | | | | | | | | | | S | S | W | G | Q | G | T | Q | V | T | V | S | S |
| S-VH5 | 93.1% | 96.6% | R | G | F | | | | | | | | | | | S | S | W | G | Q | G | T | Q | V | T | V | S | S |

10.12 Lama Glama derived VL analysis

Lambda

| Name | % Homol | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 28 |
|---|---|---|---|---|---|---|---|---|---|---|---|---|---|---|---|---|---|---|---|---|---|---|---|---|---|---|---|---|---|---|---|---|
| D86994\|IGLV3-25*02 VL25-28 | 91.3% | *S* | *Y* | *E* | *L* | *T* | *Q* | *P* | *P* | *S* | *V* | *S* | *V* | *S* | *P* | *G* | *Q* | *T* | *A* | *R* | *I* | *T* | *C* | *S* | *G* | *D* | *A* | | | | *L* |
| | | N | F | M | L | T | Q | P | S | A | L | S | V | S | V | T | S | S | T | A | K | I | T | C | Q | G | S | | | | | L |
| Z73672\|IGLV5-37*01 VL2,12,15 | 97.5% | *Q* | *P* | *V* | *L* | *T* | *Q* | *P* | *P* | *S* | *V* | *S* | *S* | *A* | *P* | *G* | *E* | *S* | *S* | *A* | *R* | *L* | *T* | *C* | *T* | *L* | *P* | *D* | *I* | | *V* |
| | | Q | A | V | L | T | Q | P | P | S | L | S | A | A | P | G | S | S | S | V | R | L | T | C | T | L | S | G | H | | V |
| Z73650\|IGLV8-61*01 VL3,5 | 90.0% | *Q* | *T* | *V* | *V* | *T* | *Q* | *E* | *P* | *S* | *F* | *L* | *S* | *V* | *P* | *G* | *G* | *T* | *T* | *V* | *T* | *L* | *T* | *C* | *G* | *L* | *S* | *G* | *S* | *V* | *T* |
| VL17-24,29-32 | 90.0% | Q | A | V | V | T | Q | Q | P | S | L | S | A | A | P | G | G | T | T | V | T | L | L | T | C | G | L | S | G | S | V | T |
| VL10 | 91.3% | Q | S | E | L | T | Q | Q | P | S | L | S | A | V | P | G | G | T | T | V | T | L | L | T | C | G | L | S | G | S | V | T |
| VL4,6,7,8,9,13,14 | 97.5% | S | Y | E | L | T | Q | D | P | S | L | S | V | V | P | G | E | T | T | V | T | L | T | C | G | L | N | G | S | V | T |

| Name | % Homol | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 51a | 51b | 51c | 51d | 52 | 53 | 54 |
|---|---|---|---|---|---|---|---|---|---|---|---|---|---|---|---|---|---|---|---|---|---|---|---|---|---|---|---|---|---|---|---|
| D86994\|IGLV3-25*02 VL25-28 | 91.3% | *P* | *K* | *Q* | *Y* | *A* | *Y* | *W* | *Y* | *Q* | *Q* | *K* | *P* | *G* | *Q* | *A* | *P* | *V* | *L* | *V* | *I* | *Y* | *K* | *D* | | | | | *S* | *E* | *R* |
| | | G | S | S | Y | A | H | W | Y | Q | Q | K | P | G | Q | A | P | V | L | V | I | Y | D | D | | | | | D | S | R |
| Z73672\|IGLV5-37*01 VL2,12,15 | 97.5% | *G* | *S* | *Y* | *N* | *I* | *Y* | *W* | *Y* | *Q* | *Q* | *K* | *P* | *A* | *S* | *S* | *P* | *R* | *Y* | *L* | *L* | *Y* | *Y* | *Y* | | | | | *D* | *G* | *Q* |
| | | G | S | Y | D | I | S | W | F | Q | Q | K | A | G | S | A | P | R | Y | L | L | Y | S | S | | | | | F | H | Q |
| Z73650\|IGLV8-61*01 VL3,5 | 90.0% | *T* | *S* | *Y* | *Y* | *P* | *S* | *W* | *Y* | *Q* | *Q* | *T* | *P* | *G* | *Q* | *A* | *P* | *R* | *T* | *L* | *I* | *Y* | *S* | *T* | | | | | *N* | *T* | *R* |
| VL17-24,29-32 | 90.0% | T | S | N | Y | P | G | W | F | Q | Q | K | P | G | Q | A | P | R | L | L | I | Y | N | T | | | | | N | S | R |
| VL10 | 91.3% | S | S | N | Y | A | A | W | Y | Q | Q | K | A | G | Q | A | P | R | L | L | M | Y | K | N | | | | | N | S | R |
| VL4,6,7,8,9,13,14 | 97.5% | S | H | N | Y | P | A | W | Y | Q | Q | K | P | G | Q | A | P | R | L | L | I | Y | N | T | | | | | N | S | R |

| Name | % Homol | 55 | 56 | 57 | 58 | 59 | 60 | 61 | 62 | 63 | 64 | 65 | 66 | 67 | 68 | 68a | 68b | 69 | 70 | 71 | 72 | 73 | 74 | 75 | 76 | 77 | 78 | 79 | 80 | 81 | 82 |
|---|---|---|---|---|---|---|---|---|---|---|---|---|---|---|---|---|---|---|---|---|---|---|---|---|---|---|---|---|---|---|---|
| D86994\|IGLV3-25*02 VL25-28 | 91.3% | *P* | *S* | *G* | *I* | *P* | *E* | *R* | *F* | *S* | *G* | *S* | *S* | *S* | *G* | | | *T* | *T* | *V* | *T* | *L* | *T* | *I* | *S* | *G* | *V* | *Q* | *A* | *E* | *D* |
| | | P | S | G | I | P | E | R | F | S | G | S | S | S | G | | | G | R | A | T | L | T | I | S | G | A | Q | A | E | D |
| Z73672\|IGLV5-37*01 VL2,12,15 | 97.5% | *G* | *S* | *G* | *V* | *P* | *S* | *R* | *F* | *S* | *G* | *S* | *K* | *D* | *A* | *S* | *A* | *N* | *T* | *G* | *I* | *L* | *L* | *I* | *S* | *G* | *L* | *Q* | *S* | *E* | *D* |
| | | G | S | G | V | P | S | R | F | S | G | S | K | D | A | S | A | N | A | G | L | L | L | I | S | G | L | Q | P | E | D |
| Z73650\|IGLV8-61*01 VL3,5 | 90.0% | *S* | *S* | *G* | *V* | *P* | *D* | *R* | *F* | *S* | *G* | *S* | *I* | *L* | *G* | | | *N* | *K* | *A* | *A* | *L* | *T* | *I* | *T* | *G* | *A* | *Q* | *A* | *D* | *D* |
| VL17-24,29-32 | 90.0% | Y | S | G | V | P | N | R | F | S | G | S | H | S | G | | | N | K | A | V | L | T | I | H | G | A | Q | P | E | D |
| VL10 | 91.3% | H | S | G | V | P | S | R | F | S | G | S | K | S | G | | | N | A | V | L | T | I | T | G | A | P | E | D | | |

-continued 10.12 Lama Glama derived VL analysis

| Name | | | 83 | 84 | 85 | 86 | 87 | 88 | 89 | 90 | 91 | 92 | 93 | 94 | 95 | 95a | 95b | 95c | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|
| | 91.3% | | Y | S | G | V | P | N | R | F | S | G | S | I | S | G | | | N | K | A | A | L | T | I | T | G | A | | P | D |
| VL10 | 97.5% | % Homol | Y | P | M | Y | Y | C | Q | S | A | D | S | S | G | | | | K | A | Y | A | L | T | | T | G | A | Q | E | D |
| VL4,6,7,8,9,13,14 | | | | | | | | | | | | | | | | | | | | | | | | | | | | | | | |
| D86994\|IGLV3-25*02 | 91.3% | | E | A | D | Y | Y | C | Q | S | A | D | S | S | G | N | | | T | A | Y | F | G | G | | T | G | | | | L |
| VL25-28 | | | | | | | | | | | | | | | | | | | | | | | | | | | | | | | |
| Z73672\|IGLV5-37*01 | 97.5% | | E | A | D | Y | Y | C | M | I | W | P | S | N | A | | | | S | P | T | F | G | G | | T | G | | | | L |
| VL2,12,15 | | | | | | | | | | | | | | | | | | | | | | | | | | | | | | | |
| Z73650\|IGLV8-61*01 | | | E | S | D | Y | Y | C | L | Y | M | G | S | G | | | | | I | A | V | V | G | G | | T | K | L | | | L |
| VL3,5 | 90.0% | | E | A | D | Y | Y | C | A | V | T | G | S | S | S | N | Y | P | A | S | V | F | G | G | | T | H | L | L | V | L |
| VL17-24,29-32 | 90.0% | | E | A | D | Y | Y | C | S | L | Y | P | G | S | D | I | | | S | P | V | F | G | G | | T | H | L | L | V | L |
| VL10 | 91.3% | | E | A | D | Y | Y | C | A | V | Y | I | G | S | G | G | Y | | P | P | V | F | G | G | | T | K | L | L | V | L |
| VL4,6,7,8,9,13,14 | 97.5% | | E | A | D | Y | Y | C | A | V | Y | K | I | R | R | T | | | L | L | E | F | G | G | | T | H | L | L | V | L |

Kappa

| Name | % Ident | % Homol | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|---|
| | | | D | I | V | M | T | Q | T | P | L | S | L | S | V | T | P | G | Q | P | A | S | I | S |
| U41644\|IGKV2D-29*02 | 86.3% | 90.0% | D | I | V | M | T | Q | T | P | L | S | L | S | V | T | P | G | E | S | A | S | I | S |
| KAPPA 33-36,38, 39,42,4 | | | | | | | | | | | | | | | | | | | | | | | | |
| KAPPA 41,43,44 | 86.3% | 90.0% | D | I | V | M | T | Q | T | P | L | S | L | S | V | V | P | G | E | S | A | S | I | S |
| KAPPA 40,44 | 86.3% | 90.0% | D | I | V | M | T | Q | T | P | L | S | L | S | V | V | P | G | E | S | A | S | I | S |
| KAPPA 37,46,48 | 83.3% | 90.0% | E | L | V | L | T | Q | S | P | L | S | L | S | V | V | P | G | T | S | A | S | I | S |

| Name | % Ident | % Homol | 23 | 24 | 25 | 26 | 27 | 27a | 27b | 27c | 27d | 27e | 28 | 29 | 30 | 31 | 32 | 33 | 34 | 35 | 36 | 37 | 38 |
|---|---|---|---|---|---|---|---|---|---|---|---|---|---|---|---|---|---|---|---|---|---|---|---|
| | | | C | K | S | S | Q | S | L | L | H | S | D | G | K | T | Y | L | Y | W | Y | L | Q |
| U41644\|IGKV2D-29*02 | 86.3% | 90.0% | C | K | S | S | Q | S | L | V | H | S | D | G | K | T | Y | L | Y | W | Y | L | Q |
| KAPPA 33-36,38, 39,42,4 | | | | | | | | | | | | | | | | | | | | | | | | |
| KAPPA 41,43,44 | 86.3% | 90.0% | C | K | A | S | Q | S | L | V | H | S | D | G | K | T | Y | L | Y | W | Y | L | Q |
| KAPPA 40,44 | 86.3% | 90.0% | C | K | A | S | Q | S | L | V | R | S | D | G | K | T | Y | L | Y | W | Y | L | Q |
| KAPPA 37,46,48 | 83.3% | 90.0% | C | K | A | S | Q | S | L | V | R | S | D | G | K | T | Y | L | Y | W | Y | L | Q |

| Name | % Ident | % Homol | 39 | 40 | 41 | 42 | 43 | 44 | 45 | 46 | 47 | 48 | 49 | 50 | 51 | 52 | 53 | 54 | 55 | 56 | 57 | 58 | 59 |
|---|---|---|---|---|---|---|---|---|---|---|---|---|---|---|---|---|---|---|---|---|---|---|---|
| | | | K | P | G | Q | S | P | Q | L | L | I | Y | Q | V | S | N | R | F | S | G | V | P |
| U41644\|IGKV2D-29*02 | 86.3% | 90.0% | K | P | G | Q | S | P | Q | R | L | H | Y | Q | V | S | N | R | G | S | G | V | P |
| KAPPA 33-36,38, 39,42,4 | | | | | | | | | | | | | | | | | | | | | | | | |
| KAPPA 41,43,44 | 86.3% | 90.0% | K | P | G | Q | S | P | Q | R | L | H | Y | Q | V | S | N | R | G | S | G | V | P |
| KAPPA 40,44 | 86.3% | 90.0% | K | P | G | Q | S | P | Q | R | L | H | Y | Q | V | S | N | R | G | S | G | V | P |
| KAPPA 37,46,48 | 83.3% | 90.0% | K | P | G | Q | S | P | Q | L | L | I | Y | Q | V | S | N | R | G | S | G | V | P |

Example 11

Analysis of Key Residues for Canonical Folds of H1 and H2 and Comparison of H1 and H2 Residues with Human Germline Structural analysis of antibodies revealed the relationship between the sequence and the shape of the binding site formed by the complementarity determining regions (Chothia and Lesk, J. Mol. Biol. 196:901-917 (1987); Tramontano et al., J. Mol. Biol. 215:175-82 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

We have analyzed the predicted canonical structures of H1 and H2 for the germline dromedary and llama VH segments based on the length of these loops and the presence of the previously mentioned key residues. The comparison was made with the key residues as they occur in the closest matching human germline in terms of the presence of identical combination of canonical folds and overall sequence homology (Table 1); in addition the amino acids compatible with the corresponding canonical fold as proposed by Morea and colleagues (Morea et al., Methods 20:267-279 (2000)) are shown. For the dromedary germline VH family IGHV1S(1-19), which has canonical fold 1 for H1 (coded as H1: 1 in Table 1) and fold 1 for H2 (H2: 1), and family IGHV1S(20, 22, 23, 24) with fold 1 for H1 (H1: 1) and fold 3 for H2 (H2: 3), and family IGHV1S(21, 25-39) with fold 1 for H1 (H1: 1) and fold 2 for H2 (H2: 2) and llama germline IGHV1S8 with fold 1 for H1 (H1: 1) and fold 2 for H2 (H2: 2), the key residues 24, 26, 27, 29, 34 and 94 for the canonical fold of H1 are shown along with these from the analogue human germline family with the same canonical fold combination (upper part of Table 1). Also for dromedary germline VH family IGHV1S(1-19) with fold 1 for H1 (H1: 1) and fold 1 for H2 (H2: 1), and family IGHV1S(20, 22, 23, 24) with fold 1 for H1 (H1: 1) and fold 3 for H2 (H2: 3), and family IGHV1S(21, 25-39) with fold 1 for H1 (H1: 1) and fold 2 for H2 (H2: 2) and llama germline IGHV1S8 with fold 1 for H1 (H1: 1) and fold 2 for H2 (H2: 1) the key residues 52a or 54 or 55 in combination with residue 71 are shown along with these from the analogue human germline families with the same canonical fold combinations (lower part Table 1).

The analysis clearly demonstrates the "human nature" of the canonical loops, since the key residues found in the camelid VH segments are identical to what is found in the corresponding human VH segments. For example, all 19 germline VH segments from dromedary coded IGHV1S(1-19) have Alanine on position 19, Glycine on 26, Phenylalanine on 27 and 29 and Methionine on 34 as they predominantly occur in human germline family 3 members, which like these dromedary germline sequences have a canonical fold type 1 for H1 and fold type 1 for H2. Position 94 is encoded only in a single germline dromedary (out of the total of 39 germline VH segments) meaning that a proper analysis is not possible. Nguyen and colleagues (Nguyen et al., EMBO J. 19:921-930 (2000)) noticed that the dromedary germline VH and VHH segments "span from the conserved octamer (i.e. recombination signal) to the Cysteine residue 92 of FR3" (end of citation), whereas the human segments encode two additional residues (93 and 94). However, we will discuss this residue during the analysis of the only six known somatically mutated VH segments derived from llama derived conventional antibodies.

There are virtually no exceptions for the perfect match with the human germline segments and the key residues proposed by Morea and colleagues (Morea et al., Methods 20:267-279 (2000)), besides residue 52a for llama germline IGHV1S6 for canonical fold type 2 for loop H2, which has Serine on this position, while the human analogue uses Threonine. It is encouraging to observe that in four of the six published llama VH derived from somatically mutated conventional antibodies (Vu et al., Mol. Immunol. 34:1121-31 (1997) Threonine is found on position 52a. It is worthwhile to mention that Serine and Threonine are closely related, since they both have a polar hydroxyl group and small sidegroups, suggesting that it might be possible to exchange both residues during humanization.

Glutamine on position 71, which occurs in 1 out of 19 dromedary germline VH segments with a canonical fold type 1 for loop H2 and in 4 out of 16 dromedary germline VH with a canonical fold type 2 for H2, seems to be rather extraordinary. The H2 loop packs against the residue at site 71 and the position of the loop relative to the framework is mainly determined by the size of the residue at this site. Canonical structures 2 and 3 are found in H2 loops with 6 residues. Structure 2 occurs when residues 52a and 71 are small or medium sized hydrophobic residues, while canonical fold 3 occurs when residue 71 is Arginine or Lysine. It can not be predicted how often the dromedary germline segments with Glutamine on position 71 will be used in somatically mutated conventional antibodies, but the humanization of this residue in antibody leads with this particular residue needs to be carefully examined. The presence of Arginine and Glutamine on position 71 in the dromedary IGHV1S(20, 22, 23, 24) family members with canonical fold 2 for H2 is rather unexpected, but on the other hand human germline VH1 family members VH1-9, VH1-10 and VH1-11 with canonical fold 2 for H2 have Arginine as well, while VH5 member 5-1 with fold 2 for H2 carries Glutamine on this position.

As Chothia and colleagues did when discussing the structural repertoire of the human VH segments (Chothia et al., J. Mol. Biol. 227:799-817 (1992)) we examined the individual amino acid residues of the H1 and H2 loops of the dromedary and llama VH segments along with the key residues and compared these with the human counterparts having the same canonical fold combination (Table 2). For dromedary germline VH family IGHV1S(1-19) with canonical fold 1 for H1 and fold 1 for H2, and family IGHV1S(20, 22, 23, 24) with fold 1 for H1 (H1: 1) and fold 3 for H2 (H2: 3), and family IGHV1S(21, 25-39) with fold 1 for H1 (H1: 1) and fold 2 for H2 (H2: 2) and llama germline IGHV1S8 with fold 1 for H1 and fold 2 for H2 the H1 residues 26 to 33 and the are shown together with the key residues 24 and 94 located outside of H1 (Table 2A). In addition, for dromedary germline VH family IGHV1S(1-19) with canonical fold 1 for H1(H1: 1) and fold 1 for H2 (H2: 1), and family IGHV1S(20, 22, 23, 24) with fold 1 for H1 (H1: 1) and fold 3 for H2 (H2: 3), and family IGHV1S(21, 25-39) with fold 1 for H1 (H1: 1) and fold 2 for H2 (H2: 2) and llama germline IGHV1S8 with fold 1 for H1 (H1: 1) and fold 2 for H2 (H2: 2) the H2 residues 52 to 56 were analyzed with key residue 71, which is located outside H2 (Table 2B).

It is surprising to see the very high degree of sequence homology in the variable loops, especially in H1 there are hardly differences with the relevant human sequences. For instance, germline dromedary family IGHV1S(1-19) with canonical fold combination H1: 1/H2: 1 contains predominantly Alanine on position 24, Glycine on 26, Phenylalanine on 27, Threonine on 28, Phenylalanine on 29, Serine on 30 and 31, Tyrosine on 33, Methionine on 34 and Serine on 35, which completely match the human germline family 3 members that share the same combination of H1 and H2 canonical folds. Exceptions are residue 27 (Phenylalanine) and 32 (Serine) of the only publicly known llama germline VH segment, but again in 4 out of 6 somatically mutated llama VH which are publicly known (Vu et al., Mol. Immunol. 34:1121-1131 (1997)). Tyrosine is present on 32 as is found in the analogue human germlines. The same high degree of sequence homology is found for the H2 loops of dromedary germline VH segments with the exception of residue 54 of family IGHV1S(1-19). Especially dromedary family IGHV1S(21, 25-39) deviates on a number positions in the H2 loop (i.e. 53, 54, 56 and 58). The H2 loop of the llama germline VH segment with the same fold scores much better, but as well contains a number of deviating residues on position 50, 52, 52a, 54, 55 and 58, but the interpretation is rather difficult, since the analysis was performed with the only known germline segment. The analysis of somatically mutated VH derived from llama shows that certain residues on these positions occur, which also appear in the corresponding human germline sequences, although infrequently (f.i. Glycine on 50, Asparagine on 52 and 58, Threonine on 52a and Glycine on 55).

We also analyzed the panel of six publicly known somatically mutated VH sequences from llama (Vu et al., Mol. Immunol. 34:1121-31 (1997)). Below the alignment with human VH3 member 3-23 is shown, demonstrating a very high degree of sequence homology: overall, only 3 deviating residues were observed, one of which is encoded by the primer used for amplification, while the other two occur in human germlines of the same class. Even the CDRs show to have a very high degree of sequence homology: CDR1 is probably identical, while only three residues of CDR2 are different. Canonical fold analysis reveals that two VH have fold 1 for H1 and fold 2 for H2, as was observed for the only available llama derived germline VH, but the other four have fold 1 for H1 and fold 3 for H2 as occurs in 3-23 and the majority of the human family VH3 germline segments. This might be suggesting that these are derived from other, not yet known germline VH segments. Examination of the key residues supporting the canonical folds gives the perfect match with those occurring in human germline with the same canonical fold combination as was already observed for the llama germline VH segment listed in Table 1. It is very interesting to see that key residue 94 in these somatically mutated sequences is Lysine (2 out of 5), Serine (1 out of 5) and Arginine (1 out of 5), which are all found in the human germlines with the same fold combination or are proposed by Morea and colleagues (Morea et al., Methods 20:267-279 (2000)).

11.1 Somatically Mutated Llama VH from Conventional Antibodies 11.1 Somatically mutated Llama VH from conventional antibodies

| IGHV gene | FR1-IMGT (1-26) | CDR1-IMGT (27-38) | FR2-IMGT (39-55) | CDR2-IMGT (56-65) | FR3-IMGT (66-104) | CDR3-IMGT (105-115) | (J1,4,5) |
|---|---|---|---|---|---|---|---|
| M99660, IGHV3-23 | EVQLLESGG.GLVQPGGSLRLSCAAS | GFTFSSYA.... | MSWVRQAPGKGLEWVSA | ISGSGGST.. | YYADSVK.GRFTISRDNSKNTLYLQMNSLRAEDTAVYYC | AK........... | WGQGTLVTVSS |
| IVH28 | EVQLVESGG.GLVQPGGSLRLSCAAS | GFAFSSYD..... | MSWVRQAPGKGLEWVSA | INBGGIST.. | YNADSMK.GRFTISRDNAKNTVYLQMNSLKPEDTAVYYC | NADTWYCDQLDSSDY | WGQGTQVTVSS |
| IVH69 | EVQLVESGG.GLVQPGRSLRVSYAAS | GFTFSSHY..... | MSWVRQDPEKGLEMVSE | IATGGTIT.. | SYADSVK.GRFTISRDNANNMLFLQMNNLKPEDTALYYC | VRRGRAIA....FDV | WGQGTLVTVSS |
| IVH47 | EVQLVESGG.GLVQPGGSLRLSCAAS | GLTFDDYA..... | MSWVRQAPGKGLEWVST | IYTHSRNT.. | YYADSVK.GRFTISRDNAKNTLYLQMNSLKPEDTAVYYC | AKEWVGSVVEGRYRG | WGQGTLVTVSS |
| IVH48 | EVQLLESGG.GLVQPGGSLRLSCAAS | GFTFSSVV..... | MSXVRQAPGKGPEWVSG | VNTDGRSI.. | TYADSVK.GRFTISRDNAKNTLYLQMNSLSPEDTAVYYC | TKICTVITGRPGYDY | WGQGTLVTVSS |
| IVH70 | EVQLVESGG.GLVQPGGSLRVSCAAS | GFTFSSLY..... | MSWVRQVPGKGLEWVST | IHTASGST.. | FYADSVQ.GRFLVSRDNAKNTLYLQMDSLKPEDTARYYC | ASAILGW.....YDY | WGQGTLVTVSS |
| IVH71 | EVQLVESGG.GLVQPGGSLRLSCAAS | GFTFSSYD..... | MSWVRQAPGKGLEWVSS | IYSDGTTT.. | YDGDSVK.GRFTISRDNAKNMLYLQMNSLKPEDAAVYYC | ASAIRGW.....YDY | WGQGTLVTVSS |

A) Sequence homology:
1) position 5 Valine (primer encoded) also found in f.i. IGHV3-15
2) position 83 Alanine is found more often in human VH3 germlines then Serine of 3-23
3) position 95/96 Lysine/Proline occurs in IGHV3-15/49/73 as Lysine/Threonine
4) CDR1 is completely human-like, in CDR2 only residues 57, 58 and 59 seem to deviate from human germline 3-23 (57 Serine, 58 Glycine, 59 Serine)
5) FR4 gives perfect match with human J1, J4 and J5

B) Canonical fold analysis
1) combination fold 1 for H1 and fold 2 for H2 for IVH28 and 1VH69 (as in 3 out of 11 human germline family VH1 members and both human germline family VH5 members)
2) for IVH47, 48, 70 and 71 combination fold 1 for H1 and fold 3 for H2 as found in 3-23 and majority of family VH3 members -continued 11.1 Somatically mutated Llama VH from conventional antibodies Examples of analysis:

IVH28:
CDR H1 Class ?
! Similar to class 1/10A, but:
! H33 (Chothia Numbering) = D (allows: YAWGTLV)
! H94 (Chothia Numbering) = A (allows: RKGSHN)

CDR H2 Class ?
! Similar to class 2/10A, but:
! H33 (Chothia Numbering) = D (allows: YWGATL)
! H59 (Chothia Numbering) = N (allows: Y)
! H71 (Chothia Numbering) = R (allows: VAL)

IVH47:
CDR H1 Class 1/10A [2fbj]
CDR H2
! Similar to class 3/10B, but:
! H52 (Chothia Numbering) = Y (allows: SFWH)
! H53 (Chothia Numbering) = H (allows: DGSN)

Example 12

Analysis Key Residues for Canonical Folds of L1(λ) and L2(λ) and Comparison of L1(λ) and L2(λ) Residues with Human Germline Also the predicted canonical structures of L1 and L2 were analyzed for the somatically mutated dromedary VLambda segments based on length of the loops and the presence of the key residues relevant for the canonical folds. The comparison was made with the key residues occurring in the closest matching human germline with the same combination of canonical folds and overall sequence homology (Table 3). For the somatically mutated dromedary VL family VL3-1 (CamvI8, 18, 19, 20 and 23), with fold 11 for L1 (L1: 11) and fold 7 for L2 (L2: 7), and somatically mutated dromedary VL family VL3-12/32 (CamvI11) with fold 11 for L1 (L1: 11) and fold 7 for L2 (L2: 7), and somatically mutated dromedary VL1-40 (CamvI44) with fold 14 for L1 (L1: 14) and fold 7 for L2 (L2: 7), and somatically mutated dromedary VL2-18 (CamvI5, 17, 30-33, 36, 52, 57, 59, 60 and 65) with fold 14 for L1 (L1: 14) and fold 7 for L2 (L2: 7) the key residues 2, 25, 29, 30, 33 and 71 relevant for the canonical fold of L1 are shown along with these from the analogue human germline family with the same canonical fold combination (upper part of Table 3). For somatically mutated dromedary VL family VL3-1 (CamvI8, 18, 19, 20 and 23), with fold 11 for L1 (L1: 11) and fold 7 for L2 (L2: 7), and somatically mutated dromedary VL family VL3-12/32 (CamvI11) with fold 11 for L1 (L1: 11) and fold 7 for L2 (L2: 7), and somatically mutated dromedary VL1-40 (CamvI44) with fold 14 for L1 (L1: 14) and fold 7 for L2 (L2: 7), and somatically mutated dromedary VL2-18 (CamvI5, 17, 30-33, 36, 52, 57, 59, 60 and 65) with fold 14 for L1 (L1: 14) and fold 7 for L2 (L2: 7) the key residues 48 and 64 important for the canonical fold of L2 are shown along with the key residues from the analogue human germline families having the same canonical fold combinations (lower part Table 3).

As observed for VH the analysis reveals the "human nature" of both canonical loops L1 and L2, because here also the key residues of the camelid VLambda segments are identical to those of the corresponding human VLambda segments. For example, in dromedary VL3-12/32, VL1-40 and VL2-18 all key residues of L1 are identical to those occurring in the corresponding human germlines, and in dromedary VL3-1, VL3-12/32 and VL2-18 the key residues of L2 completely match with the corresponding human germline VL segments. Basically there are only two exceptions. First of all, L2 key residue 64 of VL1-40 is Glutamate, which is rather different from Glycine that is present in human germline Vλ1 with the same L1/L2 combination of canonical folds as VL1-40. It is difficult to draw general conclusions, since VL1-40 only consists of an orphan (i.e. CamvI44). The second exception is VL3-1, where Phenylalanine is the most dominantly occurring L1 key residue on position 30, whereas Leucine is frequently found in human Vλ family 3 members that share fold 11 for L1 and fold 7 for L2 with VL3-1. However, Leucine is also present in one out of the five VL3-1 members.

We analyzed the individual amino acid residues of the L1 and L2 loops of the somatically mutated dromedary VLambda segments along with the key residues and made the comparison with the human counterparts sharing the same canonical fold combination (Table 4). For the somatically mutated dromedary VL family VL3-1 (CamvI8, 18, 19, 20 and 23), with fold 11 for L1 (L1: 11) and fold 7 for L2 (L2: 7), and somatically mutated dromedary VL family VL3-12/32 (CamvI11) with fold 11 for L1 (L1: 11) and fold 7 for L2 (L2: 7), the L1 residues 27 to 33 together with key residue 71 outside L1 are compared with the same residues present in the corresponding human germline Vλ with same combination of folds for L1 and L2 (upper part of Table 4A). For dromedary somatically mutated dromedary VL1-40 (CamvI44) with fold 14 for L1 (L1: 14) and fold 7 for L2 (L2: 7), and somatically mutated dromedary VL2-18 (CamvI5, 17, 30-33, 36, 52, 57, 59, 60 and 65) with fold 14 for L1 (L1: 14) and fold 7 for L2 (L2: 7) the L1 residues 26 to 33 together with key residues 2 and 71 outside L1 are compared with the same residues present in the corresponding human germline Vλ family with same combination of folds for L1 and L2 (lower part of Table A). In addition, for somatically mutated dromedary VL family VL3-1 (CamvI8, 18, 19, 20 and 23), with fold 11 for L1 (L1: 11) and fold 7 for L2 (L2: 7), and somatically mutated dromedary VL family VL3-12/32 (CamvI11) with fold 11 for L1 (L1: 11) and fold 7 for L2 (L2: 7), and somatically mutated dromedary VL1-40 (CamvI44) with fold 14 for L1 (L1: 14) and fold 7 for L2 (L2: 7), and somatically mutated dromedary VL2-18 (CamvI5, 17, 30-33, 36, 52, 57, 59, 60 and 65) with fold 14 for L1 (L1: 14) and fold 7 for L2 (L2: 7) the L2 residues 49 to 53 together with key residues 48 and 64 located outside L2 are compared with the same residues present in the corresponding human germline Vλ family with the same combination of canonical folds for L1 and L2 (Table 4B). There is a high degree of sequence homology between the L1, L2 and key residues with the human germline sequences and only few exceptions exist, which mainly can be found in the orphan members of the VL3-12/32 and VL1-40 families. For L1 of VL3-12/32 residues 27, 28, 30, 30a and 30 b deviate from the corresponding human germline Vλ family 3, while for the same loop residues 30b, 31 and 32 of VL1-40 are different from the matching human germline Vλ family 1. In the orphan member of VL3-12/32 L2 residue 50 differs from the human analogue, while for the only member of VL1-40 key residue 64 differs from the human analogue. A fundamental difference can be observed for L1 residue 28 of dromedary family VL2-18 (Asparagine or Glutamate versus Serine in analogue human Vλ family 2).

Example 13

Analysis Key Residues for Canonical Folds of L1(κ) and L2(κ)) and Comparison of L1(κ)) and L2(κ)) Residues with Human Germline The predicted canonical structures of L1(κ)) and L2(κ)) were analyzed for the somatically mutated dromedary VKappa segments based on loop length and presence of key residues. As before the comparison was made with the key residues occurring in the closest matching human germline with the same combination of canonical folds and overall sequence homology (Table 5). For the somatically mutated dromedary VK family VK2-40 (Kp1, 3, 6, 7, 10, 20 and 48), with fold 3 for L1 (L1: 3) and fold 1 for L2 (L2: 1) the key residues 2, 25, 29, 30e, 33 and 71 relevant for the canonical fold of L1 are shown along with these from the analogue human VKappa germline family 2 with the same canonical fold combination. In addition the key residues compatible with the corresponding canonical fold as proposed by Morea et al. are shown in the bottom line. There is a perfect match for key residues 2, 25, 33 and 71 and to a certain degree for residue 29. Residue 30e of the dromedary VKappa is Glutamine in stead of Glycine, but Morea and colleagues (Morea et al., Methods 20:267-279 (2000)) suggested this residue to be perfectly compatible with the fold 3 for L1.

For the same somatically mutated dromedary VK family VK2-40 (Kp1, 3, 6, 7, 10, 20 and 48) with fold 3 for L1 (L1: 3) and fold 1 for L2 (L2: 1) the key residues 48 and 64 determining the canonical fold of L1 are shown together with these from the analogue human VKappa germline family 2. Here again the match is perfect.

The individual amino acid residues of the L1 and L2 loops of the somatically mutated dromedary VKappa segments along with the key residues were compared with those occurring in the human counterpart (VK family 2) that shares the same canonical fold combination (Table 6). For the somatically mutated dromedary VK family VK2-40 (Kp1, 3, 6, 7, 10, 20 and 48) with fold 3 for L1 (L1: 3) and fold 1 for L2 (L2: 1) the L1 and L2 residues were compared with those found in germline VK family 2 that has the identical canonical loop combination. The majority of the residues are shared between the dromedary somatically mutated VK and the human germline, such as Isoleucine on position 2, Serine on 25, 26 28 and 30b, Glutamine on 27, Tyrosine on 32, Leucine on 33 and Phenylalanine on 71. However, a few differ from the human analogue, i.e. Valine on 29 (although Leucine of human germline also occurs in the dromedary VK), Phenylalanine on 30 (again human residue Leucine is found as well in dromedary VK), Serine on 30a (human residue Glutamate occurs infrequently in dromedary VK), Serine on 30c, Asparagine on 30d, Glutamine on 30e, Lysine on 30f and finally Serine on 31.

Together with the key residues the residues of the L2 loop of the somatically mutated dromedary VKappa segments were compared those occurring in the human counterpart (VK family 2) that shares the same canonical fold combination (Table 6). Here again a perfect match was observed from residue Isoleucine on 48, Tyrosine on 49, Serine on 52 and Glycine on 64, while deviations were found on position 50 (Tyrosine in stead of Threonine from human VK family 2), and 51 (Alanine on 51 instead of Leucine).

Overall Conclusion

This analysis of the camelid VH and VL sequences demonstrates a very high homology if not identity to the human key residues defining the canonical folds as well as to the residues found in the hypervariable loops themselves. This suggests that the vast majority of the camelid immunoglobulin sequences will adopt the canonical folds as found in the human germlines, not only for the individual hypervariable loops but as well as for the combination of canonical folds found in human VH and VL.

TABLE 1

Sites of key residues for determining canonical folds in germline dromedary and llama VH. Number between brackets indicates frequency of residue as found in dromedary/llama or human germline; numbering of key residues according to Kabat et al. (Sequences of Proteins of Immunological Interest, 5th ed. (1991)) and key residues proposed by Morea and colleagues. (Morea et al., Methods 2000). Ha: b indicates canonical fold type b for loop Ha.

| Sequence | Canonical structure | Closest hu GL family | H1 key residues | | | | | H2 key residues | | | | |
|---|---|---|---|---|---|---|---|---|---|---|---|---|
| | | | 24 | 26 | 27 | 29 | 34 | 94 | 52a | 54 | 55 | 71 |
| Gl Drom IGHV1S (1-19) | H1: 1 | (3-53) | A (19) | G (19) | F (19) | F (19) | M (19) | G (1); (18) | | | | |
| Hu Gl family 3 | H1: 1 | (3-23) | A (23); G (1) A (4) | G (24) G (4) | F (24) F (4) | F (22); V (2) F (4) | M (23); T (1) M (4) | R (18); K (5); T (1) | | | | |
| Gl Drom IGHV1S (20, 22, 23, 24) | H1: 1 | (V₇₄₁b) | A (23); G (1) A (16) | G (24) G (15); A(1) | F (24) F (16) | F (22); V (2) F (14); S (1); Y (1) | M (23); T (1) M (13); I (2); V (1) | R (18); K (5); T (1) | | | | |
| Hu Gl family 3 | H1: 1 | (3-23) | A (19); V (2) A (1) | G (21) G (1) | Y (18); F (1); G (2) F (1) | F (20); L (1) F (1) | M (13); I (5); L (2); V (1) M (1) | R (17); T (2); A (1) A (1) | | | | |
| Gl Drom IGHV1S (21 25-39) | H1: 1 | | | | | | | | | | | |
| Hu Gl family 1 Gl Llama IGHV1S6 | H1: 1 | | | | | | | | | | | |
| Hu Gl family 1 | H1: 1 (Morea) H2: 1 | | A (19); V (2) A, V, S; T | G (21) G | Y (18); F (1); G (2) F; Y, S; D | F (20), L (1) F; L; I | M (13), I (5); L (2); V(1) M; V; I; Y; W | R (17); T (2); A (1) R; G; N; K; S | | | | |
| Gl Drom IGHV1S (1-19) | H2: 1 (Morea) | (3-53) | | | | | | | — | — | G (19) | R (18); Q (1) |
| Hu Gl family 3 | H2: 3 | (3-23) | | | | | | | — | — | G (4) G; D | R (4) K; R; V; I R (4) |
| Gl Drom IGHV1S (20 22 23, 24) | H2: 3 (Morea) | (3-23) | | | | | | | — | G (4) | — | R (14) R; K |
| Hu Gl family 3 | H2: 2 | (V₇₄₁b) | | | | | | | — | G (13); S (3) G; S; N; D | — | R (8); K (4); Q (4) |
| Gl Drom IGHV1S (21, 25-39) | H2: 2 Hu Gl family 1 | | | | | | | | S (10); T (6) | — | G (16) | A (3); T (2); L (2) |
| Hu Gl family 1 | H2: 2 (Morea) H2: 2 | (3-23) | | | | | | | P (3); T (2); A (2) P; T; A S (1) | — | G (7) G; N; D; S S (1) | A; L; T T (1) |
| Gl Llama IGHV1S6 | H2: 2 (Morea) | | | | | | | | P (3); T (2); A (2) P; T; A | — | G (7) G; N; D; S | A (3); T (2); L (2) A; L; T |
| Hu Gl family 1 | | | | | | | | | | | | |

TABLE 2A

Comparison of H1 sequences for dromedary and llama germline VH with human germlines; numbering according to Kabat et al. (Sequences of Proteins of Immunological Interest, 5th ed. (1991)). Asterisks indicate key residues important for canonical folds.

| | | | | | | | H1: 1 residue no. | | | | | | | |
|---|---|---|---|---|---|---|---|---|---|---|---|---|---|---|
| | | | 24* | 26* | 27* | 28 | 29* | 30 | 31 | 31a | 31b | 32 | 33 | 34* | 35 | 94* |
| Family 3 | Gl Drom IGHV1S (1-19) | A (19) | G (19) | F (19) | T (19) | F (19) | S (19) | S (19) | — | — | Y (19) | Y (14); D (2); W (2); A (1) | M (19) | S (17); Y (2) | G (1) |
| | Hu GL | A (3); G (1) | G (4) | F (4) | T (4) | V (2); F (2) | S (4) | S (4) | — | — | N (2); Y (2) | Y (2); A (1); D (1) | M (4) | S (2); H (2) | R |

| | | | | | | | H1: 1 residue no. | | | | | | | |
|---|---|---|---|---|---|---|---|---|---|---|---|---|---|---|
| | | | 24* | 26* | 27* | 28 | 29* | 30 | 31 | 31a | 31b | 32 | 33 | 34* | 35 | 94* |
| Family 3 | Gl Drom IGHV1S (20, 22, 23, 24) | A (4) | G (4) | F (4) | T (4) | F (4) | S (4) | S (4) | — | — | Y (4) | W (3); Y (1) | M (4) | Y (3); S (1) | — |
| | Hu GL | A (16) | G (16) | F (16) | T (16) | F (16) | S (13); D (3) | S (11); D (4); N (1) | — | — | Y (15); H (1) | A (6); G (3); Y (2); W (2); S (1); E (1); T (1) | M (15); T (1) | H (9); S (5); N (2) | R (11); K (5) |

| | | | | | | | H1: 1 residue no. | | | | | | | |
|---|---|---|---|---|---|---|---|---|---|---|---|---|---|---|
| | | | 24* | 26* | 27* | 28 | 29* | 30 | 31 | 31a | 31b | 32 | 33 | 34* | 35 | 94* |
| Family 1 | Gl Drom IGHV1S (21, 25-39) | A (16) | G (15); A (1) | F (16) | T (16) | F (14); S (1); Y (1) | S (16) | S (16) | — | — | Y (15); C (1) | W (7); A (4); D (3); Y (1); C (1) | M (13); I (2); V (1) | Y (8); S (8) | — |
| | Hu GL | A (6); V (1) | G (7) | Y (5); G (2) | T (7) | F (7) | T (5); S (2) | S (6); D (1) | — | — | Y (7) | A (4); G (2); Y (1) | I (4); M (3) | S (4); N (2); H(1) | R (4); T (1); -(1) |

| | | | | | | | H1: 1 residue no. | | | | | | | |
|---|---|---|---|---|---|---|---|---|---|---|---|---|---|---|
| | | | 24* | 26* | 27* | 28 | 29* | 30 | 31 | 31a | 31b | 32 | 33 | 34* | 35 | 94* |
| Family 1 | Gl Llama IGHV1S6 | A (1) | G (1) | F (1) | T (1) | F (1) | S (1) | S (1) | — | — | S (1) | A (1) | M (1) | S (1) | A (1) |
| | Hu GL | A (6); V (1) | G (7) | Y (5); G (2) | T (7) | F (7) | T (5); S(2) | S (6); D (1) | — | — | Y (7) | A (4); G (2); Y (1) | I (4); M (3) | S (4); N (2); H (1) | R (4); T (1); -(1) |

TABLE 2B

Comparison of H2 sequences for dromedary and llama germline VH with human germlines; numbering according to Kabat et al. (Sequences of Proteins of Immunological Interest, 5th ed. (1991)). Asterisks indicate key residues important for canonical folds.

H2: 1 residue no.

| | | 50 | 51 | 52 | 52a | 52b | 52c | 53 | 54 | 55 | 56 | 57 | 58 | 71* |
|---|---|---|---|---|---|---|---|---|---|---|---|---|---|---|
| | Gl Drom IGHV1S (1-19) | G (17); A (2) | I (18); N (1) | Y (16); N (2); T (1) | — | — | — | S (19) | D (18); R (1) | G (19) | S (18); G (1) | T (19) | Y (17); N (1); H (1) | R (18); Q (1) |
| Family 3 | Hu GL | V (2); A (2) | I (4) | Y (2); G (2) | — | — | — | S (2); T (2) | G (3); A (1) | G (4) | S (2); G (1); D (1) | T (4) | Y (4) | R (4) |

H2: 3 residue no.

| | | 50 | 51 | 52 | 52a | 52b | 52c | 53 | 54 | 55 | 56 | 57 | 58 | 71* |
|---|---|---|---|---|---|---|---|---|---|---|---|---|---|---|
| | Gl Drom IGHV1S (20, 22, 23, 24) | T (3); G (1) | I (4) | N (4) | S (4) | — | — | G (3); D (1) | G (4) | G (3); S (1) | S (3); N (1) | T (4) | Y (4) | R (4) |
| Family 3 | Hu GL | V (5); Y (4); G (2); A (2); R (1); N (1), L (1) | I (15); S (1) | S (12); N (2); W (1); K (1) | Y (5); S (5); W (3); G (2); Q (1) | — | — | D (8); S (4); N (4) | G (13); S (3) | S (10); G (6) | S (6); N (5); T (3); Y (1); E (1) | T (6); K (6); I (4) | Y (12); G (2); T (1); N (1) | R (16) |

H2: 2 residue no.

| | | 50 | 51 | 52 | 52a | 52b | 52c | 53 | 54 | 55 | 56 | 57 | 58 | 71* |
|---|---|---|---|---|---|---|---|---|---|---|---|---|---|---|
| | Gl Drom IGHV1S (21, 25-39) | A (9); S (4); T (2); G (1) | I (16) | N (10); Y (6) | S (10); T (6) | — | — | G (14); A (2) | G (16) | G (16) | S (16) | T (16) | Y (16) | R (8); K (4); Q (4) |
| Family 1 | Hu GL | W (4); R (1); G (1); L (1) | I (6); V (1) | S (2); N (2); I (2); D (1) | P (3); T (2); A (2) | — | — | Y (2); N (2); I (2); E (1) | N (2); T (2); L (1); F (1); D (1) | G (7) | N (4); T (1); I (1); E (1) | T (3); P (2); A (2) | N (4); T (2); I (1) | A (3); L (2); T (2) |
| | Gl Llama IGHV1S6 | S (1) | I (1) | Y (1) | S (1) | — | — | Y (1) | S (1) | S (1) | N (1) | T (1) | Y (1) | T (1) |
| Family 1 | Hu GL | W (4); R (1); G (1); L (1) | I (6); V (1) | S (2); N (2); I (2); D (1) | P (3); T (2); A (2) | — | — | Y (2); N (2); I (2); E (1) | N (2); T (2); L (1); F (1); D (1) | G (7) | N (4); T (1); I (1); E (1) | T (3); P (2); A (2) | N (4); T (2); I (1) | A (3); L (2); T (2) |

TABLE 3

Sites of key residues for determining canonical folds in somatically mutated dromedary VLambda sequences; numbering according to Kabat et al. (Sequences of Proteins of Immunological Interest, 5$^{th}$ ed. (1991)) and key residues proposed by Morea and colleagues (Morea et al., Methods 2000).

| Sequence | Canonical structure | Closest hu GL family | L1 (λ) key residues | | | | | | L2 (λ) key residues | |
|---|---|---|---|---|---|---|---|---|---|---|
| | | | 2 | 25 | 29 | 30 | 33 | 71 | 46 | 64 |
| Som Mut Drom VL3-1 (Camvl8, 18, 19, 20, 23) Hu Gl Vλ family 3 | L1: 11 (or 2) | (IGLV3-1*01) | — — | G (5) G (10) | — — | F (4); L (1) L (6); I (3); M (1) | T (2); A (1); V (1); F (1) A (6); V (3); E (1) | T (4); A (1) A (5); T (3); V (2) | | |
| | L1: 2 (Morea) | | — | G | — | I | V | A | | |
| Som Mut Drom VL3-12/32 (Camvl11) Hu Gl Vλ family 3 | L1: 11 (or 2) | (IGLV3-1*01) | — — | G (1) G (10) | — — | L (1) L (6); I (3); M (1) | A (1) A (6); V (3); E (1) | T (1) A (5); T (3); V (2) | | |
| | L1: 2 (Morea) | | — | G | — | I | V | A | | |
| Som Mut Drom VL1-40 (Camvl44) Hu Gl Vλ family 1 | L1: 14 (or 6) L1: λ6 (Martin) | (IGLV1-40*01) | S (1) S (2) S | G (1) G (2) G | N (1) N (2) N | — — — | V (1) V (2) V | A (1) A (2) A | | |
| Som Mut Drom VL2-18 (Camvl5, 17, 30-33, 36, 52, 57, 59, 60, 65) Hu Gl Vλ family 2 | L1: 14 or 6 L1: λ6 (Martin) | (IGLV2-18*02) | S (11); A (1) S (6) S | G (12) G (6) G | D (12) D (6) N | — — — | V (12) V (6) V | A (11); V (1) A (6) A | | |
| Som Mut Drom VL3-1 (Camvl8, 18, 19, 20, 23) Hu Gl Vλ family 3 | L2: 7 | (IGLV3-1*01) | | | | | | | I (4); L (1) I (10) | G (3); A (2) G (10) |
| | L2: 1 (Morea) | | | | | | | | I; V | G |
| Som Mut Drom VL3-12132 (Camvl11) Hu Gl Vλ family 3 | L2: 7 | (IGLV3-1*01) | | | | | | | I (1) I (10) | G (1) G (10) |
| | L2: 1 (Morea) | | | | | | | | I; V | G |
| Som Mut Drom VL1-40 (Camvl44) Hu Gl Vλ family 1 | L2: 7 | (IGLV1-40*01) | | | | | | | I (1) I (2) | E (1) G (2) |
| | L2: 1 (Morea) | | | | | | | | I; V | G |
| Som Mut Drom VL2-18 (Camvl5, 17, 30-33, 36, 52, 57, 59, 60, 65) Hu Gl Vλ family 2 | L2: 7 | (IGLV2-18*02) | | | | | | | I (12) I (6) | G (11); S (1) G (6) |
| | L2: 6 (Morea) | | | | | | | | I; V | G |

TABLE 4A

Comparison of L1 sequences of dromedary VLambda with human germlines; numbering according to Kabat et al. (Sequences of Proteins of Immunological Interest, 5$^{th}$ ed. (1991)). Asterisks indicate key residues important for canonical folds.

| | | L1: 11 residue no. | | | | | | | | | | | |
|---|---|---|---|---|---|---|---|---|---|---|---|---|---|
| | | 02 | 26 | 27 | 28 | 29 | 30* | 30a | 30b | 30c | 31 | 32 | 33* | 71* |
| Family 3 | Som Mut Drom VL3-1 (Camvl8, 18, 19, 21, 23) | — | — | G (4); D (1) | N (3); D (1); I (1) | — | F (4); L (1) | G (5) | S (4); D (1) | Y (4); K (1) | — | Y (4); K (1) | T (2); A (1); V (1); F (1) | A (5) |
| | Hu Gl Vλ family 3 | — | — | D (6); N (3); E (1) | N (3); A (3); S (2); K (1); V (1) | — | L (6); I (3); M (1) | G (5); P (3); R (1); E (1); G (1) | S (4); D (1); N(1); E (1); S (1) | K (6); N(1); Q (1); S (1) | — | Y (7); A(1); S (1); N (1) | A (6); V (3); E (1) | A (3); T (3); V (2) |

| | | L1: 11 residue no. | | | | | | | | | | | |
|---|---|---|---|---|---|---|---|---|---|---|---|---|---|
| | | 02 | 26 | 27 | 28 | 29 | 30* | 30a | 30b | 30c | 31 | 32 | 33* | 71* |
| Family 3 | Som Mut Drom VL3-12/32 (Camvl11) | — | — | S(1) | L (1) | — | R (1) | N (1) | Y (1) | Y (19); C (1) | — | A (1) | A (1) | A (1) |
| | Hu Gl Vλ family 3 | | | D (6); N (3); | N (3); A (3); | | L (6); I (3); | G (5); P (3); | S (4); K (3); | K (6); Y (1) | | Y (7); A (1); | A (6); V (3); | A (3); T (3); |

TABLE 4A-continued

Comparison of L1 sequences of dromedary VLambda with human germlines; numbering according to Kabat et al. (Sequences of Proteins of Immunological Interest, 5th ed. (1991)). Asterisks indicate key residues important for canonical folds.

|   |   |   |   | E (1) | S (2); K (1); V (1) |   | M (1) | R (1); E (1) | D (1); E (1); G (1) | N (1); Q (1); S (1) |   | S (1); N (1) | E (1) | V (2) |
|---|---|---|---|---|---|---|---|---|---|---|---|---|---|---|

| | | colspan: L1: 14 residue no. |
|---|---|---|

|   |   | 02 | 26 | 27 | 28 | 29 | 30* | 30a | 30b | 30c | 31 | 32 | 33* | 71* |
|---|---|---|---|---|---|---|---|---|---|---|---|---|---|---|
| Family 1 | Som Mut Drom VL1-40 (Camvl44) | S (1) | S (1) | S (1) | S (1) | N (1) | I (1) | G (1) | G (1) | G (1) | S (1) | G (1) | V (1) | A (1) |
|   | Hu Gl Vλ family 1 | S (2) | S (2) | S (2) | S (2) | N (2) | I (2) | G (2) | A (2) | G (2) | Y (2) | D (1); V (1) | V (2) | A (2) |

| | | colspan: L1: 14 residue no. |
|---|---|---|

|   |   | 02 | 26 | 27 | 28 | 29 | 30* | 30a | 30b | 30c | 31 | 32 | 33* | 71* |
|---|---|---|---|---|---|---|---|---|---|---|---|---|---|---|
| Family 2 | Som Mut Drom VL2-18 (Camvl5, 17, 30-33, 36, 52, 57, 59, 60, 65) | S (11); A (1) | T (12) | S (10); R (2) | N (9); D (3) | D (11); G (1) | V (12) | G (12) | G (5); R (4); K(2); A (1) | Y (12) | N (11); A (1) | Y (12) | V (12) | A (11); V (1) |
|   | Hu Gl Vλ family 2 | S (6) | T (6) | S (6) | S (6) | D (6) | V (6) | G (6) | G (3); S (2); D (1) | Y (6) | N (5); D (1) | Y (3); R (1); L (1); V (1) | V (6) | A (6) |

TABLE 4B

Comparison of L2 sequences of dromedary VLambda with human germlines; numbering according to Kabat et al. (Sequences of Proteins of Immunological Interest, 5th ed. (1991)). Asterisks indicate key residues important for canonical folds.

| | | colspan: L2: 7 residue no. |
|---|---|---|

|   |   | 48* | 49 | 50 | 51 | 52 | 53 | 64* |
|---|---|---|---|---|---|---|---|---|
| Family 3 | Som Mut Drom VL3-1 (Camvl8, 18, 19, 20, 23) | I (4), L (1) | Y (5) | K (3); R (1); G (1) | D (4); N (1) | S (2); T (2); D (1) | A (1); L (1); E (1); N (1); S (1) | G (3); A (2) |
|   | Hu Gl Vλ family 3 | I (10) | Y (10) | E (2); K (2); D (1); Q (1); R (1); S (1); G (1); Y (1) | D (8); K (1); S (1) | S (9); N (1) | E (3); N (3); K (2); D (2) | G (10) |

| | | colspan: L2: 7 residue no. |
|---|---|---|

|   |   | 48* | 49 | 50 | 51 | 52 | 53 | 64* |
|---|---|---|---|---|---|---|---|---|
| Family 3 | Som Mut Drom VL3-12/32 (Camvl11) | I (1) | Y (1) | N (1) | D (1) | N (1) | N (1) | G (1) |
|   | Hu Gl Vλ family 3 | I (10) | Y (10) | E (2); K (2); D (1); Q (1); R (1); S (1); G (1); Y (1) | D (8); K (1); S (1) | S (9); N (1) | E (3); N (3); K (2); D (2) | G (10) |

| | | colspan: L2: 7 residue no. |
|---|---|---|

|   |   | 48* | 49 | 50 | 51 | 52 | 53 | 64* |
|---|---|---|---|---|---|---|---|---|
| Family 1 | Som Mut Drum VL1-40 (Camvl44) | I (1) | Y (1) | G (1) | N (1) | S (1) | N (1) | E (1) |
|   | Hu Gl Vλ family 1 | I (2) | Y (2) | G (2) | N (2) | S (2) | N (2) | G (2) |

| | | colspan: L2: 7 residue no. |
|---|---|---|

|   |   | 48* | 49 | 50 | 51 | 52 | 53 | 64* |
|---|---|---|---|---|---|---|---|---|
|   | Som Mut Drom VL2-18 (Camvl5, | I (12) | Y (12) | Q (11); D (1) | V (9); I (2); | N (10); S (1); | K (12) | G (11); S (1) |

TABLE 4B-continued

Comparison of L2 sequences of dromedary VLambda with human germlines; numbering according to Kabat et al. (Sequences of Proteins of Immunological Interest, 5th ed. (1991)). Asterisks indicate key residues important for canonical folds.

| | | 17, 30-33, 36, 52, 57, 59, 60, 65) | | | | D (1) | D (1) | | |
|---|---|---|---|---|---|---|---|---|---|
| Family 2 | Hu Gl Vλ family 2 | | I (6) | Y (6) | E (4); D (1); N (1) | V (6) | S (5); N (1) | K (3); N (2); T (1) | G (6) |

TABLE 5

Sites of key residues for determining canonical folds in somatically mutated dromedary VKappa sequences; numbering according to Kabat et al. (Sequences of Proteins of Immunological Interest, 5th ed. (1991)) and key residues proposed by Morea and colleagues (Morea et al., Methods 2000).

| Sequence | Canonical structure | Closest hu GL family | L1 (κ) key residues | | | | | L2 (κ) key residues | |
|---|---|---|---|---|---|---|---|---|---|
| | | | 2 | 25 | 29 | 30e | 33 | 71 | 48 | 64 |
| Som Mut Drom VK2-40 (Kp1, 3, 6, 7, 10, 20, 48) | K1: 3 | IGKV2-40 (2_1 or 011*/01) | I (7) | S (7) | V (6); L (1) | Q (7) | L (7) | F (7) | | |
| Hu Gl VK family 2 | | | I (1) | S (1) | L (1) | Q (1) | L (1) | F (1) | | |
| | K1: 3 (Morea) | | I | S | L; V | E; Q; S | L | F | | |
| Som Mut Drom VK2-40 (Kp1, 3, 6, 7, 10, 20, 48) | K2: 1 | IGKV2-40 (2_1 or 011*/01) | | | | | | | I (7) | G (7) |
| Hu Gl VK family 2 | | | | | | | | | I (1) | G (1) |
| | H2: 1 (Morea) | | | | | | | | I, V | G |

TABLE 6

Comparison of (A) L1 and (B) L2 sequences of dromedary VKappa with human germline; numbering according to Kabat et al. (Sequences of Proteins of Immunological Interest, 5th ed. (1991)). Asterisks indicate key residues important for canonical folds.

(A)

| | | L1 (κ): 11 residue no. | | | | | | | | | | | | | | | |
|---|---|---|---|---|---|---|---|---|---|---|---|---|---|---|---|---|---|
| | | 2* | 25* | 26 | 27 | 28 | 29 | 30 | 30a | 30b | 30c | 30d | 30e* | 30f | 31 | 32 | 33* | 71* |
| | Som Mut Drom VK2-40 (Kp1, 3, 6, 7, 10, 20, 48) | I (7) | S (7) | S (7) | Q (7) | S (5); N (1); H (1) | V (6); L (1) | F (3); L (2); I (1); V (1) | S (5); D (1); A (1) | S (4); D (1); T (1); V (1) | S (7) | N (4); S (2); R (1) | Q (7) | K (6); S (1) | S (7) | Y (3); L (2); Q (1); F (1) | L (7) | F (7) |
| Family 2 | Hu Gl VK family 2 (011*/01) | I (1) | S (1) | S (1) | Q (1) | S (1) | L (1) | L (1) | D (1) | S (1) | D (1) | D (1) | G (1) | | T (1) | Y (1) | L (1) | F (1) |

(B)

| | | L2 (κ): 11 residue no. | | | | | |
|---|---|---|---|---|---|---|---|
| | | 48* | 49 | 50 | 51 | 52 | 64* |
| | Som Mut Drom VK2-40 (Kp1,3, 6, 7, 10, 20, 48) | I (7) | Y (7) | Y (7) | A (7) | S (7) | G (7) |
| Family 2 | Hu Gl VK family 2 (011*/01) | I (1) | Y (1) | T (1) | L (1) | S (1) | G (1) |

Example 14

Sequence Analysis of Somatically Mutated VH, VK and VL from Llama

From four llamas peripheral blood lymphocytes were isolated, RNA extracted and random primed cDNA synthesized as described before (de Haard et al, JBC 1999). Amplification of VHCH1, VLCL and VKCK was performed and the amplicons were cloned in vector pCB3 yielding heavy chain or light chain libraries. After screening of clones with PCR to check for the presence of the antibody domain insert, individual clones were grown and plasmid DNA was purified for sequence analysis.

Section 14.A shows the lambda light chain variable regions grouped into families according to the closest human germline analogue with the same CDR1 and CDR2 length and presumable having the same canonical fold combination. The lambda germlines most frequently used in humans, i.e. VL1, VL2 and VL3, are also often found in the analyzed llama sequences and in addition VL4, VL5, VL6 (not shown in section 14.A) and VL8, meaning that 7 out of the 10 lambda families as found in humans are used as well in the llama. Section 14.B shows two of the three kappa light chain variable regions (i.e. VK1, and VK4; VK2 is not shown), which occur in about 50% of kappa containing human antibodies. Members of the VK3 family, which is used most frequently (50%) in human antibodies, were not identified, but it can well be that the used primers for amplification are responsible for this and that these have to be adapted. Section 14.0 shows the alignment of the VH sequences revealing a high sequence homology to the most often used human VH3 segment (occurs 34% in human antibodies) and VH1 (17%). It must be noted that the recent publication of Achour et al (J Immunol 2008) mentions the presence of a VH2 family in the germline of Alpaca which is most closely related to the human VH 4 family (see example 10.10).

Overall it can be concluded that camelids use a high diversity of heavy chain and light chain families similar to what is found in the human immune system, meaning that by active immunization with human disease targets an excellent choice of lead antibodies can be expected with a high sequence homology to human antibodies, which therefore can be easily engineered for therapeutic applications.

14. (A) VLAMBDA

| | FR1 | CDR1 | FR2 | CDR2 | FR3 | CDR3 | FR4 |
|---|---|---|---|---|---|---|---|
| | 1234567891234567890123 | 4567890123abc234 | 56789012345678 | 901abcde23456 | 7890123456789012345678 | 9012345abcde | |
| HuVL1-1(3/4/5) | QSVLTQPPSVSEAPRQRVTISC | SGSSSNIGNN AVN | WYQQLPGKAPKLLIY | YD DLLPS | GVSDRFSGSKSG ISASLAISGLQSEDEADYYC | AAWDDSLNG | |
| LAMBDA#14 | QPVLTQPPSVSGSPGQKFTISC | TGSSSNIGNN YVN | WYQHLPGTAPKLLIY | SN NNRAS | GVPDRFSGSKSG SSASLTITGLQAEDEAEYYC | SSWDDSLSGTV | FGGGTHLTVL |
| LAMBDA#16 | QSALIQPPSVSGSPGQKFIISC | TGSSSNIGDN YVN | WYQHLPGTAPKLLIY | SN SNRAS | GVPDRFSGSKSG SSASLTITGLQAEDEADYYC | SSWDDSLSGHPV | FGGGTKLTVL |
| LAMBDA#46 | NFMLTQPPSVSGSPGQKFTISC | TGSSSDIGNN YVN | WYQHLPGTAPKLLIY | ST DKRAS | GVPDRFSGSKSG SSASLTITGLQAEDEADYYC | SSWDDNLGTYV | FGGGTSVTVL |
| LAMBDA#45 | NFMLTQPPSVSGSPGQKFTISC | TGSSSNIGEN FVN | WYQHLPGTAPKLLIY | ST DKRAS | GVPDRFSGSKSG SSASLTITGLQAEDEADYYC | SSWDDNLGTYV | FGGGTSVTVL |
| LAMBDA#15 | NFMLTQPPSVSGSPGQKFTISC | TGSNNNIGNN YVN | WYQHLPGTAPKLLIY | SN NYRAS | GVPDRFSGSKSG SSASLTITGLQAEDEADYYC | SSWDESLSGRYV | FGGGTKLAVL |
| HuVL1-2 | QSVLTQPPSVSGAPGQRVTISC | TGSSSNIGAGYDVH | WYQQLPGTAPKLLIY | GN SNRPS | GVPDRFSGSKSG TSASLAITGLQAEDEADYYC | QSYDSSLSG | |
| LAMBDA#47 | QSALTQPPSVSVSGTLGKTVTISC | AGTSNDIGRYNYVA | WYQQLPGTAPKLLIY | AV SYRAS | GIPDRFSGSKSG NTASLTISGLQSEDEADYYC | VSYRSGGTNV | FGGGTHLTVL |
| LAMBDA#18 | QSALTQPPSVSGTLGKTLTISC | AGTSSDVGVGNYVS | WYQQLPGTAPKLLIY | RV SYRPS | GIPDRFSGSKSG NTASLTISGLQSEDEADYYC | TSYTYKGGGTAV | FGGGTHLTVL |
| LAMBDA#32 | QSALTQPPSVSVSGTLGKTVTISC | AGTRTDVGVGDYVS | WYQHVPNTAPKLLIY | AV SARAS | GIPSRFSGSKSG NTASLTISGLQSEDEADYYC | ASYRDGNYAV | FGGGTHLTVL |
| LAMBDA#28 | QAVLTQPPSVSGTLGKAVTISC | AGTGSDVGVGDYVS | WYQQLPDTAPKLLVY | AV NTRAS | GIPDRFSGRSG NTASLTISGLQSEDEGDYYC | ASYRSYNNYV | FGGGTHLTVL |
| LAMBDA#29 | NFMLTQPPSVSGSPGKTVTISC | AGTSSDVGVGNYVS | WYQQLPGMAPKLLIY | NI NKRAS | GIADRFSGSKSG NTASLTISGLQSEDEAVYYC | ASYRSGNNYV | FGGGTELTVL |
| LAMBDA#27 | QSALTQPPSVSGTLGKTVTISC | AGTNSDIGDYNFVS | WYQHLPGMAPKLLIY | DV NKRAS | GIADRFSGSKSG NTASLTISGLQSEDEADYYC | ASYRSSNNYV | FGGGTKLTVL |
| LAMBDA#17 | QAGLIQPPSVSGSLGKIIIISC | AGTRNDIGHGHVS | WYQQLPGTAPKLLIY | KI NTRAS | GIPDRFSGSKSG NTASLTISGLQSEDEADYFC | VADINGDTNV | FGGGTHLTVL |
| LAMBDA#4 | SSELTQPPSVSGSLGKTVTISC | AGTSNDIGAHNYVS | WYQQLPGTAPKLLIN | KV STRAS | GIPDRFSGSKSG NTASLTISGLQSEDEADYYC | AAYRTGDARI | FGGGTHLTVL |
| LAMBDA#7 | QPVLTQPPSVSGSPGKTVTISC | AGTSSDVGVGNYVS | WYQLLPGTAPKLLIY | DV NKRPS | GIPDRFSGSKSG NQAYLTISGLQSEDEADYYC | VSYREPNNFV | SGGGTHLVVL |
| LAMBDA#8 | QSALTQPPSVSGTLGKTVTISC | AGTIGDIGAGNYVS | WTRQTPGTAPKLLIY | EV NKRTS | GIPDRFAGSRSG NIASLIISGLQAEDEADYYC | ASYRIGSRGV | FGGGTHLTVL |
| LAMBDA#5 | QPVLIQPPSVSGSLGKIVIISC | AGTWSDIGGYNYIS | WIRQLPGTAPKLLIY | EV DKRAP | GIPDRFSGSKSG TTASLVISGLQSEDEADYYC | ASYKSSENAV | FGGGTHLTVV |

| | FR1 | CDR1 | FR2 | CDR2 | FR3 | CDR3 | FR4 |
|---|---|---|---|---|---|---|---|
| | 12345678912345678901123 | 45678901abc234 | 56789012345678 | 901abcde23456 | 78901234567ab9012345678 | 9012345abcde | |
| HuVL2-1 | QSALTQPPSASGSPGQSVTISC | IGISSDVGSYNYVS | WYQQHPGKAPKLMIY | EV SKRPS | GVPDRFSGSKSG NTASLTVSGLQAEDEADYYC | SSYAGSNNF | |
| LAMBDA#1 | QSVLTQPPSVSGTLGKTLTISC | AGTSSDVGVGNYVS | WYQQLPGTAPKLLIY | RV STRAS | GIPDRFSGSKSG NTASLTISGLQSEDEADYYC | SSYRSTGTAV | FGGGTHLTVI |

14. (A) VLAMBDA

| | FR1 | CDR1 | FR2 | CDR2 | FR3 | CDR3 | FR4 |
|---|---|---|---|---|---|---|---|
| LAMBDA#8 | QSVLTQPPSVSGTLGKTVTISC | AGTSSDVGYGNYVS | WYQKLPGTAPKLLIY | AV SYRAS | GIPDRFSGSKSG NTASLTISGLQSEDEADYYC | ASYRDSNNAV | FGGGTHLTAI |
| LAMBDA#5 | LPVLTQPPSVSGTLGKSLTISC | AGTSSDVGNGNYVS | WYQQLPGTAPKLLIY | RV ISRAS | GVPDRFSGSKSG NTASLTISGLQPEDEADYYC | ASYKRGGTSV | FGGGTHLTVI |
| LAMBDA#11 | QPVLTQPPSVSGTLGKTVTISC | AGTSTDIGGYNYVS | WYQQVPGTAPKLLIY | EV NKRPS | GIPDRFSGSKSG NTASLTISGLQSEDEADYYC | ASYRSSNNVV | FGGGTHLTVI |
| | 1234567891012345678901234 5678901abc234 | 3 | 4 | 5 01abcde23456 | 6 7 8 789012345678ab901234567890123456 78 | 9 9012345abcde | |
| HuVL3-2 | SYELTQPLSVSVALGQTARITC | GGNNIGSK | NVH WYQQKPGQAPVLVIY | RD SNRPS | GIPERFSGSNSG NTATLTISRAQAGDEADYYC | QVWDSSTA | |
| LAMBDA#13 | LPVLTQPSALSVTLGQTAKITC | QGGSLGSS | YAH WYQQKPGPAPVLVIY | DD ANRPS | GIPERFSGSRSG GTATLTISGAQAEDGDYYC | QSVDNSGNVV | FGGGTHLTVI |
| LAMBDA#40 | QAVLTQPSAVSVSLGQTARLTC | QGDNVETA | GTS WYRQKPGQAPSLIIY | GD SSRPS | EISERFSASTSG NTAILTITGAQAEDEADYYC | LSADSDLDSV | FGGGTLLTVI |
| LAMBDA#2 | QAGLTQPSAVSVSLGQTARITC | RGDSLERY | GAN WYQQKPGQARVQVIY | GD DIRPS | GIPERFSGSRLG GTATLTISGAQAEDEADYYC | QSDSSGYMND | FSSRTHLTVI |
| LAMBDA#14 | QSALTQPSAVSVSLGQTAEITC | RGRNFESG | FPH WYRQKPGQSPELVMF | IV NNRWS | GIPDRFSGTRSG DAAILIIGVQAEDEADYYC | QMWDGEGAV | FGGGTHLTVI |
| | 12345678912345678901 23 4 | 4567890labc234 | 4 | 5 01abcde23456 | 6 7 8 789012345678ab901234567890123456 78 | 9 9012345abcde | |
| HuVL4-1 | LPVLTQPPSASALLGASIKLTC | TLSSEHSTY | TIE WYQQRPGRSPQYIMK | VKSDGS HSKGD | GIPDRFMGSSSG ADRYLTFSNLQSDDEAEYHC | GESHTIDGQVG | |
| LAMBDA#10 | QSVLTQPPSASASLGASAKLTC | TLSSGYSSY | NVD WYQQVPGKSPWFLMR | VGSSGV GSKGS | GVSDRFSGSSSG LERYLTIQNVQEEDEAEYIC | GADHASSMYT | FGGGTHLTVL |
| | 12345678912345678901 23 4 | 4567890labc234 | 4 | 5 01abcde23456 | 6 7 8 789012345678ab901234567890123456 78 | 9 9012345abcde | |
| HuVL5-1 | QPVLIQPPSSSASPGESARLIC | TLPSDINVGSYNIY | WYQQKPGSPPRYLLY | YYSDSD KGQGS | GVPSRFSGSKDASANTGILLISGLQSEDEADYYC | MIWPSNAS | |
| LAMBDA#3 | LPVLTQPPSLSASPGASARLTC | SLNSGTIVGGYHIN | WYQQKAGSPPRYLLR | FYSDSN KHQGS | GVPSRFSGSKDASANAGLLLISGLQVEDEADYYC | GIYDSNTGTYV | FGGGTKLTVL |

-continued 14. (A) VLAMBDA

| | FR1 | CDR1 | FR2 | CDR2 | FR3 | CDR3 | FR4 |
|---|---|---|---|---|---|---|---|
| LAMBDA#7 | LPVLTQPPSLSASPGASARLTC | VLSSGTVVGGYHIN | WYQQKPGSPPRYLLR | FYSDSS | KQQGS GVPSRFSGSKDASANAGLLLISGLQPEDEADYYC | GTYHSNTGTYV | FGGGTKLTVL |
| LAMBDA#9 | LPVLNQPPSLSASPGESARLTC | SLSSETIVGGYQIA | WYQQTAGSPPRYLLR | FYSDSN | KHQGS GVPSRFSGSKDASANAGILFISGLQPEDEADYYC | GIYHYNSDTYV | FGGGTRLTVL |
| LAMBDA#26 | LPVLIQPPSLSASPGSSVRLIC | TLSSGKSVGMYDIS | WYQQKAGSPPRYLLY | YYSDTS | NHQGS GVPSRFSGSKDASANAGLLLISGLQPEDEADYYC | ATGDRSSNPHV | FGGGTKLTVL |
| LAMBDA#12 | QSVLTQPPSLSASPGSSVRLTC | TLSSANSVDNYYIS | WYQQKPGSPPRYLLY | YYSDSY | MQRDS GLPDRFSVSKDASINAGLLLISGLQPEDEADYYC | ASGDRNSNPHSV | FGGGTHLTVL |

| | FR1 | CDR1 | FR2 | CDR2 | FR3 | CDR3 | FR4 |
|---|---|---|---|---|---|---|---|
| | 1234567891234567890123 | 4567890 1abc234 | 567890123456 789 | 01abcde23456 | 789012345678ab901234567 8 | 9012345abcde | |
| | 1 | 2 3 | 4 | 5 | 6 7 8 | 9 | |
| HuVL8-1 | QTVVTQEPSLTVSPGGTVTLTC | ASSTGAVTSGYYPN | WFQQKPGQAPRALIY | SNKHS | WTPARFSGSLLG GKAALILSGVQPEDEAEYYC | LLYYGGAQ | |
| LAMBDA#42 | QAVVSQEPSLSVSPGGTVTLIC | GLSSGSVTTSNYPG | WFQQTPGQAPRTLIY | SSRHS | GVPSRFSGSISG NKAALTITGAQPEDEADYYC | ALDIGSYTV | FGGGTKLTVL |
| LAMBDA#31 | QTVVTQEPSLSVSPGGTVTLIC | GLTSGSVTASNLPG | WFQQTPGQAPRTLIF | IYHHS | GVPSRFSGSIAG NKATLTITGAQPEDEGDYFC | VLWMDRIEAGSIM | FGGGTHLSVV |

14.(B) VKAPPA

|  | FR1 | L1 CDR1 | FR2 | L2 CDR2 | FR3 | L3 CDR3 |  |
|---|---|---|---|---|---|---|---|
| HuVK1-1 | DIQMTQSPSSLSASVGDRVTITC | RASQSI SSYLN | WYQQKPGKAPKLLIY | AASSLQS | GVPSRFSGSGSGTDFTLTISSLQPEDFATYYC | QQSYSTP | |
| KAPPA#39 | DIQLTQSPSSLSASLGDRVTITC | QASQSI STELS | WYQQKPGQTPKLLIY | GASRLQT | GVPSRFSGSGSGTSFTLTISGLEAEDLATYYC | LQDVSSPYS | FGSGTRLEIK |
| KAPPA#22 | DIQLTQSPSSLSASLGDRVTITC | QASQSI STELS | WYQQKPGQTPKLLIY | DRSRLQI | GVPSRFSGSGSGTSFTLTISGLEAEDLATYYC | LQDDSWPYS | FGSGTRLEIK |
| KAPPA#24 | DIVMTPSSLSASLGDRVTITC | QASQSI NTELS | WYQQKPEQPPKLLIY | AASRLQT | GVPSRFSGSGSGTSFTLTISGLEAEDLATYYC | LQDSDWPLT | FGQGTKVELK |
| KAPPA#21 | DIVMTQTPSSLSASLGDRVTITC | QASQSI NTELS | WYQQKPGQPPKLLIY | EASRLQT | GVPSRFSGSGSGTSFTLTISGLEAEDLATYYC | LQDSDWPLT | FGQGTKVELK |
| KAPPA#23 | DIVMTQTPSSLSASLGDRVTITC | QATQSI STELA | WYQQKPGQTPKLLIY | GASRLQT | GVPSRFSGSGSGTSFTLTISGLEAEDLATYYC | MADLDWPLV | FGQGTKVELK |
| KAPPA#7 | AIQMTQSPSSLSASLGDRVTITC | QASQSI STELS | WYQQKPGQTPKLLIY | GASRLQT | GVPSRFSGSGSGTSFTLTISGLEAEDLATYYC | LQQSSPLT | FGQGTEVDLK |
| KAPPA#19 | DIQLTQSPSSLSASLGDRVTITC | QASQSI STELS | WYQQKPGQTPKLLIY | GASRLQT | GVPSRFSGSGSGTSFTLTISGLESEDLATYYC | LQDYSWPLT | FGQGTKVELT |
| KAPPA#25b | DIVMTQTPPSLSASLGDRVTITC | QASQSI RNELA | WYQQKPGQTPKLLIY | GASRLQT | GVPSRFSGSGSGTSFTLTISGLEAEDLATYYC | LQDYSWPRT | FGQGTKVELK |
| I-_8 | AIQMTQSPSSLSASLGDRVTITC | QASQSI SSYLA | WYQQKPGQAPKLLIY | GASRLQT | GVPSRFSGSGSGTSFTLTISGLEAEDLATYYC | LQDDSWPLT | FGQGTKVELK |
| KAPPA#43 | AIQMTQSPSSLSASLGDRVTITC | QASQSI SSYLA | WYQQKPGQAPKLLIY | GASTLQT | GVPSRFSGSGSGTSFTLTISGLEAEDLATYYC | QQYSIPVT | FGQGTKCELR |
| KAPPA#44 | VIQMTQSPSSLSASLGDRVTITC | QASQSI SNYLA | WYQQKPGQAPKLVIY | GASRLQT | GVPSRFSGSGSGTSFTLTISGLEAEDAGTYYC | QLYGSRPS | FGQGTKVELK |
| KAPPA#20b | DIQLTQSPSSLSOSLGDIVTITC | QASQSI TTELS | WYQQKPGQTPKLLIY | GAFRLQA | GVPSRFSGSGSRSGTTFTLTISGLEAEDAGTYYC | LQDYSWPPYS | FGSGTRLEIK |
| HuVK4-1 | DIVMTQSPDSLAVSLGERATINC | KSSQSVLYSSNNKNYLA | WYQQKPGQPPKLLIY | WASTRES | GVPDRFSGSGSGTDFTLTISSLQAEDVAVYYC | QQYYSTP | |
| KAPPA#53 | ETTLTQSPSSVTASVGEKVTINC | KSSQNVGGSNQKSILN | WIQQRPGSGSATDFTLTIRSVQPEDAAVYYC | YASTRDA | GIPDRFSGSGSATDFTLTIRSVQPEDAAVYYC | QQVNIAPYT | FGSGTRLEIR |
| KAPPA#50 | EIVMTQSPSSVTASAGEKVTINC | KSSQSVFQSSNQKNYLG | WYQQRIGQSPRLLIN | WASTRES | GVPDRFSGSGTTDFTLTINPFQPEDAAVYYC | QQGKSAPLT | FGSGTKVELK |
| KAPPA#20 | DIVMTQTPSSVTASIGEKVTINC | KSSQSVLYSSNQKNYLT | WYQQRLGQSPRLLIY | WASTRES | GVPDRFSGSGSGLTTFLTISSFQPEDAAVFFC | QQGYSVPLT | FGRGTKVELK |
| KAPPA#48 | ETTLTQSPSSVTASAGEKVTINC | KSSQSVLLDSNQKNYLA | WYQQRLGQSPRLLIY | WASTRQS | GVPDRFSGSGSTTDFTLTISSQPEDAAVYYC | QQGITIPVT | FGQGTKVELK |
| KAPPA#55 | EIVLTQSPSSVTASAGEKVTINC | KSSQSVLYSSDQKNYLA | WYQQRLGQSPRLLIY | WASTRES | GVPDRFSGSGSTTDFTLTISSFQPEDAAVYYC | QQGYSSPHS | FGSGTRLEIK |
| KAPPA#9 | ETTLTQSPSSVTASAGEKVTINC | KSSQSVLYRSDQKNVLS | WYQQRLGQSPRLLIY | WASTRES | GVPDRFSGSGSTTDFTLTISSFQPEDAAVYYC | QQGYSRPYS | FGNGTRLEIK |
| KAPPA#51 | DIVMTQTPSSVTASAGEKVTINC | KSSQSVLNNSDQKIYLA | WYQQRLGQSPRLLIY | WASTRES | GVPDRFSGSGSTTDFTLTISSFQPEDAAVYYC | QQEYSAPAS | FGSGTRLEIK |
| KAPPA#10 | DIVMTQSPGVSTASTGENITINC | KSSQNVLLSSDQKNYLN | WYQQRLGQSPRLLIY | WASTRKS | GIPDRFSGRGSTTDFTLTINSFQPEDAAVYYC | QQGYSIPHT | FGGGTRLEIK |

-continued 14.(B) VKAPPA

| | | | | | | |
|---|---|---|---|---|---|---|
| KAPPA#54 | DIVMTQTPTSVTASAGEKVTINC | KSSQSLLYSANQKVYLA | WYQQRLGQSPRLLFR | WTSTRQP | GIPDRFSGSGSTTDFTLTISRVQPEDAAVYYC | QQAYARPHT FGSGTRLEIK |
| KAPPA#49 | DIVMTQTPTSVTASAGEKVTINC | KSSQSLLYSANQKVYLA | WYQQRLGQSPRLLFR | WTSTRQP | GIPDRFSGSVSGSTTDFTLTINSSVQPEDAAVYYC | QQAYARPHT FGSGTRLEIK |
| KAPPA#52 | EIVMTQSPTSVTASVGEKVTINC | KSSQSLLYSANQKVYLA | WYQQRLGQSPRLLFY | WTSTRQS | GIPDRFSGSGSTSFTLTISSVQPEDAAVYYC | QQAYTRPHT FGSGTRLEIR |
| KAPPA#13 | EIVLTQSPSSVTASVGEKVTINC | KSSQSVVKSGSNQITYLN | WYQQTPGQSPRLLIY | YASTQEL | GIPDRFSGSGSTTDFTLTISSVQPEDAAVYYC | QQAYSAPFS FGSGTRLEIK |
| KAPPA#11 | ETLLTQSPSSVTASVGEKVTINC | KSSQSVVSGSNQKIYLN | WYQQRPGQSPRLLIY | YASTQES | GIPDRFSGSGSTTDFTLTISSVQPEDAAVYYC | QQGASAPVS FGSGTRLEIK |
| KAPPA#36 | DIVMTQTPSSVTASVGETVIGC | KSSQSVVSGSSQKSFLN | WYQQRPGQSPRLLIY | YASTLEL | GIPDRFSGSGSTTDFTLTISSVQPEDAAVYYC | QQAYSTPST FGPGTKLEIR |
| KAPPA#25 | DIVMTQTPRSVTASVGEKVTINC | KSSQSVLSGSNQKSYLN | WYQTRPGQSPRLLIY | YASTQES | GIPDRFSGSGSTTDFTLTISGVQPEDAAVYYC | QQAYSAPAT FGQGTTVEVI |
| KAPPA#12 | DVVMTQSPSSVTASVGETVGTINC | KSSQSVVSGSSQKSFLN | WYQQRPGQSPRLLIY | YASTQES | GIPDRFSGSGSTTDFTLTISSVQPEDAAVYYC | QQAYSYPIT FGQGTKVELK |
| KAPPA#34 | DVVMTQSPSSVTASVGEKVTIDC | KSSQILVSGSDQKSYLS | WYQQRPGQSPRLLIY | YASTQKL | GIPDRFSGSGSTTDFTLTISSVQPEDAAVYYC | QQTYEAPYS FGNGTRLEIK |
| KAPPA#48b | EIVMTQTPSSVTASVGEKVTINC | KSSQSVVLASNQKTYLN | WYQQRPGQSPRLLIY | YASTQQL | GIPDRFSGSGSTTDFTLTISSVQPEDAAVYYC | QQALSAPYS FGSGTRLEIK |
| KAPPA#21 | DVVMTQSPSSVTASVGEKVTINC | KSSQSVVSGSNQKSYLN | WYQQRPGQSPRLLIY | YASTQEL | GIPDRFSGSGSTTDFTLTISSVQPEDAAVYYC | QQAYSTPYS FGSGTRLEIK |
| KAPPA#24 | EIVMTQSPSTVTASVGEKVTINC | KSSQSVVSGSNQKTYLN | WYQQRPEQSPRLLMY | YAATPEL | GIPDRFSGSGSTTDFTLTINSVQPEDAAVYYC | QQTYSPPN FGSGTRLEIA |
| KAPPA#22b | DVVMTQSPSSVTASAGEKVTINC | KSSQSLLWSDNKKNYLS | WYQQRLGQSPRLLIY | WASTRES | GAPDRFSGSGSTTDFTLTISNFQPEDAAVYYC | QQGYSIPIT FGQGTKVELS |
| KAPPA#45 | DIVLTQSPSSVTASAGEKVTITC | ESSQSVLRSSNQRNYLN | WYQQRLGQSPRLLIY | WASTRES | GVPDRFSGSGSTTDFTLTISSFQPEDAAVYYC | QQASSLPFT FGQGTKVELK |
| KAPPA#46 | EIVLTQSPSSVTASAGEKVTINC | KSSQSVLYSSNQNYLA | WYQQRLGQSPRLLIY | WASTRES | GVPDRFSGSGSTTDFTLTISSFQPEDAAVYYC | QQYLSGVT FGQGTKVELK |

14.(C) VH

| | FR1 | CDR1 | FR2 | CDR2 | FR3 | |
|---|---|---|---|---|---|---|
| | H1 | | | H2 | | |
| | 1234567890123456789012345678901234567890 | 1ab2345 | 6789012345 | 012abc345678901234 5 | 6789012345678901 2abc345678901234 | |
| VH1(1-02) | QVQLVQSGAEVKKPGASVKVSCKASGYTFT | G--YYMH | WVRQAPGQGLEWMG | WINP--NSGGTNYAQKFQG | RVTMTRDTSISTAYMELSRLRSDTAVYYCAR | |
| 1C2 | EVQLVQSGAELRNPGASVKVSCKASGYTFT | S--YYID | WVRQAPGQGLEWMG | RIDP--EDGGTKYAPKFQG | RVTFTADTSTSTAYVELSSLRSEDTAVYYCAR | SGRYELDY WGQGTQVTVSS |
| 1G5 | EVQLVQSGAELRNPGASVKVSCKASGYTFT | S--YYIE | WVRQAPGQGLEWMG | RIDP--EDGGTKYAQKFQG | RVIFTADTSTSTAYVELSSLRSEDTAVYFCAT | SGATMSDLDSFGS WGQGTQVTVSS |
| VH3(3-23) | EVQLVESGGGLVQPGGSLRLSCAASGFTFS | S--YAMS | WVRQAPGKGLEWVS | AISG--SGGSTYYADSVKG | RFTISRDNSKNTLYLQMNSLRAEDTAVYYCAK | |
| 5B12 | EVQLVESGGGLVQPGGSLRLSCTTSGFTFE | D--YPMN | WVRQAPGKGLEWVS | VISR--NGGSTYYAESMKG | RFTISRDNAKNTLYIVMNSLISEDTAVYYCIK | PSTSWSTNYGMDY WGKGTQVTVSS |
| 1G4 | EVQLVESGGGLVQPGGSLRLSCAASGFTFD | D--YGMS | WVRQAPGKGLEWVS | GITW--NGGTTNYADSVKG | RFTISRDSAKNMVHLQMDSLKSEDTAVYYCAK | AVRGST LGQGTQVTVSS |
| 5G7 | EVQLVESGGGLVQPGGSLRLSCAASGFTFS | T--YYMS | WVRQAPGKGLEWVS | GINT--GGDSTYYADSVMG | RFTISRDNAKNTLSLQMNSLKPEDTALYYCAR | DLRDYSDYTFVN WGQGTQVTVSS |
| VH_99 | EVQLVESGGGLVQPGGSLRLSCSASGFRFS | T--YAMT | WVRQAPGKGLEWVS | TVDA--SGATTSYAESVKG | RFTISRDNTKGALYLYLQMNSLKPEDTAVYYCGT | RSGTWRGSYIYTESENG WGQGTQVTVSS |
| VH_76 | EVQLVESGGGLVQPGGSLRLSCSASGFTFS | D--YAMI | WVRQAPGKGLEWVS | SINN--GGWSTRYADSVKG | RFTISRDNAKNTLYLQMNSLKPEDTALYYCAR | EGYYSDYAAVGHAYDY WGQGTQVTVSS |
| VH_86 | EVQLVESGGGLVQPGGSLRLSCAASGFTFS | R--YSMS | WVRQAPGKGLEWVS | YIDS--DGATTTYADSVKG | RFTISRDNAKNTLNLQMNSLKPDDAGVYYCAS | FGSSAYSWGYLGMDH WGKGALVTVFS |
| VH_98 | EVQLVESGGGLVQPGGSLRLSCAASGFTFS | I--YGMS | WVRQAPGKGLEWVS | VINS--GGDSTSYADSVKG | RFTISRDNAKNTLYLQMNNLKPEDTAVYYCAK | GGVLGHSNYYAMDY WGKGTLVTVSS |
| VH_89 | EVQLVESGGGLVQPGGSLRLSCSASGLTAS | N--TAMA | WVRQVPGKQLEWVS | DINS--LGNNIFYSKSVKG | RFTIARDKTKNTLVLSMNSLSPEDTAVYYCVA | DASALSWSRPALEV WGQGTLVTVSD |
| VH_82 | EVQLVESGGGLAQPGGSLRLSCAASGFTLS | N--HWMY | WVRQAPGKGLEWVS | AISS--SGGSTYYIDSVKG | RFTISRDNAKNTLYLQMNSLKAEDKGVYYCGK | DESRGIEPGWGSIY WGGGTLVVVSS |
| VH_68 | EVQLVESGGGLVQPGGSLRLSCAASGFAFS | S--SDMS | WVRQAPTKGLEWVS | GINS--GGGSTYYGESMKG | RFTISRDNAKNTLYLQMSSLKPEDTAVYYCTR | YDSFGWNVRYGMDY WGKGTLVTVSS |
| VH_73 | EVQLVQSGGDLVQPGGSLRLSCAASGFAFS | S--YHIS | WVRQAPGKGLEWVS | IIGR--WGADIYYADSVKG | RLTISRDNAKNTVVILQMNSLKPEDTAVYYCTA | ELNWEPENAYSDH WGQGTLVTVSS |
| VH_107 | EVQLVESGGGLVQPGGSLRLSCVGSGITFS | K--YAMS | WVRQPPGKGLEWVS | NIDA--NSELTTYEDTVKG | RFTISRDNVKNTLYLQMNSLKPEDTAVYYCIK | DPRNSWYTYGMDY GGKGTLVVVSS |
| VH_94 | EVQLVESGGGLVQPGGSLRLSCAASGFTFS | S--YYMN | WVRQPPGKGLEWLS | VISS--SGGNTKYSDSVKG | RFTISRDNAKNMVILQMNSLKPEDTAVYYCAK | RIEGGMGYGMDY WGKGTPVTVSS |
| VH_90 | EVQLVESGGGLVQPGGSLRLSCAASGFTFD | D--YGKT | WVRQAPGKGLEWVS | SIYI--FVGNTYYADSVKG | RFTISRDNAGNTLYLQMINLKPEDTAKYFCVK | SPEWTYYYGMDS WGKGTLVTVSS |
| VH_77 | EVQLVESGGGLVQPGGSLRLSCAASGFTFS | S--YAMS | WVRQAPGKGLEWVS | TISS--GGASTTYADSVKG | RFTISRDNAKNTVYLQNSLKPEDTAVYYCAK | SFGLVTGVYFGS WGQGTLVTVSS |
| VH_74 | EVQLVQSGGGLVQPGGSLRLSCAASGFAFS | D--YDMS | WVRQAPGKGLEWVS | IHVS--GDGRIFYADSMKG | RFTISRDNAKNTMVLQLNSLKPEDTAVYYCAA | DSYHAATGYLEQ WGQGTLVTVSS |
| VH_67 | EVQLVESGGGLVQPGGSLRLSCAASGFRFT | D--YYMG | WIRQTPGKGLEWVS | SIYS--LGDPTYYADSVKG | RFTISRDNGKDTVYLEMNSLKSDDTGLYYCAR | DHRGWGTIRYDY WGQGTLVTVSS |
| VH_79 | EVQLVESGGGLVQPGGSLRLSCAASGFAFS | R--YWMY | WVRQAPGKGLEWVS | GMTT--GSDYIYSAVSVKG | RFTISRDNAKNTLYLQMNSLKFEDTAVYYCAK | GGVIDADHFES WGQGTQVTVSS |

-continued 14. (C) VH

| | | | | | | | |
|---|---|---|---|---|---|---|---|
| VH_75 | EVQLVGVWGRLGAPGGSLRLSCAASGFPFS | I--YFMS | WFRQRPEKGARMVS | DIDK--SGGRTTYAPSVKG | RFTASRDNAKNTLYLTINTLEPNDTAVYYCAK | PTSSMWSPGDY | WGQGTQVTVAS |
| VH_110 | EVQLVQSGGGLVQPGGSLRVSCAVSGFTFI | Y--YGMS | WVRQAPGKGLEWVS | TISN--GGSTANYADSVKG | RFTISRDNAKNTLYLEMNDLKPEDTALYYCAK | ISTELGNTLDA | WGQGTLVTVSS |
| VH_109 | EVQLVESGGGLVQPGGSLRLSCTASGFTFS | S--YGIS | WVRQAPGKGLEWVS | SVTG--DGLSTTAIDSVKG | RFTITRDNAKNTVYLQMNNLKLDDTAVYYCAK | LDVYVDYGMDY | WGKGTLVTVSS |
| VH_103 | EVQLVESGGGLVQPGGSLRLSCAASGFTFR | S--YYMN | WVRQAPGKGLEWVS | VSSS--GGGTTYYADSVKG | RFTISRDNAQNTLYLQMNSLKPEDTALYYCAR | ESGGPGMDLEV | WGQGTLVTVSS |
| VH_84 | EVQLVESGGGLVQPGGSLRLSCAASGFTFS | S--YAMS | WVRQAPGKGLEWVS | GINS--GGGSTSYADSVKG | RFTISRDNAKNTLYLQMNSLKPEDTAVYYCAK | WEVVTLDFGS | WGQGTLVTVSS |
| VH_113 | EVQLVESGGGLVQPGRSLRLSCAAAGFTFS | T--YWMY | WIRQAPGKGLEWVA | TITS--LGGSQWYVDSVKG | RFTISRDNAKNTLYLQMNSLKPEDMAQYYCVR | GGLYGDYEH | WGQGTQVTVSS |
| VH_87 | EVQLVESGGGLVKPGGSLRLSCAASGFTFS | S--AYMN | WVRQAPGKGLEWVS | GLTN--YGSTSYYADSVKG | RFTISRDNTVNTVYLQLNSLKPEDTGLYYCAR | VGNMWSSDY | WGQGTQVTVSS |
| VH_105 | EVQLVESGGGLVQPGGSLRLSCAASGFTFS | N--YWMY | WVRQAPGKGLEWVS | SIDT--SGGITMYADSVKG | RFTISRDNAKNTLYLQMNSLKSEDTALYYCAK | ALGYNAPDA | WGRGTLVTVSS |
| VH_101 | EVQLVESGGGLVQPGVSLRLSCTTSGFTFS | T--QGMN | WVRQPPEKGLEWVS | GIDS--RGNTNYADSVKG | RFTISRDNAKNALYLQMNDLRPDDTAMYYCTN | TGPWYTYNY | WGQGTQVTVSS |
| VH_108 | EVQLVESGGGLVQPGGSLRLSCAASGFTFS | S--YWMY | WVRQAPGKGLDWIS | GISV--GGASTYYARSVQD | RFTISRDNTKNTLYLQMSSLRSEDTAVYWCTR | GGNTPYDY | WGQGTQVTVSS |
| VH_106 | EVQLVESGGGLVQPGGSLRLSCAASGENFD | D--YPMT | WIRQAPGKGLEWVA | SIYS--GISTTYYPDSVKG | RFTISTNDAKNTVYLQMNDLKSDDTAVYYCAN | PRRNY | WGQGTQVTVSS |
| VH3(3-13) | EVQLVESGGGLVQPGGSLRLSCAASGFTFS | S--YDMH | WVRQATGKGLEWVS | AIG---TAGDTYYPGSVKG | RFTISRENAKNSLYLQMNSLRAGDTAVYYCAR | | |
| VH_115 | EVQLVESGGGLVQPGGSLRLSCAASGFTFS | T--YAMS | WVRQGPGKALEWVS | TIN---GADFTSYVDSVKG | RFTISRDNTKNTLYLQMNSLKPEDTAVYYCAK | GLSGLNWYGFGDY | WGQGTQVTVSS |
| VH_85 | EVQLVESGGGLVQPGGSLRLSCAASGFTFS | T--YWMY | WVRQAPGKGLEYVG | SID---NDGFTYYSEDVKG | RFTISGDNARNTLYLQINSVKPEDTALYYCVR | GVYYMDYEPRMDY | WGKGTLVTVSS |
| VH_114 | EVQLVESGGGLVQPGGSLRLSCTASGFTFS | T--HTMS | WVRQAPGKGLEWVS | GIN---SAYGTIYIDSVKG | RFTISRDNAKNTLYLQMNSLKPDDTAVYYCVQ | VVDTWDEYDY | WGQGTQVTVSS |
| VH_78 | EVQLVESGGGLVQPGGSLRLSCAASRFTFG | T--SGMT | WVRQAPGKGLEWVS | TIN---SGGLTTSADSVKG | RFTISRDNGKNTLYLQMDSLKPDDTAVYYCAN | LLELGH | WGRGTQVTVSS |
| 3B5 | EVQLVQSGGGLVQPGGSLRLSCAASGFTFS | S--YWMY | WVRQAPGKGLEWVS | TIT---KGGSTYYSDSVKG | RFTISRDNAKNTLYLQMNSLKSEDTAVYYCAK | SNSGTHWYEYYGMDY | WGKGTLVTVSS |
| 3A3 | EVQLVESGGGLVQPGDSLRLSCAASGFTFG | N--YDMS | WVRQAPGKGPEWVS | GIN---SGGKTYSADSVKG | RFTISRDNAKNTLYLQMNNLKPEDTAVYYCIL | GIVTLGS | WGQGTQVTVSS |

Example 15

Generating Fabs Against IL-1 Beta

Unless otherwise indicated, the materials and protocols used in the following study were analogous to those used in examples 1-9.

Llamas were Successfully Immunized with IL-1 Beta

Two llamas (*Lama glama*) were immunized with human IL-1 Beta according to a standard protocol (as described in Example 1).

Sera from both llamas were tested for the presence of antibodies against IL-1 Beta by ELISA prior (day 0) and after immunization (day 28). As shown in FIG. 1, a specific signal against IL-1 Beta was observed in ELISA after immunization, even after 10,000 fold dilution of the serum. This high antibody titer indicates a specific and appropriate immune response.

Fab Libraries with Good Diversity were Constructed

PBLs isolated from both immunized llamas were used for RNA extraction, RT-PCR and PCR-cloning of Fab in a phagemid using the strategy described by de Haard et al (JBC 1999), to obtain a diverse library of good diversity ($2-5 \times 10^8$).

The following primers were used:

| Name | Sequence |
|---|---|
| Primers for cloning of lambda light chain | |
| HuVl1A-BACK-ApaLl | GCC TCC ACC AGT GCA CAGTCTGTGYTGACKCAGCC |
| HuVl1B-BACK-ApaLl | GCC TCC ACC AGT GCA CAGTCTGTGYTGACGCAGCC |
| HuVl1C-BACK-ApaLl | GCC TCC ACC AGT GCA CAGTCTGTCGTGACGCAGCC |
| HuVl2-BACK-ApaLl | GCC TCC ACC AGT GCA CAGTCTGCCCTGACTCAGCC |
| HuVl3A-BACK-ApaLl | GCC TCC ACC AGT GCA CTT TCCTATGAGCTGACWCAGCC |
| HuVl3B-BACK-ApaLl | GCC TCC ACC AGT GCA CTT TCTTCTGAGCTGACTCAGGA |
| HuVl4-BACK-ApaLl | GCC TCC ACC AGT GCA CAGCYTGTGCTGACTCAATC |
| HuVl5-BACK-ApaLl | GCC TCC ACC AGT GCA CAGGCTGTGCTGACTCAGCC |
| HuVl6-BACK-ApaLl | GCC TCC ACC AGT GCA CTT AATTTTATGCTGACTCAGCC |
| HuVl7/8-BACK-ApaLl | GCC TCC ACC AGT GCA CAGRCTGTGGTGACYCAGGA |
| HuVl9-BACK-ApaLl | GCC TCC ACC AGT GCA CWGCCTGTGCTGACTCAGCC |
| HuVl10-BACK-ApaLl | GCC TCC ACC AGT GCA CAGGCAGGGCTGACTCAGCC |
| caClambda1-FOR | CTAACACTGGGAGGGGGACACCGTCTTCTC |
| caClambda2-FOR | CTAACACTGGGAGGGNCTCACNGTCTTCTC |
| Primers for cloning of kappa light chain | |
| HuVk1B-BACK-ApaLl | GCC TCC ACC AGT GCA CTT GACATCCAGWTGACCCAGTCTCC |
| HuVk2-BACK-ApaLl | GCC TCC ACC AGT GCA CTT GATGTTGTGATGACTCAGTCTCC |
| HuVk3B-BACK-ApaLl | GCC TCC ACC AGT GCA CTT GAAATTGTGWTGACRCAGTCTCC |
| HuVk2/4-BACK-ApaLl | GCC TCC ACC AGT GCA CTT GAYATYGTGATGACCCAGWCTCC |
| HuVk5-BACK-ApaLl | GCC TCC ACC AGT GCA CTT GAAACGACACTCACGCAGTCTCC |
| HuVk6-BACK-ApaLl | GCC TCC ACC AGT GCA CTT GAAATTGTGCTGACTCAGTCTCC |
| HuVk4B-BACK-ApaLl | GCC TCC ACC AGT GCA CTT GATATTGTGATGACCCAGACTCC |
| caCHkapFOR-AscI | GCC TCC ACC GGG CGC GCC TTA TTAGCAGTGTCTCCGGTCGAAGCTCCT |
| caCHkap2FOR-AscI | GCC TCC ACC GGG CGC GCC TTA TTARCARTGYCTNCGRTCRAA |
| Non-tagged primers for cloning of Heavy chain (step 1) | |
| VH1 a-BACK | CAGGTKCAGCTGGTGCAGTCTGG |
| VH5a-BACK | GARGTGCAGCTGGTGCAGTCTGG |
| VH4a-BACK | CAGSTGCAGCTGCAGGAGTCTGG |
| VH4b-BACK | CAGGTGCAGCTACAGCAGTCTGG |
| VH2b-BACK | CAGGTCACCTTGARGGAGTCTGG |
| Tagged primers for cloning of Heavy chain (step 2) | |
| VH1 a-BACK-SfiI | CTC GCA ACT GCG GCC CAG CCG GCC ATG GCCCAGGTKCAGCTGGTGCAGTCTGG |
| VH5a-BACK-SfiI | CTC GCA ACT GCG GCC CAG CCG GCC ATG GCCGARGTGCAGCTGGTGCAGTCTGG |
| VH4a-BACK-SfiI | CTC GCA ACT GCG GCC CAG CCG GCC ATG GCCCAGSTGCAGCTGCAGGAGTCTGG |
| VH4b-BACK-SfiI | CTC GCA ACT GCG GCC CAG CCG GCC ATG GCCCAGGTGCAGCTACAGCAGTCTGG |
| VH2b-BACK-SfiI | CTC GCA ACT GCG GCC CAG CCG GCC ATG GCCCAGGTCACCTTGARGGAGTCTGG |

Independent VλCλ and VκCκ libraries were constructed using a single (tagged)-PCR step (30 cycles) to conserve a greater clonal diversity.

The VHCH1 libraries were built in parallel using a two step PCR (25 cycles with non tagged primers (step 1) followed by 10 cycles of tagged primers (step 2)).

Next, the light chain from the VλCλ and VκCκ libraries are re-cloned separately in the VHCH1-expressing vector to create the "Lambda" and "Kappa" llama Fab-library respectively (two for each immunized llama). Quality control of the libraries was routinely performed using PCR.

Up to 93% of the clones tested randomly contained full length Fab sequences, indicating a high quality of the libraries.

Human IL-1 Beta Specific Fabs were Selected

Phage display was used to identify a large diversity of llama Fabs binding to biotinylated IL-1 Beta. Biotinylated IL-1 Beta was used for capturing to conserve the active conformation of the protein. After two rounds of selection, a good enrichment compared to control was observed. Phage ELISA revealed presence of clones expressing cytokine specific Fabs (data not shown).

The phage binding to biotinylated IL-1 Beta were eluted by pH shock. Sequential dilutions of the output ($10^{-1}$ to $10^{-5}$) were used to infect fresh E. coli TG1 cells. The number of colonies obtained indicate the number of phage bound during the selection. In the example above, 5 µl of output gave around $10^5$ phage when selection was done with 100 nM and 10 nM of biot-IL-1 Beta. Compared to the $10^2$ phages obtained by non-specific binding, this gives a 1000 fold enrichment.

94 Single clones were grown and used to produce monoclonal phage. These phage were used in a phage ELISA. Many phage showed good binding to biot-IL-1 Beta after two rounds of selection on biotinylated IL-1 Beta.

Human IL-1 Beta Specific Fabs have High Starting Homology to Human Germline

Target specific VH and Vλ domains were matched with those common human germlines showing an identical CDR1 and CDR2 length and corresponding canonical folds. Subsequently the closest human germline was selected based on sequence homology in their framework regions. Non-matching amino acid residues were checked for their presence in other, related human germlines. In case there was no match, these residues were counted as foreign.

TABLE 7

Overall sequence homology of llama VH to human germline

| Closest Human Germline | Matching Clones | % Sequence Homology |
|---|---|---|
| IGHV1-2 | 1C2/2B7/2C12 | 93 |
| | 2D8 | 94 |
| | 1G5/2D7 | 93 |
| | 2E12/2G7 | 94 |
| IGHV3-23 | 1F2 | 98 |
| | 1G4 | 92 |
| | 5G7 | 95 |
| | 5B12 | 92 |
| | 1A1/2B8/2B9 | 98 |
| | 1C3/1E3/2A7 | 98 |
| IGHV3-13 | 1E2 | 94 |
| | 3A3/3B6/3E2/3E3 | 95 |
| | 3B5/4F1 | 98 |
| IGHV3-20 | 4H1 | 94 |
| | 4H4 | 93 |

TABLE 8

Overall sequence homology of llama VL to human germline

| Closest Human Germline | Matching Clones | % Sequence Homology |
|---|---|---|
| IGLV8-61 | 1E2 | 90 |
| | 1F2 | 90 |
| | 3E2/3E3/3A3 | 86 |
| | 3B5/4F1 | 86 |
| IGLV2-18 | 3B6 | 91 |
| IGLV5-52 | 1G4 VL | 96 |
| IGLV3-19 | 1C2/2B7/2D7 | 95 |
| | 2E12/2G7 | 96 |
| | 2D8 | 95 |

Discussion and Conclusions:

A total of 14 target specific VH families, 9 target specific Vλ families and 3 Vκ families were identified based on this very first selection This initial panel of 14 anti-IL-1 Beta WT VH's and 12 anti-IL-1 Beta WT VL's shows a remarkably high sequence homology to the human germline.

33% of those VH domains have a starting homology of 95% or more to the human situation and about 44% of the VL domains have a starting homology of 95% or more to the human situation, eliminating the need for further humanization.

VH domain 2D8 is a humanized version of VH 1C2 because it has one deviating amino acid residue less as compared to the closest human germline. Its corresponding VL domain (VL 2D8), had a starting homology of 95% which was further increased to 96% by 1 back mutation (VL 2G7) to the closest human germline.

All VH and VL domains, without a single exception, exhibited human 3-D binding site structures (i.e. identical combinations of canonical folds for CDR1 and CDR2 as occurring in the matching human germline segments) when assessed using the methodology described above (data not shown).

Humanization of Fabs 1E2 and 1F2

Figure 2:
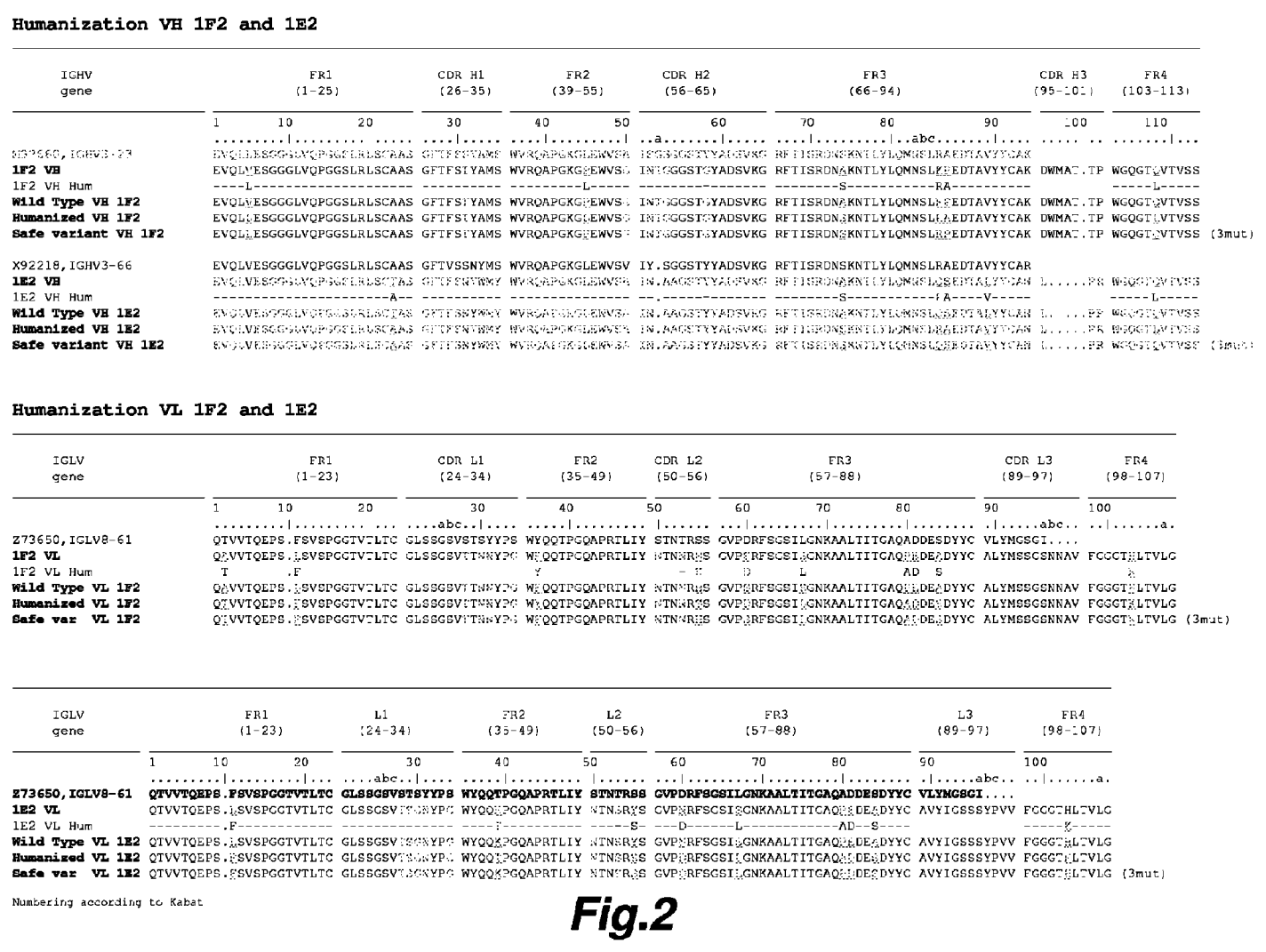

Humanization was performed on two IL-1 Beta specific Fabs coded 1E2 and 1F2. Based on the alignment against the closest human germlines, mutations in their VH and VΛ framework regions were proposed (FIG. 2). The germlining of VH matching to the human VH3 family will often involve a number of residues, which already deviate in publically known Lama glama, Lama pacos or Camelus dromedarius derived germline sequences. For instance, Alanine on position 71 (numbering according to Kabat) and Lysine on 83 and Proline on 84 might be changed into Serine (although Alanine exists in certain human germline VH3 members), Arginine (although Lysine is used by a number of human VH3 germlines) and Alanine, respectively. For light chain variable sequences no germline sequences are available for Camelids, but it is very likely that a number of deviations in FRs from human germline exists that will be changed in the majority of lead antibodies. Besides the fully humanized (hum) and the wild type (wt) V regions, also a "safe variant" with only three wild type residues remaining was proposed (safe).

Fab 1E2 was formatted in a step-by-step approach, whereby the different versions (wt, safe and fully humanized) of the Vλ fused to the human constant domain were combined with various versions of the VH fused to the human constant CH1 domain to generate the Fabs indicated in Table 9.

TABLE 9

Fab 1E2 formats

|  |  | VH 1E2 + hum CH1 | | |
|---|---|---|---|---|
|  |  | wt | safe | hum |
| VL1E2 + humCL | wt | wt 1E2 | wt/safe | wt/hum |
|  | safe | safe/wt | safe 1E2 | safe/hum |
|  | hum | hum/wt | hum/safe | hum 1E2 |

Figure 3:
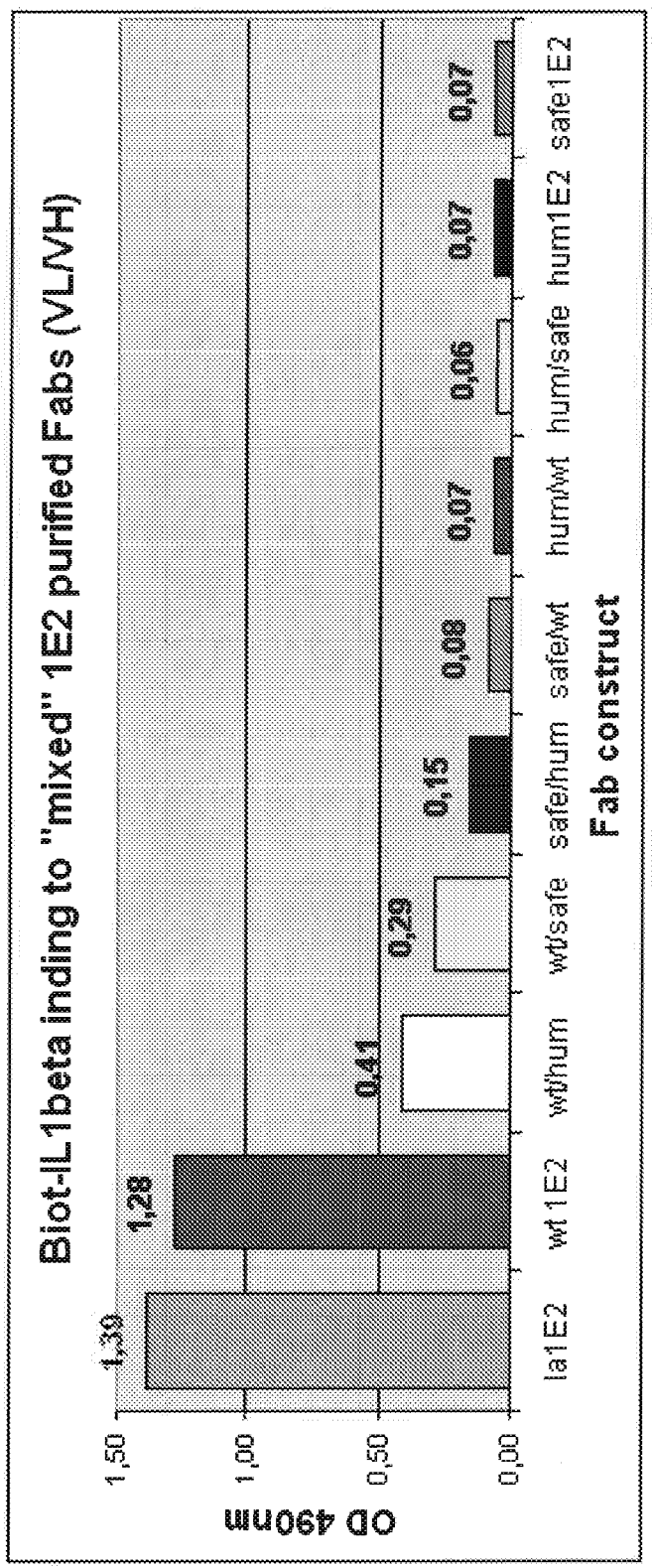
FIG. 3—shows the results of an ELISA in which recombinantly expressed Fabs were tested for their ability to bind biot-IL-1 Beta. For this the Fabs were captured on an anti-myc coated Maxisorp plate. Biotinylated human IL-1 Beta was added and bound cytokine was detected using HRP-conjugated streptavidin.

The genes of these Fabs were ordered as synthetic genes with GeneArt (Germany) and were subsequently produced in *E. coli*, purified and tested for their ability to bind biot-IL-1 Beta. For this the Fabs were captured on an anti-myc coated Maxisorp plate. Biotinylated human IL-1 Beta was added and bound cytokine was detected using HRP-conjugated streptavidin. The read out of this assay is represented in FIG. 3 below.

The replacement of the wild type constant domains CH1 and CA by their human counterpart did not affect the binding capacity.

Partial (wt VA/safe VH) and complete (wt VA/hum VH) humanization of the VH domain of 1E2 generated a functional Fab.

Figure 4:
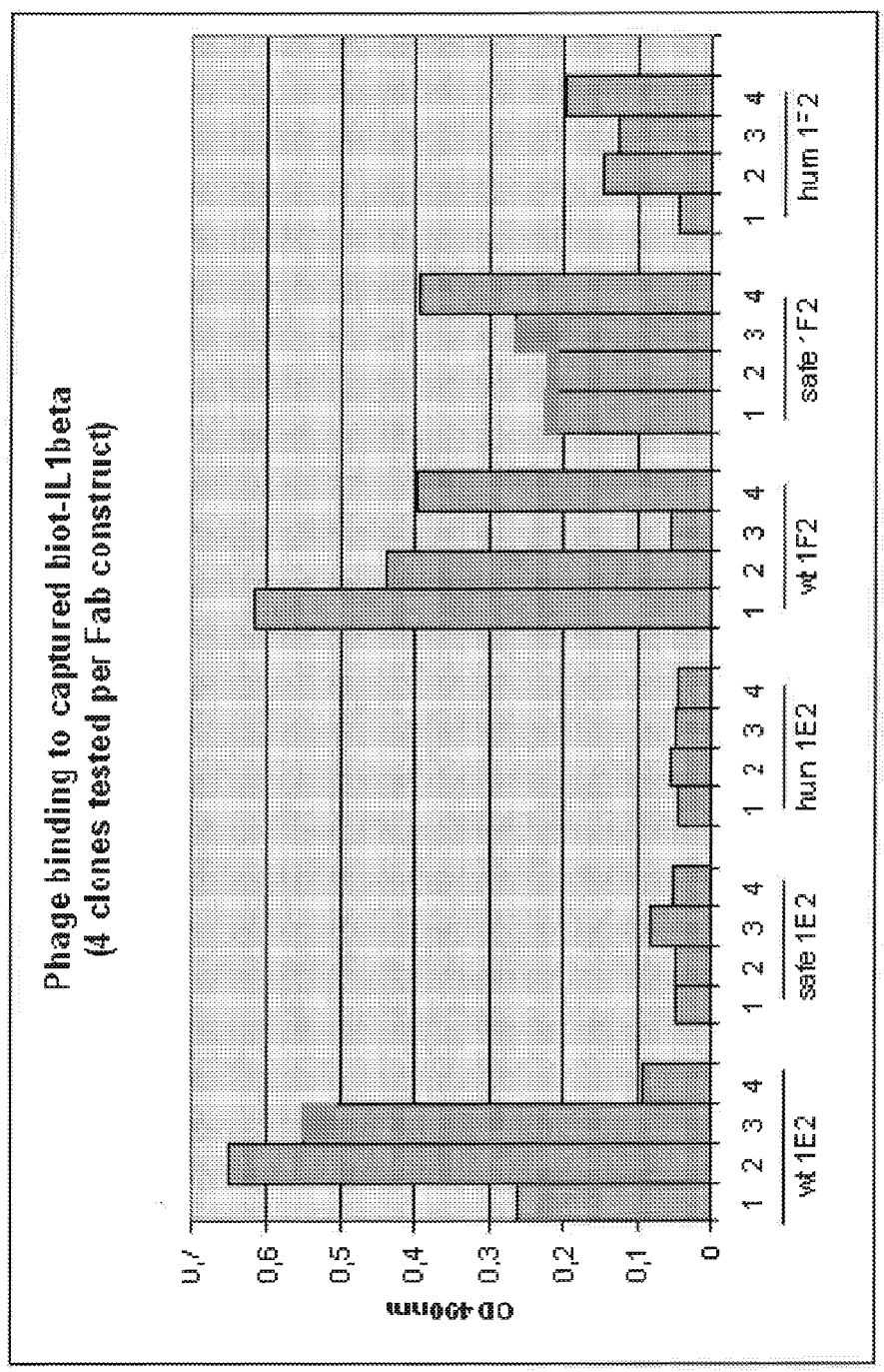

The humanized variants of clone 1F2 were tested with phage expressing gene3-Fabs fusions (FIG. 4). Phage were produced from 4 independent clones for each construct:
wt 1F2 and wt 1E2 (llama Vλ and VH fused to human CA and CH1)
safe variant 1F2 and safe variant 1E2 (partially humanized Vλ fused to human CA and CH1)
hum 1F2 and hum 1E2 (fully humanized Vλ and VH fused to human CA and CH1)

Four clones for each Fab were tested to overcome clonal variation (due to bacterial growth, phage production efficiency and toxicity etc. . . . ). Phage ELISA was performed by capturing of biotinylated IL-1 Beta on neutravidin coated Maxisorp plate and subsequent incubation of crude phage extract (i.e. bacterial medium). After extensive washing, bound phages were detected with an anti-M13-HRP monoclonal antibody. The same phage preparations when tested on neutravidin coated wells (without biotinylated IL-1 Beta) did not give signals (data not shown).

Back mutations in the framework regions of 1F2 VL and VH domains to the closest human germline successfully yield partially (safe) and fully (hum) humanized variants, maintaining antigen specificity.

Successful Formatting of Camelid Variable Domains with Human Constant Domains

The VL and VH variable domains of the IL-1 Beta specific clone 1E2 were successfully fused to the human Cλ and CH1 constant domains, resulting in a "chimeric" Fab which was produced and purified.

This chimeric 1E2 Fab was produced by performing the induction for 4 h at 37° C. (o/d) or for 16 h and 28° C. (o/n) from the pCB5 phagemid (Δgene3). The wild type llama 1E2 Fab was produced by performing induction for 16 h at 30° C. from pCB3 (gene3 containing phagemid). After purification, these Fabs were loaded on SDS-PAGE with (reducing) or without (non-reducing) DTT. Coomassie staining was performed, nicely showing the presence of these Fabs or their composing light and heavy chains at the expected molecular weight band (not shown).

Figure 5:
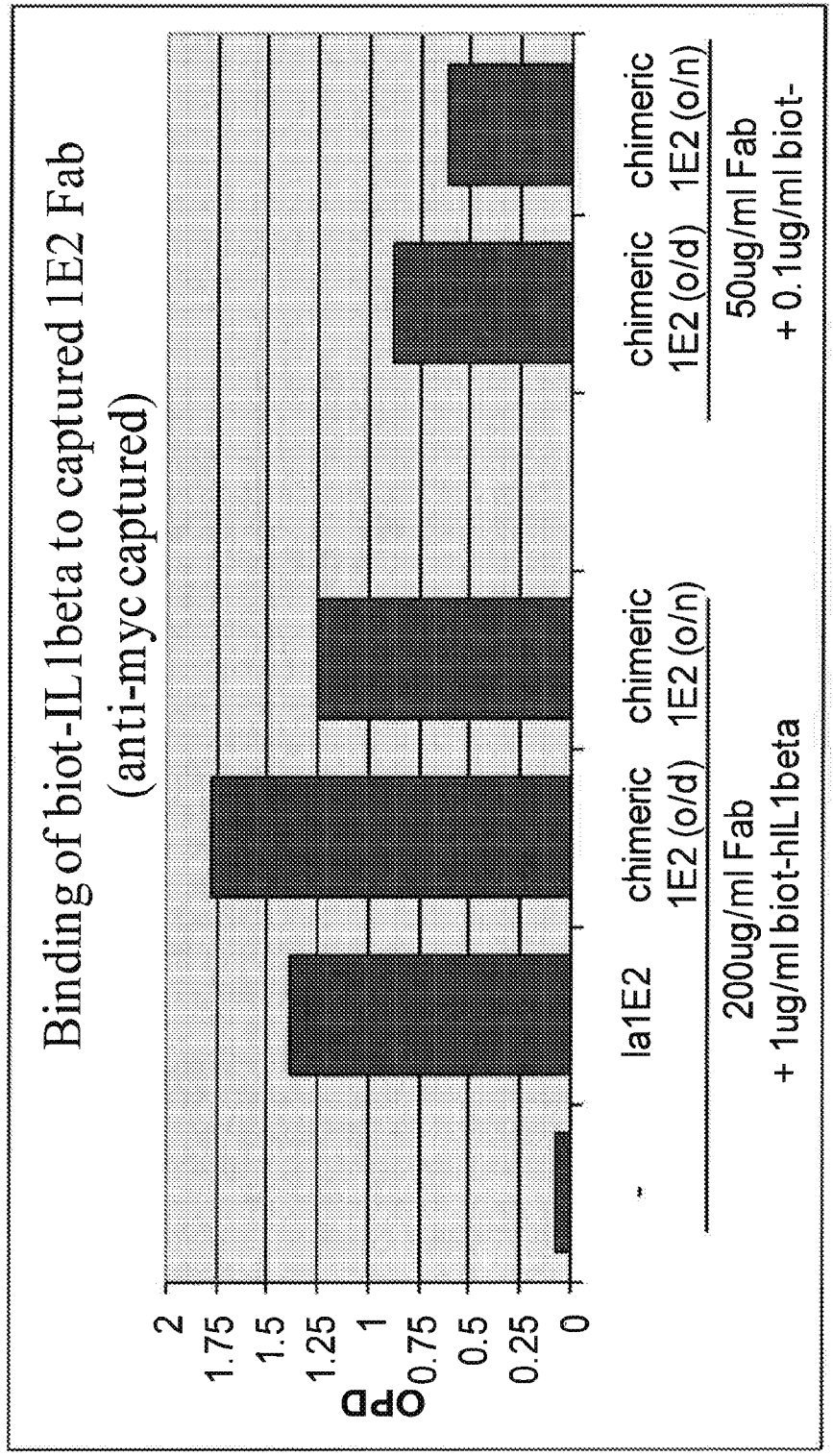

The purified llama and chimeric 1E2 Fabs described above were captured on anti-myc coated maxisorp plates. After incubation with biotinylated human IL-1 Beta and extensive washing, the biotinylated IL-1 Beta bound to the Fab was detected using HRP-conjugated streptavidin. Both the purified llama and chimeric 1E2 Fabs exhibited functional target binding (FIG. 5). This finding demonstrates the feasibility to associate Camelid derived variable domains with the constant domains of human IgGs A Subset of Fabs Showed Functional Inhibition of the Target The table below shows the OD values resulting from the following ELISA experiment. Wells were coated with a mouse monoclonal antibody known to inhibit the binding of IL1-Beta with its receptor (provided by Diaclone SAS).

Biotinylated IL-1 Beta was added to the wells together with periplasmic extracts of Fabs identified after 2 rounds of selection against biotinylated IL-1 Beta. Detection of the bound biotinylated IL-1 Beta happened through HRP labeled streptavidin. A reduced signal indicated the competition of a specific Fab with the blocking mouse monoclonal antibody, suggesting antagonism.

A positive control was included in well G12 by spiking in a large amount of the competing mouse monoclonal (well 12G in Table 10).

TABLE 10

Results of competition assay

| | 6A | | | | | | 6C | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 0.205 | 0.621 | 0.670 | 0.691 | 0.704 | 0.823 | 0.353 | 0.737 | 0.726 | 0.544 | 0.551 | 0.626 |
| B | 0.668 | 0.546 | 0.444 | 0.632 | 0.614 | 0.627 | 0.442 | 0.641 | 0.558 | 0.693 | 0.565 | 0.548 |
| C | 0.756 | 0.541 | 0.386 | 0.572 | 0.763 | 0.593 | 0.517 | 0.537 | 0.518 | 0.588 | 0.473 | 0.435 |
| D | 0.521 | 0.790 | 0.203 | 0.792 | 0.801 | 0.263 | 0.619 | 0.483 | 0.631 | 0.592 | 0.455 | 0.603 |
| E | 0.798 | 0.545 | 0.359 | 0.528 | 0.281 | 0.655 | 0.618 | 0.519 | 0.651 | 0.493 | 0.575 | 0.367 |
| F | 0.747 | 0.611 | 0.520 | 0.599 | 0.203 | 0.204 | 0.605 | 0.373 | 0.550 | 0.516 | 0.602 | 0.392 |
| G | 0.498 | 0.477 | 0.539 | 0.693 | 0.663 | 0.197 | 0.554 | 0.589 | 0.807 | 0.528 | 0.634 | 0.063 |
| H | 0.628 | 0.493 | 0.552 | 0.900 | 0.858 | 0.635 | 0.170 | 0.574 | 0.559 | 0.598 | 0.593 | 0.378 |

A number of Fabs were identified which successfully compete with the blocking mouse monoclonal antibody (indicated by shaded cells in Table 10). Sequence analysis of the competing clones revealed the presence of three Fabs with different VH, which were present in 48 screened clones (part of the plate coded 6A in Table 10). The sequence alignments against the closest human germline and the structural homology analysis of the VH of the antagonistic Fab 1A1 (giving a signal of 0.205 in the competition assay of Table 10), 1B3 (signal of 0.444) and the related clone 1G1 (signal of 0.498) and finally 1C3 (signal of 0.386) are shown below.

All three have a very high degree of sequence homology with the matching human germline and have the identical canonical fold combinations as found in the human germline. This was also observed for the lambda light chain in the three antagonistic leads (data not shown). Fab 1A1 competes strongly with the antagonistic reference monoclonal antibody (IC50 of 12 µg/ml in ELISA based competition assay), whereas Fab 1C3 hardly shows competition (only at concentrations of more than 50 µg/ml). However, in the bioassay 1C3 is more potent (IC50 of 3 µg/ml) than 1A1 (IC50 of 10 µg/ml), which suggests a different epitope recognition. The high frequency of different antagonistic Fabs (3 different antibodies in 48 screened clones) and the difference in epitope recognition as found for two of these illustrates the high diversity of antibodies as the result of the outbred nature of the *lama*. The high degree of sequence homology with human germline V regions combined with the high diversity of (potent) antibodies and the broad epitope coverage enables the identification of panels of therapeutic antibodies from immunized camelids.

```
IGHV gene                    FR1-Kabat                        CDR1         FR2-Kabat          CDR2
Kabat FR/CDR                                                  Kabat                           Kabat IMGT numbering    1         10        20        30            40           50        60       70
             .........|.........|.........|       .........|    .........|....  .....|.........|....
M99660, IGHV3-23  EVQLLESGG.GLVQPGGSLRLSCAASGFTF  SSYA....MS   WVRQAPGKGLEWVS   AISGSGGST..YYADSVK.G VH-1A1, 3B8, 3D9  EVQLVESGG.GLVQPGGSLRLSCAASGFTF  DDYA....MS   WVRQAPGKGLEWVS   TISWNGGAT..YYAESMK.G IGHV gene                FR3-Kabat                            CDR3         FR4(IGHJ)
Kabat FR/CDR                                                  Kabat IMGT numbering     80        90       100                    110          120       130
             ....|.........|.........|......       ...|.........|.  .........|..
M99660, IGHV3-23  RFTISRDNSKNTLYLQMNSLRAEDTAVYYCAK

VH-1A1, 3E8, 3D9  RFTISRDNAKNTLYLQMNSLKSEDTAVYYCAK PYYSDYVGVEYDY..  WGQGTQVTVSS

5 V         primer encoded and also in all other class 3 except 3-23

83 A         occurs in all VH3 family members except 3-23

95 K         also in IGHV3.13/49/66/72 and classes 5 and 7

96 S         not in class 3 but in class 1

127 Q         not in human germline

Overall homology
84/86 framework residues = 98% homology
Canonical folds analysis
CDR H1 Class 1/10A [2fbj]
CDR2 Class ?
! Similar to class 3/10B, but:

!    H66 (Chothia Numbering) = A (allows: SYTNDR)
```

```
IGHV gene                    FR1-Kabat                        CDR1         FR2-Kabat          CDR2
Kabat FR/CDR                                                  Kabat                           Kabat IMGT numbering    1         10        20        30            40           50        60       70
             .........|.........|.........|       .........|    .........|....  .....|.........|....
M99660, IGHV3-23  EVQLLESGG.GLVQPGGSLRLSCAASGFTF  SSYA....MS   WVRQAPGKGLEWVS   AISGSGGST..YYADSVK.G VH-1C3, 1E3, 2A7  EVQLVESGG.GLVQPGGSLRLSCAASGFTF  SSYW....MY   WVRQAPGKGLEWVS   AINTGGGRT..YYADSVK.G IGHV gene                FR3-Kabat                            CDR3         FR4(IGHJ)
Kabat FR/CDR                                                  Kabat IMGT numbering     80        90       100                    110          120       130
             ....|.........|.........|......       ...|.........|.  .........|..
M99660, IGHV3-23  RFTISRDNSKNTLYLQMNSLRAEDTAVYYCAK VH-1C3, 1E3, 2A7  RFTISRDNAKNTLYLQMNSLKSEDTAVYYCAK GTSADGSSWYVPADPYDY WGQGTQVTVSS 5 V         primer encoded and also in all other class 3 except 3-23

83 A         occurs in all VH3 family members except 3-23

95 K         also in IGHV3.13/49/66/72 and classes 5 and 7

96 S         not in class 3 but in class 1

127 Q         not in human germline
```

```
Overall homology
84/86 framework residues = 98% homology
Canonical folds analysis
CDR H1 Class 1/10A [2fbj]
CDR2 Class ?
! Similar to class 2/10A, but:

!    H71 (Chothia Numbering) = R (allows: VAL)
```

| IGHV gene<br>Kabat FR/CDR | FR1-Kabat | CDR1<br>Kabat | FR2-Kabat | CDR2<br>Kabat |
|---|---|---|---|---|
| IMGT numbering | 1        10        20        30 | 40 | 50        60 | 70 |
| X07448, IGHV1-2 | QVQLVQSGA.EVKKPGASVKVSCKASGYTF | TGYYMH.... | WVRQAPGQGLEWMG | RINPNSGGT..NYAQKFQ.G |
| VM-1B3, 1G2, 2D8 | EVQLVQSGA.ELRNPGASVKVSCKASGYTF | TSYYID.... | WVRQAPGQGLEWMG | RIDPEDGGT..KYAQKFQ.G |
| VM-1G1, 2B7 | EVQLVQSGA.ELRNPGASVKVSCKASGYTF | TSYYTD.... | WVRQAPGQGLEWMG | RIDPEDGDT..KYAQKFQ.G |

| IGHV gene<br>Kabat FR/CDR | FR3-Kabat | CDR3<br>Kabat | FR4(IGHJ) |
|---|---|---|---|
| IMGT numbering | 80        90        100 | 110        120        130 | |
| X07448, IGHV1-2 | RVTSTRDTSISTAYMELSRLRSDDTVVYYCAR | | |
| VM-1B3, 1G2, 2D8 | RVTFTADTSTSTAYVELSSLRSEDTAVYYCAR | SGRYELDY....... | WGQGTQVTVSS |
| VM-1G1, 2B7 | RVTFTADTSTSTAYVELTSLRSEDTAVYYCLR | SGAYELDY....... | WGQGTQVTVSS |

```
  1 E        primer encoded, occurs as well in IGHV1-f

11 L        occurs in class 2, 3, 4, 6 and 7

12 R        not in human germline

13 N        not in human germline

78 F        occurs in class 7

85 G        occurs in class 7

80 A        present in two class 1 members

84 T        occurs in half of class 1 members

89 V        not in human germline

93 S        present in majority of class 1 members

97 E        present in majority of class 1 members

127 Q        not in human germline

Overall homology
79/86 framework residues = 92% homology
Canonical folds analysis
CDR H1 Class ?
! Similar to class 1/10A, but:
!    H35 (Chothia Numbering) = D (allows: HENQSYT)

!    H80 (Chothia Numbering) = V (allows: LM)

CDR H2 Class ?
! Similar to class 2/10A, but:

!    H53 (Chothia Numbering) = E (allows: AGYSKTN)
```

Example 16

The following example demonstrates the functional diversity which can be achieved with the current invention, in comparison with the established mouse monoclonal antibody approach.

10 BALB/c mice were immunized with a recombinant produced cytokine with a small molecular weight. After completion of the immunization protocol, the animals were sacrificed, and hybridomas were generated by immortalizing their spleen cells. Supernatant of the resulting hybridomas was tested in the cytokine binding ELISA and subsequently in a suitable bioassay. One highly potent antagonist and one weaker antagonist could be identified.

Also, 4 llamas were immunized with the same recombinant produced cytokine, using the general protocol described herein. After completion of the immunization protocol, peripheral B lymphocytes were harvested and their RNA was extracted and purified. Using a set of llama specific primers, Fab libraries were generated using the phage display technique. Those Fabs were tested in the cytokine/cytokine receptor binding ELISA. 5 different VH families could be identified from the first 2 llamas, and 6 additional different VH families from the next 2 llamas, which blocked the cytokine/receptor interaction with high potency, meaning that those VH domains contained uniquely different CDRs, both in length and amino acid sequence.

Thus a higher functional diversity could be achieved from a small number of outbred llamas as opposed to a higher number of inbred BALB/c mice. All VH families obtained by active immunisation of llamas exhibited an extraordinary sequence homology as compared to the closest human germline and had the same canonical fold combinations for CDR1 and CDR2 as the matching human germlines.

Example 17

The following table summarises the results of amino acid sequence homology comparisons between germline VH domains of alpaca (*Lama pacos*) and the closest matching human germline VH domains. % homology was calculated using the same algorithm as described herein for *Lama glama*. Raw VH sequence data for *Lama pacos* is not shown:

TABLE 11 amino acid sequence homology germline VH of *Lama pacos* vs human

| Alpaca (*Lama pacos*) germline VH family | Frequency | % amino acid sequence homology with closest matching human germline VH |
|---|---|---|
| VH3 | 70% (36/51) | ≥95% |
| VH1 | 10% (5/51) | 90-92% |
| VH2 (NB Lama pacos VH2 aligns to human VH4) | 20% (10/51) | 81-88% |

The following table is provided to cross-reference nucleotide and amino acid sequences listed herein with the sequence listing submitted in ST.25 format for searching purposes.

TABLE 12 cross-reference to sequence identifiers

| SEQ ID No. | Sequence name |
|---|---|
| 1 | M99679, IGHV3-53 |
| 2 | AF000603, IGHV1S1 |
| 3 | AJ245151, IGHV1S2 |
| 4 | AJ245152, IGHV1S3 |
| 5 | AJ245153, IGHV1S4 |
| 6 | AJ245154, IGHV1S5 |
| 7 | AJ245155, IGHV1S6 |
| 8 | AJ245157, IGHV1S7 |
| 9 | AJ245158, IGHV1S8 |
| 10 | AJ245159, IGHV1S9 |
| 11 | AJ245160, IGHV1S10 |
| 12 | AJ245164, IGHV1S11 |

TABLE 12-continued cross-reference to sequence identifiers

| SEQ ID No. | Sequence name |
|---|---|
| 13 | AJ245165, IGHV1S12 |
| 14 | AJ245167, IGHV1S13 |
| 15 | AJ245168, IGHV1S14 |
| 16 | AJ245170, IGHV1S15 |
| 17 | AJ245171, IGHV1S16 |
| 18 | AJ245173, IGHV1S17 |
| 19 | AJ245174, IGHV1S18 |
| 20 | AJ245156, IGHV1S19 |
| 21 | M99660, IGHV3-23 |
| 22 | AJ245177, IGHV1S20 |
| 23 | AJ245178, IGHV1S21 |
| 24 | AJ245183, IGHV1S22 |
| 25 | AJ245185, IGHV1S23 |
| 26 | AJ245186, IGHV1S24 |
| 27 | AJ245187, IGHV1S25 |
| 28 | AJ245189, IGHV1S26 |
| 29 | AJ245191, IGHV1S27 |
| 30 | AJ245192, IGHV1S28 |
| 31 | AJ245193, IGHV1S29 |
| 32 | AJ245194, IGHV1S30 |
| 33 | AJ245195, IGHV1S31 |
| 34 | AJ245179, IGHV1S32 |
| 35 | AJ245180, IGHV1S33 |
| 36 | AJ245182, IGHV1S34 |
| 37 | AJ245190, IGHV1S35 |
| 38 | AJ245196, IGHV1S36 |
| 39 | AJ245197, IGHV1S37 |
| 40 | AJ245181, IGHV1S38 |
| 41 | AJ245198, IGHV1S39 |
| 42 | AJ245199, IGHV1S4OP |
| 43 | AF305949, IGHV1S6 |
| 44 | M94116, IGLV1-40 |
| 45 | Camv144 |
| 46 | Z73642, IGLV2-18 |
| 47 | Camv117 |
| 48 | Camv133 |
| 49 | Camv136 |
| 50 | Camv159 |
| 51 | Camv130 |
| 52 | Camv132 |
| 53 | Camv157 |
| 54 | Camv15 |
| 55 | Camv165 |
| 56 | Camv151 |
| 57 | Camv131 |
| 58 | Camv160 |
| 59 | Camv152 |
| 60 | X57826, IGLV3-1 |
| 61 | Camv119 |
| 62 | Camv120 |
| 63 | Camv18 |
| 64 | Camv118 |
| 65 | Camv123 |
| 66 | Z73658, IGLV3-12 |
| 67 | Camv111 |
| 68 | X59314, IGKV2-40 |
| 69 | Kp6 |
| 70 | Kp48 |
| 71 | Kp3 |
| 72 | Kp20 |
| 73 | Kp7 |
| 74 | Kp10 |
| 75 | Kp1 |
| 76 | J00256, IGHJ1 |
| 77 | J00256, IGHJ2 |
| 78 | J00256, IGHJ3 |
| 79 | J00256, IGHJ4 |
| 80 | J00256, IGHJ5 |
| 81 | J00256, IGHJ6 |
| 82 | AF305952, IGHJ2 |
| 83 | AF305952, IGHJ3 |
| 84 | AF305952, IGHJ4 |
| 85 | AF305952, IGHJ5 |
| 86 | AF305952, IGHJ6 (1) |
| 87 | X04457, IGLJ1 |
| 88 | M15641, IGLJ2 |

TABLE 12-continued cross-reference to sequence identifiers

| SEQ ID No. | Sequence name |
|---|---|
| 89 | M15642, IGLJ3 |
| 90 | X51755, IGLJ4 |
| 91 | X51755, IGLJ5 |
| 92 | M18338, IGLJ6 |
| 93 | X51755, IGLJ7 |
| 94 | Camv119 etc. |
| 95 | Camv18/18/4 |
| 96 | Camv158/28/5 |
| 97 | J00242, IGKJ1 |
| 98 | J00242, IGKJ2 |
| 99 | J00242, IGKJ3 |
| 100 | J00242, IGKJ4 |
| 101 | J00242, IGKJ5 |
| 102 | Kp6/48/3/20/10/1 |
| 103 | Kp7 (1/7 analyzed) |
| 104 | M99660, IGHV3-23 |
| 105 | IVH28 |
| 106 | IVH69 |
| 107 | IVH47 |
| 108 | IVH48 |
| 109 | IVH70 |
| 110 | IVH71 |
| 111 | HuVL1-1(3/4/5) |
| 112 | LAMBDA#14 |
| 113 | LAMBDA#16 |
| 114 | LAMBDA#46 |
| 115 | LAMBDA#45 |
| 116 | LAMBDA#15 |
| 117 | HuVL1-2 |
| 118 | LAMBDA#47 |
| 119 | LAMBDA#18 |
| 120 | LAMBDA#32 |
| 121 | LAMBDA#28 |
| 122 | LAMBDA#29 |
| 123 | LAMBDA#27 |
| 124 | LAMBDA#17 |
| 125 | LAMBDA#4 |
| 126 | LAMBDA#7 |
| 127 | LAMBDA#8 |
| 128 | LAMBDA#5 |
| 129 | HuVL2-1 |
| 130 | LAMBDA#1 |
| 131 | LAMBDA#8 (2) |
| 132 | LAMBDA#5 (2) |
| 133 | LAMBDA#11 |
| 134 | HuVL3-2 |
| 135 | LAMBDA#13 |
| 136 | LAMBDA#40 |
| 137 | LAMBDA#2 |
| 138 | LAMBDA#14 (2) |
| 139 | HuVL4-1 |
| 140 | LAMBDA#10 |
| 141 | HuVL5-1 |
| 142 | LAMBDA#3 |
| 143 | LAMBDA#7 (2) |
| 144 | LAMBDA#9 |
| 145 | LAMBDA#26 |
| 146 | LAMBDA#12 |
| 147 | HuVL8-1 |
| 148 | LAMBDA#42 |
| 149 | LAMBDA#31 |
| 150 | HuVK1-1 |
| 151 | KAPPA#39 |
| 152 | KAPPA#22 |
| 153 | KAPPA#24 |
| 154 | KAPPA#21 |
| 155 | KAPPA#23 |
| 156 | KAPPA#7 |
| 157 | KAPPA#19 |
| 158 | KAPPA#25b |
| 159 | I-_8 |
| 160 | KAPPA#43 |
| 161 | KAPPA#44 |
| 162 | KAPPA#20b |
| 163 | HuVK4-1 |
| 164 | KAPPA#53 |
| 165 | KAPPA#50 |
| 166 | KAPPA#20 |
| 167 | KAPPA#48 |
| 168 | KAPPA#55 |
| 169 | KAPPA#9 |
| 170 | KAPPA#51 |
| 171 | KAPPA#10 |
| 172 | KAPPA#54 |
| 173 | KAPPA#49 |
| 174 | KAPPA#52 |
| 175 | KAPPA#13 |
| 176 | KAPPA#11 |
| 177 | KAPPA#36 |
| 178 | KAPPA#25 |
| 179 | KAPPA#12 |
| 180 | KAPPA#34 |
| 181 | KAPPA#48b |
| 182 | KAPPA#21 (2) |
| 183 | KAPPA#24 (2) |
| 184 | KAPPA#22b |
| 185 | KAPPA#45 |
| 186 | KAPPA#46 |
| 187 | VH1 (1-02) |
| 188 | 1C2 |
| 189 | 1G5 |
| 190 | VH3 (3-23) |
| 191 | 5B12 |
| 192 | 1G4 |
| 193 | 5G7 |
| 194 | VH_99 |
| 195 | VH_76 |
| 196 | VH_86 |
| 197 | VH_98 |
| 198 | VH_89 |
| 199 | VH_82 |
| 200 | VH_68 |
| 201 | VH_73 |
| 202 | VH_107 |
| 203 | VH_94 |
| 204 | VH_90 |
| 205 | VH_77 |
| 206 | VH_74 |
| 207 | VH_67 |
| 208 | VH_79 |
| 209 | VH_75 |
| 210 | VH_110 |
| 211 | VH_109 |
| 212 | VH_103 |
| 213 | VH_84 |
| 214 | VH_113 |
| 215 | VH_87 |
| 216 | VH_105 |
| 217 | VH_101 |
| 218 | VH_108 |
| 219 | VH_106 |
| 220 | VH3 (3-13) |
| 221 | VH_115 |
| 222 | VH_85 |
| 223 | VH_114 |
| 224 | VH_78 |
| 225 | 3B5 |
| 226 | 3A3 |
| 227 | HuV11A-BACK-ApaLI |
| 228 | HuV11B-BACK-ApaLI |
| 229 | HuV11C-BACK-ApaLI |
| 230 | HuV12-BACK-ApaLI |
| 231 | HuV13A-BACK-ApaLI |
| 232 | HuV13B-BACK-ApaLI |
| 233 | HuV14-BACK-ApaLI |
| 234 | HuV15-BACK-ApaLI |
| 235 | HuV16-BACK-ApaLI |
| 236 | HuV17/8-BACK-ApaLI |
| 237 | HuV19-BACK-ApaLI |
| 238 | HuV110-BACK-ApaLI |
| 239 | caClambda1-FOR |
| 240 | caClambda2-FOR |

TABLE 12-continued cross-reference to sequence identifiers

| SEQ ID No. | Sequence name |
|---|---|
| 241 | HuVk1B-BACK-ApaLI |
| 242 | HuVk2-BACK-ApaLI |
| 243 | HuVk3B-BACK-ApaLI |
| 244 | HuVk2/4-BACK-ApaLI |
| 245 | HuVk5-BACK-ApaLI |
| 246 | HuVk6-BACK-ApaLI |
| 247 | HuVk4B-BACK-ApaLI |
| 248 | caCHkapFOR-AscI |
| 249 | caCHkap2FOR-AscI |
| 250 | VH-1A1, 2B8, 2B9 |
| 251 | VH-1C3, 1E3, 2A7 |
| 252 | VH-1B3, 1G2, 2D8 |
| 253 | VH-1G1, 2B7 |
| 254 | X07448, IGHV1-2 |
| 255 | 1F2 VH |
| 256 | Humanized VH 1F2 |
| 257 | Safe Variant VH 1F2 |
| 258 | X92218, IGHV3-66 |
| 259 | 1E2 VH |
| 260 | Humanized VH 1E2 |
| 261 | Safe Variant VH 1E2 |
| 262 | Z73650, IGLV8-61 |
| 263 | 1F2 VL |
| 264 | Humanized 1F2 VL |
| 265 | Safe Variant VL 1F2 |
| 266 | 1E2 VL |
| 267 | Humanized VL 1E2 |
| 268 | Safe Variant VL 1E2 |
| 269 | X92343 | IGHV1-46*01 |
| 270 | LpVH1-s6 (AM939701) |
| 271 | LpVH1-s2 (AM939697) |
| 272 | LpVH1-s3 (AM939698) |
| 273 | LpVH1-s4 (AM939699) |
| 274 | LpVH1-s5 Ps (AM939700) |
| 275 | M99660 | IGHV3-23*01 |
| 276 | AM939712 |
| 277 | AM939713 |
| 278 | AM939730 |
| 279 | AM939731 |
| 280 | AM939744 |
| 281 | AM939726 |
| 282 | AM939727 |
| 283 | AM939739 |
| 284 | AM939740 |
| 285 | AM939741 |
| 286 | AM939742 |
| 287 | AM939743 |
| 288 | u29481 | IGliv3-23*03 |
| 289 | AM939716 |
| 290 | AM939728 |
| 291 | AM939738 |
| 292 | AM939710 |
| 293 | AM939748 |
| 294 | AM939750 |
| 295 | AM939751 |
| 296 | AM939767 |
| 297 | AM939768 |
| 298 | AM939707 |
| 299 | AM939708 |

TABLE 12-continued cross-reference to sequence identifiers

| SEQ ID No. | Sequence name |
|---|---|
| 300 | AM939709 |
| 301 | AM939732 |
| 302 | AM939733 |
| 303 | AM939717 |
| 304 | AM939734 |
| 305 | AM939735 |
| 306 | AM939736 |
| 307 | AM939737 |
| 308 | L33851 | IGHV3-74*01 |
| 309 | AM939749 |
| 310 | AM939724 |
| 311 | AM939725 |
| 312 | AM939745 |
| 313 | AM939723 |
| 314 | X92229 | IGHV4-30-2*03 |
| 315 | LpVH2-s7 (AM939704) |
| 316 | Z14238 | IGHV4-30-4*01 |
| 317 | LpVH2-s2 (AM939769) |
| 318 | LpVH2-s3 (AM939770) |
| 319 | LpVH2-s4 (AM939771) |
| 320 | LpVH2-s5 (AM939772) |
| 321 | LpVH2-s6 (AM939773) |
| 322 | LpVH2-sll Ps (AM939703) |
| 323 | LpVH2-s8 (AM939705) |
| 324 | LpVH2-s9 Ps (AM939706) |
| 325 | LpVH2-s10 (AM939702) |
| 326 | AJ879486 | IGliv3-23*04 |
| 327 | S-VH1 |
| 328 | S-VH3 |
| 329 | S-VH4 |
| 330 | S-VH2 |
| 331 | S-VH6 |
| 332 | S-VH5 |
| 333 | D86994 | IGIN3-25*02 |
| 334 | VL25-28 |
| 335 | z73672 | IGIN5-37*01 |
| 336 | VL2,12,15 |
| 337 | z73650 | IGIN8-61*01 |
| 338 | VL3,5 |
| 339 | VL17-24,29-32 |
| 340 | vL10 |
| 341 | v1,4,6,7,8,9,13,14 |
| 342 | U41644 | IGKV2D-29*02 |
| 343 | KAPPA 33-36,38,39,42,4 |
| 344 | KAPPA 41,43,44 |
| 345 | KAPPA 40,44 |
| 346 | KAPPA 37,46,48 |
| 347 | VH1a-BACK |
| 348 | VH5a-BACK |
| 349 | VH4a-BACK |
| 350 | VH4b-BACK |
| 351 | VH2b-BACK |
| 352 | VH1a-BACK-SfiI |
| 353 | VH5a-BACK-SfiI |
| 354 | VH4a-BACK-SfiI |
| 355 | VH4b-BACK-SfiI |
| 356 | VH2b-BACK-SfiI |

The invention claimed is:

1. A polynucleotide molecule encoding a VH domain and/or a VL domain of an antigen binding polypeptide, said VH domain comprising hypervariable loops H1, H2 and H3, and said VL domain comprising hypervariable loops L1, L2 and L3, wherein said VH domain and/or said VL domain are each fused to one or more IgG constant domains of a human antibody, wherein each of the hypervariable loops H1-H3 and L1-L3 are obtained from a conventional antibody of a *Lama* species by active immunization of the *Lama* species with the human target antigen, wherein said conventional antibody is a heterotetrameric IgG antibody composed of two identical light chains and two identical heavy chains, and wherein at least one of the hypervariable loops H1, H2, L1, L2 and L3 exhibits a predicted or actual canonical fold structure which is identical or substantially identical to a canonical fold structure of a corresponding H1, H2, L1, L2 or L3 hypervariable loop which occurs in a human antibody.

2. An expression vector comprising the polynucleotide molecule of claim 1 operably linked to regulatory sequences which permit expression of the antigen binding polypeptide in a host cell or cell-free expression system.

3. A host cell or cell-free expression system containing the expression vector of claim 2.

4. A method of producing a recombinant antigen binding polypeptide which comprises culturing the host cell or cell free expression system of claim 3 under conditions which permit expression of the antigen binding polypeptide and recovering the expressed antigen binding polypeptide.

* * * * *